(12) United States Patent
Maehata et al.

(10) Patent No.: US 9,185,910 B2
(45) Date of Patent: Nov. 17, 2015

(54) AMIDE COMPOUND

(71) Applicant: Sumitomo Chemical Company, Limited, Tokyo (JP)

(72) Inventors: Ryota Maehata, Takarazuka (JP); Hajime Mizuno, Takarazuka (JP); Chie Shimizu, Takarazuka (JP); Yoshihiko Nokura, Takarazuka (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 0 days.

(21) Appl. No.: 14/417,374

(22) PCT Filed: Jul. 29, 2013

(86) PCT No.: PCT/JP2013/071083
§ 371 (c)(1),
(2) Date: Jan. 26, 2015

(87) PCT Pub. No.: WO2014/021468
PCT Pub. Date: Feb. 6, 2014

(65) Prior Publication Data
US 2015/0189880 A1    Jul. 9, 2015

(30) Foreign Application Priority Data

Jul. 31, 2012   (JP) .................. 2012-169305

(51) Int. Cl.

| | | |
|---|---|---|
| *A61K 31/44* | (2006.01) | |
| *A01N 43/40* | (2006.01) | |
| *A01N 47/02* | (2006.01) | |
| *C07D 213/81* | (2006.01) | |
| *C07D 213/89* | (2006.01) | |
| *A61K 47/10* | (2006.01) | |
| *A61K 47/18* | (2006.01) | |
| *A61K 9/02* | (2006.01) | |
| *A61K 9/08* | (2006.01) | |
| *A61K 9/10* | (2006.01) | |
| *A61K 9/107* | (2006.01) | |
| *A61K 9/14* | (2006.01) | |
| *A61K 9/16* | (2006.01) | |
| *A61K 9/20* | (2006.01) | |
| *A61K 9/48* | (2006.01) | |
| *A61K 31/4412* | (2006.01) | |
| *A61K 31/444* | (2006.01) | |

(52) U.S. Cl.
CPC ............. *A01N 43/40* (2013.01); *A01N 47/02* (2013.01); *A61K 9/02* (2013.01); *A61K 9/08* (2013.01); *A61K 9/10* (2013.01); *A61K 9/107* (2013.01); *A61K 9/143* (2013.01); *A61K 9/145* (2013.01); *A61K 9/1611* (2013.01); *A61K 9/1641* (2013.01); *A61K 9/2027* (2013.01); *A61K 9/2054* (2013.01); *A61K 9/2059* (2013.01); *A61K 9/4816* (2013.01); *A61K 31/44* (2013.01); *A61K 31/444* (2013.01); *A61K 31/4412* (2013.01); *A61K 47/10* (2013.01); *A61K 47/18* (2013.01); *C07D 213/81* (2013.01); *C07D 213/89* (2013.01)

(58) Field of Classification Search
None
See application file for complete search history.

(56) References Cited

U.S. PATENT DOCUMENTS

| | | | |
|---|---|---|---|
| 9,018,134 B2 * | 4/2015 | Takahashi et al. ............ 504/246 |
| 2003/0191113 A1 | 10/2003 | Nieto-Roman et al. | |
| 2004/0142977 A1 | 7/2004 | Hutin et al. | |
| 2006/0040995 A1 | 2/2006 | Bacque et al. | |
| 2012/0149910 A1 | 6/2012 | Mihara et al. | |
| 2013/0012380 A1 | 1/2013 | Le Vezouet et al. | |
| 2013/0180014 A1 | 7/2013 | Soergel et al. | |

FOREIGN PATENT DOCUMENTS

| | | |
|---|---|---|
| JP | 2003-034671 A | 2/2003 |
| WO | 2008044713 A1 | 4/2008 |

OTHER PUBLICATIONS

Int'l Search Report issued Aug. 27, 2013 in Int'l Application No. PCT/JP2013/071083.

* cited by examiner

*Primary Examiner* — Heidi Reese
(74) *Attorney, Agent, or Firm* — Panitch Schwarze Belisario & Nadel LLP

(57) ABSTRACT

A fused heterocyclic compound represented by formula (I) has an excellent pest control effect. In the formula, $R^1$ represents a $C_1$-$C_6$ chain hydrocarbon group or the like; $R^2$, $R^3$ and $R^4$ may be the same or different, and each represents a $C_1$-$C_6$ chain hydrocarbon group or the like; $R^5$ represents a $C_1$-$C_6$ chain hydrocarbon group or the like; $G^1$, $G^2$, $G^3$, $G^4$ and $G^5$ may be the same or different, and each represents a nitrogen atom or the like; Q represents an oxygen atom or a sulfur atom; and n represents 0, 1 or 2.

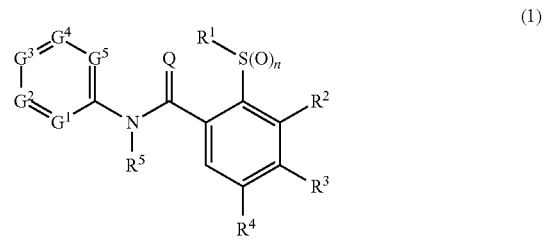

(1)

18 Claims, No Drawings

AMIDE COMPOUND

CROSS-REFERENCE TO RELATED APPLICATION

This application is a Section 371 of International Application No. PCT/JP2013/071083, filed Jul. 29, 2013, which was published in the Japanese language on Feb. 6, 2014, under International Publication No. WO 2014/021468 A1, and the disclosure of which is incorporated herein by reference.

TECHNICAL FIELD

The present invention relates to an amide compound and a use thereof for pest control.

BACKGROUND ART

It is known that a certain kind of amide compound has a use as a fungicide. (WO2001/049666)

SUMMARY OF THE INVENTION

The present invention provides a compound having an excellent control effect on pests and a method for controlling pests using the compound.

According to the present invention, an amide compound represented by the following formula (1) has an excellent control effect on pests.

More specifically, the present invention is as described below.

[1] An amide compound represented by formula (1) or an N-oxide thereof,

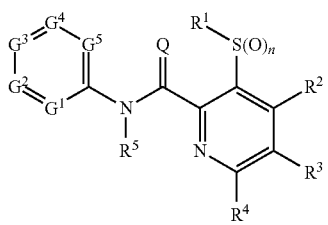

(1)

wherein $R^1$ represents a C1 to C6 chain hydrocarbon group optionally having one or more atoms or groups selected from group X or a C3 to C9 alicyclic hydrocarbon group optionally having one or more atoms or groups selected from group Y, $R^2$, $R^3$ and $R^4$ are the same or different and represent a C1 to C6 chain hydrocarbon group optionally having one or more atoms or groups selected from group X, a C3 to C9 alicyclic hydrocarbon group optionally having one or more atoms or groups selected from group Y, a phenyl group optionally having one or more atoms or groups selected from group Z, a 5- or 6-membered heterocyclic group optionally having one or more atoms or groups selected from group Z, $OR^{11}$, $S(O)_mR^{11}$, $S(O)_2NR^{11}R^{12}$, $NR^{11}R^{12}$, $NR^{15}C(O)R^{11}$, $NR^{15}C(O)OR^{11}$, $NR^{15}C(O)NR^{11}R^{12}$, $NR^{16}S(O)_2R^{13}$, $C(O)R^{11}$, $C(O)OR^{11}$, $C(O)NR^{11}R^{12}$, $C(O)NR^{11}NR^{15}R^{16}$, $SF_5$, a cyano group, a nitro group, a halogen atom or a hydrogen atom, $R^5$ represents a C1 to C6 chain hydrocarbon group optionally having one or more atoms or groups selected from group W, a C3 to C9 alicyclic hydrocarbon group optionally having one or more atoms or groups selected from group Y, a C1 to C6 chain hydrocarbon group having one phenyl group (wherein the phenyl group optionally has one or more atoms or groups selected from group Z), a C1 to C6 chain hydrocarbon group having one 5- or 6-membered heterocyclic group (wherein the 5- or 6-membered heterocyclic group optionally has one or more atoms or groups selected from group Z), $C(O)R^{11}$, $C(O)OR^{11}$, $C(O)NR^{11}R^{12}$ or a hydrogen atom, $G^1$ represents a nitrogen atom or $CR^6$,
$G^2$ represents a nitrogen atom or $CR^7$,
$G^3$ represents a nitrogen atom or $CR^8$,
$G^4$ represents a nitrogen atom or $CR^9$,
$G^5$ represents a nitrogen atom or $CR^{10}$ (wherein not all of $G^2$, $G^3$ and $G^4$ represent a nitrogen atom), $R^6$ and $R^{10}$ are the same or different and represent a C1 to C6 chain hydrocarbon group optionally having one or more atoms or groups selected from group X, a C3 to C9 alicyclic hydrocarbon group optionally having one or more atoms or groups selected from group Y, $OR^{14}$, $S(O)_mR^{14}$, a fluorine atom or a hydrogen atom, $R^7$, $R^8$ and $R^9$ are the same or different and represent a C1 to C6 chain hydrocarbon group optionally having one or more atoms or groups selected from group X, a C3 to C9 alicyclic hydrocarbon group optionally having one or more atoms or groups selected from group Y, a phenyl group optionally having one or more atoms or groups selected from group Z, a 5- or 6-membered heterocyclic group optionally having one or more atoms or groups selected from group Z, $OR^{14}$, $S(O)_mR^{11}$, $S(O)_2NR^{11}R^{12}$, $NR^{11}R^{12}$, $NR^{11}C(O)R^{12}$, $NR^{11}C(O)OR^{12}$, $NR^{11}S(O)_2R^{13}$, $C(O)R^{11}$, $C(O)OR^{11}$, $C(O)NR^{11}R^{12}$, $SF_5$, a hydroxy group, a cyano group, a nitro group, a halogen atom or a hydrogen atom (wherein at least one of $R^7$, $R^8$ and $R^9$ represents a C1 to C6 chain hydrocarbon group optionally having one or more atoms or groups selected from group X, a C3 to C9 alicyclic hydrocarbon group optionally having one or more atoms or groups selected from group Y, a phenyl group optionally having one or more atoms or groups selected from group Z, a 5- or 6-membered heterocyclic group optionally having one or more atoms or groups selected from group Z, $OR^{14}$, $S(O)_mR^{11}$, $S(O)_2NR^{11}R^{12}$, $NR^{11}R^{12}$, $NR^{11}C(O)R^{12}$, $NR^{11}C(O)OR^{12}$, $NR^{11}S(O)_2R^{13}$, $C(O)R^{11}$, $C(O)OR^{11}$, $C(O)NR^{11}R^{12}$, $SF_5$, a cyano group, a nitro group, or a halogen atom), $R^{11}$ and $R^{12}$ are the same or different and represent a C1 to C6 chain hydrocarbon group optionally having one or more atoms or groups selected from group V, a C3 to C9 alicyclic hydrocarbon group optionally having one or more atoms or groups selected from group Y, a phenyl group optionally having one or more atoms or groups selected from group Z, a 4-, 5- or 6-membered heterocyclic group optionally having one or more atoms or groups selected from group Z or a hydrogen atom, $R^{13}$ represents a C1 to C6 chain hydrocarbon group optionally having one or more atoms or groups selected from group V, a C3 to C9 alicyclic hydrocarbon group optionally having one or more atoms or groups selected from group Y, a phenyl group optionally having one or more atoms or groups selected from group Z or a 4-, 5- or 6-membered heterocyclic group optionally having one or more atoms or groups selected from group Z, $R^{14}$ represents a C1 to C6 chain hydrocarbon group optionally having one or more atoms or groups selected from the group consisting of halogen atoms and C3 to C9 alicyclic hydrocarbon groups (wherein the C3 to C9 alicyclic hydrocarbon group optionally has one or more halogen atoms or one or more C1 to C3 alkyl groups) or a C3 to C9 alicyclic hydrocarbon group optionally having one or more atoms or groups selected from the group consisting of halogen atoms and C1 to C3 alkyl groups, $R^{15}$ represents a C1 to C6 chain hydrocarbon group optionally having one or more atoms or groups selected from group V, a C3 to C9 alicyclic hydrocarbon group optionally having one or more atoms or groups selected from group Y, a phenyl group optionally having one or more atoms or groups selected from group Z, a 5- or 6-membered heterocyclic group optionally having one or more atoms or groups selected from group Z, $C(O)R^{11}$, $C(O)OR^{11}$, $C(O)NR^{11}R^{12}$ or a hydrogen atom, $R^{16}$ represents a C1 to C6 chain hydrocarbon group optionally having one or more atoms or groups selected from group V, a C3 to C9 alicyclic hydrocarbon group optionally having one or more atoms or groups selected from group Y, a phenyl group optionally having one or more atoms or groups selected from group Z, a 5- or 6-membered heterocyclic group optionally having one or more atoms or groups selected from group Z, $C(O)R^{11}$, $C(O)OR^{11}$, $C(O)NR^{11}R^{12}$, $S(O)_2R^{11}$, $S(O)_2NR^{11}R^{12}$ or a hydrogen atom, Q represents an oxygen atom or a sulfur atom, m represents 0, 1 or 2, and n represents 0, 1 or 2;

Group X: a group consisting of C3 to C9 alicyclic hydrocarbon groups optionally having one or more atoms or groups selected from the group consisting of halogen atoms and C1 to C3 alkyl groups, C1 to C6 alkoxy groups optionally having one or more halogen atoms, C1 to C6 alkylsulfanyl groups optionally having one or more halogen atoms, C1 to C6 alkylsulfinyl groups optionally having one or more halogen atoms, C1 to C6 alkylsulfonyl groups optionally having one or more halogen atoms, C2 to C6 alkylcarbonyl groups optionally having one or more halogen atoms, C2 to C6 alkoxycarbonyl groups optionally having one or more halogen atoms, hydroxy groups, mercapto groups, cyano groups, and halogen atoms, Group Y: a group consisting of C1 to C6 alkyl groups optionally having one or more halogen atoms, C1 to C6 alkoxy groups optionally having one or more halogen atoms, C1 to C6 alkylsulfanyl groups optionally having one or more halogen atoms, C1 to C6 alkylsulfinyl groups optionally having one or more halogen atoms, C1 to C6 alkylsulfonyl groups optionally having one or more halogen atoms, and halogen atoms, Group Z: a group consisting of C1 to C6 alkyl groups optionally having one or more halogen atoms, C1 to C6 alkoxy groups optionally having one or more halogen atoms, C1 to C6 alkylsulfanyl groups optionally having one or more halogen atoms, C1 to C6 alkylsulfinyl groups optionally having one or more halogen atoms, C1 to C6 alkylsulfonyl groups optionally having one or more halogen atoms, C1 to C6 alkylamino groups optionally having one or more halogen atoms, C2 to C8 dialkylamino groups optionally having one or more halogen atoms, C2 to C6 alkylcarbonyl groups optionally having one or more halogen atoms, C2 to C6 alkoxycarbonyl groups optionally having one or more halogen atoms, hydroxy groups, mercapto groups, amino groups, cyano groups, nitro groups, and halogen atoms, Group W: a group consisting of C3 to C9 alicyclic hydrocarbon groups optionally having one or more atoms or groups selected from the group consisting of halogen atoms and C1 to C3 alkyl groups, C1 to C6 alkoxy groups optionally having one or more halogen atoms, C1 to C6 alkylsulfanyl groups optionally having one or more halogen atoms, C1 to C6 alkylsulfinyl groups optionally having one or more halogen atoms, C1 to C6 alkylsulfonyl groups optionally having one or more halogen atoms, C2 to C6 alkylcarbonyl groups optionally having one or more halogen atoms, C2 to C6 alkoxycarbonyl groups optionally having one or more halogen atoms, hydroxy groups, cyano groups, and halogen atoms, Group V: a group consisting of C3 to C9 alicyclic hydrocarbon groups optionally having one or more atoms or groups selected from group Y, a phenyl group optionally having one or more atoms or groups selected from group Z, a 5- or 6-membered heterocyclic group optionally having one or more atoms or groups selected from group Z, a C1 to C6 alkoxy group optionally having one or more halogen atoms, a C2 to C6 alkenyloxy group optionally having one or more halogen atoms, a C2 to C6 alkynyloxy group optionally having one or more halogen atoms, a C1 to C6 alkylsulfanyl group optionally having one or more halogen atoms, a C1 to C6 alkylsulfinyl group optionally having one or more halogen atoms, a C1 to C6 alkylsulfonyl group optionally having one or more halogen atoms, a C1 to C6 alkylaminosulfonyl group optionally having one or more halogen atoms, a C2 to C8 dialkylaminosulfonyl group optionally having one or more halogen atoms, a C1 to C6 alkylamino group optionally having one or more halogen atoms, a C2 to C8 dialkylamino group optionally having one or more halogen atoms, a C2 to C6 alkylcarbonylamino group optionally having one or more halogen atoms, a C2 to C6 alkoxycarbonylamino group optionally having one or more halogen atoms, a C2 to C6 alkylcarbonyl group optionally having one or more halogen atoms, a C2 to C6 alkoxycarbonyl group optionally having one or more halogen atoms, a C2 to C6 alkylaminocarbonyl group optionally having one or more halogen atoms, a C3 to C10 dialkylaminocarbonyl group optionally having one or more halogen atoms, cyano groups, hydroxy groups, and halogen atoms;

when m is 1 or 2 in $S(O)_mR^{11}$, $R^{11}$ does not represent a hydrogen atom (hereinafter, the amide compound represented by the formula (1) and the N-oxide thereof are referred to as the compound of the present invention).

[2] The compound according to [1] described above, wherein $R^1$ is a C1 to C6 alkyl group optionally having one or more atoms or groups selected from the group consisting of halogen atoms and cyclopropyl groups (wherein the cyclopropyl group optionally has one or more halogen atoms or one or more C1 to C3 alkyl groups), a C3 to C6 cycloalkyl group optionally having one or more atoms or groups selected from the group consisting of halogen atoms and C1 to C3 alkyl groups, a C2 to C6 alkenyl group optionally having one or more halogen atoms or a C2 to C6 alkynyl group optionally having one or more halogen atoms, $R^2$, $R^3$ and $R^4$ are the same or different and are a C1 to C6 chain hydrocarbon group optionally having one or more atoms or groups selected from group X, a phenyl group optionally having one or more atoms or groups selected from group Z, a 5- or 6-membered heterocyclic group optionally having one or more atoms or groups selected from group Z, $OR^{11}$, $S(O)_mR^{11}$, $S(O)_2NR^{11}R^{12}$, $NR^{11}R^{12}$, $NR^{15}C(O)R^{11}$, $NR^{15}C(O)OR^{11}$, $NR^{15}C(O)NR^{11}R^{12}$, $NR^{16}S(O)_2R^{13}$, $C(O)R^{11}$, $C(O)OR^{11}$, $C(O)NR^{11}R^{12}$, $C(O)NR^{11}NR^{15}R^{16}$, a cyano group, a halogen atom or a hydrogen atom, $R^5$ is a C1 to C6 alkyl group optionally having one or more atoms or groups selected from the group consisting of halogen atoms and cyclopropyl groups (wherein the cyclopropyl group optionally has one or more halogen atoms or one or more C1 to C3 alkyl groups), a C3 to C6 cycloalkyl group optionally having one or more atoms or groups selected from the group consisting of halogen atoms and C1 to C3 alkyl groups, a (C1 to C6 alkoxy)C1 to C6 alkyl group optionally having one or more halogen atoms, a C2 to C6 alkenyl group optionally having one or more halogen atoms, a C2 to C6 alkynyl group optionally having one or more halogen atoms, a C1 to C6 alkyl group having one thiazolyl group (wherein the thiazolyl group optionally has one or more atoms or groups selected from the group consisting of C1 to C3 alkyl groups optionally having one or more halogen atoms and halogen atoms), a C1 to C6 alkyl group having one pyridyl group (wherein the pyridyl group optionally has one or more atoms or groups selected from the group consisting of C1 to C3 alkyl groups optionally having one or more halogen atoms and halogen atoms), $C(O)R^{11}$, $C(O)OR^{11}$ or a hydrogen atom, $R^6$ and $R^{10}$ are the same or different and are a C1 to C6 alkyl group optionally having one or more halogen atoms, a fluorine atom or a hydrogen atom, $R^7$, $R^8$ and $R^9$ are the same or different and are a C1 to C6 chain hydrocarbon group optionally having one or more atoms or groups selected from group X, a C1 to C6 alkoxy group optionally having one or more halogen atoms, $OR^{14}$, $S(O)_mR^{11}$, a halogen atom or a hydrogen atom (wherein at least one of $R^7$, $R^8$ and $R^9$ represents a C1 to C6 chain hydrocarbon group optionally having one or more atoms or groups selected from group X, a C1 to C6 alkoxy group optionally having one or more halogen atoms, $OR^{14}$, $S(O)_mR^{11}$, or a halogen atom), $R^{11}$ and $R^{12}$ are the same or different and are a C1 to C6 alkyl group optionally having one or more halogen atoms, a phenyl group optionally having one or more atoms or groups selected from the group consisting of C1 to C3 alkyl groups optionally having one or more halogen atoms and halogen atoms, a 5- or 6-membered heterocyclic group optionally having one or more atoms or groups selected from the group consisting of C1 to C3 alkyl groups optionally having one or more halogen atoms and halogen atoms, a C3 to C6 cycloalkyl group optionally having one or more atoms or groups selected from the group consisting of halogen atoms and C1 to C3 alkyl groups or a hydrogen atom, and Q is an oxygen atom.

[3] The compound according to [1] described above, wherein $R^1$ is a C3 to C6 cycloalkyl group optionally having one or more atoms or groups selected from the group consisting of halogen atoms and C1 to C3 alkyl groups, a C1 to C6 alkyl group optionally having one or more halogen atoms or a (C3 to C6 cycloalkyl)C1 to C3 alkyl group optionally having one or more halogen atoms, $R^2$, $R^3$ and $R^4$ are the same or different and are a C1 to C6 alkyl group optionally having one or more halogen atoms, a 5- or 6-membered heterocyclic group optionally having one or more atoms or groups selected from C1 to C3 alkyl groups optionally having one or more halogen atoms and halogen atoms, $OR^{11}$, $S(O)_mR^{11}$, $NR^{11}R^{12}$, $NR^{15}C(O)R^{11}$, $NR^{15}C(O)OR^{11}$, $NR^{15}C(O)NR^{11}R^{12}$, $NR^{16}S(O)_2R^{13}$, $C(O)OR^{11}$, $C(O)NR^{11}R^{12}$, $C(O)NR^{11}NR^{15}R^{16}$, a cyano group, a halogen atom or a hydrogen atom, $R^5$ is a C1 to C6 alkyl group optionally having one or more atoms or groups selected from the group consisting of halogen atoms and cyclopropyl groups (wherein the cyclopropyl group optionally has one or more halogen atoms or one or more C1 to C3 alkyl groups), a C3 to C6 cycloalkyl group optionally having one or more atoms or groups selected from the group consisting of halogen atoms and C1 to C3 alkyl groups, a (C1 to C6 alkoxy)C1 to C6 alkyl group optionally having one or more halogen atoms, a C2 to C6 alkenyl group optionally having one or more halogen atoms, a C2 to C6 alkynyl group optionally having one or more halogen atoms, a C2 to C6 alkylcarbonyl group optionally having one or more halogen atoms, a C2 to C6 alkoxycarbonyl group optionally having one or more halogen atoms, or a hydrogen atom, $R^6$ and $R^{10}$ are the same or different and are a fluorine atom or a hydrogen atom, $R^7$, $R^8$ and $R^9$ are the same or different and are a C1 to C6 alkyl group optionally having one or more atoms or groups selected from the group consisting of C1 to C3 alkoxy groups and halogen atoms, a C2 to C6 alkenyl group optionally having one or more halogen atoms, a C2 to C6 alkynyl group optionally having one or more halogen atoms, a C1 to C6 alkoxy group optionally having one or more halogen atoms, a C1 to C6 alkylsulfanyl group optionally having one or more halogen atoms, a C1 to C6 alkylsulfinyl group optionally having one or more halogen atoms, a C1 to C6 alkylsulfonyl group optionally having one or more halogen atoms, a halogen atom or a hydrogen atom (wherein at least one of $R^7$, $R^8$ and $R^9$ represents a C1 to C6 alkyl group optionally having one or more atoms or groups selected from the group consisting of C1 to C3 alkoxy groups and halogen atoms, a C2 to C6 alkenyl group optionally having one or more halogen atoms, a C2 to C6 alkynyl group optionally having one or more halogen atoms, a C1 to C6 alkoxy group optionally having one or more halogen atoms, a C1 to C6 alkylsulfanyl group optionally having one or more halogen atoms, a C1 to C6 alkylsulfinyl group optionally having one or more halogen atoms, a C1 to C6 alkylsulfonyl group optionally having one or more halogen atoms, or a halogen atom), $R^{11}$ is a C1 to C6 alkyl group optionally having one or more halogen atoms or a hydrogen atom, and Q is an oxygen atom.

[4] The compound according to [1] described above, wherein $R^1$ is a C1 to C6 alkyl group, a cyclopropyl group or a cyclopropylmethyl group, $R^2$, $R^3$ and $R^4$ are the same or different and are a C1 to C3 alkyl group optionally having one or more halogen atoms, a C1 to C3 alkylsulfanyl group optionally having one or more halogen atoms, a C1 to C3 alkylsulfinyl group optionally having one or more halogen atoms, a C1 to C3 alkylsulfonyl group optionally having one or more halogen atoms, an amino group, a C1 to C3 alkylamino group optionally having one or more halogen atoms, a C2 to C6 dialkylamino group optionally having one or more halogen atoms, a C2 to C6 alkylcarbonylamino group optionally having one or more halogen atoms, a C2 to C6 alkoxycarbonylamino group optionally having one or more halogen atoms, a C2 to C6 alkylaminocarbonyl group optionally having one or more halogen atoms, a C2 to C6 dialkylaminocarbonyl group optionally having one or more halogen atoms, a C2 to C6 alkoxycarbonyl group optionally having one or more halogen atoms, a 5- or 6-membered heterocyclic group optionally having one or more atoms or groups selected from the group consisting of C1 to C3 alkyl groups optionally having one or more halogen atoms and halogen atoms, a halogen atom or a hydrogen atom, $R^5$ is a C1 to C6 alkyl group optionally having one or more atoms or groups selected from the group consisting of halogen atoms and cyclopropyl groups (wherein the cyclopropyl group optionally has one or more halogen atoms or one or more C1 to C3 alkyl groups), a C3 to C6 cycloalkyl group optionally having one or more atoms or groups selected from the group consisting of halogen atoms and C1 to C3 alkyl groups, a C2 to C6 alkenyl group optionally having one or more halogen atoms, a C2 to C6 alkynyl group optionally having one or more halogen atoms, a (C1 to C6 alkoxy)C1 to C6 alkyl group optionally having one or more halogen atoms, a C2 to C6 alkylcarbonyl group optionally having one or more halogen atoms, a C2 to C6 alkoxycarbonyl group optionally having one or more halogen atoms or a hydrogen atom, $R^6$ and $R^{10}$ are the same or different and are a fluorine atom or a hydrogen atom, $R^7$, $R^8$ and $R^9$ are the same or different and are a C1 to C6 haloalkyl group, a C2 to C6 haloalkenyl group, a C1 to C6 haloalkoxy group, a C1 to C6 haloalkylsulfanyl group, a C1 to C6 haloalkylsulfinyl group, a C1 to C6 haloalkylsulfonyl group, a halogen atom or a hydrogen atom, and Q is an oxygen atom.

[5] The compound according to any of [1] to [4] described above, wherein $R^5$ is a C1 to C6 alkyl group optionally having one or more atoms or groups selected from the group consisting of halogen atoms and cyclopropyl groups (wherein the cyclopropyl group optionally has one or more halogen atoms or one or more C1 to C3 alkyl groups), a C2 to C6 alkenyl group optionally having one or more halogen atoms, a C2 to C6 alkynyl group optionally having one or more halogen atoms, a (C1 to C6 alkoxy)C1 to C6 alkyl group optionally having one or more halogen atoms, a C3 to C6 cycloalkyl group optionally having one or more atoms or groups selected from the group consisting of halogen atoms and C1 to C3 alkyl groups, a C2 to C6 alkylcarbonyl group optionally having one or more halogen atoms or a C2 to C6 alkoxycarbonyl group optionally having one or more halogen atoms.

[6] The compound according to any of [1] to [4] described above, wherein $R^5$ is a hydrogen atom.

[7] The compound according to any of [1] to [6] described above, wherein one or two of $G^1$, $G^2$, $G^3$, $G^4$ and $G^5$ are a nitrogen atom.

[8] The compound according to [7] described above, wherein $G^1$ is a nitrogen atom or $CR^6$, $G^2$ is a nitrogen atom or $CR^7$, $G^3$ is $CR^8$, $G^4$ is $CR^9$, $G^5$ is a nitrogen atom or $CR^{10}$, and one or two of $G^1$, $G^2$ and $G^5$ are a nitrogen atom.

[9] The compound according to [7] described above, wherein $G^1$ is a nitrogen atom or CH, $G^5$ is a nitrogen atom or CH (wherein one or two of $G^1$, $G^2$ and $G^5$ represent a nitrogen atom), and $R^7$, $R^8$ and $R^9$ are the same or different and are a C1 to C6 haloalkyl group, a C2 to C6 haloalkenyl group, a C1 to C6 haloalkoxy group, a C1 to C6 haloalkylsulfanyl group, a C1 to C6 haloalkylsulfinyl group, a C1 to C6 haloalkylsulfonyl group, a halogen atom or a hydrogen atom.

[10] The compound according to [7] described above, wherein $G^1$ is a nitrogen atom or CH, $G^5$ is a nitrogen atom or CH (wherein one or two of $G^1$, $G^2$ and $G^5$ represent a nitrogen atom), and $R^7$, $R^8$ and $R^9$ are the same or different and are a C1 to C3 perfluoroalkyl group, a C1 to C3 perfluoroalkoxy group, a C1 to C3 perfluoroalkylsulfanyl group, a C1 to C3 perfluoroalkylsulfinyl group, a C1 to C3 perfluoroalkylsulfonyl group, a halogen atom or a hydrogen atom.

[11] The compound as defined in any of [7] to [10] described above, wherein one of $G^1$, $G^2$ and $G^5$ is a nitrogen atom.

[12] The compound as defined in any of [7] to [10] described above, wherein $G^1$ is a nitrogen atom, $G^2$ is $CR^7$, $G^3$ is $CR^8$, $G^4$ is $CR^9$, and $G^5$ is $CR^{10}$.

[13] The compound as defined in any of [7] to [10] described above, wherein $G^1$ is $CR^6$, $G^2$ is a nitrogen atom, $G^3$ is $CR^8$, $G^4$ is $CR^9$, and $G^5$ is $CR^{10}$.

[14] The compound as defined in any of [1] to [6] described above, wherein $G^1$ is $CR^6$, $G^2$ is $CR^7$, $G^3$ is $CR^7$, $G^4$ is $CR^9$, and $G^5$ is $CR^{10}$.

[15] The compound according to [14] described above, wherein $G^1$ is CH, $G^2$ is $CR^7$, $G^3$ is $CR^8$, $G^4$ is $CR^9$, and $G^5$ is CH, and $R^7$, $R^8$ and $R^9$ are the same or different and are a C1 to C6 haloalkyl group, a C2 to C6 haloalkenyl group, a C1 to C6 haloalkoxy group, a C1 to C6 haloalkylsulfanyl group, a C1 to C6 haloalkylsulfinyl group, a C1 to C6 haloalkylsulfonyl group, a halogen atom or a hydrogen atom.

[16] The compound according to [14] described above, wherein $G^1$ is CH, $G^2$ is $CR^7$, $G^3$ is $CR^8$, $G^4$ is $CR^9$, and $G^5$ is CH, and $R^7$, $R^8$ and $R^9$ are the same or different and are a C1 to C3 perfluoroalkyl group, a C1 to C3 perfluoroalkoxy group, a C1 to C3 perfluoroalkylsulfanyl group, a C1 to C3 perfluoroalkylsulfinyl group, a C1 to C3 perfluoroalkylsulfonyl group, a halogen atom or a hydrogen atom.

[17] A pest control composition comprising the compound as defined in any of [1] to [16] described above, and an inert carrier.

[18] A method for controlling pests comprising applying an effective amount of the compound as defined in any of [1] to [16] described above to a pest or a pest-infested area.

MODE FOR CARRYING OUT THE INVENTION

In the compound of the present invention, an N-oxide is a compound in which the nitrogen atom constituting the ring on the heterocyclic group is oxidized. Examples of the heterocyclic group that may form an N-oxide include a pyridine ring.

The groups used in the description of the present specification will be described below with examples.

The "halogen atom" in the present invention refers to a fluorine atom, a chlorine atom, a bromine atom, or an iodine atom.

The "C1 to C6 chain hydrocarbon group" in the present invention represents a C1 to C6 alkyl group, a C2 to C6 alkenyl group, and a C2 to C6 alkynyl group.

Examples of the C1 to C6 alkyl group include a methyl group, an ethyl group, a propyl group, an isopropyl group, a butyl group, an isobutyl group, a sec-butyl group, a tert-butyl group, a pentyl group, a neopentyl group and a hexyl group, examples of the C2 to C6 alkenyl group include a vinyl group, a 1-propenyl group, a 2-propenyl group, a 1-methylvinyl group, a 2-methyl-1-propenyl group, a 1-butenyl group, a 2-butenyl group, a 3-butenyl group, a 1-pentenyl group and a 1-hexenyl group; and examples of the C2 to C6 alkynyl group include an ethynyl group, a propargyl group, a 2-butynyl group, a 3-butynyl group, a 1-pentynyl group and a 1-hexynyl group.

The notation of the "C1 to C6 chain hydrocarbon group optionally having one or more atoms or groups selected from group X" in the present invention represents a straight-chain or branched-chain hydrocarbon group comprising a carbon atom number of 1 to 6, in which a hydrogen atom bound to the carbon atom is optionally substituted by an atom or group selected from group X, and at that time, when having two or more atoms or groups selected from group X, the atoms or groups selected from group X may be the same or different from each other.

Examples of the "C1 to C6 chain hydrocarbon group optionally having one or more atoms or groups selected from group X" include C1 to C6 alkyl groups optionally having one or more atoms or groups selected from group X such as a methyl group, an ethyl group, a propyl group, an isopropyl group, a butyl group, an isobutyl group, a sec-butyl group, a tert-butyl group, a pentyl group, a neopentyl group, a hexyl group, a methoxymethyl group, an ethoxymethyl group, a propoxymethyl group, an isopropoxymethyl group, a butoxymethyl group, a sec-butoxymethyl group, a tert-butoxymethyl group, a 2-methoxyethyl group, a 2-ethoxyethyl group, a 2-propoxyethyl group, a 2-isopropoxyethyl group, a 2-butoxyethyl group, a 2-sec-butoxyethyl group, a 2-tert-butoxyethyl group, a trifluoromethyl group, a trichloromethyl group, a 2-fluoroethyl group, a 2,2-difluoroethyl group, a 2,2,2-trifluoroethyl group, a pentafluoroethyl group, a methylsulfanylethyl group, an ethylsulfanylethyl group, a methylsulfinylethyl group, a methylsulfonylethyl group, a cyclopropylmethyl group, a 1-methylcyclopropylmethyl group and a 2,2-difluorocyclopropylmethyl group; C2 to C6 alkenyl groups optionally having one or more atoms or groups selected from group X such as a vinyl group, a 1-propenyl group, a 2-propenyl group, a 1-methylvinyl group, a 2-methyl-1-propenyl group, a 1-butenyl group, a 2-butenyl group, a 3-butenyl group, a 1-pentenyl group, a 1-hexenyl group, a 1,1-difluoroallyl group and a pentafluoroallyl group; and C2 to C6 alkynyl groups optionally having one or more atoms or groups selected from group X such as an ethynyl group, a propargyl group, a 2-butynyl group, a 3-butynyl group, a 1-pentynyl group, a 1-hexynyl group and a 4,4,4-trifluoro-2-butynyl group.

The notation of the "C1 to C6 chain hydrocarbon group optionally having one or more atoms or groups selected from group W" in the present invention represents a straight-chain or branched-chain hydrocarbon group comprising a carbon atom number of 1 to 6, in which a hydrogen atom bound to the carbon atom is optionally substituted by an atom or group selected from group W, and at that time, when having two or more atoms or groups selected from group W, the atoms or groups selected from group W may be the same or different from each other.

Examples of the "C1 to C6 chain hydrocarbon group optionally having one or more atoms or groups selected from group W" include C1 to C6 alkyl groups optionally having one or more atoms or groups selected from group W such as a methyl group, an ethyl group, a propyl group, an isopropyl group, a butyl group, an isobutyl group, a sec-butyl group, a tert-butyl group, a pentyl group, a neopentyl group, a hexyl group, a trifluoromethyl group, a trichloromethyl group, a 2-fluoroethyl group, a 2,2-difluoroethyl group, a 2,2,2-trifluoroethyl group, a pentafluoroethyl group, a methoxymethyl group, an ethoxymethyl group, a propoxymethyl group, an isopropoxymethyl group, a butoxymethyl group, a sec-butoxymethyl group, an isobutoxymethyl group, a tert-butoxymethyl group, a methoxyethyl group, an ethoxyethyl group, a propoxyethyl group, an isopropoxyethyl group, a butoxyethyl group, a sec-butoxyethyl group, an isobutoxyethyl group, a tert-butoxyethyl group, a methylsulfanylethyl group, an ethylsulfanylethyl group, a methylsulfinylethyl group, a methylsulfonylethyl group, a methoxycarbonylmethyl group, a methoxycarbonylethyl group, a 2-cyanoethyl group, a cyclopropylmethyl group and a cyclohexylmethyl group; C2 to C6 alkenyl groups optionally having one or more atoms or groups selected from group W such as a vinyl group, a 1-propenyl group, a 2-propenyl group, a 1-methylvinyl group, a 2-methyl-1-propenyl group, a 1-butenyl group, a 2-butenyl group, a 3-butenyl group, a 1-pentenyl group, a 1-hexenyl group, a 1,1-difluoroallyl group and a pentafluoroallyl group; and C2 to C6 alkynyl groups optionally having one or more atoms or groups selected from group W such as an ethynyl group, a propargyl group, a 2-butynyl group, a 3-butynyl group, a 1-pentynyl group, a 1-hexynyl group and a 4,4,4-trifluoro-2-butynyl group.

The notation of the "C1 to C6 chain hydrocarbon group optionally having one or more atoms or groups selected from group V" in the present invention represents a straight-chain or branched-chain hydrocarbon group comprising a carbon atom number of 1 to 6, in which a hydrogen atom bound to the carbon atom is optionally substituted by an atom or group selected from group V, and at that time, when having two or more atoms or groups selected from group V, the atoms or groups selected from group V may be the same or different from each other.

Examples of the "C1 to C6 chain hydrocarbon group optionally having one or more atoms or groups selected from group V" include C1 to C6 alkyl groups optionally having one or more atoms or groups selected from group V such as a methyl group, an ethyl group, a propyl group, an isopropyl group, a butyl group, an isobutyl group, a sec-butyl group, a tert-butyl group, a pentyl group, a neopentyl group, a hexyl group, a trifluoromethyl group, a trichloromethyl group, a 2-fluoroethyl group, a 2,2-difluoroethyl group, a 2,2,2-trifluoroethyl group, a pentafluoroethyl group, a methoxymethyl group, an ethoxymethyl group, a propoxymethyl group, an isopropoxymethyl group, a butoxymethyl group, a sec-butoxymethyl group, a tert-butoxymethyl group, a 2-methoxyethyl group, a 2-ethoxyethyl group, a 2-propoxyethyl group, a 2-isopropoxyethyl group, a 2-butoxyethyl group, a 2-sec-butoxyethyl group, a 2-tert-butoxyethyl group, a cyclopropylmethyl group, a 1-methylcyclopropylmethyl group, a 2,2-difluorocyclopropylmethyl group, a 2-(methylsulfanyl)ethyl group, a 2-(ethylsulfanyl)ethyl group, a 2-(methylsulfinyl)ethyl group, a 2-(methylsulfonyl)ethyl group, a 2-hydroxyethyl group, a 2-(methylamino)ethyl group, a 2-(dimethylamino)ethyl group, a 2-(acetylaminocarbonyl)ethyl group, a 2-(methoxycarbonylamino)ethyl group, a 2-(methylaminocarbonyl)ethyl group, a 2-(dimethylaminocarbonyl)ethyl group, a phenylmethyl group, a 4-chlorophenylmethyl group, a 4-trifluorophenylmethyl group, a tetrahydrofuran-2-ylmethyl group, a tetrahydropyran-2-ylmethyl group, a tetrahydropyran-2-ylmethyl group, a thiazol-5-ylmethyl group, a 2-chlorothiazol-5-ylmethyl group, a pyridin-3-ylmethyl group, a 6-chloropyridin-3-ylmethyl group and a 6-trifluoromethylpyridin-3-ylmethyl group; C2 to C6 alkenyl groups optionally having one or more atoms or groups selected from group V such as a vinyl group, a 1-propenyl group, a 2-propenyl group, a 1-methylvinyl group, a 2-methyl-1-propenyl group, a 1-butenyl group, a 2-butenyl group, a 3-butenyl group, a 1-pentenyl group, a 1-hexenyl group, a 2-cyclopropylvinyl group, a 2-phenylvinyl group, a 3-phenyl-2-propenyl group, a 2-(pyridin-3-yl)vinyl group and 3-(dimethylamino)-2-propenyl; and C2 to C6 alkynyl groups optionally having one or more atoms or groups selected from group V such as an ethynyl group, a propargyl group, a 2-butynyl group, a 3-butynyl group, a 1-pentynyl group, a 1-hexynyl group, a 2-phenylethynyl group and a 2-(pyridin-3-yl)ethynyl group.

Examples of the "C1 to C6 chain hydrocarbon group having one phenyl group (wherein the phenyl group optionally has one or more atoms or groups selected from group Z)" in the present invention include a phenylmethyl group, a 4-chlorophenylmethyl group, and a 4-trifluoromethylphenylmethyl group. At that time, when having two or more atoms or groups selected from group Z, the atoms or groups selected from group Z may be the same or different from each other.

Examples of the "C1 to C6 chain hydrocarbon group having one 5- or 6-membered heterocyclic group (wherein the 5- or 6-membered heterocyclic group optionally has one or more atoms or groups selected from group Z)" in the present invention include a (thiazol-5-yl)methyl group, a (2-chlorothiazol-5-yl)methyl group, a 1-(2-chlorothiazol-5-yl)ethyl group, a (pyridin-5-yl)methyl group, a (2-chloropyridin-5-yl) methyl group, a 1-(2-chloropyridin-5-yl)ethyl group, a (2-trifluoromethylpyridin-5-yl)methyl group, a (pyrimidin-2-yl) methyl group, and a tetrahydro-3-furylmethyl group.

Examples of the "C1 to C6 alkyl group having one thiazolyl group (wherein the thiazolyl group optionally has one or more atoms or groups selected from the group consisting of C1 to C3 alkyl groups optionally having one or more halogen atoms and halogen atoms)" in the present invention include a (thiazol-5-yl)methyl group, a (2-chlorothiazol-5-yl)methyl group, and a 1-(2-chlorothiazol-5-yl)ethyl group.

Examples of the "C1 to C6 alkyl group having one pyridyl group (wherein the pyridyl group optionally has one or more atoms or groups selected from the group consisting of C1 to C3 alkyl groups optionally having one or more halogen atoms and halogen atoms)" in the present invention include a (pyridin-5-yl)methyl group, a (2-chloropyridin-5-yl)methyl group, a 1-(2-chloropyridin-5-yl)ethyl group, and a (2-trifluoromethylpyridin-5-yl)methyl group.

Examples of the "C1 to C6 chain hydrocarbon group optionally having one or more atoms or groups selected from the group consisting of halogen atoms and C3 to C9 alicyclic hydrocarbon groups (wherein the C3 to C9 alicyclic hydrocarbon group optionally has one or more halogen atoms or one or more C1 to C3 alkyl groups)" in the present invention include a methyl group, an ethyl group, a propyl group, an isopropyl group, a butyl group, an isobutyl group, a sec-butyl group, a tert-butyl group, a pentyl group, a neopentyl group, a hexyl group, a fluoromethyl group, a chloromethyl group, a bromomethyl group, an iodomethyl group, a difluoromethyl group, a dichloromethyl group, a trifluoromethyl group, a chlorodifluoromethyl group, a bromodifluoromethyl group, a trichloromethyl group, a 2-fluoroethyl group, a 2-chloroethyl group, a 2-bromoethyl group, a 2,2-difluoroethyl group, a 2,2,2,-trifluoroethyl group, a pentafluoroethyl group, a heptafluoropropyl group, a heptafluoroisopropyl group, a cyclopropylmethyl group, a 1-methylcyclopropylmethyl group, a 2,2-difluorocyclopropylmethyl group, a 2-cyclopropylethyl group, and a 1-cyclopropylethyl group.

Examples of the "C1 to C6 alkyl group optionally having one or more atoms or groups selected from the group consisting of halogen atoms and cyclopropyl groups (wherein the cyclopropyl group optionally has one or more halogen atoms or one or more C1 to C3 alkyl groups)" in the present invention include a methyl group, an ethyl group, a propyl group, an isopropyl group, a butyl group, an isobutyl group, a sec-butyl group, a tert-butyl group, a pentyl group, a neopentyl group, a hexyl group, a trifluoromethyl group, a trichloromethyl group, a 2-fluoroethyl group, a 2,2-difluoroethyl group, a 2,2,2,-trifluoroethyl group, a pentafluoroethyl group, a heptafluoroisopropyl group, a cyclopropylmethyl group, a 2-cyclopropylethyl group, a 1-cyclopropylethyl group, a 1-methylcyclopropylmethyl group, a 2,2-dimethylcyclopropylmethyl group, and a 2,2-difluorocyclopropylmethyl group.

Examples of the "C1 to C6 alkyl group optionally having one or more halogen atoms" in the present invention include a methyl group, an ethyl group, a propyl group, an isopropyl group, a butyl group, an isobutyl group, a sec-butyl group, a tert-butyl group, a pentyl group, a neopentyl group, a hexyl group, a fluoromethyl group, a chloromethyl group, a bromomethyl group, an iodomethyl group, a difluoromethyl group, a dichloromethyl group, a trifluoromethyl group, a chlorodifluoromethyl group, a bromodifluoromethyl group, a trichloromethyl group, a 2-fluoroethyl group, a 2-chloroethyl group, a 2-bromoethyl group, a 2,2-difluoroethyl group, a 2,2,2-trifluoroethyl group, a pentafluoroethyl group, a heptafluoropropyl group, and a heptafluoroisopropyl group.

Examples of the "C1 to C3 alkyl groups optionally having one or more halogen atoms" in the present invention include a methyl group, an ethyl group, a propyl group, an isopropyl group, a trifluoromethyl group, a trichloromethyl group, a 2,2-difluoroethyl group, and a 2,2,2-trifluoroethyl group.

Examples of the "C2 to C6 alkenyl group optionally having one or more halogen atoms" in the present invention include a vinyl group, a 1-propenyl group, a 2-propenyl group, a 1-methylvinyl group, a 2-methyl-1-propenyl group, a 1-butenyl group, a 2-butenyl group, a 3-butenyl group, a 1-pentenyl group, a 1-hexenyl group, a 1,1-difluoroallyl group, and a pentafluoroallyl group.

Examples of the "C2 to C6 alkynyl group optionally having one or more halogen atoms" in the present invention include an ethynyl group, a propargyl group, a 2-butynyl group, a 3-butynyl group, a 1-pentynyl group, a 1-hexynyl group, and a 4,4,4-trifluoro-2-butynyl group.

The notation of the "(C1 to C6 alkoxy)C1 to C6 alkyl group optionally having one or more halogen atoms" in the present invention represents a C1 to C6 alkyl group having one C1 to C6 alkoxy group optionally having one or more halogen atoms, and when the C1 to C6 alkoxy group has two or more halogen atoms, those halogen atoms may be the same or different from each other.

Examples of the "(C1 to C6 alkoxy)C1 to C6 alkyl group optionally having one or more halogen atoms" include a methoxymethyl group, an ethoxymethyl group, a 1-(methoxy)ethyl group, a 2-(methoxy)ethyl group, a 1-(ethoxy)ethyl group, a 2-(ethoxy)ethyl group, and a (2,2,2-trifluoroethoxy)methyl group.

The notation of the "(C3 to C6 cycloalkyl)C1 to C3 alkyl group optionally having one or more halogen atoms" in the present invention represents a C1 to C3 alkyl group having one C3 to C6 cycloalkyl group optionally having one or more halogen atoms, and when the C3 to C6 cycloalkyl group has two or more halogen atoms, those halogen atoms may be the same or different from each other.

Examples of the "(C3 to C6 cycloalkyl)C1 to C3 alkyl groups optionally having one or more halogen atoms" include a cyclopropylmethyl group, a 2-cyclopropylethyl group, a 1-cyclopropylethyl group, and a 2,2-difluorocyclopropylmethyl group.

Examples of the "C1 to C6 alkyl group optionally having one or more atoms or groups selected from the group consisting of C1 to C3 alkoxy groups and halogen atoms" in the present invention include a methyl group, an ethyl group, a propyl group, an isopropyl group, a butyl group, an isobutyl group, a sec-butyl group, a tert-butyl group, a pentyl group, a neopentyl group, a hexyl group, a methoxymethyl group, an ethoxymethyl group, a propoxymethyl group, an isopropoxymethyl group, a 2-methoxyethyl group, a 2-ethoxyethyl group, a 2-propoxyethyl group, a 2-isopropoxyethyl group, a trifluoromethyl group, a trichloromethyl group, a 2-fluoroethyl group, a 2,2-difluoroethyl group, a 2,2,2-trifluoroethyl group, a pentafluoroethyl group, and the like.

The notation of the "C1 to C6 haloalkyl group" in the present invention represents a C1 to C6 alkyl group in which one or more hydrogen atoms bound to the carbon atom are substituted by a halogen atom, and at that time, when having two or more halogen atoms, those halogen atoms may be the same or different from each other.

Examples of the "C1 to C6 haloalkyl group" include a fluoromethyl group, a chloromethyl group, a bromomethyl group, an iodomethyl group, a difluoromethyl group, a dichloromethyl group, a trifluoromethyl group, a chlorodifluoromethyl group, a bromodifluoromethyl group, a trichloromethyl group, a 2-fluoroethyl group, a 2-chloroethyl group, a 2-bromoethyl group, a 2,2-difluoroethyl group, a 2,2,2-trifluoroethyl group, a pentafluoroethyl group, a heptafluoropropyl group, and a heptafluoroisopropyl group.

The notation of the "C2 to C6 haloalkenyl group" in the present invention represents a C2 to C6 alkenyl group in which one or more hydrogen atoms bound to the carbon atom are substituted by a halogen atom, and at that time, when having two or more halogen atoms, those halogen atoms may be the same or different from each other.

Examples of the "C2 to C6 haloalkenyl group" include a 3,3-dichloro-2-propenyl group and a 3,3-dibromo-2-propenyl group.

The notation of the "C1 to C3 perfluoroalkyl group" in the present invention represents a C1 to C3 alkyl group in which all hydrogen atoms bound to the carbon atom are substituted by a fluorine atom.

Examples of the "C1 to C3 perfluoroalkyl group" include a trifluoromethyl group, a pentafluoroethyl group, a heptafluoropropyl group, and a heptafluoroisopropyl group.

The "C3 to C9 alicyclic hydrocarbon group" in the present invention represents a C3 to C9 cycloalkyl group and a C3 to C9 cycloalkenyl group.

Examples of the "C3 to C9 cycloalkyl group" in the present invention include a cyclopropyl group, a cyclobutyl group, a cyclopentyl group, a cyclohexyl group, and a cycloheptyl group.

Examples of the "C3 to C9 cycloalkenyl group" in the present invention include a cyclopropenyl group, a cyclobutenyl group, a cyclopentenyl group, and a cyclohexenyl group.

The notation of the "C3 to C9 alicyclic hydrocarbon group optionally having one or more atoms or groups selected from group Y" in the present invention represents a cyclic alkyl group or alkenyl group comprising a carbon atom number of 3 to 9, in which a hydrogen atom bound to the carbon atom is optionally substituted by an atom or group selected from group Y and at that time, when having two or more atoms or groups selected from group Y, the atoms or groups selected from group Y may be the same or different from each other.

Examples of the "C3 to C9 alicyclic hydrocarbon group optionally having one or more atoms or groups selected from group Y" include a cyclopropyl group, a cyclobutyl group, a cyclopentyl group, a cyclohexyl group, a cycloheptyl group, a 1-methylcyclohexyl group, a 2-methylcyclohexyl group, a 3-methylcyclohexyl group, a 4-methylcyclohexyl group, a 2-methoxylcyclohexyl group, a 3-methoxylcyclohexyl group, a 4-methoxylcyclohexyl group, a 1-fluorocyclohexyl group, a 2-fluorocyclohexyl group, a 3-fluorocyclohexyl group, and a 4-fluorocyclohexyl group.

Examples of the "C3 to C9 alicyclic hydrocarbon groups optionally having one or more atoms or groups selected from the group consisting of halogen atoms and C1 to C3 alkyl groups" in the present invention include a cyclopropyl group, a 1-methylcyclopropyl group, a 2-methylcyclopropyl group, a 1-fluorocyclopropyl group, a 2,2-difluorocyclopropyl group, a 2,2-dichlorocyclopropyl group, a 2,2-dibromocyclopropyl group, a cyclobutyl group, a cyclopentyl group, a cyclohexyl group, and a cycloheptyl group.

Examples of the "C3 to C6 cycloalkyl groups optionally having one or more atoms or groups selected from the group consisting of halogen atoms and C1 to C3 alkyl groups" in the present invention include a cyclopropyl group, a 1-methylcyclopropyl group, a 2-methylcyclopropyl group, a 1-fluorocyclopropyl group, a 2,2-difluorocyclopropyl group, a 2,2-dichlorocyclopropyl group, a 2,2-dibromocyclopropyl group, a cyclobutyl group, a cyclopentyl group, and a cyclohexyl group.

The notation of the "phenyl group optionally having one or more atoms or groups selected from group Z" in the present invention represents a phenyl group in which a hydrogen atom bound to the carbon atom is optionally substituted by an atom or group selected from group Z, and at that time, when having two or more atoms or groups selected from group Z, the atoms or groups selected from group Z may be the same or different from each other.

Examples of the "phenyl group optionally having one or more atoms or groups selected from group Z" include a phenyl group, a 2-fluorophenyl group, a 3-fluorophenyl group, a 4-fluorophenyl group, a 2,3-difluorophenyl group, a 2,4-difluorophenyl group, a 2,5-difluorophenyl group, a 2,6-difluorophenyl group, a 3,4-difluorophenyl group, a 3,5-difluorophenyl group, a 2,3,4,5,6-pentafluorophenyl group, a 2-chlorophenyl group, a 3-chlorophenyl group, a 4-chlorophenyl group, a 2-bromophenyl group, a 3-bromophenyl group, a 4-bromophenyl group, a 2-iodophenyl group, a 3-iodophenyl group, a 4-iodophenyl group, a 2-trifluoromethylphenyl group, a 3-trifluoromethylphenyl group, a 4-trifluoromethylphenyl group, a 2-trifluoromethoxyphenyl group, a 3-trifluoromethoxyphenyl group, a 4-trifluoromethoxyphenyl group, a 2-trifluoromethylsulfanylphenyl group, a 3-trifluoromethylsulfanylphenyl group, a 4-trifluoromethylsulfanylphenyl group, a 4-methoxycarbonylphenyl group, a 4-nitrophenyl group, a 4-cyanophenyl group, a 4-methylaminophenyl group, a 4-dimethylaminophenyl group, a 4-methylsulfinylphenyl group, a 4-methylsulfonylphenyl group, a 4-acetylphenyl group, and a 4-methoxycarbonylphenyl group.

Examples of the "phenyl group optionally having one or more atoms or groups selected from the group consisting of C1 to C3 alkyl groups optionally having one or more halogen atoms and halogen atoms" in the present invention include a phenyl group, a 2-fluorophenyl group, a 3-fluorophenyl group, a 4-fluorophenyl group, a 2,3-difluorophenyl group, a 2,4-difluorophenyl group, a 2,5-difluorophenyl group, a 2,6-difluorophenyl group, a 3,4-difluorophenyl group, a 3,5-difluorophenyl group, a 2,3,4,5,6-pentafluorophenyl group, a 2-chlorophenyl group, a 3-chlorophenyl group, a 4-chlorophenyl group, a 2-bromophenyl group, a 3-bromophenyl group, a 4-bromophenyl group, a 2-iodophenyl group, a 3-iodophenyl group, a 4-iodophenyl group, a 2-trifluoromethylphenyl group, a 3-trifluoromethylphenyl group, and a 4-trifluoromethylphenyl group.

The "heterocyclic group" in the present invention represents a heterocyclic compound residue containing one or more nitrogen atoms, oxygen atoms or sulfur atoms, other than carbon atoms, as ring-constituting atoms. Examples of the "heterocyclic ring" include 4-membered nonaromatic heterocyclic rings such as a thietane ring and an azetidine ring, 5-membered nonaromatic heterocyclic rings such as a pyrrolidine ring, a tetrahydrofuran ring and a tetrahydrothiophene ring, 5-membered aromatic heterocyclic rings such as a pyrrole ring, a pyrazole ring, an imidazole ring, a furan ring, a thiophene ring, an oxazole ring and a thiazole ring, 6-membered nonaromatic heterocyclic rings such as a piperidine ring, a tetrahydropyran ring, a tetrahydrothiopyran ring, a piperazine ring and a morpholine group, and 6-membered aromatic heterocyclic rings such as a pyridine ring, a pyrimidine ring, a pyridazine ring and a pyrazine ring.

In the present invention, a 5-membered heterocyclic group means a 5-membered nonaromatic heterocyclic group or a 5-membered aromatic heterocyclic group, and a 6-membered heterocyclic group means a 6-membered nonaromatic heterocyclic group or a 6-membered aromatic heterocyclic group. In addition, in the present invention, a 5- or 6-membered heterocyclic group means a 5- or 6-membered aromatic heterocyclic group or a 5- or 6-membered nonaromatic heterocyclic group. In addition, in the present invention, a 4-, 5- or 6-membered heterocyclic group means a 5- or 6-membered aromatic heterocyclic group or a 4-, 5- or 6-membered nonaromatic heterocyclic group.

The notation of the "5- or 6-membered heterocyclic group optionally having one or more atoms or groups selected from group Z" in the present invention represents a 5- or 6-membered heterocyclic group in which a hydrogen atom bound to the carbon atom is optionally substituted by an atom or group selected from group Z, and at that time, when having two or more atoms or groups selected from group Z, the atoms or groups selected from group Z may be the same or different from each other.

Examples of the "5- or 6-membered heterocyclic group optionally having one or more atoms or groups selected from group Z" include 5- or 6-membered nonaromatic heterocyclic groups optionally having one or more atoms or groups selected from group Z such as a pyrrolidin-1-yl group, a 3,3,4,4-tetrafluoropyrrolidin-1-yl group, a tetrahydrofuran-2-yl group, a piperidyl group, a morpholyl group and a thiomorpholyl group; and 5- or 6-membered aromatic heterocyclic groups optionally having one or more atoms or groups selected from group Z such as a 2-pyrrolyl group, a 2-furyl group, a 3-furyl group, a 5-pyrazolyl group, a 4-pyrazolyl group, a 1-pyrrolyl group, a 1-methyl-2-pyrrolyl group, a 2-methylsulfanyl-1-pyrrolyl group, a 2-methylsulfinyl-1-pyrrolyl group, a 2-methylsulfonyl-1-pyrrolyl group, a 2-methylamino-1-pyrrolyl group, a 2-dimethylamino-1-pyrrolyl group, a 5-bromo-2-furyl group, a 5-nitro-2-furyl group, a 5-cyano-2-furyl group, a 5-methoxy-2-furyl group, a 5-acetyl-2-furyl group, a 5-methoxycarbonyl-2-furyl group, a 2-methyl-3-furyl group, a 2,5-dimethyl-3-furyl group, a 2,4-dimethyl-3-furyl group, a 5-methyl-2-thienyl group, a 3-methyl-2-thienyl group, a 1-methyl-3-trifluoromethyl-5-pyrazolyl group, a 5-chloro-1,3-dimethyl-4-pyrazolyl group, a pyrazol-1-yl group, a 3-chloro-pyrazol-1-yl group, a 3-bromopyrazol-1-yl group, a 4-chloropyrazol-1-yl group, a 4-bromopyrazol-1-yl group, an imidazole-1-yl group, a 1,2,4-triazole-1-yl group, a 3-chloro-1,2,4-triazole-1-yl group, a 1,2,3,4-tetrazol-1-yl group, a 1,2,3,5-tetrazol-1-yl group, a 2-thienyl group, a 3-thienyl group, a 3-trifluoromethyl-1,2,4-triazol-1-yl group, a 4-trifluoromethylpyrazol-1-yl group, a pyrazinyl group, a 4-pyrimidinyl group, a 5-pyrimidinyl group, a 2-pyridyl group, a 3-pyridyl group, a 4-pyridyl group, a 3-fluoro-2-pyridyl group, a 4-fluoro-2-pyridyl group, a 5-fluoro-2-pyridyl group, a 6-fluoro-2-pyridyl group, a 2-pyrimidinyl group, a 3-chloro-5-trifluoromethylpyridin-2-yl group and a 5-trifluoromethylpyridin-2-yl group.

The notation of the "4-, 5- or 6-membered heterocyclic group optionally having one or more atoms or groups selected from group Z" in the present invention represents a 4-, 5- or 6-membered heterocyclic group in which a hydrogen atom bound to the carbon atom is optionally substituted by an atom or group selected from group Z, and at that time, when having two or more atoms or groups selected from group Z, the atoms or groups selected from group Z may be the same or different from each other.

Examples of the "4-, 5- or 6-membered heterocyclic group optionally having one or more atoms or groups selected from group Z" include 4-, 5- or 6-membered nonaromatic heterocyclic groups optionally having one or more atoms or groups selected from group Z such as a thietan-3-yl group, an azetidin-1-yl group, a pyrrolidin-1-yl group, a 3,3,4,4-tetrafluoropyrrolidin-1-yl group, a tetrahydrofuran-2-yl group, a piperidyl group, a morpholyl group and a thiomorpholyl group; and 5- or 6-membered aromatic heterocyclic groups optionally having one or more atoms or groups selected from group Z such as a 2-pyrrolyl group, a 2-furyl group, a 3-furyl group, a 5-pyrazolyl group, a 4-pyrazolyl group, a 1-pyrrolyl group, a 1-methyl-2-pyrrolyl group, a 2-methylsulfanyl-1-pyrrolyl group, a 2-methylsulfinyl-1-pyrrolyl group, a 2-methylsulfonyl-1-pyrrolyl group, a 2-methylamino-1-pyrrolyl group, a 2-dimethylamino-1-pyrrolyl group, a 5-bromo-2-furyl group, a 5-nitro-2-furyl group, a 5-cyano-2-furyl group, a 5-methoxy-2-furyl group, a 5-acetyl-2-furyl group, a 5-methoxycarbonyl-2-furyl group, a 2-methyl-3-furyl group, a 2,5-dimethyl-3-furyl group, a 2,4-dimethyl-3-furyl group, a 5-methyl-2-thienyl group, a 3-methyl-2-thienyl group, a 1-methyl-3-trifluoromethyl-5-pyrazolyl group, a 5-chloro-1,3-dimethyl-4-pyrazolyl group, a pyrazol-1-yl group, a 3-chloro-pyrazol-1-yl group, a 3-bromopyrazol-1-yl group, a 4-chloropyrazol-1-yl group, a 4-bromopyrazol-1-yl group, an imidazole-1-yl group, a 1,2,4-triazole-1-yl group, a 3-chloro-1,2,4-triazole-1-yl group, a 1,2,3,4-tetrazol-1-yl group, a 1,2,3,5-tetrazol-1-yl group, a 2-thienyl group, a 3-thienyl group, a 3-trifluoromethyl-1,2,4-triazol-1-yl group, a 4-trifluoromethylpyrazol-1-yl group, a pyrazinyl group, a 4-pyrimidinyl group, a 5-pyrimidinyl group, a 2-pyridyl group, a 3-pyridyl group, a 4-pyridyl group, a 3-fluoro-2-pyridyl group, a 4-fluoro-2-pyridyl group, a 5-fluoro-2-pyridyl group, a 6-fluoro-2-pyridyl group, a 2-pyrimidinyl group, a 3-chloro-5-trifluoromethylpyridin-2-yl group and a 5-trifluoromethylpyridin-2-yl group.

Examples of the "phenyl group optionally having one or more atoms or groups selected from the group consisting of C1 to C3 alkyl groups optionally having one or more halogen atoms and halogen atoms" in the present invention include a phenyl group, a 2-fluorophenyl group, a 3-fluorophenyl group, a 4-fluorophenyl group, a 2,3-difluorophenyl group, a 2,4-difluorophenyl group, a 2,5-difluorophenyl group, a 2,6-difluorophenyl group, a 3,4-difluorophenyl group, a 3,5-difluorophenyl group, a 2,3,4,5,6-pentafluorophenyl group, a 2-chlorophenyl group, a 3-chlorophenyl group, a 4-chlorophenyl group, a 2-bromophenyl group, a 3-bromophenyl group, a 4-bromophenyl group, a 2-iodophenyl group, a 3-iodophenyl group, a 4-iodophenyl group, a 2-trifluoromethylphenyl group, a 3-trifluoromethylphenyl group, and a 4-trifluoromethylphenyl group.

Examples of the "5- or 6-membered heterocyclic group optionally having one or more atoms or groups selected from the group consisting of C1 to C3 alkyl groups optionally having one or more halogen atoms and halogen atoms" in the present invention include 5- or 6-membered nonaromatic heterocyclic groups such as a pyrrolidin-1-yl group, a 3,3,4,4-tetrafluoropyrrolidin-1-yl group, a tetrahydrofuran-2-yl group, a piperidyl group, a morpholyl group and a thiomorpholyl group; and 5- or 6-membered aromatic heterocyclic groups such as a 2-pyrrolyl group, a 2-furyl group, a 3-furyl group, a 5-pyrazolyl group, a 4-pyrazolyl group, a 1-pyrrolyl group, a 1-methyl-2-pyrrolyl group, a 5-bromo-2-furyl group, a 2-methyl-3-furyl group, a 2,5-dimethyl-3-furyl group, a 2,4-dimethyl-3-furyl group, a 5-methyl-2-thienyl group, a 3-methyl-2-thienyl group, a 1-methyl-3-trifluoromethyl-5-pyrazolyl group, a 5-chloro-1,3-dimethyl-4-pyrazolyl group, a pyrazol-1-yl group, a 3-chloro-pyrazol-1-yl group, a 3-bromopyrazol-1-yl group, a 4-chloropyrazol-1-yl group, a 4-bromopyrazol-1-yl group, an imidazole-1-yl group, a 1,2,4-triazole-1-yl group, a 3-chloro-1,2,4-triazole-1-yl group, a 1,2,3,4-tetrazol-1-yl group, a 1,2,3,5-tetrazol-1-yl group, a 2-thienyl group, a 3-thienyl group, a 3-trifluoromethyl-1,2,4-triazol-1-yl group, a 4-trifluoromethylpyrazol-1-yl group, a pyrazinyl group, a 4-pyrimidinyl group, a 5-pyrimidinyl group, a 2-pyridyl group, a 3-pyridyl group, a 4-pyridyl group, a 3-fluoro-2- pyridyl group, a 4-fluoro-2-pyridyl group, a 5-fluoro-2-pyridyl group, a 6-fluoro-2-pyridyl group, a 2-pyrimidinyl group, a 3-chloro-5-trifluoromethylpyridin-2-yl group and a 5-trifluoromethylpyridin-2-yl group.

Examples of the "C1 to C6 alkoxy groups optionally having one or more halogen atoms" in the present invention include a methoxy group, a trifluoromethoxy group, an ethoxy group, a 2,2,2-trifluoroethoxy group, a propoxy group, an isopropoxy group, a butoxy group, an isobutoxy group, a sec-butoxy group, a tert-butoxy group, a pentyloxy group, and a hexyloxy group.

The notation of the "C1 to C6 haloalkoxy group" in the present invention represents a C1 to C6 alkoxy group in which one or more hydrogen atoms bound to the carbon atom are substituted by a halogen atom, and at that time, when having two or more halogen atoms, those halogen atoms may be the same or different from each other.

Examples of the "C1 to C6 haloalkoxy group" include a trifluoromethoxy group, a 2,2,2-trifluoroethoxy group, a 2,2,2-trichoroethoxy group, a 2,2,3,3-tetrafluoropropoxy group, and a 2,2,3,4,4,4-hexafluorobutoxy group.

The notation of the "C1 to C3 perfluoroalkoxy group" in the present invention represents a C1 to C3 alkoxy group in which all hydrogen atoms bound to the carbon atom are substituted by a fluorine atom.

Examples of the "C1 to C3 perfluoroalkoxy group" include a trifluoromethoxy group, a pentafluoroethoxy group, a heptafluoropropoxy group, and a heptafluoroisopropoxy group.

Examples of the "C1 to C6 alkylsulfanyl groups optionally having one or more halogen atoms" in the present invention include a methylsulfanyl group, an ethylsulfanyl group, a propylsulfanyl group, an isopropylsulfanyl group, a butylsulfanyl group, a pentylsulfanyl group, a hexylsulfanyl group, a trifluoromethylsulfanyl group, a 2,2,2-trifluoroethylsulfanyl group, and a pentafluoroethylsulfanyl group.

The notation of the "C1 to C6 haloalkylsulfanyl group" in the present invention represents a C1 to C6 alkylsulfanyl group in which one or more hydrogen atoms bound to the carbon atom are substituted by a halogen atom, and at that time, when having two or more halogen atoms, those halogen atoms may be the same or different from each other.

Examples of the "C1 to C6 haloalkylsulfanyl group" include a trifluoromethylsulfany group, a 2,2,2-trifluoroethylsulfanyl group, a 2,2,2-trichoroethylsulfanyl group, a 2,2,3,3-tetrafluoropropylsulfanyl group, and a 2,2,3,4,4,4-hexafluorobutylsulfanyl group.

The notation of the "C1 to C3 perfluoroalkylsulfanyl group" in the present invention represents a C1 to C3 alkylsulfanyl group in which all hydrogen atoms bound to the carbon atom are substituted by a fluorine atom.

Examples of the "C1 to C3 perfluoroalkylsulfanyl group" include a trifluoromethylsulfanyl group, a pentafluoroethylsulfanyl group, a heptafluoropropylsulfanyl group, and a heptafluoroisopropylsulfanyl group.

Examples of the "C1 to C6 alkylsulfinyl groups optionally having one or more halogen atoms" in the present invention include a methylsulfinyl group, an ethylsulfinyl group, a propylsulfinyl group, an isopropylsulfinyl group, a butylsulfinyl group, a pentylsulfinyl group, a hexylsulfinyl group, a trifluoromethylsulfinyl group, a 2,2,2-trifluoroethylsulfinyl group, and a pentafluoroethylsulfinyl group.

The notation of the "C1 to C6 haloalkylsulfinyl group" in the present invention represents a C1 to C6 alkylsulfinyl group in which one or more hydrogen atoms bound to the carbon atom are substituted by a halogen atom, and at that time, when having two or more halogen atoms, those halogen atoms may be the same or different from each other.

Examples of the "C1 to C6 haloalkylsulfinyl group" include a trifluoromethylsulfiny group, a 2,2,2-trifluoroethylsulfinyl group, a 2,2,2-trichoroethylsulfinyl group, a 2,2,3,3-tetrafluoropropylsulfinyl group, and a 2,2,3,4,4,4-hexafluorobutylsulfinyl group.

The notation of the "C1 to C3 perfluoroalkylsulfinyl group" in the present invention represents a C1 to C3 alkylsulfinyl group in which all hydrogen atoms bound to the carbon atom are substituted by a fluorine atom.

Examples of the "C1 to C3 perfluoroalkylsulfinyl group" include a trifluoromethylsulfinyl group, a pentafluoroethylsulfinyl group, a heptafluoropropylsulfinyl group, and a heptafluoroisopropylsulfinyl group.

Examples of the "C1 to C6 alkylsulfonyl groups optionally having one or more halogen atoms" in the present invention include a methylsulfonyl group, an ethylsulfonyl group, a propylsulfonyl group, an isopropylsulfonyl group, a butylsulfonyl group, a pentylsulfonyl group, a hexylsulfonyl group, a trifluoromethylsulfonyl group, a 2,2,2-trifluoroethylsulfonyl group, and a pentafluoroethylsulfonyl group.

The notation of the "C1 to C6 haloalkylsulfonyl group" in the present invention represents a C1 to C6 alkylsulfonyl group in which one or more hydrogen atoms bound to the carbon atom are substituted by a halogen atom, and at that time, when having two or more halogen atoms, those halogen atoms may be the same or different from each other.

Examples of the "C1 to C6 haloalkylsulfonyl group" include a trifluoromethylsulfony group, a 2,2,2-trifluoroethylsulfonyl group, a 2,2,2-trichoroethylsulfonyl group, a 2,2,3,3-tetrafluoropropylsulfonyl group, and a 2,2,3,4,4,4-hexafluorobutylsulfonyl group.

The notation of the "C1 to C3 perfluoroalkylsulfonyl group" in the present invention represents a C1 to C3 alkylsulfonyl in which all hydrogen atoms bound to the carbon atom are substituted by a fluorine atom.

Examples of the "C1 to C3 perfluoroalkylsulfonyl group" include a trifluoromethylsulfonyl group, a pentafluoroethylsulfonyl group, a heptafluoropropylsulfonyl group, and a heptafluoroisopropylsulfonyl group.

Examples of the "C2 to C6 alkylcarbonyl groups optionally having one or more halogen atoms" in the present invention include an acetyl group, a propionyl group, a butyryl group, a pentanoyl group, a hexanoyl group, and a trifluoroacetyl group.

Examples of the "C2 to C6 alkoxycarbonyl groups optionally having one or more halogen atoms" in the present invention include a methoxycarbonyl group, an ethoxycarbonyl group, a propoxycarbonyl group, a butoxycarbonyl group, a pentyloxycarbonyl group, a tert-butyloxycarbonyl group, and a 2,2,2-trifluoroethoxycarbonyl group.

Examples of the "C1 to C6 alkylamino groups optionally having one or more halogen atoms" in the present invention include a methylamino group, an ethylamino group, a 2,2,2-trifluoroethylamino group, a propylamino group, and an isopropylamino group.

Examples of the "C2 to C8 dialkylamino groups optionally having one or more halogen atoms" in the present invention include a dimethylamino group, a diethylamino group, a bis(2,2,2-trifluoroethyl)amino group, and a dipropylamino group.

Examples of the "C2 to C6 alkenyloxy groups optionally having one or more halogen atoms" in the present invention include a 2-propenyloxy group, a 2-methyl-2-propenyloxy group, a 2-butenyloxy group, a 3-butenyloxy group, a 2-pentenyloxy group, a 2-hexenyloxy group, a 3,3-difluoroallyloxy group, and a 3,3-dichloroallyloxy group.

Examples of the "C2 to C6 alkynyloxy groups optionally having one or more halogen atoms" in the present invention include a propargyloxy group, a 2-butynyloxy group, a 3-butynyloxy group, a 2-pentynyloxy group, a 2-hexynyloxy group, and a 4,4,4-trifluoro-2-butynyloxy group.

Examples of the "C1 to C6 alkylaminosulfonyl groups optionally having one or more halogen atoms" in the present invention include a methylaminosulfonyl group, an ethylaminosulfonyl group, a 2,2,2-trifluoroethylaminosulfonyl group, a propylaminosulfonyl group, and an isopropylaminosulfonyl group.

Examples of the "C2 to C8 dialkylaminosulfonyl groups optionally having one or more halogen atoms" in the present invention include a dimethylaminosulfonyl group, a diethylaminosulfonyl group, a bis(2,2,2-trifluoroethyl)aminosulfonyl group, and a dipropylaminosulfonyl group.

Examples of the "C2 to C6 alkylcarbonylamino groups optionally having one or more halogen atoms" in the present invention include an acetylamino group, a propionylamino group, a butyrylamino group, a pentanoylamino group, a hexanoylamino group, and a trifluoroacetylamino group.

Examples of the "C2 to C6 alkoxycarbonylamino groups optionally having one or more halogen atoms" in the present invention include a methoxycarbonylamino group, an ethoxycarbonylamino group, a propoxycarbonylamino group, a butoxycarbonylamino group, a pentyloxycarbonylamino group, a tert-butoxycarbonylamino group, and a 2,2,2-trifluoroethoxycarbonylamino group.

Examples of the "C2 to C6 alkylaminocarbonyl groups optionally having one or more halogen atoms" in the present invention include a methylaminocarbonyl group, an ethylaminocarbonyl group, a 2,2,2-trifluoroethylaminocarbonyl group, a propylaminocarbonyl group, and an isopropylaminocarbonyl group.

Examples of the "C3 to C10 dialkylaminocarbonyl groups optionally having one or more halogen atoms" in the present invention include a dimethylaminocarbonyl group, a diethylaminocarbonyl group, a bis(2,2,2-trifluoroethyl)aminocarbonyl group, and a dipropylaminocarbonyl group.

Examples of the compound of the present invention include the following compounds.

In the formula (1), compounds wherein $R^1$ is a C1 to C6 chain hydrocarbon group optionally having one or more atoms or groups selected from group X.

In the formula (1), compounds wherein $R^1$ is a C3 to C9 alicyclic hydrocarbon group optionally having one or more atoms or groups selected from group Y.

In the formula (1), compounds wherein $R^1$ is a C1 to C6 alkyl group optionally having one or more atoms or groups selected from the group consisting of halogen atoms and cyclopropyl groups (wherein the cyclopropyl group optionally has one or more halogen atoms or one or more C1 to C3 alkyl groups), a C2 to C6 alkenyl group optionally having one or more halogen atoms, a C2 to C6 alkynyl group optionally having one or more halogen atoms, or C3 to C6 cycloalkyl group optionally having one or more atoms or groups selected from the group consisting of halogen atoms and C1 to C3 alkyl groups.

In the formula (1), compounds wherein $R^1$ is a C1 to C6 alkyl group optionally having one or more atoms or groups selected from the group consisting of halogen atoms and cyclopropyl groups (wherein the cyclopropyl group optionally has one or more halogen atoms or one or more C1 to C3 alkyl groups), a C2 to C6 alkenyl group optionally having one or more halogen atoms, or a C2 to C6 alkynyl group optionally having one or more halogen atoms.

In the formula (1), compounds wherein $R^1$ is a C1 to C6 alkyl group optionally having one or more atoms or groups selected from the group consisting of halogen atoms and cyclopropyl groups (wherein the cyclopropyl group optionally has one or more halogen atoms or one or more C1 to C3 alkyl groups).

In the formula (1), compounds wherein $R^1$ is a C3 to C6 cycloalkyl group optionally having one or more atoms or groups selected from the group consisting of halogen atoms and C1 to C3 alkyl groups.

In the formula (1), compounds wherein $R^1$ is a C2 to C6 alkyl group optionally having one or more atoms or groups selected from the group consisting of halogen atoms and cyclopropyl groups (wherein the cyclopropyl group optionally has one or more halogen atoms or one or more C1 to C3 alkyl groups) or a C3 to C6 cycloalkyl group optionally having one or more atoms or groups selected from the group consisting of halogen atoms and C1 to C3 alkyl groups.

In the formula (1), compounds wherein $R^1$ is a C2 to C6 alkyl group optionally having one or more atoms or groups selected from the group consisting of halogen atoms and cyclopropyl groups (wherein the cyclopropyl group optionally has one or more halogen atoms or one or more C1 to C3 alkyl groups).

In the formula (1), compounds wherein $R^1$ is a C3 to C6 cycloalkyl group optionally having one or more atoms or groups selected from the group consisting of halogen atoms and C1 to C3 alkyl groups, a C1 to C6 alkyl group optionally having one or more halogen atoms, or a (C3 to C6 cycloalkyl)C1 to C3 alkyl group optionally having one or more halogen atoms.

In the formula (1), compounds wherein $R^1$ is a C2 to C6 alkyl group optionally having one or more halogen atoms, a (C3 to C6 cycloalkyl)C1 to C3 alkyl group optionally having one or more halogen atoms, or a C3 to C6 cycloalkyl group optionally having one or more atoms or groups selected from the group consisting of halogen atoms and C1 to C3 alkyl groups.

In the formula (1), compounds wherein $R^1$ is a C2 to C6 alkyl group optionally having one or more halogen atoms.

In the formula (1), compounds wherein $R^1$ is a (C3 to C6 cycloalkylalkyl)C1 to C3 alkyl group optionally having one or more halogen atoms.

In the formula (1), compounds wherein $R^1$ is a C2 to C6 alkyl group.

In the formula (1), compounds wherein $R^1$ is a (C3 to C6 cycloalkylalkyl)C1 to C3 alkyl group.

In the formula (1), compounds wherein $R^1$ is a C2 to C6 alkyl group, a C2 to C6 alkenyl group, or a C2 to C6 alkynyl group.

In the formula (1), compounds wherein $R^1$ is a C1 to C6 alkyl group, a cyclopropyl group, or a cyclopropylmethyl group.

In the formula (1), compounds wherein $R^1$ is a C2 to C6 alkyl group, a cyclopropyl group, or a cyclopropylmethyl group.

In the formula (1), compounds wherein $R^1$ is a methyl group, an ethyl group, a propyl group, an isopropyl group, a butyl group, a propargyl group, a trifluoromethyl group, a 2,2,2-trifluoroethyl group, a cyclopropyl group, a cyclobutyl group, a cyclopropylmethyl group, or a cyclobutylmethyl group.

In the formula (1), compounds wherein $R^1$ is an ethyl group, a cyclopropyl group, or a cyclopropylmethyl group.

In the formula (1), compounds wherein $R^1$ is an ethyl group.

In the formula (1), compounds wherein $R^1$ is a cyclopropyl group.

In the formula (1), compounds wherein $R^1$ is a cyclopropylmethyl group.

In the formula (1), compounds wherein $R^2$, $R^3$ and $R^4$ are the same or different and are a C1 to C6 chain hydrocarbon group optionally having one or more atoms or groups selected from group X, a C3 to C6 cycloalkyl group optionally having one or more atoms or groups selected from group Y, or a hydrogen atom.

In the formula (1), compounds wherein $R^2$, $R^3$ and $R^4$ are the same or different and are a phenyl group optionally having one or more atoms or groups selected from group Z, a 5- or 6-membered heterocyclic group optionally having one or more atoms or groups selected from group Z, or a hydrogen atom.

In the formula (1), compounds wherein $R^2$, $R^3$ and $R^4$ are the same or different and are a C1 to C6 chain hydrocarbon group optionally having one or more atoms or groups selected from group X or a hydrogen atom.

In the formula (1), compounds wherein $R^2$, $R^3$ and $R^4$ are the same or different and are a C3 to C6 cycloalkyl group optionally having one or more atoms or groups selected from group Y or a hydrogen atom.

In the formula (1), compounds wherein $R^2$, $R^3$ and $R^4$ are the same or different and are a phenyl group optionally having one or more atoms or groups selected from group Z or a hydrogen atom.

In the formula (1), compounds wherein $R^2$, $R^3$ and $R^4$ are the same or different and are a 5- or 6-membered heterocyclic group optionally having one or more atoms or groups selected from group Z or a hydrogen atom.

In the formula (1), compounds wherein $R^2$, $R^3$ and $R^4$ are the same or different and are $OR^{11}$ or a hydrogen atom.

In the formula (1), compounds wherein $R^2$, $R^3$ and $R^4$ are the same or different and are $S(O)_m R^{11}$ or a hydrogen atom.

In the formula (1), compounds wherein $R^2$, $R^3$ and $R^4$ are the same or different and are $S(O)_2 NR^{11}R^{12}$ or a hydrogen atom.

In the formula (1), compounds wherein $R^2$, $R^3$ and $R^4$ are the same or different and are $NR^{11}R^{12}$ or a hydrogen atom.

In the formula (1), compounds wherein $R^2$, $R^3$ and $R^4$ are the same or different and are $NR^{15}C(O)R^{11}$ or a hydrogen atom.

In the formula (1), compounds wherein $R^2$, $R^3$ and $R^4$ are the same or different and are $NR^{15}C(O)OR^{11}$ or a hydrogen atom.

In the formula (1), compounds wherein $R^2$, $R^3$ and $R^4$ are the same or different and are $NR^{15}C(O)NR^{11}R^{12}$ or a hydrogen atom.

In the formula (1), compounds wherein $R^2$, $R^3$ and $R^4$ are the same or different and are $NR^{16}S(O)_2R^{13}$ or a hydrogen atom.

In the formula (1), compounds wherein $R^2$, $R^3$ and $R^4$ are the same or different and are $C(O)R^{11}$ or a hydrogen atom.

In the formula (1), compounds wherein $R^2$, $R^3$ and $R^4$ are the same or different and are $C(O)OR^{11}$ or a hydrogen atom.

In the formula (1), compounds wherein $R^2$, $R^3$ and $R^4$ are the same or different and are $C(O)NR^{11}R^{12}$ or a hydrogen atom.

In the formula (1), compounds wherein $R^2$, $R^3$ and $R^4$ are the same or different and are $C(O)NR^{11}NR^{15}R^{16}$ or a hydrogen atom.

In the formula (1), compounds wherein $R^2$, $R^3$ and $R^4$ are the same or different and are a halogen atom or a hydrogen atom.

In the formula (1), compounds wherein $R^2$, $R^3$ and $R^4$ are a hydrogen atom.

In the formula (1), compounds wherein $R^2$, $R^3$ and $R^4$ are the same or different and are a C1 to C6 chain hydrocarbon group optionally having one or more atoms or groups selected from group X, a phenyl group optionally having one or more atoms or groups selected from group Z, a 5- or 6-membered heterocyclic group optionally having one or more atoms or groups selected from group Z, $OR^{11}$, $S(O)_m R^{11}$, $S(O)_2 NR^{11}R^{12}$, $NR^{11}R^{12}$, $NR^{15}C(O)R^{11}$, $NR^{15}C(O)OR^{11}$, $NR^{15}C(O)NR^{11}R^{12}$, $NR^{16}S(O)_2R^{13}$, $C(O)R^{11}$, $C(O)OR^{11}$, $C(O)NR^{11}R^{12}$, $C(O)NR^{11}NR^{15}R^{16}$, a cyano group, a halogen atom, or a hydrogen atom.

In the formula (1), compounds wherein $R^2$, $R^3$ and $R^4$ are the same or different and are a C1 to C6 alkyl group optionally having one or more halogen atoms, a phenyl group optionally having one or more atoms or groups selected from the group consisting of C1 to C3 alkyl groups optionally having one or more halogen atoms and halogen atoms, a 5- or 6-membered heterocyclic group optionally having one or more atoms or groups selected from the group consisting of C1 to C3 alkyl groups optionally having one or more halogen atoms and halogen atoms, $OR^{11}$, $S(O)_m R^{11}$, $NR^{11}R^{12}$, $NR^{15}C(O)R^{11}$, $NR^{15}C(O)OR^{11}$, $NR^{15}C(O)NR^{11}R^{12}$, $NR^{16}S(O)_2R^{13}$, $C(O)OR^{11}$, $C(O)NR^{11}R^{12}$, $C(O)NR^{11}NR^{15}R^{16}$, a cyano group, a halogen atom, or a hydrogen atom.

In the formula (1), compounds wherein $R^2$, $R^3$ and $R^4$ are the same or different and are a C1 to C3 alkyl group optionally having one or more halogen atoms, a C1 to C6 alkoxy group optionally having one or more halogen atoms, a C1 to C3 alkylsulfanyl group optionally having one or more halogen atoms, a C1 to C3 alkylsulfinyl group optionally having one or more halogen atoms, a C1 to C3 alkylsulfonyl group optionally having one or more halogen atoms, an amino group, a C1 to C3 alkylamino group optionally having one or more halogen atoms, a C2 to C6 dialkylamino group optionally having one or more halogen atoms, a C2 to C6 alkylcarbonylamino group optionally having one or more halogen atoms, a C2 to C6 alkoxycarbonylamino group optionally having one or more halogen atoms, a C2 to C6 alkylaminocarbonyl group optionally having one or more halogen atoms, a C3 to C10 dialkylaminocarbonyl group optionally having one or more halogen atoms, a C2 to C6 alkoxycarbonyl group optionally having one or more halogen atoms, a phenyl group optionally having one or more atoms or groups selected from the group consisting of C1 to C3 alkyl groups optionally having one or more halogen atoms and halogen atoms, a 5- or 6-membered heterocyclic group optionally having one or more atoms or groups selected from the group consisting of C1 to C3 alkyl groups optionally having one or more halogen atoms and halogen atoms, a halogen atom, or a hydrogen atom.

In the formula (1), compounds wherein $R^2$ and $R^4$ are the same or different and are a C1 to C6 alkyl group optionally having one or more halogen atoms, $OR^{11}$, $S(O)_m R^{11}$, a halogen atom or a hydrogen atom, and $R^3$ is a C1 to C6 chain hydrocarbon group optionally having one or more atoms or groups selected from group X, a C3 to C6 cycloalkyl group optionally having one or more atoms or groups selected from group Y, a phenyl group optionally having one or more atoms or groups selected from group Z, a 5- or 6-membered heterocyclic group optionally having one or more atoms or groups selected from group Z, $OR^{11}$, $S(O)_m R^{11}$, $C(O)R^{11}$, $CO_2R^{11}$, $C(O)NR^{11}R^{12}$, $SF_5$, a cyano group, a nitro group, a halogen atom or a hydrogen atom.

In the formula (1), compounds wherein $R^2$ and $R^4$ are the same or different and are a halogen atom or a hydrogen atom, and $R^3$ is a C1 to C6 chain hydrocarbon group optionally having one or more atoms or groups selected from group X, a C3 to C6 cycloalkyl group optionally having one or more atoms or groups selected from group Y, a phenyl group optionally having one or more atoms or groups selected from group Z, a 5- or 6-membered heterocyclic group optionally having one or more atoms or groups selected from group Z, $OR^{11}$, $S(O)_mR^{11}$, $C(O)R^{11}$, $CO_2R^{11}$, $C(O)NR^{11}R^{12}$, $SF_5$, a cyano group, a nitro group, a halogen atom or a hydrogen atom.

In the formula (1), compounds wherein $R^2$ and $R^4$ are a hydrogen atom, and $R^3$ is a C1 to C6 chain hydrocarbon group optionally having one or more atoms or groups selected from group X, a C3 to C6 cycloalkyl group optionally having one or more atoms or groups selected from group Y, a phenyl group optionally having one or more atoms or groups selected from group Z, a 5- or 6-membered heterocyclic group optionally having one or more atoms or groups selected from group Z, $OR^{11}$, $S(O)_mR^{11}$, $C(O)R^{11}$, $CO_2R^{11}$, $C(O)NR^{11}R^{12}$, $SF_5$, a cyano group, a nitro group, a halogen atom or a hydrogen atom.

In the formula (1), compounds wherein $R^2$ and $R^4$ are a hydrogen atom, and $R^3$ is a C1 to C6 chain hydrocarbon group optionally having one or more atoms or groups selected from group X or a hydrogen atom.

In the formula (1), compounds wherein $R^2$ and $R^4$ are a hydrogen atom, and $R^3$ is a phenyl group optionally having one or more atoms or groups selected from group Z or a hydrogen atom.

In the formula (1), compounds wherein $R^2$ and $R^4$ are a hydrogen atom, and $R^3$ is a 5- or 6-membered heterocyclic group optionally having one or more atoms or groups selected from group Z or a hydrogen atom.

In the formula (1), compounds wherein $R^2$ and $R^4$ are a hydrogen atom, and $R^3$ is $OR^{11}$ or a hydrogen atom.

In the formula (1), compounds wherein $R^2$ and $R^4$ are a hydrogen atom, and $R^3$ is $S(O)_mR^{11}$ or a hydrogen atom.

In the formula (1), compounds wherein $R^2$ and $R^4$ are a hydrogen atom, and $R^3$ is $S(O)_2NR^{11}R^{12}$ or a hydrogen atom.

In the formula (1), compounds wherein $R^2$ and $R^4$ are a hydrogen atom, and $R^3$ is $NR^{11}R^{12}$ or a hydrogen atom.

In the formula (1), compounds wherein $R^2$ and $R^4$ are a hydrogen atom, and $R^3$ is $NR^{15}C(O)R^{11}$ or a hydrogen atom.

In the formula (1), compounds wherein $R^2$ and $R^4$ are a hydrogen atom, and $R^3$ is $NR^{15}C(O)OR^{11}$ or a hydrogen atom.

In the formula (1), compounds wherein $R^2$ and $R^4$ are a hydrogen atom, and $R^3$ is $NR^{15}C(O)NR^{11}R^{12}$ or a hydrogen atom.

In the formula (1), compounds wherein $R^2$ and $R^4$ are a hydrogen atom, and $R^3$ is $NR^{16}S(O)_2R^{13}$ or a hydrogen atom.

In the formula (1), compounds wherein $R^2$ and $R^4$ are a hydrogen atom, and $R^3$ is $C(O)R^{11}$ or a hydrogen atom.

In the formula (1), compounds wherein $R^2$ and $R^4$ are a hydrogen atom, and $R^3$ is $C(O)OR^{11}$ or a hydrogen atom.

In the formula (1), compounds wherein $R^2$ and $R^4$ are a hydrogen atom, and $R^3$ is $C(O)NR^{11}R^{12}$ or a hydrogen atom.

In the formula (1), compounds wherein $R^2$ and $R^4$ are a hydrogen atom, and $R^3$ is $C(O)NR^{11}NR^{15}R^{16}$ or a hydrogen atom.

In the formula (1), compounds wherein $R^2$ and $R^4$ are a hydrogen atom, and $R^3$ is a halogen atom or a hydrogen atom.

In the formula (1), compounds wherein $R^2$ and $R^4$ are a hydrogen atom, and $R^3$ is a C1 to C6 chain hydrocarbon group optionally having one or more atoms or groups selected from group X.

In the formula (1), compounds wherein $R^2$ and $R^4$ are a hydrogen atom, and $R^3$ is a phenyl group optionally having one or more atoms or groups selected from group Z.

In the formula (1), compounds wherein $R^2$ and $R^4$ are a hydrogen atom, and $R^3$ is a 5- or 6-membered heterocyclic group optionally having one or more atoms or groups selected from group Z.

In the formula (1), compounds wherein $R^2$ and $R^4$ are a hydrogen atom, and $R^3$ is $OR^{11}$.

In the formula (1), compounds wherein $R^2$ and $R^4$ are a hydrogen atom, and $R^3$ is $S(O)_mR^{11}$.

In the formula (1), compounds wherein $R^2$ and $R^4$ are a hydrogen atom, and $R^3$ is $S(O)_2NR^{11}R^{12}$.

In the formula (1), compounds wherein $R^2$ and $R^4$ are a hydrogen atom, and $R^3$ is $NR^{11}R^{12}$.

In the formula (1), compounds wherein $R^2$ and $R^4$ are a hydrogen atom, and $R^3$ is $NR^{15}C(O)R^{11}$.

In the formula (1), compounds wherein $R^2$ and $R^4$ are a hydrogen atom, and $R^3$ is $NR^{15}C(O)OR^{11}$.

In the formula (1), compounds wherein $R^2$ and $R^4$ are a hydrogen atom, and $R^3$ is $NR^{15}C(O)NR^{11}R^{12}$.

In the formula (1), compounds wherein $R^2$ and $R^4$ are a hydrogen atom, and $R^3$ is $NR^{16}S(O)_2R^{13}$.

In the formula (1), compounds wherein $R^2$ and $R^4$ are a hydrogen atom, and $R^3$ is $C(O)R^{11}$.

In the formula (1), compounds wherein $R^2$ and $R^4$ are a hydrogen atom, and $R^3$ is $C(O)OR^1$.

In the formula (1), compounds wherein $R^2$ and $R^4$ are a hydrogen atom, and $R^3$ is $C(O)NR^{11}R^{12}$.

In the formula (1), compounds wherein $R^2$ and $R^4$ are a hydrogen atom, and $R^3$ is $C(O)NR^{11}NR^{15}R^{16}$.

In the formula (1), compounds wherein $R^2$ and $R^4$ are a hydrogen atom, and $R^3$ is a halogen atom.

In the formula (1), compounds wherein $R^2$ and $R^4$ are the same or different and are a halogen atom or a hydrogen atom, and $R^3$ is a C1 to C6 alkyl group optionally having one or more halogen atoms, a C2 to C6 alkenyl group optionally having one or more halogen atoms, a C2 to C6 alkynyl group optionally having one or more halogen atoms, a 5- or 6-membered heterocyclic group (wherein the 5- or 6-membered heterocyclic group optionally has one or more atoms or groups selected from the group consisting of C1 to C3 alkyl groups optionally having one or more halogen atoms and halogen atoms), $OR^{11}$, $S(O)_mR^{11}$, a halogen atom or a hydrogen atom.

In the formula (1), compounds wherein $R^2$ and $R^4$ are a hydrogen atom, and $R^3$ is a C1 to C6 alkyl group optionally having one or more halogen atoms, a C2 to C6 alkenyl group optionally having one or more halogen atoms, a C2 to C6 alkynyl group optionally having one or more halogen atoms, a 5- or 6-membered heterocyclic group (wherein the 5- or 6-membered heterocyclic group optionally has one or more atoms or groups selected from the group consisting of C1 to C3 alkyl groups optionally having one or more halogen atoms and halogen atoms), $OR^{11}$, $S(O)_mR^{11}$, a halogen atom or a hydrogen atom.

In the formula (1), compounds wherein $R^2$ and $R^4$ are a hydrogen atom, and $R^3$ is a C1 to C6 alkyl group optionally having one or more halogen atoms or a hydrogen atom.

In the formula (1), compounds wherein $R^2$ and $R^4$ are a hydrogen atom, and $R^3$ is a 5- or 6-membered heterocyclic group (wherein the 5- or 6-membered heterocyclic group optionally has one or more atoms or groups selected from the group consisting of C1 to C3 alkyl groups optionally having one or more halogen atoms and halogen atoms) or a hydrogen atom.

In the formula (1), compounds wherein $R^2$ and $R^4$ are a hydrogen atom, and $R^3$ is a C1 to C6 alkyl group optionally having one or more halogen atoms.

In the formula (1), compounds wherein $R^2$ and $R^4$ are a hydrogen atom, and $R^3$ is a 5- or 6-membered heterocyclic group (wherein the 5- or 6-membered heterocyclic group optionally has one or more atoms or groups selected from the group consisting of C1 to C3 alkyl groups optionally having one or more halogen atoms and halogen atoms).

In the formula (1), compounds wherein $R^2$ and $R^4$ are a hydrogen atom, and $R^3$ is a C1 to C3 alkyl group optionally having one or more halogen atoms, a C1 to C3 alkoxy group optionally having one or more halogen atoms, a C1 to C3 alkylsulfanyl group optionally having one or more halogen atoms, a C1 to C3 alkylsulfinyl group optionally having one or more halogen atoms, a C1 to C3 alkylsulfonyl group optionally having one or more halogen atoms, a pyridyl group (wherein the pyridyl group optionally has one or more atoms or groups selected from the group consisting of C1 to C3 alkyl groups optionally having one or more halogen atoms and halogen atoms), a pyrimidinyl group (wherein the pyrimidinyl group optionally has one or more atoms or groups selected from the group consisting of C1 to C3 alkyl groups optionally having one or more halogen atoms and halogen atoms), a halogen atom or a hydrogen atom.

In the formula (1), compounds wherein $R^2$ and $R^4$ are a hydrogen atom, and $R^3$ is a C1 to C3 alkyl group optionally having one or more halogen atoms.

In the formula (1), compounds wherein $R^2$ and $R^4$ are a hydrogen atom, and $R^3$ is a C1 to C3 alkoxy group optionally having one or more halogen atoms.

In the formula (1), compounds wherein $R^2$ and $R^4$ are a hydrogen atom, and $R^3$ is a C1 to C3 alkylsulfanyl group optionally having one or more halogen atoms, a C1 to C3 alkylsulfinyl group optionally having one or more halogen atoms or a C1 to C3 alkylsulfonyl group optionally having one or more halogen atoms.

In the formula (1), compounds wherein $R^2$ and $R^4$ are a hydrogen atom, and $R^3$ is a pyridyl group (wherein the pyridyl group optionally has one or more atoms or substituents selected from the group consisting of halogen atoms and C1 to C3 alkyl groups optionally having one or more halogen atoms) or a pyrimidinyl group (wherein the pyrimidinyl group optionally has one or more atoms or substituents selected from the group consisting of halogen atoms and C1 to C3 alkyl groups optionally having one or more halogen atoms).

In the formula (1), compounds wherein $R^2$ and $R^4$ are a hydrogen atom, and $R^3$ is a pyridyl group (wherein the pyridyl group optionally has one or more atoms or substituents selected from the group consisting of halogen atoms and C1 to C3 alkyl groups optionally having one or more halogen atoms).

In the formula (1), compounds wherein $R^2$ and $R^4$ are a hydrogen atom, and $R^3$ is a pyrimidinyl group (wherein the pyrimidinyl group optionally has one or more atoms or substituents selected from the group consisting of halogen atoms and C1 to C3 alkyl groups optionally having one or more halogen atoms).

In the formula (1), compounds wherein $R^2$ and $R^4$ are a hydrogen atom, and $R^3$ is a methyl group, an ethyl group, a vinyl group, a propyl group, an isopropyl group, a cyclopropyl group, a propargyl group, a trifluoromethyl group, a pentafluoroethyl group, a heptafluoropropyl group, a heptafluoroisopropyl group, a methoxy group, a trifluoromethoxy group, a methylsulfanyl group, a trifluoromethylsulfanyl group, a methylsulfinyl group, a trifluoromethylsulfinyl group, a methylsulfonyl group, a trifluoromethylsulfonyl group, a 2-pyridyl group, a 2-pyrimidinyl group, a 5-trifluoromethyl-2-pyridyl group, a 3-chloro-5-trifluoromethyl-2-pyridyl group, a fluorine atom, a chlorine atom, a bromine atom, an iodine atom or a hydrogen atom.

In the formula (1), compounds wherein $R^2$ and $R^4$ are a hydrogen atom, and $R^3$ is a methyl group, an ethyl group, a vinyl group, a propyl group, an isopropyl group, a cyclopropyl group, a propargyl group, a trifluoromethyl group, a pentafluoroethyl group, a heptafluoropropyl group, a heptafluoroisopropyl group, a methoxy group, a trifluoromethoxy group, a methylsulfanyl group, a trifluoromethylsulfanyl group, a methylsulfinyl group, a trifluoromethylsulfinyl group, a methylsulfonyl group, a trifluoromethylsulfonyl group, a fluorine atom, a chlorine atom, a bromine atom, an iodine atom or a hydrogen atom.

In the formula (1), compounds wherein $R^2$ is a hydrogen atom.

In the formula (1), compounds wherein $R^3$ is a hydrogen atom.

In the formula (1), compounds wherein $R^4$ is a hydrogen atom.

In the formula (1), compounds wherein $R^2$ and $R^3$ are a hydrogen atom.

In the formula (1), compounds wherein $R^2$ and $R^4$ are a hydrogen atom.

In the formula (1), compounds wherein $R^3$ and $R^4$ are a hydrogen atom.

In the formula (1), compounds wherein $R^2$, $R^3$ and $R^4$ are a hydrogen atom.

In the formula (1), compounds wherein $R^5$ is a C1 to C6 chain hydrocarbon group optionally having one or more atoms or groups selected from group W, a C3 to C9 alicyclic hydrocarbon group optionally having one or more atoms or groups selected from group Y, a C1 to C6 chain hydrocarbon group having one phenyl group (wherein the phenyl group optionally has one or more atoms or groups selected from group Z), a C1 to C6 chain hydrocarbon group having one 5- or 6-membered heterocyclic group (wherein the 5- or 6-membered heterocyclic group optionally has one or more atoms or groups selected from group Z), $C(O)R^{11}$, $C(O)OR^{11}$, or $C(O)NR^{11}R^{12}$.

In the formula (1), compounds wherein $R^5$ is a C1 to C6 chain hydrocarbon group optionally having one or more atoms or groups selected from group W.

In the formula (1), compounds wherein $R^5$ is a C3 to C9 alicyclic hydrocarbon group optionally having one or more atoms or groups selected from group Y.

In the formula (1), compounds wherein $R^5$ is a C1 to C6 chain hydrocarbon group optionally having one or more atoms or groups selected from group W or a C3 to C9 alicyclic hydrocarbon group optionally having one or more atoms or groups selected from group Y.

In the formula (1), compounds wherein $R^5$ is a C1 to C6 chain hydrocarbon group having one phenyl group (wherein the phenyl group optionally has one or more atoms or groups selected from group Z) or a C1 to C6 chain hydrocarbon group having one 5- or 6-membered heterocyclic group (wherein the 5- or 6-membered heterocyclic group optionally has one or more atoms or groups selected from group Z).

In the formula (1), compounds wherein $R^5$ is a $C(O)R^{11}$, $C(O)OR^{11}$, or $C(O)NR^{11}R^{12}$.

In the formula (1), compounds wherein $R^5$ is a hydrogen atom.

In the formula (1), compounds wherein $R^5$ is a C1 to C6 alkyl group optionally having one or more atoms or groups selected from the group consisting of halogen atoms and cyclopropyl groups (wherein the cyclopropyl group optionally has one or more halogen atoms or one or more C1 to C3 alkyl groups), a (C1 to C6 alkoxy)C1 to C6 alkyl group optionally having one or more halogen atoms, a C2 to C6 alkenyl group optionally having one or more halogen atoms, a C2 to C6 alkynyl group optionally having one or more halogen atoms, a C3 to C6 cycloalkyl group optionally having one or more atoms or groups selected from the group consisting of halogen atoms and C1 to C3 alkyl groups, a C1 to C6 alkyl group having one thiazolyl group (wherein the thiazolyl group optionally has one or more atoms or groups selected from the group consisting of C1 to C3 alkyl groups optionally having one or more halogen atoms and halogen atoms), a C1 to C6 alkyl group having one pyridyl group (wherein the pyridyl group optionally has one or more atoms or groups selected from the group consisting of C1 to C3 alkyl groups optionally having one or more halogen atoms and halogen atoms), $C(O)R^{11}$, $C(O)OR^{11}$, or a hydrogen atom.

In the formula (1), compounds wherein $R^5$ is a C1 to C6 alkyl group optionally having one or more atoms or groups selected from the group consisting of halogen atoms and cyclopropyl groups (wherein the cyclopropyl group optionally has one or more halogen atoms or one or more C1 to C3 alkyl groups), a (C1 to C6 alkoxy)C1 to C6 alkyl group optionally having one or more halogen atoms, a C2 to C6 alkenyl group optionally having one or more halogen atoms, a C2 to C6 alkynyl group optionally having one or more halogen atoms, a C1 to C6 alkyl group having one thiazolyl group (wherein the thiazolyl group optionally has one or more atoms or groups selected from the group consisting of C1 to C3 alkyl groups optionally having one or more halogen atoms and halogen atoms), a C1 to C6 alkyl group having one pyridyl group (wherein the pyridyl group optionally has one or more atoms or groups selected from the group consisting of C1 to C3 alkyl groups optionally having one or more halogen atoms and halogen atoms), $C(O)R^{11}$, $C(O)OR^{11}$, or a hydrogen atom.

In the formula (1), compounds wherein $R^5$ is a C1 to C6 alkyl group optionally having one or more atoms or groups selected from the group consisting of halogen atoms and cyclopropyl groups (wherein the cyclopropyl group optionally has one or more halogen atoms or one or more C1 to C3 alkyl groups).

In the formula (1), compounds wherein $R^5$ is a (C1 to C6 alkoxy)C1 to C6 alkyl group optionally having one or more halogen atoms.

In the formula (1), compounds wherein $R^5$ is a C2 to C6 alkenyl group optionally having one or more halogen atoms.

In the formula (1), compounds wherein $R^5$ is a C2 to C6 alkynyl group optionally having one or more halogen atoms.

In the formula (1), compounds wherein $R^5$ is a C1 to C6 alkyl group having one thiazolyl group (wherein the thiazolyl group optionally has one or more atoms or groups selected from the group consisting of C1 to C3 alkyl groups optionally having one or more halogen atoms and halogen atoms) or a C1 to C6 alkyl group having one pyridyl group (wherein the pyridyl group optionally has one or more atoms or groups selected from the group consisting of C1 to C3 alkyl groups optionally having one or more halogen atoms and halogen atoms).

In the formula (1), compounds wherein $R^5$ is a C1 to C6 alkyl group optionally having one or more atoms or groups selected from the group consisting of halogen atoms and cyclopropyl groups (wherein the cyclopropyl group optionally has one or more halogen atoms or one or more C1 to C3 alkyl groups) or a propargyl group.

In the formula (1), compounds wherein $R^5$ is a C1 to C6 alkyl group optionally having one or more atoms or groups selected from the group consisting of halogen atoms and cyclopropyl groups (wherein the cyclopropyl group optionally has one or more halogen atoms or one or more C1 to C3 alkyl groups), a (C1 to C6 alkoxy)C1 to C6 alkyl group optionally having one or more halogen atoms, a C2 to C6 alkenyl group optionally having one or more halogen atoms, a C2 to C6 alkynyl group optionally having one or more halogen atoms, a C3 to C6 cycloalkyl group optionally having one or more atoms or groups selected from the group consisting of halogen atoms and C1 to C3 alkyl groups, a C2 to C6 alkylcarbonyl group optionally having one or more halogen atoms, a C2 to C6 alkoxycarbonyl group optionally having one or more halogen atoms, or a hydrogen atom.

In the formula (1), compounds wherein $R^5$ is a C1 to C6 alkyl group optionally having one or more atoms or groups selected from the group consisting of halogen atoms and cyclopropyl groups (wherein the cyclopropyl group optionally has one or more halogen atoms or one or more C1 to C3 alkyl groups), a (C1 to C6 alkoxy)C1 to C6 alkyl group optionally having one or more halogen atoms, a C2 to C6 alkenyl group optionally having one or more halogen atoms, a C2 to C6 alkynyl group optionally having one or more halogen atoms, a C2 to C6 alkylcarbonyl group optionally having one or more halogen atoms, a C2 to C6 alkoxycarbonyl group optionally having one or more halogen atoms, or a hydrogen atom.

In the formula (1), compounds wherein $R^5$ is a C2 to C6 alkylcarbonyl group optionally having one or more halogen atoms.

In the formula (1), compounds wherein $R^5$ is a C2 to C6 alkoxycarbonyl group optionally having one or more halogen atoms.

In the formula (1), compounds wherein $R^5$ is a methyl group, an ethyl group, a propyl group, an isopropyl group, a butyl group, an isobutyl group, a hexyl group, a propargyl group, a cyclopropyl group, a cyclobutyl group, a cyclohexyl group, a cyclopropylmethyl group, a cyclobutylmethyl group, a 2,2,2-trifluoroethyl group, a benzyl group, a 6-chloropyridin-3-ylmethyl group, a 2-chlorothiazolyl-5-ylmethyl group, a methoxymethyl group, an ethoxymethyl group, a methoxycarbonyl group, or an ethoxycarbonyl group.

In the formula (1), compounds wherein $R^5$ is a methyl group, an ethyl group, a propyl group, an isopropyl group, a butyl group, an isobutyl group, a hexyl group, a propargyl group, a cyclopropyl group, a cyclobutyl group, a cyclohexyl group, a cyclopropylmethyl group, a cyclobutylmethyl group, a 2,2,2-trifluoroethyl group, a benzyl group, a 6-chloropyridin-3-ylmethyl group, or a 2-chlorothiazol-5-ylmethyl group.

In the formula (1), compounds wherein $R^5$ is a methyl group, an ethyl group, a propyl group, an isopropyl group, a butyl group, an isobutyl group, or a hexyl group.

In the formula (1), compounds wherein $R^5$ is a cyclopropyl group, a cyclobutyl group, a cyclohexyl group, a cyclopropylmethyl group, or a cyclobutylmethyl group.

In the formula (1), compounds wherein $R^5$ is a benzyl group, a 6-chloropyridin-3-ylmethyl group, or a 2-chlorothiazol-5-ylmethyl group.

In the formula (1), compounds wherein $R^5$ is a methoxymethyl group, an ethoxymethyl group, a methoxycarbonyl group, or an ethoxycarbonyl group.

In the formula (1), compounds wherein $R^5$ is a methyl group, an ethyl group, a cyclopropyl group, or a cyclopropylmethyl group.

In the formula (1), compounds wherein $R^5$ is a methyl group.

In the formula (1), compounds wherein $R^5$ is an ethyl group.

In the formula (1), compounds wherein $R^5$ is a cyclopropyl group.

In the formula (1), compounds wherein $R^5$ is a cyclopropylmethyl group.

In the formula (1), compounds wherein $R^6$ and $R^{10}$ are the same or different and are a C1 to C6 chain hydrocarbon group optionally having one or more atoms or groups selected from group X, $OR^{14}$, $S(O)_m R^{14}$, a fluorine atom, or a hydrogen atom.

In the formula (1), compounds wherein $R^6$ and $R^{10}$ are the same or different and are a C1 to C6 chain hydrocarbon group optionally having one or more atoms or groups selected from group X or a hydrogen atom.

In the formula (1), compounds wherein $R^6$ and $R^{10}$ are the same or different and are $OR^{14}$ or a hydrogen atom.

In the formula (1), compounds wherein $R^6$ and $R^{10}$ are the same or different and are $S(O)_m R^{14}$ or a hydrogen atom.

In the formula (1), compounds wherein $R^6$ and $R^{10}$ are the same or different and are a fluorine atom or a hydrogen atom.

In the formula (1), compounds wherein $R^6$ and $R^{10}$ are a hydrogen atom.

In the formula (1), compounds wherein $R^6$ is a hydrogen atom.

In the formula (1), compounds wherein $R^{10}$ is a hydrogen atom.

In the formula (1), compounds wherein $R^6$ and $R^{10}$ are the same or different and are a C1 to C6 alkyl group optionally having one or more halogen atoms, $OR^{14}$, $S(O)_m R^{14}$, a fluorine atom, or a hydrogen atom.

In the formula (1), compounds wherein $R^6$ and $R^{10}$ are the same or different and are a C1 to C6 alkyl group optionally having one or more halogen atoms or a hydrogen atom.

In the formula (1), compounds wherein $R^7$, $R^8$ and $R^9$ are the same or different and are a C1 to C6 chain hydrocarbon group optionally having one or more atoms or groups selected from group X, $OR^{14}$, $S(O)_m R^{11}$, a halogen atom, or a hydrogen atom.

In the formula (1), compounds wherein $R^7$, $R^8$ and $R^9$ are the same or different and are a C1 to C6 chain hydrocarbon group optionally having one or more atoms or groups selected from group X, a halogen atom, or a hydrogen atom.

In the formula (1), compounds wherein $R^7$, $R^8$ and $R^9$ are the same or different and are a phenyl group optionally having one or more atoms or groups selected from group Z, a halogen atom, or a hydrogen atom.

In the formula (1), compounds wherein $R^7$, $R^8$ and $R^9$ are the same or different and are a 5- or 6-membered heterocyclic group optionally having one or more atoms or groups selected from group Z, a halogen atom, or a hydrogen atom.

In the formula (1), compounds wherein $R^7$, $R^8$ and $R^9$ are the same or different and are $OR^{14}$, a halogen atom, or a hydrogen atom.

In the formula (1), compounds wherein $R^7$, $R^8$ and $R^9$ are the same or different and are $S(O)_m R^{11}$, a halogen atom, or a hydrogen atom.

In the formula (1), compounds wherein $R^7$, $R^8$ and $R^9$ are the same or different and are a C1 to C6 chain hydrocarbon group optionally having one or more atoms or groups selected from group X or a hydrogen atom.

In the formula (1), compounds wherein $R^7$, $R^8$ and $R^9$ are the same or different and are a phenyl group optionally having one or more atoms or groups selected from group Z or a hydrogen atom.

In the formula (1), compounds wherein $R^7$, $R^8$ and $R^9$ are the same or different and are a 5- or 6-membered heterocyclic group optionally having one or more atoms or groups selected from group Z or a hydrogen atom.

In the formula (1), compounds wherein $R^7$, $R^8$ and $R^9$ are the same or different and are $OR^{14}$ or a hydrogen atom.

In the formula (1), compounds wherein $R^7$, $R^8$ and $R^9$ are the same or different and are $S(O)_m R^{11}$ or a hydrogen atom.

In the formula (1), compounds wherein $R^7$, $R^8$ and $R^9$ are the same or different and are a C1 to C6 chain hydrocarbon group optionally having one or more atoms or groups selected from group X, $OR^{14}$, $S(O)_m R^{11}$, $SF_5$, a halogen atom, or a hydrogen atom.

In the formula (1), compounds wherein $R^7$, $R^8$ and $R^9$ are the same or different and are a C1 to C6 alkyl group optionally having one or more halogen atoms, a C2 to C6 alkenyl group optionally having one or more halogen atoms, a C2 to C6 alkynyl group optionally having one or more halogen atoms, $OR^{14}$, $S(O)_m R^{11}$, a halogen atom, or a hydrogen atom.

In the formula (1), compounds wherein $R^7$, $R^8$ and $R^9$ are the same or different and are a C1 to C6 alkyl group optionally having one or more halogen atoms, $OR^{14}$, $S(O)_m R^{11}$, a halogen atom, or a hydrogen atom.

In the formula (1), compounds wherein $R^7$, $R^8$ and $R^9$ are the same or different and are a C1 to C6 alkyl group optionally having one or more halogen atoms, a halogen atom, or a hydrogen atom.

In the formula (1), compounds wherein $R^7$, $R^8$ and $R^9$ are the same or different and are a C1 to C6 alkyl group optionally having one or more halogen atoms, or a hydrogen atom.

In the formula (1), compounds wherein $R^7$, $R^8$ and $R^9$ are the same or different and are a C1 to C6 haloalkyl group, a C2 to C6 haloalkenyl group, a C1 to C6 haloalkoxy group, a C1 to C6 haloalkylsulfanyl group, a C1 to C6 haloalkylsulfinyl group, a C1 to C6 haloalkylsulfonyl group, a halogen atom, or a hydrogen atom.

In the formula (1), compounds wherein $R^7$, $R^8$ and $R^9$ are the same or different and are a C1 to C6 haloalkyl group, a halogen atom, or a hydrogen atom.

In the formula (1), compounds wherein $R^7$, $R^8$ and $R^9$ are the same or different and are a C1 to C6 haloalkoxy group, a halogen atom, or a hydrogen atom.

In the formula (1), compounds wherein $R^7$, $R^8$ and $R^9$ are the same or different and are a C1 to C6 haloalkylsulfanyl group, a C1 to C6 haloalkylsulfinyl group, a C1 to C6 haloalkylsulfonyl group, a halogen atom, or a hydrogen atom.

In the formula (1), compounds wherein $R^7$, $R^8$ and $R^9$ are the same or different and are a C1 to C6 haloalkyl group or a hydrogen atom.

In the formula (1), compounds wherein $R^7$, $R^8$ and $R^9$ are the same or different and are a C1 to C6 haloalkoxy group or a hydrogen atom.

In the formula (1), compounds wherein $R^7$, $R^8$ and $R^9$ are the same or different and are a C1 to C6 haloalkylsulfanyl group, a C1 to C6 haloalkylsulfinyl group, a C1 to C6 haloalkylsulfonyl group, or a hydrogen atom.

In the formula (1), compounds wherein $R^7$, $R^8$ and $R^9$ are the same or different and are a C1 to C3 perfluoroalkyl group, a C1 to C3 perfluoroalkoxy group, a C1 to C3 perfluoroalkylsulfanyl group, a C1 to C3 perfluoroalkylsulfinyl group, a C1 to C3 perfluoroalkylsulfonyl group, a halogen atom, or a hydrogen atom.

In the formula (1), compounds wherein $R^7$, $R^8$ and $R^9$ are the same or different and are a C1 to C3 perfluoroalkyl group, a halogen atom, or a hydrogen atom.

In the formula (1), compounds wherein $R^7$, $R^8$ and $R^9$ are the same or different and are a C1 to C3 perfluoroalkoxy group, a halogen atom, or a hydrogen atom.

In the formula (1), compounds wherein $R^7$, $R^8$ and $R^9$ are the same or different and are a C1 to C3 perfluoroalkylsulfanyl group, a C1 to C3 perfluoroalkylsulfinyl group, a C1 to C3 perfluoroalkylsulfonyl group, a halogen atom, or a hydrogen atom.

In the formula (1), compounds wherein $R^7$, $R^8$ and $R^9$ are the same or different and are a C1 to C3 perfluoroalkyl group or a hydrogen atom.

In the formula (1), compounds wherein $R^7$, $R^8$ and $R^9$ are the same or different and are a C1 to C3 perfluoroalkoxy group or a hydrogen atom.

In the formula (1), compounds wherein $R^7$, $R^8$ and $R^9$ are the same or different and are a C1 to C3 perfluoroalkylsulfanyl group, a C1 to C3 perfluoroalkylsulfinyl group, a C1 to C3 perfluoroalkylsulfonyl group, or a hydrogen atom.

In the formula (1), compounds wherein $R^7$ is a hydrogen atom.

In the formula (1), compounds wherein $R^8$ is a hydrogen atom.

In the formula (1), compounds wherein $R^9$ is a hydrogen atom.

In the formula (1), compounds wherein $R^7$ and $R^9$ are a hydrogen atom.

In the formula (1), compounds wherein $R^6$, $R^7$, $R^8$ and $R^9$ are a hydrogen atom.

In the formula (1), compounds wherein $R^6$ and $R^{10}$ are the same or different and are a C1 to C6 alkyl group optionally having one or more halogen atoms, $OR^{14}$, $S(O)_m R^{14}$, a fluorine atom or a hydrogen atom, and $R^7$, $R^8$ and $R^9$ are the same or different and are a C1 to C6 chain hydrocarbon group optionally having one or more atoms or groups selected from group X, $OR^{14}$, $S(O)_m R^{11}$, $SF_5$, a halogen atom or a hydrogen atom.

In the formula (1), compounds wherein $R^6$ and $R^{10}$ are the same or different and are a fluorine atom or a hydrogen atom, and $R^7$, $R^8$ and $R^9$ are the same or different and are a C1 to C6 chain hydrocarbon group optionally having one or more atoms or groups selected from group X, $OR^{14}$, $S(O)_m R^{11}$, $SF_5$, a halogen atom or a hydrogen atom.

In the formula (1), compounds wherein $R^6$ and $R^{10}$ are a hydrogen atom, and $R^7$, $R^8$ and $R^9$ are the same or different and are a C1 to C6 chain hydrocarbon group optionally having one or more atoms or groups selected from group X, $OR^{14}$, $S(O)_m R^{11}$, $SF_5$, a halogen atom or a hydrogen atom.

In the formula (1), compounds wherein $R^6$ and $R^{10}$ are a hydrogen atom, and $R^7$, $R^8$ and $R^9$ are the same or different and are a C1 to C6 chain hydrocarbon group optionally having one or more atoms or groups selected from group X, a halogen atom or a hydrogen atom.

In the formula (1), compounds wherein $R^6$ and $R^{10}$ are a hydrogen atom, and $R^7$, $R^8$ and $R^9$ are the same or different and are $OR^{14}$, a halogen atom or a hydrogen atom.

In the formula (1), compounds wherein $R^6$ and $R^{10}$ are a hydrogen atom, and $R^7$, $R^8$ and $R^9$ are the same or different and are $S(O)_m R^{11}$, a halogen atom or a hydrogen atom.

In the formula (1), compounds wherein $R^6$ and $R^{10}$ are a hydrogen atom, and $R^7$, $R^8$ and $R^9$ are the same or different and are a C1 to C6 chain hydrocarbon group optionally having one or more atoms or groups selected from group X or a hydrogen atom.

In the formula (1), compounds wherein $R^6$ and $R^{10}$ are a hydrogen atom, and $R^7$, $R^8$ and $R^9$ are the same or different and are $OR^{14}$ or a hydrogen atom.

In the formula (1), compounds wherein $R^6$ and $R^{10}$ are a hydrogen atom, and $R^7$, $R^8$ and $R^9$ are the same or different and are $S(O)_m R^{11}$ or a hydrogen atom.

In the formula (1), compounds wherein $R^6$ and $R^{10}$ are a hydrogen atom, and $R^7$, $R^8$ and $R^9$ are the same or different and are a halogen atom or a hydrogen atom.

In the formula (1), compounds wherein $R^6$ and $R^{10}$ are a hydrogen atom, $R^7$ and $R^9$ are the same or different and are a halogen atom or a hydrogen atom, and $R^8$ is a C1 to C6 chain hydrocarbon group optionally having one or more atoms or groups selected from group X, $OR^{14}$, $S(O)_m R^{11}$, $SF_5$ or a halogen atom.

In the formula (1), compounds wherein $R^6$ and $R^{10}$ are a hydrogen atom, $R^7$ and $R^9$ are the same or different and are a halogen atom or a hydrogen atom, and $R^8$ is a C1 to C6 chain hydrocarbon group optionally having one or more atoms or groups selected from group X.

In the formula (1), compounds wherein $R^6$ and $R^{10}$ are a hydrogen atom, $R^8$ is a halogen atom or a hydrogen atom, and $R^7$ and $R^9$ are the same or different and are a C1 to C6 chain hydrocarbon group optionally having one or more atoms or groups selected from group X.

In the formula (1), compounds wherein $R^6$ and $R^{10}$ are a hydrogen atom, $R^7$ and $R^9$ are the same or different and are a halogen atom or a hydrogen atom, and $R^8$ is $OR^{14}$.

In the formula (1), compounds wherein $R^6$ and $R^{10}$ are a hydrogen atom, $R^7$ and $R^9$ are the same or different and are a halogen atom or a hydrogen atom, and $R^8$ is $S(O)_m R^{11}$.

In the formula (1), compounds wherein $R^6$ and $R^{10}$ are the same or different and are a fluorine atom or a hydrogen atom, and $R^7$, $R^8$ and $R^9$ are the same or different and are a C1 to C6 alkyl group optionally having one or more halogen atoms, a C2 to C6 alkenyl group optionally having one or more halogen atoms, a C2 to C6 alkynyl group optionally having one or more halogen atoms, $OR^{14}$, $S(O)_m R^{11}$, a halogen atom or a hydrogen atom.

In the formula (1), compounds wherein $R^6$ and $R^{10}$ are the same or different and are a fluorine atom or a hydrogen atom, and $R^7$, $R^8$ and $R^9$ are the same or different and are a C1 to C6 alkyl group optionally having one or more halogen atoms, a C2 to C6 alkenyl group optionally having one or more halogen atoms, a halogen atom or a hydrogen atom.

In the formula (1), compounds wherein $R^6$ and $R^{10}$ are the same or different and are a fluorine atom or a hydrogen atom, and $R^7$, $R^8$ and $R^9$ are the same or different and are a C1 to C6 alkyl group optionally having one or more halogen atoms, a halogen atom or a hydrogen atom.

In the formula (1), compounds wherein $R^6$ and $R^{10}$ are the same or different and are a fluorine atom or a hydrogen atom, and $R^7$, $R^8$ and $R^9$ are the same or different and are a C1 to C6 alkyl group optionally having one or more halogen atoms or a hydrogen atom.

In the formula (1), compounds wherein $R^6$ and $R^{10}$ are a hydrogen atom, and $R^7$, $R^8$ and $R^9$ are the same or different and are a C1 to C6 haloalkyl group, a C2 to C6 haloalkenyl group, a C1 to C6 haloalkoxy group, a C1 to C6 haloalkylsulfanyl group, a C1 to C6 haloalkylsulfinyl group, a C1 to C6 haloalkylsulfonyl group, a halogen atom or a hydrogen atom.

In the formula (1), compounds wherein $R^6$ and $R^{10}$ are a hydrogen atom, and $R^7$, $R^8$ and $R^9$ are the same or different and are a C1 to C6 haloalkyl group, a C2 to C6 haloalkenyl group, a halogen atom or a hydrogen atom.

In the formula (1), compounds wherein $R^6$ and $R^{10}$ are a hydrogen atom, and $R^7$, $R^8$ and $R^9$ are the same or different and are a C1 to C6 haloalkyl group, a halogen atom or a hydrogen atom.

In the formula (1), compounds wherein $R^6$ and $R^{10}$ are a hydrogen atom, and $R^7$, $R^8$ and $R^9$ are the same or different and are a C1 to C6 haloalkoxy group, a halogen atom or a hydrogen atom.

In the formula (1), compounds wherein $R^6$ and $R^{10}$ are a hydrogen atom, and $R^7$, $R^8$ and $R^9$ are the same or different and are a C1 to C6 haloalkylsulfanyl group, a C1 to C6 haloalkylsulfinyl group, a C1 to C6 haloalkylsulfonyl group, a halogen atom or a hydrogen atom.

In the formula (1), compounds wherein $R^6$ and $R^{10}$ are a hydrogen atom, $R^7$ and $R^9$ are the same or different and are a halogen atom or a hydrogen atom, and $R^8$ is a C1 to C6 haloalkyl group, a C2 to C6 haloalkenyl group, a C1 to C6 haloalkoxy group, a C1 to C6 haloalkylsulfanyl group, a C1 to C6 haloalkylsulfinyl group, a C1 to C6 haloalkylsulfonyl group, a halogen atom or a hydrogen atom.

In the formula (1), compounds wherein $R^6$ and $R^{10}$ are a hydrogen atom, $R^7$ and $R^9$ are the same or different and are a halogen atom or a hydrogen atom, and $R^8$ is a C1 to C6 haloalkyl group.

In the formula (1), compounds wherein $R^6$ and $R^{10}$ are a hydrogen atom, $R^7$ and $R^9$ are the same or different and are a halogen atom or a hydrogen atom, and $R^8$ is a C1 to C6 haloalkoxy group.

In the formula (1), compounds wherein $R^6$ and $R^{10}$ are a hydrogen atom, $R^7$ and $R^9$ are the same or different and are a halogen atom or a hydrogen atom, and $R^8$ is a C1 to C6 haloalkylsulfanyl group, a C1 to C6 haloalkylsulfinyl group or a C1 to C6 haloalkylsulfonyl group.

In the formula (1), compounds wherein $R^6$ and $R^{10}$ are a hydrogen atom, and $R^7$, $R^8$ and $R^9$ are the same or different and are a C1 to C3 perfluoroalkyl group, a C1 to C3 perfluoroalkoxy group, a C1 to C3 perfluoroalkylsulfanyl group, a C1 to C3 perfluoroalkylsulfinyl group, a C1 to C3 perfluoroalkylsulfonyl group, a halogen atom or a hydrogen atom.

In the formula (1), compounds wherein $R^6$ and $R^{10}$ are a hydrogen atom, and $R^7$, $R^8$ and $R^9$ are the same or different and are a C1 to C3 perfluoroalkyl group, a halogen atom or a hydrogen atom.

In the formula (1), compounds wherein $R^6$ and $R^{10}$ are a hydrogen atom, and $R^7$, $R^8$ and $R^9$ are the same or different and are a C1 to C3 perfluoroalkoxy group, a halogen atom or a hydrogen atom.

In the formula (1), compounds wherein $R^6$ and $R^{10}$ are a hydrogen atom, and $R^7$, $R^8$ and $R^9$ are the same or different and are a C1 to C3 perfluoroalkylsulfanyl group, a C1 to C3 perfluoroalkylsulfinyl group, a C1 to C3 perfluoroalkylsulfonyl group, a halogen atom or a hydrogen atom.

In the formula (1), compounds wherein $R^6$ and $R^{10}$ are a hydrogen atom, $R^7$ and $R^9$ are the same or different and are a halogen atom or a hydrogen atom, and $R^8$ is a C1 to C3 perfluoroalkyl group.

In the formula (1), compounds wherein $R^6$ and $R^{10}$ are a hydrogen atom, $R^7$ and $R^9$ are the same or different and are a halogen atom or a hydrogen atom, and $R^8$ is a C1 to C3 perfluoroalkoxy group.

In the formula (1), compounds wherein $R^6$ and $R^{10}$ are a hydrogen atom, $R^7$ and $R^9$ are the same or different and are a halogen atom or a hydrogen atom, and $R^8$ is a C1 to C3 perfluoroalkylsulfanyl group, a C1 to C3 perfluoroalkylsulfinyl group or a C1 to C3 perfluoroalkylsulfonyl group.

In the formula (1), compounds wherein $R^6$ and $R^{10}$ are a hydrogen atom, and $R^7$, $R^8$ and $R^9$ are the same or different and are a trifluoromethyl group, a pentafluoroethyl group, a heptafluoropropyl group, a heptafluoroisopropyl group, a trifluoromethoxy group, a trifluoromethylsulfanyl group, a trifluoromethylsulfinyl group, a trifluoromethylsulfonyl group, a fluorine atom, a chlorine atom, a bromine atom, an iodine atom or a hydrogen atom.

In the formula (1), compounds wherein $R^6$ and $R^{10}$ are a hydrogen atom, $R^7$ and $R^9$ are the same or different and are a halogen atom or a hydrogen atom, and $R^8$ is a trifluoromethyl group, a pentafluoroethyl group, a heptafluoropropyl group, a heptafluoroisopropyl group, a trifluoromethoxy group, a trifluoromethylsulfanyl group, a trifluoromethylsulfinyl group or a trifluoromethylsulfonyl group.

In the formula (1), compounds wherein one or two of $G^1$, $G^2$, $G^3$, $G^4$ and $G^5$ are a nitrogen atom.

In the formula (1), compounds wherein two of $G^1$, $G^2$, $G^3$, $G^4$ and $G^5$ are a nitrogen atom.

In the formula (1), compounds wherein one of $G^1$, $G^2$, $G^3$, $G^4$ and $G^5$ is a nitrogen atom.

In the formula (1), compounds wherein one or two of $G^1$, $G^2$, $G^4$ and $G^5$ are a nitrogen atom, and $G^3$ is =$CR^8$—.

In the formula (1), compounds wherein $G^1$ is a nitrogen atom.

In the formula (1), compounds wherein $G^2$ is a nitrogen atom.

In the formula (1), compounds wherein $G^3$ is a nitrogen atom.

In the formula (1), compounds wherein $G^4$ is a nitrogen atom.

In the formula (1), compounds wherein $G^5$ is a nitrogen atom.

In the formula (1), compounds wherein $G^1$ is $CR^6$, $G^2$ is $CR^7$, $G^3$ is $CR^8$, $G^4$ is $CR^9$, and $G^5$ is $CR^{10}$.

In the formula (1), compounds wherein $G^1$ is a nitrogen atom, $G^2$ is $CR^7$, $G^3$ is $CR^8$, $G^4$ is $CR^9$, and $G^5$ is $CR^{10}$.

In the formula (1), compounds wherein $G^1$ is $CR^6$, $G^2$ is a nitrogen atom, $G^3$ is $CR^8$, $G^4$ is $CR^9$, and $G^5$ is $CR^{10}$.

In the formula (1), compounds wherein $G^1$ is $CR^6$, $G^2$ is $CR^7$, $G^3$ is a nitrogen atom, $G^4$ is $CR^9$, and $G^5$ is $CR^{10}$.

In the formula (1), compounds wherein $G^1$ is a nitrogen atom, $G^2$ is $CR^7$, $G^3$ is a nitrogen atom, $G^4$ is $CR^9$, and $G^5$ is $CR^{10}$.

In the formula (1), compounds wherein $G^1$ is $CR^6$, $G^2$ is a nitrogen atom, $G^3$ is $CR^8$, $G^4$ is a nitrogen atom, and $G^5$ is $CR^{10}$.

In the formula (1), compounds wherein $G^1$ is a nitrogen atom, $G^2$ is a nitrogen atom, $G^3$ is $CR^8$, $G^4$ is $CR^9$, and $G^5$ is $CR^{10}$.

In the formula (1), compounds wherein $G^1$ is $CR^6$, $G^2$ is a nitrogen atom, $G^3$ is a nitrogen atom, $G^4$ is $CR^8$, and $G^5$ is $CR^{10}$.

In the formula (1), compounds wherein $G^1$ is a nitrogen atom, $G^2$ is $CR^7$, $G^3$ is $CR^8$, $G^4$ is a nitrogen atom, and $G^5$ is $CR^{10}$.

In the formula (1), compounds wherein $G^1$ is a nitrogen atom or $CR^6$, $G^2$ is a nitrogen atom or $CR^7$, $G^3$ is $CR^8$, $G^4$ is $CR^9$, $G^5$ is a nitrogen atom or $CR^{10}$, and one or two of $G^1$, $G^2$ and $G^5$ are a nitrogen atom.

In the formula (1), compounds wherein $G^1$ is a nitrogen atom or $CR^6$, $G^2$ is a nitrogen atom or $CR^7$, $G^3$ is $CR^8$, $G^4$ is $CR^9$, $G^5$ is a nitrogen atom or $CR^{10}$, and two of $G^1$, $G^2$ and $G^5$ are a nitrogen atom.

In the formula (1), compounds wherein $G^1$ is a nitrogen atom or $CR^6$, $G^2$ is a nitrogen atom or $CR^7$, $G^3$ is $CR^8$, $G^4$ is $CR^9$, $G^5$ is a nitrogen atom or $CR^{10}$, and one of $G^1$, $G^2$ and $G^5$ is a nitrogen atom.

In the formula (1), compounds wherein Q is an oxygen atom.

In the formula (1), compounds wherein Q is a sulfur atom.

In the formula (1), compounds wherein m is 0.

In the formula (1), compounds wherein m is 1.
In the formula (1), compounds wherein m is 2.
In the formula (1), compounds wherein n is 0.
In the formula (1), compounds wherein n is 1.
In the formula (1), compounds wherein n is 2.
Compounds represented by formula (H1):

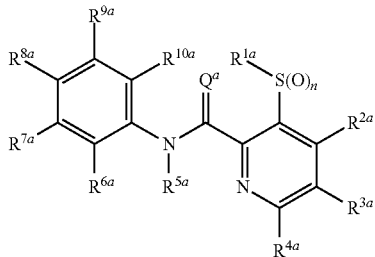

(H1)

wherein
$R^{1a}$ represents a C1 to C6 alkyl group optionally having one or more halogen atoms, a (C3 to C6 cycloalkyl)C1 to C3 alkyl group optionally having one or more halogen atoms or a C3 to C6 cycloalkyl group optionally having one or more atoms or groups selected from the group consisting of halogen atoms and C1 to C3 alkyl groups, $R^{2a}$, $R^{3a}$ and $R^{4a}$ are the same or different and represent a C1 to C6 alkyl group optionally having one or more halogen atoms, a phenyl group optionally having one or more atoms or groups selected from the group consisting of C1 to C3 alkyl groups optionally having one or more halogen atoms and halogen atoms, a 5- or 6-membered heterocyclic group optionally having one or more atoms or groups selected from the group consisting of C1 to C3 alkyl groups optionally having one or more halogen atoms and halogen atoms, $OR^{11}$, $S(O)_m R^{11}$, $NR^{11}R^{12}$, $NR^{15}C(O)R^{11}$, $NR^{15}C(O)OR^{11}$, $NR^{15}C(O)NR^{11}R^{12}$, $NR^{16}S(O)_2R^{13}$, $C(O)OR^{11}$, $C(O)NR^{11}R^{12}$, $C(O)NR^{11}NR^{15}R^{16}$, a cyano group, a halogen atom or a hydrogen atom, $R^{5a}$ represents a C1 to C6 alkyl group optionally having one or more atoms or groups selected from the group consisting of halogen atoms and cyclopropyl groups (wherein the cyclopropyl group optionally has one or more halogen atoms or one or more C1 to C3 alkyl groups), a (C1 to C6 alkoxy)C1 to C6 alkyl group optionally having one or more halogen atoms, a C2 to C6 alkenyl group optionally having one or more halogen atoms, a C2 to C6 alkynyl group optionally having one or more halogen atoms, a C3 to C6 cycloalkyl group optionally having one or more atoms or groups selected from the group consisting of halogen atoms and C1 to C3 alkyl groups, a C2 to C6 alkylcarbonyl group optionally having one or more halogen atoms, a C2 to C6 alkoxycarbonyl group optionally having one or more halogen atoms, or a hydrogen atom, $R^{6a}$ and $R^{10a}$ are the same or different and represent a fluorine atom or a hydrogen atom, $R^{7a}$, $R^{8a}$ and $R^{9a}$ are the same or different and represent a C1 to C6 alkyl group optionally having one or more atoms or groups selected from the group consisting of C1 to C3 alkoxy groups and halogen atoms, a C2 to C6 alkenyl group optionally having one or more halogen atoms, a C2 to C6 alkynyl group optionally having one or more halogen atoms, a C1 to C6 alkoxy group optionally having one or more halogen atoms, a C1 to C6 alkylsulfanyl group optionally having one or more halogen atoms, a C1 to C6 alkylsulfinyl group optionally having one or more halogen atoms, a C1 to C6 alkylsulfonyl group optionally having one or more halogen atoms, a halogen atom or a hydrogen atom (wherein $R^{7a}$, $R^{8a}$ and $R^{9a}$ do not represent a hydrogen atom at the same time), $Q^a$ represents an oxygen atom or a sulfur atom,
n represents 0, 1 or 2 and
m represents 0, 1 or 2, or N-oxides thereof.

In the formula (H1), compounds wherein $R^{2a}$ and $R^{4a}$ are the same or different and are a halogen atom or a hydrogen atom, and $R^{3a}$ is a C1 to C6 alkyl group optionally having one or more halogen atoms, a C2 to C6 alkenyl group optionally having one or more halogen atoms, a C2 to C6 alkynyl group optionally having one or more halogen atoms, a 5- or 6-membered heterocyclic group (wherein the 5- or 6-membered heterocyclic group optionally has one or more atoms or groups selected from the group consisting of C1 to C3 alkyl groups optionally having one or more halogen atoms and halogen atoms), a C1 to C6 alkoxy group optionally having one or more halogen atoms, a C1 to C6 alkylsulfanyl group optionally having one or more halogen atoms, a C1 to C6 alkylsulfinyl group optionally having one or more halogen atoms, a C1 to C6 alkylsulfonyl group optionally having one or more halogen atoms, a halogen atom or a hydrogen atom, or N-oxides thereof.

In the formula (H1), compounds wherein $R^{1a}$ is a C2 to C3 alkyl group, a cyclopropyl group, or a cyclopropylmethyl group.

In the formula (H1), compounds wherein $R^{2a}$ and $R^{4a}$ are a hydrogen atom, and $R^{3a}$ is a C1 to C6 alkyl group optionally having one or more halogen atoms, a halogen atom or a hydrogen atom.

In the formula (H1), compounds wherein $R^{5a}$ is a C1 to C6 alkyl group optionally having one or more atoms or groups selected from the group consisting of halogen atoms and cyclopropyl groups.

In the formula (H1), compounds wherein $R^{5a}$ is a hydrogen atom.

In the formula (H1), compounds wherein $R^{6a}$ and $R^{10a}$ are a hydrogen atom.

In the formula (H1), $R^{6a}$ and $R^{10a}$ are a hydrogen atom, and $R^{7a}$, $R^{8a}$ and $R^{9a}$ are the same or different and are a C1 to C6 alkyl group optionally having one or more halogen atoms, a C2 to C6 alkenyl group optionally having one or more halogen atoms, a C2 to C6 alkynyl group optionally having one or more halogen atoms, a C1 to C6 alkoxy group optionally having one or more halogen atoms, a C1 to C6 alkylsulfanyl group optionally having one or more halogen atoms, a C1 to C6 alkylsulfinyl group optionally having one or more halogen atoms, a C1 to C6 alkylsulfonyl group optionally having one or more halogen atoms, a halogen atom or a hydrogen atom.

In the formula (H1), compounds wherein $R^{6a}$ and $R^{10a}$ are a hydrogen atom, and $R^{7a}$, $R^{8a}$ and $R^{9a}$ are the same or different and are a C1 to C6 haloalkyl group, a C1 to C6 haloalkoxy group, a C1 to C6 haloalkylsulfanyl group, a C1 to C6 haloalkylsulfinyl group, a C1 to C6 haloalkylsulfonyl group, a halogen atom or a hydrogen atom.

In the formula (H1), compounds wherein $R^{6a}$ and $R^{10a}$ are a hydrogen atom, and $R^{7a}$, $R^{8a}$ and $R^{9a}$ are the same or different and are a C1 to C3 perfluoroalkyl group, a C1 to C3 perfluoroalkoxy group, a C1 to C3 perfluoroalkylsulfanyl group, a C1 to C3 perfluoroalkylsulfinyl group, a C1 to C3 perfluoroalkylsulfonyl group, a halogen atom or a hydrogen atom.

In the formula (H1), compounds wherein $Q^a$ is an oxygen atom.

In the formula (H1), compounds wherein
$R^{1a}$ is a C2 to C3 alkyl group, a cyclopropyl group or a cyclopropylmethyl group, $R^{2a}$ and $R^{4a}$ are a hydrogen atom,
$R^{3a}$ is a C1 to C6 alkyl group optionally having one or more halogen atoms, a halogen atom or a hydrogen atom,
$R^{5a}$ is a C1 to C6 alkyl group optionally having one or more atoms or groups selected from the group consisting of halogen atoms and cyclopropyl groups or a C3 to C6 cycloalkyl group optionally having one or more atoms or groups selected from the group consisting of halogen atoms and C1 to C3 alkyl groups,
$R^{6a}$ and $R^{10a}$ are a hydrogen atom,
$R^{7a}$, $R^{8a}$ and $R^{9a}$ are the same or different and are a C1 to C3 perfluoroalkyl group, a C1 to C3 perfluoroalkoxy group, a C1 to C3 perfluoroalkylsulfanyl group, a C1 to C3 perfluoroalkylsulfinyl group, a C1 to C3 perfluoroalkylsulfonyl group, a halogen atom or a hydrogen atom, and
$Q^a$ is an oxygen atom.

Compounds represented by formula (H2):

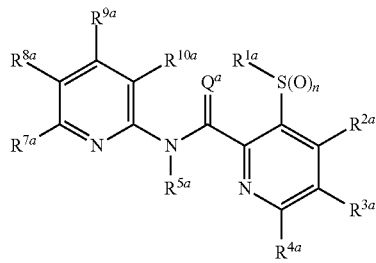

(H2)

wherein $R^{1a}$ represents a C1 to C6 alkyl group optionally having one or more halogen atoms, a (C3 to C6 cycloalkyl)C1 to C3 alkyl group optionally having one or more halogen atoms or a C3 to C6 cycloalkyl group optionally having one or more atoms or groups selected from the group consisting of halogen atoms and C1 to C3 alkyl groups, $R^{2a}$, $R^{3a}$ and $R^{4a}$ are the same or different and represent a C1 to C6 alkyl group optionally having one or more halogen atoms, a phenyl group optionally having one or more atoms or groups selected from the group consisting of C1 to C3 alkyl groups optionally having one or more halogen atoms and halogen atoms, a 5- or 6-membered heterocyclic group optionally having one or more atoms or groups selected from the group consisting of C1 to C3 alkyl groups optionally having one or more halogen atoms and halogen atoms, $OR^{11}$, $S(O)_m R^{11}$, $NR^{11}R^{12}$, $NR^{15}C(O)R^{11}$, $NR^{15}C(O)OR^{11}$, $NR^{15}C(O)NR^{11}R^{12}$, $NR^{16}S(O)_2R^{13}$, $C(O)OR^{11}$, $C(O)NR^{11}R^{12}$, $C(O)NR^{11}NR^{15}R^{16}$, a cyano group, a halogen atom or a hydrogen atom, $R^{5a}$ represents a C1 to C6 alkyl group optionally having one or more atoms or groups selected from the group consisting of halogen atoms and cyclopropyl groups (wherein the cyclopropyl group optionally has one or more halogen atoms or one or more C1 to C3 alkyl groups), a (C1 to C6 alkoxy)C1 to C6 alkyl group optionally having one or more halogen atoms, a C2 to C6 alkenyl group optionally having one or more halogen atoms, a C2 to C6 alkynyl group optionally having one or more halogen atoms, a C3 to C6 cycloalkyl group optionally having one or more atoms or groups selected from the group consisting of halogen atoms and C1 to C3 alkyl groups, a C2 to C6 alkylcarbonyl group optionally having one or more halogen atoms, a C2 to C6 alkoxycarbonyl group optionally having one or more halogen atoms or a hydrogen atom, $R^{10a}$ represents a fluorine atom or a hydrogen atom, $R^{7a}$, $R^{8a}$ and $R^{9a}$ are the same or different and represent a C1 to C6 alkyl group optionally having one or more atoms or groups selected from the group consisting of C1 to C3 alkoxy groups and halogen atoms, a C2 to C6 alkenyl group optionally having one or more halogen atoms, a C2 to C6 alkynyl group optionally having one or more halogen atoms, a C1 to C6 alkoxy group optionally having one or more halogen atoms, a C1 to C6 alkylsulfanyl group optionally having one or more halogen atoms, a C1 to C6 alkylsulfinyl group optionally having one or more halogen atoms, a C1 to C6 alkylsulfonyl group optionally having one or more halogen atoms, a halogen atom or a hydrogen atom (wherein $R^{7a}$, $R^{8a}$ and $R^{9a}$ do not represent a hydrogen atom at the same time), $Q^a$ represents an oxygen atom or a sulfur atom, n represents 0, 1 or 2 and m represents 0, 1 or 2, or N-oxides thereof.

In the formula (H2), compounds wherein $R^{2a}$ and $R^{4a}$ are the same or different and are a halogen atom or a hydrogen atom, and $R^{3a}$ is a C1 to C6 alkyl group optionally having one or more halogen atoms, a C2 to C6 alkenyl group optionally having one or more halogen atoms, a C2 to C6 alkynyl group optionally having one or more halogen atoms, a 5- or 6-membered heterocyclic group (wherein the 5- or 6-membered heterocyclic group optionally has one or more atoms or groups selected from the group consisting of C1 to C3 alkyl groups optionally having one or more halogen atoms and halogen atoms), a C1 to C6 alkoxy group optionally having one or more halogen atoms, a C1 to C6 alkylsulfanyl group optionally having one or more halogen atoms, a C1 to C6 alkylsulfinyl group optionally having one or more halogen atoms, a C1 to C6 alkylsulfonyl group optionally having one or more halogen atoms, a halogen atom or a hydrogen atom, or N-oxides thereof.

In the formula (H2), compounds wherein $R^{1a}$ is a C2 to C3 alkyl group, a cyclopropyl group, or a cyclopropylmethyl group.

In the formula (H2), compounds wherein $R^{2a}$ and $R^{4a}$ are a hydrogen atom, and $R^{3a}$ is a C1 to C6 alkyl group optionally having one or more halogen atoms, a halogen atom or a hydrogen atom.

In the formula (H2), compounds wherein $R^{5a}$ is a C1 to C6 alkyl group optionally having one or more atoms or groups selected from the group consisting of halogen atoms and cyclopropyl groups.

In the formula (H2), compounds wherein $R^{5a}$ is a hydrogen atom.

In the formula (H2), compounds wherein $R^{6a}$ is a hydrogen atom.

In the formula (H2), $R^{6a}$ is a hydrogen atom, and $R^{7a}$, $R^{8a}$ and $R^{9a}$ are the same or different and are a C1 to C6 alkyl group optionally having one or more halogen atoms, a C2 to C6 alkenyl group optionally having one or more halogen atoms, a C2 to C6 alkynyl group optionally having one or more halogen atoms, a C1 to C6 alkoxy group optionally having one or more halogen atoms, a C1 to C6 alkylsulfanyl group optionally having one or more halogen atoms, a C1 to C6 alkylsulfinyl group optionally having one or more halogen atoms, a C1 to C6 alkylsulfonyl group optionally having one or more halogen atoms, a halogen atom or a hydrogen atom.

In the formula (H2), compounds wherein $R^{6a}$ is a hydrogen atom, and $R^{7a}$, $R^{8a}$ and $R^{9a}$ are the same or different and are a C1 to C6 haloalkyl group, a C1 to C6 haloalkoxy group, a C1 to C6 haloalkylsulfanyl group, a C1 to C6 haloalkylsulfinyl group, a C1 to C6 haloalkylsulfonyl group, a halogen atom or a hydrogen atom.

In the formula (H2), compounds wherein $R^{6a}$ is a hydrogen atom, and $R^{7a}$, $R^{8a}$ and $R^{9a}$ are the same or different and are a C1 to C3 perfluoroalkyl group, a C1 to C3 perfluoroalkoxy group, a C1 to C3 perfluoroalkylsulfanyl group, a C1 to C3 perfluoroalkylsulfinyl group, a C1 to C3 perfluoroalkylsulfonyl group, a halogen atom or a hydrogen atom.

In the formula (H2), compounds wherein $Q^a$ is an oxygen atom.

In the formula (H2), compounds wherein $R^{1a}$ is a C2 to C3 alkyl group, a cyclopropyl group or a cyclopropylmethyl group, $R^{2a}$ and $R^{4a}$ are a hydrogen atom, $R^{3a}$ is a C1 to C6 alkyl group optionally having one or more halogen atoms, a halogen atom or a hydrogen atom, $R^{5a}$ is a C1 to C6 alkyl group optionally having one or more atoms or groups selected from the group consisting of halogen atoms and cyclopropyl groups or a C3 to C6 cycloalkyl group optionally having one or more atoms or groups selected from the group consisting of halogen atoms and C1 to C3 alkyl groups, $R^{10a}$ is a hydrogen atom, $R^{7a}$, $R^{8a}$ and $R^{9a}$ are the same or different and are a C1 to C3 perfluoroalkyl group, a C1 to C3 perfluoroalkoxy group, a C1 to C3 perfluoroalkylsulfanyl group, a C1 to C3 perfluoroalkylsulfinyl group, a C1 to C3 perfluoroalkylsulfonyl group, a halogen atom or a hydrogen atom, and $Q^a$ is an oxygen atom.

Compounds represented by formula (H3):

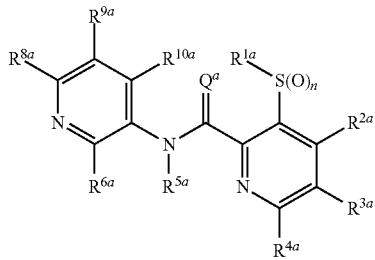

(H3)

wherein $R^{1a}$ represents a C1 to C6 alkyl group optionally having one or more halogen atoms, a (C3 to C6 cycloalkyl)C1 to C3 alkyl group optionally having one or more halogen atoms or a C3 to C6 cycloalkyl group optionally having one or more atoms or groups selected from the group consisting of halogen atoms and C1 to C3 alkyl groups, $R^{2a}$, $R^{3a}$ and $R^{4a}$ are the same or different and represent a C1 to C6 alkyl group optionally having one or more halogen atoms, a phenyl group optionally having one or more atoms or groups selected from the group consisting of C1 to C3 alkyl groups optionally having one or more halogen atoms and halogen atoms, a 5- or 6-membered heterocyclic group optionally having one or more atoms or groups selected from the group consisting of C1 to C3 alkyl groups optionally having one or more halogen atoms and halogen atoms, $OR^{11}$, $S(O)_m R^{11}$, $NR^{11}R^{12}$, $NR^{15}C(O)R^{11}$, $NR^{15}C(O)OR^{11}$, $NR^{15}C(O)NR^{11}R^{12}$, $NR^{16}S(O)_2 R^{13}$, $C(O)OR^{11}$, $C(O)NR^{11}R^{12}$, $C(O)NR^{11}NR^{15}R^{16}$, a cyano group, a halogen atom or a hydrogen atom, $R^{5a}$ represents a C1 to C6 alkyl group optionally having one or more atoms or groups selected from the group consisting of halogen atoms and cyclopropyl groups (wherein the cyclopropyl group optionally has one or more halogen atoms or one or more C1 to C3 alkyl groups), a (C1 to C6 alkoxy)C1 to C6 alkyl group optionally having one or more halogen atoms, a C2 to C6 alkenyl group optionally having one or more halogen atoms, a C2 to C6 alkynyl group optionally having one or more halogen atoms, a C3 to C6 cycloalkyl group optionally having one or more atoms or groups selected from the group consisting of halogen atoms and C1 to C3 alkyl groups, a C2 to C6 alkylcarbonyl group optionally having one or more halogen atoms, a C2 to C6 alkoxycarbonyl group optionally having one or more halogen atoms, or a hydrogen atom, $R^{6a}$ and $R^{11a}$ are the same or different and represent a fluorine atom or a hydrogen atom, $R^{8a}$ and $R^{9a}$ are the same or different and represent a C1 to C6 alkyl group optionally having one or more atoms or groups selected from the group consisting of C1 to C3 alkoxy groups and halogen atoms, a C2 to C6 alkenyl group optionally having one or more halogen atoms, a C2 to C6 alkynyl group optionally having one or more halogen atoms, a C1 to C6 alkoxy group optionally having one or more halogen atoms, a C1 to C6 alkylsulfanyl group optionally having one or more halogen atoms, a C1 to C6 alkylsulfinyl group optionally having one or more halogen atoms, a C1 to C6 alkylsulfonyl group optionally having one or more halogen atoms, a halogen atom or a hydrogen atom (wherein $R^{8a}$ and $R^{9a}$ do not represent a hydrogen atom at the same time), $Q^a$ represents an oxygen atom or a sulfur atom, n represents 0, 1 or 2 and m represents 0, 1 or 2, or N-oxides thereof.

In the formula (H3), compounds wherein $R^{2a}$ and $R^{4a}$ are the same or different and are a halogen atom or a hydrogen atom, and $R^{3a}$ is a C1 to C6 alkyl group optionally having one or more halogen atoms, a C2 to C6 alkenyl group optionally having one or more halogen atoms, a C2 to C6 alkynyl group optionally having one or more halogen atoms, a 5- or 6-membered heterocyclic group (wherein the 5- or 6-membered heterocyclic group optionally has one or more atoms or groups selected from the group consisting of C1 to C3 alkyl groups optionally having one or more halogen atoms and halogen atoms), a C1 to C6 alkoxy group optionally having one or more halogen atoms, a C1 to C6 alkylsulfanyl group optionally having one or more halogen atoms, a C1 to C6 alkylsulfinyl group optionally having one or more halogen atoms, a C1 to C6 alkylsulfonyl group optionally having one or more halogen atoms, a halogen atom or a hydrogen atom, or N-oxides thereof.

In the formula (H3), compounds wherein $R^{1a}$ is a C2 to C3 alkyl group, a cyclopropyl group, or a cyclopropylmethyl group.

In the formula (H3), compounds wherein $R^{2a}$ and $R^{4a}$ are a hydrogen atom, and $R^{3a}$ is a C1 to C6 alkyl group optionally having one or more halogen atoms, a halogen atom or a hydrogen atom.

In the formula (H3), compounds wherein $R^{5a}$ is a C1 to C6 alkyl group optionally having one or more atoms or groups selected from the group consisting of halogen atoms and cyclopropyl groups.

In the formula (H3), compounds wherein $R^{5a}$ is a hydrogen atom.

In the formula (H3), compounds wherein $R^{6a}$ and $R^{10a}$ are a hydrogen atom.

In the formula (H3), $R^{6a}$ and $R^{10}$ are a hydrogen atom, $R^{8a}$ and $R^{9a}$ are the same or different and are a C1 to C6 alkyl group optionally having one or more halogen atoms, a C2 to C6 alkenyl group optionally having one or more halogen atoms, a C2 to C6 alkynyl group optionally having one or more halogen atoms, a C1 to C6 alkoxy group optionally having one or more halogen atoms, a C1 to C6 alkylsulfanyl group optionally having one or more halogen atoms, a C1 to C6 alkylsulfinyl group optionally having one or more halogen atoms, a C1 to C6 alkylsulfonyl group optionally having one or more halogen atoms, a halogen atom or a hydrogen atom.

In the formula (H3), compounds wherein $R^{6a}$ and $R^{10a}$ are a hydrogen atom, and $R^{8a}$ and $R^{9a}$ are the same or different and are a C1 to C6 haloalkyl group, a C1 to C6 haloalkoxy group, a C1 to C6 haloalkylsulfanyl group, a C1 to C6 haloalkylsulfinyl group, a C1 to C6 haloalkylsulfonyl group, a halogen atom or a hydrogen atom.

In the formula (H3), compounds wherein $R^{6a}$ and $R^{10a}$ are a hydrogen atom, and $R^{8a}$ and $R^{9a}$ are the same or different and are a C1 to C3 perfluoroalkyl group, a C1 to C3 perfluoroalkoxy group, a C1 to C3 perfluoroalkylsulfanyl group, a C1 to C3 perfluoroalkylsulfinyl group, a C1 to C3 perfluoroalkylsulfonyl group, a halogen atom or a hydrogen atom.

In the formula (H3), compounds wherein $Q^a$ is an oxygen atom.

In the formula (H3), compounds wherein $R^{1a}$ is a C2 to C3 alkyl group, a cyclopropyl group or a cyclopropylmethyl group, $R^{2a}$ and $R^{4a}$ are a hydrogen atom, $R^{3a}$ is a C1 to C6 alkyl group optionally having one or more halogen atoms, a halogen atom or a hydrogen atom, $R^{5a}$ is a C1 to C6 alkyl group optionally having one or more atoms or groups selected from the group consisting of halogen atoms and cyclopropyl groups or a C3 to C6 cycloalkyl group optionally having one or more atoms or groups selected from the group consisting of halogen atoms and C1 to C3 alkyl groups, $R^{6a}$ and $R^{10a}$ are a hydrogen atom, $R^{8a}$ and $R^{9a}$ are the same or different and are a C1 to C3 perfluoroalkyl group, a C1 to C3 perfluoroalkoxy group, a C1 to C3 perfluoroalkylsulfanyl group, a C1 to C3 perfluoroalkylsulfinyl group, a C1 to C3 perfluoroalkylsulfonyl group, a halogen atom or a hydrogen atom, and $Q^a$ is an oxygen atom.

Compounds represented by formula (H4):

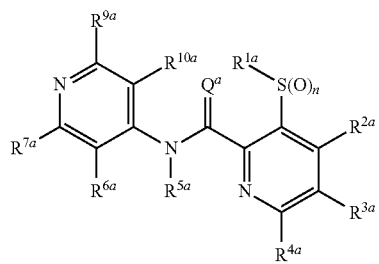

(H4)

wherein $R^{1a}$ represents a C1 to C6 alkyl group optionally having one or more halogen atoms, a (C3 to C6 cycloalkyl)C1 to C3 alkyl group optionally having one or more halogen atoms or a C3 to C6 cycloalkyl group optionally having one or more atoms or groups selected from the group consisting of halogen atoms and C1 to C3 alkyl groups, $R^{2a}$, $R^{3a}$ and $R^{4a}$ are the same or different and represent a C1 to C6 alkyl group optionally having one or more halogen atoms, a phenyl group optionally having one or more atoms or groups selected from the group consisting of C1 to C3 alkyl groups optionally having one or more halogen atoms and halogen atoms, a 5- or 6-membered heterocyclic group optionally having one or more atoms or groups selected from the group consisting of C1 to C3 alkyl groups optionally having one or more halogen atoms and halogen atoms, $OR^{11}$, $S(O)_mR^{11}$, $NR^{11}R^{12}$, $NR^{15}C(O)R^{11}$, $NR^{15}C(O)OR^{11}$, $NR^{15}C(O)NR^{11}R^{12}$, $NR^{16}S(O)_2R^{13}$, $C(O)OR^{11}$, $C(O)NR^{11}R^{12}$, $C(O)NR^{11}NR^{15}R^{16}$, a cyano group, a halogen atom or a hydrogen atom, $R^{5a}$ represents a C1 to C6 alkyl group optionally having one or more atoms or groups selected from the group consisting of halogen atoms and cyclopropyl groups (wherein the cyclopropyl group optionally has one or more halogen atoms or one or more C1 to C3 alkyl groups), a (C1 to C6 alkoxy)C1 to C6 alkyl group optionally having one or more halogen atoms, a C2 to C6 alkenyl group optionally having one or more halogen atoms, a C2 to C6 alkynyl group optionally having one or more halogen atoms, a C3 to C6 cycloalkyl group optionally having one or more atoms or groups selected from the group consisting of halogen atoms and C1 to C3 alkyl groups, a C2 to C6 alkylcarbonyl group optionally having one or more halogen atoms, a C2 to C6 alkoxycarbonyl group optionally having one or more halogen atoms or a hydrogen atom, $R^{6a}$ and $R^{10a}$ are the same or different and represent a fluorine atom or a hydrogen atom, $R^{7a}$ and $R^{9a}$ are the same or different and represent a C1 to C6 alkyl group optionally having one or more atoms or groups selected from the group consisting of C1 to C3 alkoxy groups and halogen atoms, a C2 to C6 alkenyl group optionally having one or more halogen atoms, a C2 to C6 alkynyl group optionally having one or more halogen atoms, a C1 to C6 alkoxy group optionally having one or more halogen atoms, a C1 to C6 alkylsulfanyl group optionally having one or more halogen atoms, a C1 to C6 alkylsulfinyl group optionally having one or more halogen atoms, a C1 to C6 alkylsulfonyl group optionally having one or more halogen atoms, a halogen atom or a hydrogen atom (wherein $R^{7a}$ and $R^{9a}$ do not represent a hydrogen atom at the same time), $Q^a$ represents an oxygen atom or a sulfur atom, n represents 0, 1 or 2 and m represents 0, 1 or 2, or N-oxides thereof.

In the formula (H4), compounds wherein $R^{2a}$ and $R^{4a}$ are the same or different and are a halogen atom or a hydrogen atom, and $R^{3a}$ is a C1 to C6 alkyl group optionally having one or more halogen atoms, a C2 to C6 alkenyl group optionally having one or more halogen atoms, a C2 to C6 alkynyl group optionally having one or more halogen atoms, a 5- or 6-membered heterocyclic group (wherein the 5- or 6-membered heterocyclic group optionally has one or more atoms or groups selected from the group consisting of C1 to C3 alkyl groups optionally having one or more halogen atoms and halogen atoms), a C1 to C6 alkoxy group optionally having one or more halogen atoms, a C1 to C6 alkylsulfanyl group optionally having one or more halogen atoms, a C1 to C6 alkylsulfinyl group optionally having one or more halogen atoms, a C1 to C6 alkylsulfonyl group optionally having one or more halogen atoms, a halogen atom or a hydrogen atom, or N-oxides thereof.

In the formula (H4), compounds wherein $R^{1a}$ is a C2 to C3 alkyl group, a cyclopropyl group, or a cyclopropylmethyl group.

In the formula (H4), compounds wherein $R^{2a}$ and $R^{4a}$ are a hydrogen atom, and $R^{3a}$ is a C1 to C6 alkyl group optionally having one or more halogen atoms, a halogen atom or a hydrogen atom.

In the formula (H4), compounds wherein $R^{5a}$ is a C1 to C6 alkyl group optionally having one or more atoms or groups selected from the group consisting of halogen atoms and cyclopropyl groups.

In the formula (H4), compounds wherein $R^{5a}$ is a hydrogen atom.

In the formula (H4), compounds wherein $R^{6a}$ and $R^{10a}$ are a hydrogen atom.

In the formula (H4), $R^{6a}$ and $R^{10a}$ are a hydrogen atom, $R^{7a}$ and $R^{9a}$ are the same or different and are a C1 to C6 alkyl group optionally having one or more halogen atoms, a C2 to C6 alkenyl group optionally having one or more halogen atoms, a C2 to C6 alkynyl group optionally having one or more halogen atoms, a C1 to C6 alkoxy group optionally having one or more halogen atoms, a C1 to C6 alkylsulfanyl group optionally having one or more halogen atoms, a C1 to C6 alkylsulfinyl group optionally having one or more halogen atoms, a C1 to C6 alkylsulfonyl group optionally having one or more halogen atoms, a halogen atom or a hydrogen atom.

In the formula (H4), compounds wherein $R^{6a}$ and $R^{10a}$ are a hydrogen atom, and $R^{7a}$ and $R^{9a}$ are the same or different and are a C1 to C6 haloalkyl group, a C1 to C6 haloalkoxy group, a C1 to C6 haloalkylsulfanyl group, a C1 to C6 haloalkylsulfinyl group, a C1 to C6 haloalkylsulfonyl group, a halogen atom or a hydrogen atom.

In the formula (H4), compounds wherein $R^{6a}$ and $R^{10a}$ are a hydrogen atom, and $R^{7a}$ and $R^{9a}$ are the same or different and are a C1 to C3 perfluoroalkyl group, a C1 to C3 perfluoroalkoxy group, a C1 to C3 perfluoroalkylsulfanyl group, a C1 to C3 perfluoroalkylsulfinyl group, a C1 to C3 perfluoroalkylsulfonyl group, a halogen atom or a hydrogen atom.

In the formula (H4), compounds wherein $Q^a$ is an oxygen atom.

In the formula (H4), compounds wherein $R^{1a}$ is a C2 to C3 alkyl group, a cyclopropyl group or a cyclopropylmethyl group, $R^{2a}$ and $R^{4a}$ are a hydrogen atom, $R^{3a}$ is a C1 to C6 alkyl group optionally having one or more halogen atoms, a halogen atom or a hydrogen atom, $R^{5a}$ is a C1 to C6 alkyl group optionally having one or more atoms or groups selected from the group consisting of halogen atoms and cyclopropyl groups or a C3 to C6 cycloalkyl group optionally having one or more atoms or groups selected from the group consisting of halogen atoms and C1 to C3 alkyl groups, $R^{6a}$ and $R^{10a}$ are a hydrogen atom, $R^{7a}$ and $R^{9a}$ are the same or different and are a C1 to C3 perfluoroalkyl group, a C1 to C3 perfluoroalkoxy group, a C1 to C3 perfluoroalkylsulfanyl group, a C1 to C3 perfluoroalkylsulfinyl group, a C1 to C3 perfluoroalkylsulfonyl group, a halogen atom or a hydrogen atom, and $Q^a$ is an oxygen atom.

Compounds represented by formula (H5):

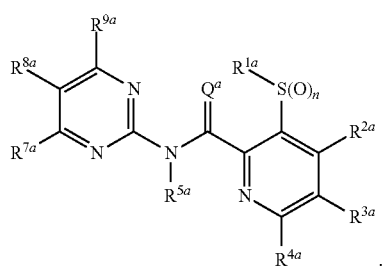

(H5)

wherein $R^{1a}$ represents a C1 to C6 alkyl group optionally having one or more halogen atoms, a (C3 to C6 cycloalkyl)C1 to C3 alkyl group optionally having one or more halogen atoms or a C3 to C6 cycloalkyl group optionally having one or more atoms or groups selected from the group consisting of halogen atoms and C1 to C3 alkyl groups, $R^{2a}$, $R^{3a}$ and $R^{4a}$ are the same or different and represent a C1 to C6 alkyl group optionally having one or more halogen atoms, a phenyl group optionally having one or more atoms or groups selected from the group consisting of C1 to C3 alkyl groups optionally having one or more halogen atoms and halogen atoms, a 5- or 6-membered heterocyclic group optionally having one or more atoms or groups selected from the group consisting of C1 to C3 alkyl groups optionally having one or more halogen atoms and halogen atoms, $OR^{11}$, $S(O)_m R^{11}$, $NR^{11}R^{12}$, $NR^{15}C(O)R^{11}$, $NR^{15}C(O)OR^{11}$, $NR^{15}C(O)NR^{11}R^{12}$, $NR^{16}S(O)_2R^{13}$, $C(O)OR^{11}$, $C(O)NR^{11}R^{12}$, $C(O)NR^{11}NR^{15}R^{16}$, a cyano group, a halogen atom or a hydrogen atom, $R^{5a}$ represents a C1 to C6 alkyl group optionally having one or more atoms or groups selected from the group consisting of halogen atoms and cyclopropyl groups (wherein the cyclopropyl group optionally has one or more halogen atoms or one or more C1 to C3 alkyl groups), a (C1 to C6 alkoxy)C1 to C6 alkyl group optionally having one or more halogen atoms, a C2 to C6 alkenyl group optionally having one or more halogen atoms, a C2 to C6 alkynyl group optionally having one or more halogen atoms, a C3 to C6 cycloalkyl group optionally having one or more atoms or groups selected from the group consisting of halogen atoms and C1 to C3 alkyl groups, a C2 to C6 alkylcarbonyl group optionally having one or more halogen atoms, a C2 to C6 alkoxycarbonyl group optionally having one or more halogen atoms or a hydrogen atom, $R^{7a}$, $R^{8a}$ and $R^{9a}$ are the same or different and represent a C1 to C6 alkyl group optionally having one or more atoms or groups selected from the group consisting of C1 to C3 alkoxy groups and halogen atoms, a C2 to C6 alkenyl group optionally having one or more halogen atoms, a C2 to C6 alkynyl group optionally having one or more halogen atoms, a C1 to C6 alkoxy group optionally having one or more halogen atoms, a C1 to C6 alkylsulfanyl group optionally having one or more halogen atoms, a C1 to C6 alkylsulfinyl group optionally having one or more halogen atoms, a C1 to C6 alkylsulfonyl group optionally having one or more halogen atoms, a halogen atom or a hydrogen atom (wherein $R^{7a}$, $R^{8a}$ and $R^{9a}$ do not represent a hydrogen atom at the same time), $Q^a$ represents an oxygen atom or a sulfur atom, n represents 0, 1 or 2 and m represents 0, 1 or 2, or N-oxides thereof.

In the formula (H5), compounds wherein $R^{2a}$ and $R^{4a}$ are the same or different and are a halogen atom or a hydrogen atom, and $R^{3a}$ is a C1 to C6 alkyl group optionally having one or more halogen atoms, a C2 to C6 alkenyl group optionally having one or more halogen atoms, a C2 to C6 alkynyl group optionally having one or more halogen atoms, a 5- or 6-membered heterocyclic group (wherein the 5- or 6-membered heterocyclic group optionally has one or more atoms or groups selected from the group consisting of C1 to C3 alkyl groups optionally having one or more halogen atoms and halogen atoms), a C1 to C6 alkoxy group optionally having one or more halogen atoms, a C1 to C6 alkylsulfanyl group optionally having one or more halogen atoms, a C1 to C6 alkylsulfinyl group optionally having one or more halogen atoms, a C1 to C6 alkylsulfonyl group optionally having one or more halogen atoms, a halogen atom or a hydrogen atom, or N-oxides thereof.

In the formula (H5), compounds wherein $R^{1a}$ is a C2 to C3 alkyl group, a cyclopropyl group, or a cyclopropylmethyl group.

In the formula (H5), compounds wherein $R^{2a}$ and $R^{4a}$ are a hydrogen atom, and $R^{3a}$ is a C1 to C6 alkyl group optionally having one or more halogen atoms, a halogen atom or a hydrogen atom.

In the formula (H5), compounds wherein $R^{5a}$ is a C1 to C6 alkyl group optionally having one or more atoms or groups selected from the group consisting of halogen atoms and cyclopropyl groups.

In the formula (H5), compounds wherein $R^{5a}$ is a hydrogen atom.

In the formula (H5), $R^{7a}$, $R^{8a}$ and $R^{9a}$ are the same or different and are a C1 to C6 alkyl group optionally having one or more halogen atoms, a C2 to C6 alkenyl group optionally having one or more halogen atoms, a C2 to C6 alkynyl group optionally having one or more halogen atoms, a C1 to C6 alkoxy group optionally having one or more halogen atoms, a C1 to C6 alkylsulfanyl group optionally having one or more halogen atoms, a C1 to C6 alkylsulfinyl group optionally having one or more halogen atoms, a C1 to C6 alkylsulfonyl group optionally having one or more halogen atoms, a halogen atom, or a hydrogen atom.

In the formula (H5), compounds wherein $R^{7a}$, $R^{8a}$ and $R^{9a}$ are the same or different and are a C1 to C6 haloalkyl group, a C1 to C6 haloalkoxy group, a C1 to C6 haloalkylsulfanyl group, a C1 to C6 haloalkylsulfinyl group, a C1 to C6 haloalkylsulfonyl group, a halogen atom, or a hydrogen atom.

In the formula (H5), compounds wherein $R^{7a}$, $R^{8a}$ and $R^{9a}$ are the same or different and are a C1 to C3 perfluoroalkyl group, a C1 to C3 perfluoroalkoxy group, a C1 to C3 perfluoroalkylsulfanyl group, a C1 to C3 perfluoroalkylsulfinyl group, a C1 to C3 perfluoroalkylsulfonyl group, a halogen atom, or a hydrogen atom.

In the formula (H5), compounds wherein $Q^a$ is an oxygen atom.

In the formula (H5), compounds wherein $R^{1a}$ is a C2 to C3 alkyl group, a cyclopropyl group or a cyclopropylmethyl group, $R^{2a}$ and $R^{4a}$ are a hydrogen atom, $R^{3a}$ is a C1 to C6 alkyl group optionally having one or more halogen atoms, a halogen atom or a hydrogen atom, $R^{5a}$ is a C1 to C6 alkyl group optionally having one or more atoms or groups selected from the group consisting of halogen atoms and cyclopropyl groups or a C3 to C6 cycloalkyl group optionally having one or more atoms or groups selected from the group consisting of halogen atoms and C1 to C3 alkyl groups, $R^{7a}$, $R^{8a}$ and $R^{9a}$ are the same or different and are a C1 to C3 perfluoroalkyl group, a C1 to C3 perfluoroalkoxy group, a C1 to C3 perfluoroalkylsulfanyl group, a C1 to C3 perfluoroalkylsulfinyl group, a C1 to C3 perfluoroalkylsulfonyl group, a halogen atom or a hydrogen atom, and $Q^a$ is an oxygen atom.

Compounds represented by formula (H6):

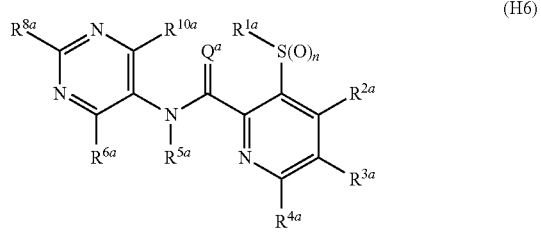

(H6)

wherein $R^{1a}$ represents a C1 to C6 alkyl group optionally having one or more halogen atoms, a (C3 to C6 cycloalkyl)C1 to C3 alkyl group optionally having one or more halogen atoms or a C3 to C6 cycloalkyl group optionally having one or more atoms or groups selected from the group consisting of halogen atoms and C1 to C3 alkyl groups, $R^{2a}$, $R^{3a}$ and $R^{4a}$ are the same or different and represent a C1 to C6 alkyl group optionally having one or more halogen atoms, a phenyl group optionally having one or more atoms or groups selected from the group consisting of C1 to C3 alkyl groups optionally having one or more halogen atoms and halogen atoms, a 5- or 6-membered heterocyclic group optionally having one or more atoms or groups selected from the group consisting of C1 to C3 alkyl groups optionally having one or more halogen atoms and halogen atoms, $OR^{11}$, $S(O)_m R^{11}$, $NR^{11}R^{12}$, $NR^{15}C(O)R^{11}$, $NR^{15}C(O)OR^{11}$, $NR^{15}C(O)NR^{11}R^{12}$, $NR^{16}S(O)_2R^{13}$, $C(O)OR^{11}$, $C(O)NR^{11}R^{12}$, $C(O)NR^{11}NR^{15}R^{16}$, a cyano group, a halogen atom or a hydrogen atom, $R^{5a}$ represents a C1 to C6 alkyl group optionally having one or more atoms or groups selected from the group consisting of halogen atoms and cyclopropyl groups (wherein the cyclopropyl group optionally has one or more halogen atoms or one or more C1 to C3 alkyl groups), a (C1 to C6 alkoxy)C1 to C6 alkyl group optionally having one or more halogen atoms, a C2 to C6 alkenyl group optionally having one or more halogen atoms, a C2 to C6 alkynyl group optionally having one or more halogen atoms, a C3 to C6 cycloalkyl group optionally having one or more atoms or groups selected from the group consisting of halogen atoms and C1 to C3 alkyl groups, a C2 to C6 alkylcarbonyl group optionally having one or more halogen atoms, a C2 to C6 alkoxycarbonyl group optionally having one or more halogen atoms or a hydrogen atom, $R^{6a}$ and $R^{10a}$ are the same or different and represent a fluorine atom or a hydrogen atom, $R^{8a}$ represents a C1 to C6 alkyl group optionally having one or more atoms or groups selected from the group consisting of C1 to C3 alkoxy groups and halogen atoms, a C2 to C6 alkenyl group optionally having one or more halogen atoms, a C2 to C6 alkynyl group optionally having one or more halogen atoms, a C1 to C6 alkoxy group optionally having one or more halogen atoms, a C1 to C6 alkylsulfanyl group optionally having one or more halogen atoms, a C1 to C6 alkylsulfinyl group optionally having one or more halogen atoms, a C1 to C6 alkylsulfonyl group optionally having one or more halogen atoms or a halogen atom, $Q^a$ represents an oxygen atom or a sulfur atom, n represents 0, 1 or 2 and m represents 0, 1 or 2, or N-oxides thereof.

In the formula (H6), compounds wherein $R^{1a}$ is a C2 to C3 alkyl group, a cyclopropyl group, or a cyclopropylmethyl group.

In the formula (H6), compounds wherein $R^{2a}$ and $R^{4a}$ are the same or different and are a halogen atom or a hydrogen atom, and $R^{3a}$ is a C1 to C6 alkyl group optionally having one or more halogen atoms, a C2 to C6 alkenyl group optionally having one or more halogen atoms, a C2 to C6 alkynyl group optionally having one or more halogen atoms, a 5- or 6-membered heterocyclic group (wherein the 5- or 6-membered heterocyclic group optionally has one or more atoms or groups selected from the group consisting of C1 to C3 alkyl groups optionally having one or more halogen atoms and halogen atoms), a C1 to C6 alkoxy group optionally having one or more halogen atoms, a C1 to C6 alkylsulfanyl group optionally having one or more halogen atoms, a C1 to C6 alkylsulfinyl group optionally having one or more halogen atoms, a C1 to C6 alkylsulfonyl group optionally having one or more halogen atoms, a halogen atom or a hydrogen atom, or N-oxides thereof.

In the formula (H6), compounds wherein $R^{2a}$ and $R^{4a}$ are a hydrogen atom, and $R^{3a}$ is a C1 to C6 alkyl group optionally having one or more halogen atoms, a halogen atom or a hydrogen atom.

In the formula (H6), compounds wherein $R^{5a}$ is a C1 to C6 alkyl group optionally having one or more atoms or groups selected from the group consisting of halogen atoms and cyclopropyl groups.

In the formula (H6), compounds wherein $R^{5a}$ is a hydrogen atom.

In the formula (H6), compounds wherein $R^{6a}$ and $R^{10a}$ are a hydrogen atom.

In the formula (H6), $R^{6a}$ and $R^{10a}$ are a hydrogen atom, and $R^{8a}$ is a C1 to C6 alkyl group optionally having one or more halogen atoms, a C2 to C6 alkenyl group optionally having one or more halogen atoms, a C2 to C6 alkynyl group optionally having one or more halogen atoms, a C1 to C6 alkoxy group optionally having one or more halogen atoms, a C1 to C6 alkylsulfanyl group optionally having one or more halogen atoms, a C1 to C6 alkylsulfinyl group optionally having one or more halogen atoms, a C1 to C6 alkylsulfonyl group optionally having one or more halogen atoms or a halogen atom.

In the formula (H6), compounds wherein $R^{6a}$ and $R^{11a}$ are a hydrogen atom, and $R^{8a}$ is a C1 to C6 haloalkyl group, a C1 to C6 haloalkoxy group, a C1 to C6 haloalkylsulfanyl group, a C1 to C6 haloalkylsulfinyl group, a C1 to C6 haloalkylsulfonyl group or a halogen atom.

In the formula (H6), compounds wherein $R^{6a}$ and $R^{1a}$ are a hydrogen atom, and $R^{8a}$ is a C1 to C3 perfluoroalkyl group, a C1 to C3 perfluoroalkoxy group, a C1 to C3 perfluoroalkylsulfanyl group, a C1 to C3 perfluoroalkylsulfinyl group, a C1 to C3 perfluoroalkylsulfonyl group or a halogen atom.

In the formula (H6), compounds wherein $Q^a$ is an oxygen atom.

In the formula (H6), compounds wherein $R^{1a}$ is a C2 to C3 alkyl group, a cyclopropyl group or a cyclopropylmethyl group, $R^{2a}$ and $R^{4a}$ are a hydrogen atom, $R^{3a}$ is a C1 to C6 alkyl group optionally having one or more halogen atoms, a halogen atom or a hydrogen atom, $R^{5a}$ is a C1 to C6 alkyl group optionally having one or more atoms or groups selected from the group consisting of halogen atoms and cyclopropyl groups or a C3 to C6 cycloalkyl group optionally having one or more atoms or groups selected from the group consisting of halogen atoms and C1 to C3 alkyl groups, $R^{6a}$ and $R^{10a}$ are a hydrogen atom, $R^{8a}$ is a C1 to C3 perfluoroalkyl group, a C1 to C3 perfluoroalkoxy group, a C1 to C3 perfluoroalkylsulfanyl group, a C1 to C3 perfluoroalkylsulfinyl group, a C1 to C3 perfluoroalkylsulfonyl group or a halogen atom, and $Q^a$ is an oxygen atom.

Compounds represented by formula (H7):

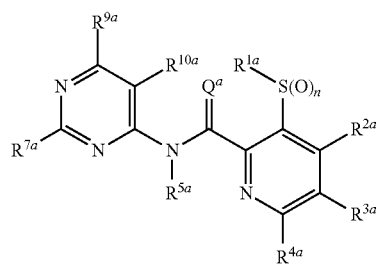

(H7)

wherein $R^{1a}$ represents a C1 to C6 alkyl group optionally having one or more halogen atoms, a (C3 to C6 cycloalkyl)C1 to C3 alkyl group optionally having one or more halogen atoms or a C3 to C6 cycloalkyl group optionally having one or more atoms or groups selected from the group consisting of halogen atoms and C1 to C3 alkyl groups, $R^{2a}$, $R^{3a}$ and $R^{4a}$ are the same or different and represent a C1 to C6 alkyl group optionally having one or more halogen atoms, a phenyl group optionally having one or more atoms or groups selected from the group consisting of C1 to C3 alkyl groups optionally having one or more halogen atoms and halogen atoms, a 5- or 6-membered heterocyclic group optionally having one or more atoms or groups selected from the group consisting of C1 to C3 alkyl groups optionally having one or more halogen atoms and halogen atoms, $OR^{11}$, $S(O)_mR^{11}$, $NR^{11}R^{12}$, $NR^{15}C(O)R^{11}$, $NR^{15}C(O)OR^{11}$, $NR^{15}C(O)NR^{11}R^{12}$, $NR^{16}S(O)_2R^{13}$, $C(O)OR^{11}$, $C(O)NR^{11}R^{12}$, $C(O)NR^{11}NR^{15}R^{16}$, a cyano group, a halogen atom or a hydrogen atom, $R^{5a}$ represents a C1 to C6 alkyl group optionally having one or more atoms or groups selected from the group consisting of halogen atoms and cyclopropyl groups (wherein the cyclopropyl group optionally has one or more halogen atoms or one or more C1 to C3 alkyl groups), a (C1 to C6 alkoxy)C1 to C6 alkyl group optionally having one or more halogen atoms, a C2 to C6 alkenyl group optionally having one or more halogen atoms, a C2 to C6 alkynyl group optionally having one or more halogen atoms, a C3 to C6 cycloalkyl group optionally having one or more atoms or groups selected from the group consisting of halogen atoms and C1 to C3 alkyl groups, a C2 to C6 alkylcarbonyl group optionally having one or more halogen atoms, a C2 to C6 alkoxycarbonyl group optionally having one or more halogen atoms or a hydrogen atom, $R^{10a}$ represents a fluorine atom or a hydrogen atom, $R^{7a}$ and $R^{9a}$ are the same or different and represent a C1 to C6 alkyl group optionally having one or more atoms or groups selected from the group consisting of C1 to C3 alkoxy groups and halogen atoms, a C2 to C6 alkenyl group optionally having one or more halogen atoms, a C2 to C6 alkynyl group optionally having one or more halogen atoms, a C1 to C6 alkoxy group optionally having one or more halogen atoms, a C1 to C6 alkylsulfanyl group optionally having one or more halogen atoms, a C1 to C6 alkylsulfinyl group optionally having one or more halogen atoms, a C1 to C6 alkylsulfonyl group optionally having one or more halogen atoms, a halogen atom or a hydrogen atom (wherein $R^{7a}$ and $R^{9a}$ do not represent a hydrogen atom at the same time), $Q^a$ represents an oxygen atom or a sulfur atom, n represents 0, 1 or 2 and m represents 0, 1 or 2, or N-oxides thereof.

In the formula (H7), compounds wherein $R^{2a}$ and $R^{4a}$ are the same or different and are a halogen atom or a hydrogen atom, and $R^{3a}$ is a C1 to C6 alkyl group optionally having one or more halogen atoms, a C2 to C6 alkenyl group optionally having one or more halogen atoms, a C2 to C6 alkynyl group optionally having one or more halogen atoms, a 5- or 6-membered heterocyclic group (wherein the 5- or 6-membered heterocyclic group optionally has one or more atoms or groups selected from the group consisting of C1 to C3 alkyl groups optionally having one or more halogen atoms and halogen atoms), a C1 to C6 alkoxy group optionally having one or more halogen atoms, a C1 to C6 alkylsulfanyl group optionally having one or more halogen atoms, a C1 to C6 alkylsulfinyl group optionally having one or more halogen atoms, a C1 to C6 alkylsulfonyl group optionally having one or more halogen atoms, a halogen atom or a hydrogen atom, or N-oxides thereof.

In the formula (H7), compounds wherein $R^{1a}$ is a C2 to C3 alkyl group, a cyclopropyl group, or a cyclopropylmethyl group.

In the formula (H7), compounds wherein $R^{2a}$ and $R^{4a}$ are a hydrogen atom, and $R^{3a}$ is a C1 to C6 alkyl group optionally having one or more halogen atoms, a halogen atom or a hydrogen atom.

In the formula (H7), compounds wherein $R^{5a}$ is a C1 to C6 alkyl group optionally having one or more atoms or groups selected from the group consisting of halogen atoms and cyclopropyl groups.

In the formula (H7), compounds wherein $R^{5a}$ is a hydrogen atom.

In the formula (H7), compounds wherein $R^{10a}$ is a hydrogen atom.

In the formula (H7), $R^{10a}$ is a hydrogen atom, and $R^{7a}$ and $R^{9a}$ are the same or different and are a C1 to C6 alkyl group optionally having one or more halogen atoms, a C2 to C6 alkenyl group optionally having one or more halogen atoms, a C2 to C6 alkynyl group optionally having one or more halogen atoms, a C1 to C6 alkoxy group optionally having one or more halogen atoms, a C1 to C6 alkylsulfanyl group optionally having one or more halogen atoms, a C1 to C6 alkylsulfinyl group optionally having one or more halogen atoms, a C1 to C6 alkylsulfonyl group optionally having one or more halogen atoms, a halogen atom or a hydrogen atom.

In the formula (H7), compounds wherein $R^{10a}$ is a hydrogen atom, and $R^{7a}$ and $R^{9a}$ are the same or different and are a C1 to C6 haloalkyl group, a C1 to C6 haloalkoxy group, a C1 to C6 haloalkylsulfanyl group, a C1 to C6 haloalkylsulfinyl group, a C1 to C6 haloalkylsulfonyl group, a halogen atom or a hydrogen atom.

In the formula (H7), compounds wherein $R^{10a}$ is a hydrogen atom, and $R^{7a}$ and $R^{9a}$ are the same or different and are a C1 to C3 perfluoroalkyl group, a C1 to C3 perfluoroalkoxy group, a C1 to C3 perfluoroalkylsulfanyl group, a C1 to C3 perfluoroalkylsulfinyl group, a C1 to C3 perfluoroalkylsulfonyl group, a halogen atom or a hydrogen atom.

In the formula (H7), compounds wherein $Q^a$ is an oxygen atom.

In the formula (H7), compounds wherein $R^{1a}$ is a C2 to C3 alkyl group, a cyclopropyl group or a cyclopropylmethyl group, $R^{2a}$ and $R^{4a}$ are a hydrogen atom, $R^{3a}$ is a C1 to C6 alkyl group optionally having one or more halogen atoms, a halogen atom or a hydrogen atom, $R^{5a}$ is a C1 to C6 alkyl group optionally having one or more atoms or groups selected from the group consisting of halogen atoms and cyclopropyl groups or a C3 to C6 cycloalkyl group optionally having one or more atoms or groups selected from the group consisting of halogen atoms and C1 to C3 alkyl groups, $R^{10a}$ is a hydrogen atom, $R^{7a}$ and $R^{9a}$ are the same or different and are a C1 to C3 perfluoroalkyl group, a C1 to C3 perfluoroalkoxy group, a C1 to C3 perfluoroalkylsulfanyl group, a C1 to C3 perfluoroalkylsulfinyl group, a C1 to C3 perfluoroalkylsulfonyl group, a halogen atom or a hydrogen atom, and $Q^a$ is an oxygen atom.

Compounds represented by formula (H8):

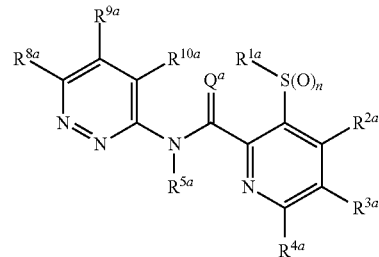

(H8)

wherein $R^{1a}$ represents a C1 to C6 alkyl group optionally having one or more halogen atoms, a (C3 to C6 cycloalkyl)C1 to C3 alkyl group optionally having one or more halogen atoms or a C3 to C6 cycloalkyl group optionally having one or more atoms or groups selected from the group consisting of halogen atoms and C1 to C3 alkyl groups, $R^{2a}$, $R^{3a}$ and $R^{4a}$ are the same or different and represent a C1 to C6 alkyl group optionally having one or more halogen atoms, a phenyl group optionally having one or more atoms or groups selected from the group consisting of C1 to C3 alkyl groups optionally having one or more halogen atoms and halogen atoms, a 5- or 6-membered heterocyclic group optionally having one or more atoms or groups selected from the group consisting of C1 to C3 alkyl groups optionally having one or more halogen atoms and halogen atoms, $OR^{11}$, $S(O)_m R^{11}$, $NR^{11}R^{12}$, $NR^{15}C(O)R^{11}$, $NR^{15}C(O)OR^{11}$, $NR^{15}C(O)NR^{11}R^{12}$, $NR^{16}S(O)_2R^{13}$, $C(O)OR^{11}$, $C(O)NR^{11}R^{12}$, $C(O)NR^{11}NR^{15}R^{16}$, a cyano group, a halogen atom or a hydrogen atom, $R^{5a}$ represents a C1 to C6 alkyl group optionally having one or more atoms or groups selected from the group consisting of halogen atoms and cyclopropyl groups (wherein the cyclopropyl group optionally has one or more halogen atoms or one or more C1 to C3 alkyl groups), a (C1 to C6 alkoxy)C1 to C6 alkyl group optionally having one or more halogen atoms, a C2 to C6 alkenyl group optionally having one or more halogen atoms, a C2 to C6 alkynyl group optionally having one or more halogen atoms, a C3 to C6 cycloalkyl group optionally having one or more atoms or groups selected from the group consisting of halogen atoms and C1 to C3 alkyl groups, a C2 to C6 alkylcarbonyl group optionally having one or more halogen atoms, a C2 to C6 alkoxycarbonyl group optionally having one or more halogen atoms or a hydrogen atom, $R^{10a}$ represents a fluorine atom or a hydrogen atom, $R^{8a}$ and $R^{9a}$ are the same or different and represent a C1 to C6 alkyl group optionally having one or more atoms or groups selected from the group consisting of C1 to C3 alkoxy groups and halogen atoms, a C2 to C6 alkenyl group optionally having one or more halogen atoms, a C2 to C6 alkynyl group optionally having one or more halogen atoms, a C1 to C6 alkoxy group optionally having one or more halogen atoms, a C1 to C6 alkylsulfanyl group optionally having one or more halogen atoms, a C1 to C6 alkylsulfinyl group optionally having one or more halogen atoms, a C1 to C6 alkylsulfonyl group optionally having one or more halogen atoms, a halogen atom or a hydrogen atom (wherein $R^{8a}$ and $R^{9a}$ do not represent a hydrogen atom at the same time), $Q^a$ represents an oxygen atom or a sulfur atom, n represents 0, 1 or 2 and m represents 0, 1 or 2, or N-oxides thereof.

In the formula (H8), compounds wherein $R^{2a}$ and $R^{4a}$ are the same or different and are a halogen atom or a hydrogen atom, and $R^{3a}$ is a C1 to C6 alkyl group optionally having one or more halogen atoms, a C2 to C6 alkenyl group optionally having one or more halogen atoms, a C2 to C6 alkynyl group optionally having one or more halogen atoms, a 5- or 6-membered heterocyclic group (wherein the 5- or 6-membered heterocyclic group optionally has one or more atoms or groups selected from the group consisting of C1 to C3 alkyl groups optionally having one or more halogen atoms and halogen atoms), a C1 to C6 alkoxy group optionally having one or more halogen atoms, a C1 to C6 alkylsulfanyl group optionally having one or more halogen atoms, a C1 to C6 alkylsulfinyl group optionally having one or more halogen atoms, a C1 to C6 alkylsulfonyl group optionally having one or more halogen atoms, a halogen atom or a hydrogen atom, or N-oxides thereof.

In the formula (H8), compounds wherein $R^{1a}$ is a C2 to C3 alkyl group, a cyclopropyl group, or a cyclopropylmethyl group.

In the formula (H8), compounds wherein $R^{2a}$ and $R^{4a}$ are a hydrogen atom, and $R^{3a}$ is a C1 to C6 alkyl group optionally having one or more halogen atoms, a halogen atom or a hydrogen atom.

In the formula (H8), compounds wherein $R^{5a}$ is a C1 to C6 alkyl group optionally having one or more atoms or groups selected from the group consisting of halogen atoms and cyclopropyl groups.

In the formula (H8), compounds wherein $R^{5a}$ is a hydrogen atom.

In the formula (H8), compounds wherein $R^{10a}$ is a hydrogen atom.

In the formula (H8), $R^{10a}$ is a hydrogen atom, and $R^{8a}$ and $R^{9a}$ are the same or different and are a C1 to C6 alkyl group optionally having one or more halogen atoms, a C2 to C6 alkenyl group optionally having one or more halogen atoms, a C2 to C6 alkynyl group optionally having one or more halogen atoms, a C1 to C6 alkoxy group optionally having one or more halogen atoms, a C1 to C6 alkylsulfanyl group optionally having one or more halogen atoms, a C1 to C6 alkylsulfinyl group optionally having one or more halogen atoms, a C1 to C6 alkylsulfonyl group optionally having one or more halogen atoms, a halogen atom or a hydrogen atom.

In the formula (H8), compounds wherein $R^{10a}$ is a hydrogen atom, and $R^{8a}$ and $R^{9a}$ are the same or different and are a C1 to C6 haloalkyl group, a C1 to C6 haloalkoxy group, a C1 to C6 haloalkylsulfanyl group, a C1 to C6 haloalkylsulfinyl group, a C1 to C6 haloalkylsulfonyl group, a halogen atom or a hydrogen atom.

In the formula (H8), compounds wherein $R^{10a}$ is a hydrogen atom, and $R^{8a}$ and $R^{9a}$ are the same or different and are a C1 to C3 perfluoroalkyl group, a C1 to C3 perfluoroalkoxy group, a C1 to C3 perfluoroalkylsulfanyl group, a C1 to C3 perfluoroalkylsulfinyl group, a C1 to C3 perfluoroalkylsulfonyl group, a halogen atom or a hydrogen atom.

In the formula (H8), compounds wherein $Q^a$ is an oxygen atom.

In the formula (H8), compounds wherein $R^{1a}$ is a C2 to C3 alkyl group, a cyclopropyl group or a cyclopropylmethyl group, $R^{2a}$ and $R^{4a}$ are a hydrogen atom, $R^{3a}$ is a C1 to C6 alkyl group optionally having one or more halogen atoms, a halogen atom or a hydrogen atom, $R^{5a}$ is a C1 to C6 alkyl group optionally having one or more atoms or groups selected from the group consisting of halogen atoms and cyclopropyl groups or a C3 to C6 cycloalkyl group optionally having one or more atoms or groups selected from the group consisting of halogen atoms and C1 to C3 alkyl groups, $R^{10a}$ is a hydrogen atom, $R^{8a}$ and $R^{9a}$ are the same or different and are a C1 to C3 perfluoroalkyl group, a C1 to C3 perfluoroalkoxy group, a C1 to C3 perfluoroalkylsulfanyl group, a C1 to C3 perfluoroalkylsulfinyl group, a C1 to C3 perfluoroalkylsulfonyl group, a halogen atom or a hydrogen atom, and $Q^a$ is an oxygen atom.

Compounds represented by formula (H9):

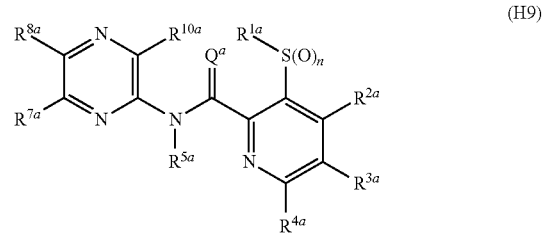

(H9)

wherein $R^{1a}$ represents a C12 to C6 alkyl group optionally having one or more halogen atoms, a (C3 to C6 cycloalkyl)C1 to C3 alkyl group optionally having one or more halogen atoms or a C3 to C6 cycloalkyl group optionally having one or more atoms or groups selected from the group consisting of halogen atoms and C1 to C3 alkyl groups, $R^{2a}$, $R^{3a}$ and $R^{4a}$ are the same or different and represent a C1 to C6 alkyl group optionally having one or more halogen atoms, a phenyl group optionally having one or more atoms or groups selected from the group consisting of C1 to C3 alkyl groups optionally having one or more halogen atoms and halogen atoms, a 5- or 6-membered heterocyclic group optionally having one or more atoms or groups selected from the group consisting of C1 to C3 alkyl groups optionally having one or more halogen atoms and halogen atoms, $OR^{11}$, $S(O)_mR^{11}$, $NR^{11}R^{12}$, $NR^{15}C(O)R^{11}$, $NR^{15}C(O)OR^{11}$, $NR^{15}C(O)NR^{11}R^{12}$, $NR^{16}S(O)_2R^{13}$, $C(O)OR^{11}$, $C(O)NR^{11}R^{12}$, $C(O)NR^{11}NR^{15}R^{16}$, a cyano group, a halogen atom or a hydrogen atom, $R^{5a}$ represents a C1 to C6 alkyl group optionally having one or more atoms or groups selected from the group consisting of halogen atoms and cyclopropyl groups (wherein the cyclopropyl group optionally has one or more halogen atoms or one or more C1 to C3 alkyl groups), a (C1 to C6 alkoxy)C1 to C6 alkyl group optionally having one or more halogen atoms, a C2 to C6 alkenyl group optionally having one or more halogen atoms, a C2 to C6 alkynyl group optionally having one or more halogen atoms, a C3 to C6 cycloalkyl group optionally having one or more atoms or groups selected from the group consisting of halogen atoms and C1 to C3 alkyl groups, a C2 to C6 alkylcarbonyl group optionally having one or more halogen atoms, a C2 to C6 alkoxycarbonyl group optionally having one or more halogen atoms or a hydrogen atom, $R^{10a}$ represents a fluorine atom or a hydrogen atom, $R^{7a}$ and $R^{8a}$ are the same or different and represent a C1 to C6 alkyl group optionally having one or more atoms or groups selected from the group consisting of C1 to C3 alkoxy groups and halogen atoms, a C2 to C6 alkenyl group optionally having one or more halogen atoms, a C2 to C6 alkynyl group optionally having one or more halogen atoms, a C1 to C6 alkoxy group optionally having one or more halogen atoms, a C1 to C6 alkylsulfanyl group optionally having one or more halogen atoms, a C1 to C6 alkylsulfinyl group optionally having one or more halogen atoms, a C1 to C6 alkylsulfonyl group optionally having one or more halogen atoms, a halogen atom or a hydrogen atom (wherein $R^{7a}$ and $R^{8a}$ do not represent a hydrogen atom at the same time), $Q^a$ represents an oxygen atom or a sulfur atom, n represents 0, 1 or 2 and m represents 0, 1 or 2, or N-oxides thereof.

In the formula (H9), compounds wherein $R^{2a}$ and $R^{4a}$ are the same or different and are a halogen atom or a hydrogen atom, and $R^{3a}$ is a C1 to C6 alkyl group optionally having one or more halogen atoms, a C2 to C6 alkenyl group optionally having one or more halogen atoms, a C2 to C6 alkynyl group optionally having one or more halogen atoms, a 5- or 6-membered heterocyclic group (wherein the 5- or 6-membered heterocyclic group optionally has one or more atoms or groups selected from the group consisting of C1 to C3 alkyl groups optionally having one or more halogen atoms and halogen atoms), a C1 to C6 alkoxy group optionally having one or more halogen atoms, a C1 to C6 alkylsulfanyl group optionally having one or more halogen atoms, a C1 to C6 alkylsulfinyl group optionally having one or more halogen atoms, a C1 to C6 alkylsulfonyl group optionally having one or more halogen atoms, a halogen atom or a hydrogen atom, or N-oxides thereof.

In the formula (H9), compounds wherein $R^{1a}$ is a C2 to C3 alkyl group, a cyclopropyl group, or a cyclopropylmethyl group.

In the formula (H9), compounds wherein $R^{2a}$ and $R^{4a}$ are a hydrogen atom, and $R^{3a}$ is a C1 to C6 alkyl group optionally having one or more halogen atoms, a halogen atom or a hydrogen atom.

In the formula (H9), compounds wherein $R^{5a}$ is a C1 to C6 alkyl group optionally having one or more atoms or groups selected from the group consisting of halogen atoms and cyclopropyl groups.

In the formula (H9), compounds wherein $R^{5a}$ is a hydrogen atom.

In the formula (H9), compounds wherein $R^{10a}$ is a hydrogen atom.

In the formula (H9), $R^{10a}$ is a hydrogen atom, and $R^{7a}$ and $R^{8a}$ are the same or different and are a C1 to C6 alkyl group optionally having one or more halogen atoms, a C2 to C6 alkenyl group optionally having one or more halogen atoms, a C2 to C6 alkynyl group optionally having one or more halogen atoms, a C1 to C6 alkoxy group optionally having one or more halogen atoms, a C1 to C6 alkylsulfanyl group optionally having one or more halogen atoms, a C1 to C6 alkylsulfinyl group optionally having one or more halogen atoms, a C1 to C6 alkylsulfonyl group optionally having one or more halogen atoms, a halogen atom or a hydrogen atom.

In the formula (H9), compounds wherein $R^{10a}$ is a hydrogen atom, and $R^{7a}$ and $R^{8a}$ are the same or different and are a C1 to C6 haloalkyl group, a C1 to C6 haloalkoxy group, a C1 to C6 haloalkylsulfanyl group, a C1 to C6 haloalkylsulfinyl group, a C1 to C6 haloalkylsulfonyl group, a halogen atom or a hydrogen atom.

In the formula (H9), compounds wherein $R^{10a}$ is a hydrogen atom, and $R^{7a}$ and $R^{8a}$ are the same or different and are a C1 to C3 perfluoroalkyl group, a C1 to C3 perfluoroalkoxy group, a C1 to C3 perfluoroalkylsulfanyl group, a C1 to C3 perfluoroalkylsulfinyl group, a C1 to C3 perfluoroalkylsulfonyl group, a halogen atom or a hydrogen atom.

In the formula (H9), compounds wherein $Q^a$ is an oxygen atom.

In the formula (H9), compounds wherein $R^{1a}$ is a C2 to C3 alkyl group, a cyclopropyl group or a cyclopropylmethyl group, $R^{2a}$ and $R^{4a}$ are a hydrogen atom, $R^{3a}$ is a C1 to C6 alkyl group optionally having one or more halogen atoms, a halogen atom or a hydrogen atom, $R^{5a}$ is a C1 to C6 alkyl group optionally having one or more atoms or groups selected from the group consisting of halogen atoms and cyclopropyl groups or a C3 to C6 cycloalkyl group optionally having one or more atoms or groups selected from the group consisting of halogen atoms and C1 to C3 alkyl groups, $R^{10a}$ is a hydrogen atom, $R^{7a}$ and $R^{8a}$ are the same or different and are a C1 to C3 perfluoroalkyl group, a C1 to C3 perfluoroalkoxy group, a C1 to C3 perfluoroalkylsulfanyl group, a C1 to C3 perfluoroalkylsulfinyl group, a C1 to C3 perfluoroalkylsulfonyl group, a halogen atom or a hydrogen atom, and $Q^a$ is an oxygen atom.

In the formula (1), compounds wherein $R^1$ is a C1 to C6 chain hydrocarbon group optionally having one or more atoms or groups selected from group X or a C3 to C6 cycloalkyl group optionally having one or more atoms or groups selected from group Y, $R^2$, $R^3$ and $R^4$ are the same or different and are a C1 to C6 chain hydrocarbon group optionally having one or more atoms or groups selected from group X, a C3 to C6 cycloalkyl group optionally having one or more atoms or groups selected from group Y, a phenyl group optionally having one or more atoms or groups selected from group Z, a 5- or 6-membered heterocyclic group optionally having one or more atoms or groups selected from group Z, $OR^{11}$, $S(O)_mR^{11}$, $S(O)_2NR^{11}R^{12}$, $NR^{11}R^{12}$, $NR^{11}C(O)R^{12}$, $NR^{11}CO_2R^{12}$, $NR^{11}S(O)_2R^{13}$, $C(O)R^{11}$, $CO_2R^{11}$, $C(O)NR^{11}R^{12}$, $SF_5$, a cyano group, a nitro group, a halogen atom or a hydrogen atom, $R^5$ is a C1 to C6 chain hydrocarbon group optionally having one or more atoms or groups selected from group W, a C3 to C6 cycloalkyl group optionally having one or more atoms or groups selected from group Y, a C1 to C6 chain hydrocarbon group having one phenyl group (wherein the phenyl group optionally has one or more atoms or groups selected from group Z), a C1 to C6 chain hydrocarbon group having one 5- or 6-membered heterocyclic group (wherein the 5- or 6-membered heterocyclic group optionally has one or more atoms or groups selected from group Z), $C(O)R^{11}$, $C(O)OR^{11}$, $C(O)NR^{11}R^{12}$ or a hydrogen atom, $G^1$ is a nitrogen atom or $CR^6$, $G^2$ is a nitrogen atom or $CR^7$, $G^3$ is a nitrogen atom or $CR^8$, $G^4$ is a nitrogen atom or $CR^9$, $G^5$ is a nitrogen atom or $CR^{10}$ (wherein not all of $G^2$, $G^3$ and $G^4$ represent a nitrogen atom), $R^6$ and $R^{10}$ are the same or different and are a C1 to C6 chain hydrocarbon group optionally having one or more atoms or groups selected from group X, a C3 to C6 cycloalkyl group optionally having one or more atoms or groups selected from group Y, $OR^{14}$, $S(O)_mR^{14}$, a fluorine atom or a hydrogen atom, $R^7$, $R^8$ and $R^9$ are the same or different and are a C1 to C6 chain hydrocarbon group optionally having one or more atoms or groups selected from group X, a C3 to C6 cycloalkyl group optionally having one or more atoms or groups selected from group Y, a phenyl group optionally having one or more atoms or groups selected from group Z, a 5- or 6-membered heterocyclic group optionally having one or more atoms or groups selected from group Z, $OR^{14}$, $S(O)_mR^{11}$, $S(O)_2NR^{11}R^{12}$, $NR^{11}R^{12}$, $NR^{11}C(O)R^{12}$, $NR^{11}CO_2R^{12}$, $NR^{11}S(O)_2R^{13}$, $C(O)R^{11}$, $CO_2R^{11}$, $C(O)NR^{11}R^{12}$, $SF_5$, a hydroxy group, a cyano group, a nitro group, a halogen atom or a hydrogen atom (wherein at least one of $R^7$, $R^8$ and $R^9$ represents a C1 to C6 chain hydrocarbon group optionally having one or more atoms or groups selected from group X, a C3 to C6 cycloalkyl group optionally having one or more atoms or groups selected from group Y, a phenyl group optionally having one or more atoms or groups selected from group Z, a 5- or 6-membered heterocyclic group optionally having one or more atoms or groups selected from group Z, $OR^{14}$, $S(O)_mR^{11}$, $S(O)_2NR^{11}R^{12}$, $NR^{11}R^{12}$, $NR^{11}C(O)R^{12}$, $NR^{11}CO_2R^{12}$, $NR^{11}S(O)_2R^{13}$, $C(O)R^{11}$, $CO_2R^{11}$, $C(O)NR^{11}R^{12}$, $SF_5$, a cyano group, a nitro group, or a halogen atom), $R^{11}$ and $R^{12}$ are the same or different and are a C1 to C6 chain hydrocarbon group optionally having one or more halogen atoms, a phenyl group optionally having one or more atoms or groups selected from group Z, a 5- or 6-membered heterocyclic group optionally having one or more atoms or groups selected from group Z or a hydrogen atom, $R^{13}$ is a C1 to C6 chain hydrocarbon group optionally having one or more halogen atoms, a phenyl group optionally having one or more atoms or groups selected from group Z or a 5- or 6-membered heterocyclic group optionally having one or more atoms or groups selected from group Z, $R^{14}$ is a C1 to C6 chain hydrocarbon group optionally having one or more halogen atoms, Q is an oxygen atom or a sulfur atom, m is 0, 1 or 2, and n is 0, 1 or 2, or N-oxides thereof.

In the formula (1), compounds wherein $R^1$ is a C1 to C6 alkyl group optionally having one or more atoms or groups selected from the group consisting of halogen atoms and cyclopropyl groups (wherein the cyclopropyl group optionally has one or more halogen atoms or one or more C1 to C3 alkyl groups), a C2 to C6 alkenyl group optionally having one or more halogen atoms, a C2 to C6 alkynyl group optionally having one or more halogen atoms or a C3 to C6 cycloalkyl group optionally having one or more atoms or groups selected from the group consisting of halogen atoms and C1 to C3 alkyl groups, $R^2$ and $R^4$ are the same or different and are a C1 to C6 alkyl group optionally having one or more halogen atoms, $OR^{11}$, $S(O)_mR^{11}$, a halogen atom or a hydrogen atom, $R^3$ is a C1 to C6 chain hydrocarbon group optionally having one or more atoms or groups selected from group X, a C3 to C6 cycloalkyl group optionally having one or more atoms or groups selected from group Y, a phenyl group optionally having one or more atoms or groups selected from group Z, a 5- or 6-membered heterocyclic group optionally having one or more atoms or groups selected from group Z, $OR^{11}$, $S(O)_mR^{11}$, $C(O)R^{11}$, $CO_2R^{11}$, $C(O)NR^{11}R^{12}$ $SF_5$, a cyano group, a nitro group, a halogen atom or a hydrogen atom, $R^5$ is a C1 to C6 alkyl group optionally having one or more atoms or groups selected from the group consisting of halogen atoms and cyclopropyl groups (wherein the cyclopropyl group optionally has one or more halogen atoms or one or more C1 to C3 alkyl groups), a (C1 to C6 alkoxy)C1 to C6 alkyl group optionally having one or more halogen atoms, a C2 to C6 alkenyl group optionally having one or more halogen atoms, a C2 to C6 alkynyl group optionally having one or more halogen atoms, a C1 to C6 alkyl group having one thiazolyl group (wherein the thiazolyl group optionally has one or more atoms or groups selected from the group consisting of C1 to C3 alkyl groups optionally having one or more halogen atoms and halogen atoms), a C1 to C6 alkyl group having one pyridyl group (wherein the pyridyl group optionally has one or more atoms or groups selected from the group consisting of C1 to C3 alkyl groups optionally having one or more halogen atoms and halogen atoms), $C(O)R^{11}$, $C(O)OR^{11}$ or a hydrogen atom, $G^1$ is a nitrogen atom or $CR^6$, $G^2$ is a nitrogen atom or $CR^7$, $G^3$ is a nitrogen atom or $CR^8$, $G^4$ is a nitrogen atom or $CR^9$, $G^5$ is a nitrogen atom or $CR^{10}$, $R^6$ and $R^{10}$ are the same or different and are a C1 to C6 alkyl group optionally having one or more halogen atoms, $OR^{14}$, $S(O)_mR^{14}$, a fluorine atom or a hydrogen atom, $R^7$, $R^8$ and $R^9$ are the same or different and are a C1 to C6 chain hydrocarbon group optionally having one or more atoms or groups selected from group X, $OR^{14}$, $S(O)_mR^{11}$, $SF_5$, a halogen atom or a hydrogen atom, $R^{11}$ and $R^{12}$ are the same or different and are a C1 to C6 alkyl group optionally having one or more halogen atoms, a phenyl group (wherein the phenyl group optionally has one or more atoms or groups selected from the group consisting of C1 to C3 alkyl groups optionally having one or more halogen atoms and halogen atoms), a 5- or 6-membered heterocyclic group (wherein the 5- or 6-membered heterocyclic group optionally has one or more atoms or groups selected from the group consisting of C1 to C3 alkyl groups optionally having one or more halogen atoms and halogen atoms) or a hydrogen atom, Q is an oxygen atom, or N-oxides thereof.

In the formula (1), compounds wherein $R^1$ is a C2 to C6 alkyl group optionally having one or more halogen atoms, a (C3 to C6 cycloalkyl)C1 to C3 alkyl group optionally having one or more halogen atoms or a C3 to C6 cycloalkyl group optionally having one or more atoms or groups selected from the group consisting of halogen atoms and C1 to C3 alkyl groups, $R^2$ and $R^4$ are the same or different and are a halogen atom or a hydrogen atom, $R^3$ is a C1 to C6 alkyl group optionally having one or more halogen atoms, a C2 to C6 alkenyl group optionally having one or more halogen atoms, a C2 to C6 alkynyl group optionally having one or more halogen atoms, a 5- or 6-membered heterocyclic group (wherein the 5- or 6-membered heterocyclic group optionally has one or more atoms or groups selected from the group consisting of C1 to C3 alkyl groups optionally having one or more halogen atoms and halogen atoms), $—OR^{11}$, $—S(O)_mR^{11}$, a halogen atom or a hydrogen atom, $R^5$ is a C1 to C6 alkyl group optionally having one or more atoms or groups selected from the group consisting of halogen atoms and cyclopropyl groups (wherein the cyclopropyl group optionally has one or more halogen atoms or one or more C1 to C3 alkyl groups), a (C1 to C6 alkoxy)C1 to C6 alkyl group optionally having one or more halogen atoms, a C2 to C6 alkenyl group optionally having one or more halogen atoms, a C2 to C6 alkynyl group optionally having one or more halogen atoms, a C2 to C6 alkylcarbonyl group optionally having one or more halogen atoms, a C2 to C6 alkoxycarbonyl group optionally having one or more halogen atoms or a hydrogen atom, $G^1$ is a nitrogen atom or $CR^6$, $G^2$ is a nitrogen atom or $CR^7$, $G^3$ is a nitrogen atom or $CR^8$,
$G^4$ is a nitrogen atom or $CR^9$,
$G^5$ is a nitrogen atom or $CR^{10}$,
$R^6$ and $R^{10}$ are the same or different and are a fluorine atom or a hydrogen atom,
$R^7$, $R^8$ and $R^9$ are the same or different and are a C1 to C6 alkyl group optionally having one or more halogen atoms, a C2 to C6 alkenyl group optionally having one or more halogen atoms, a C2 to C6 alkynyl group optionally having one or more halogen atoms, $OR^{14}$, $S(O)_m R^{11}$, a halogen atom or a hydrogen atom,
$R^{11}$ is a C1 to C6 alkyl group optionally having one or more halogen atoms or a hydrogen atom, and
Q is an oxygen atom, or an N-oxide thereof.
In the formula (1), compounds wherein
$R^1$ is a C2 to C6 alkyl group, a cyclopropyl group or a cyclopropylmethyl group,
$R^2$ and $R^4$ are a hydrogen atom,
$R^3$ is a C1 to C3 alkyl group optionally having one or more halogen atoms, a C1 to C3 alkoxy group optionally having one or more halogen atoms, a C1 to C3 alkylsulfanyl group optionally having one or more halogen atoms, a C1 to C3 alkylsulfinyl group optionally having one or more halogen atoms, a C1 to C3 alkylsulfonyl group optionally having one or more halogen atoms, a pyridyl group (wherein the pyridyl group optionally has one or more atoms or groups selected from the group consisting of C1 to C3 alkyl groups optionally having one or more halogen atoms and halogen atoms), a pyrimidinyl group (wherein the pyrimidinyl group optionally has one or more atoms or groups selected from the group consisting of C1 to C3 alkyl groups optionally having one or more halogen atoms and halogen atoms), a halogen atom or a hydrogen atom,
$R^5$ is a C1 to C6 alkyl group optionally having one or more atoms or groups selected from the group consisting of halogen atoms and cyclopropyl groups (wherein the cyclopropyl group optionally has one or more halogen atoms or one or more C1 to C3 alkyl groups), a C2 to C6 alkenyl group optionally having one or more halogen atoms, a C2 to C6 alkynyl group optionally having one or more halogen atoms, a (C1 to C6 alkoxy)C1 to C6 alkyl group optionally having one or more halogen atoms, a C2 to C6 alkylcarbonyl group optionally having one or more halogen atoms, a C2 to C6 alkoxycarbonyl group optionally having one or more halogen atoms or a hydrogen atom,
$G^1$ is a nitrogen atom or CH,
$G^2$ is a nitrogen atom or $CR^7$,
$G^3$ is a nitrogen atom or $CR^8$,
$G^4$ is a nitrogen atom or $CR^9$,
$G^5$ is a nitrogen atom or CH,
$R^7$, $R^8$ and $R^9$ are the same or different and are a C1 to C6 haloalkyl group, a C2 to C6 haloalkenyl group, a C1 to C6 haloalkoxy group, a C1 to C6 haloalkylsulfanyl group, a C1 to C6 haloalkylsulfinyl group, a C1 to C6 haloalkylsulfonyl group, a halogen atom or a hydrogen atom, and
Q is an oxygen atom, or N-oxides thereof.
In the formula (1), compounds wherein
$R^1$ is an ethyl group, a cyclopropyl group or a cyclopropylmethyl group,
$R^2$ and $R^4$ are a hydrogen atom,
$R^3$ is a methyl group, a trifluoromethyl group, a pentafluoroethyl group, a methoxy group, a trifluoromethoxy group, a methylsulfanyl group, a trifluoromethylsulfanyl group, a methylsulfinyl group, a trifluoromethylsulfinyl group, a methylsulfonyl group, a trifluoromethylsulfonyl group, a 2-pyridyl group, a 2-pyrimidinyl group, a 5-trifluoromethyl-2-pyridyl group, a 3-chloro-5-trifluoromethyl-2-pyridyl group, a chlorine atom, a bromine atom, an iodine atom or a hydrogen atom,
$R^5$ is a methyl group, an ethyl group, a propyl group, an isopropyl group, a butyl group, an isobutyl group, a hexyl group, a propargyl group, a cyclopropyl group, a cyclobutyl group, a cyclohexyl group, a cyclopropylmethyl group, a cyclobutylmethyl group, a 2,2,2-trifluoroethyl group, a benzyl group, a 6-chloropyridin-3-ylmethyl group, a 2-chlorothiazolyl-5-ylmethyl group, a methoxymethyl group, an ethoxymethyl group, a methoxycarbonyl group, an ethoxycarbonyl group or a hydrogen atom,
$G^1$ is a nitrogen atom or CH,
$G^2$ is a nitrogen atom or $CR^7$,
$G^3$ is a nitrogen atom or $CR^8$,
$G^4$ is a nitrogen atom or $CR^9$,
$G^5$ is a nitrogen atom or CH,
$R^7$, $R^8$ and $R^9$ are the same or different and are a trifluoromethyl group, a pentafluoroethyl group, a heptafluoropropyl group, a heptafluoroisopropyl group, a trifluoromethoxy group, a trifluoromethylsulfanyl group, a trifluoromethylsulfinyl group, a trifluoromethylsulfonyl group, a fluorine atom, a chlorine atom, a bromine atom, an iodine group or a hydrogen atom, and
Q is an oxygen atom.
In the formula (1), compounds wherein
$R^1$ is a C1 to C6 chain hydrocarbon group optionally having one or more atoms or groups selected from group X,
$R^2$ and $R^4$ are a hydrogen atom,
$R^3$ is a C1 to C6 chain hydrocarbon group optionally having one or more atoms or groups selected from group X or a hydrogen atom,
$R^5$ is a C1 to C6 chain hydrocarbon group optionally having one or more atoms or groups selected from group W, a C3 to C6 cycloalkyl group optionally having one or more atoms or groups selected from group Y or a hydrogen atom,
$G^1$ is a nitrogen atom or $CR^6$,
$G^2$ is a nitrogen atom or $CR^7$,
$G^3$ is a nitrogen atom or $CR^8$,
$G^4$ is a nitrogen atom or $CR^9$,
$G^5$ is a nitrogen atom or $CR^{10}$,
$R^6$, $R^7$, $R^9$ and $R^{10}$ are the same or different and are a C1 to C6 chain hydrocarbon group optionally having one or more atoms or groups selected from group X or a hydrogen atom,
$R^8$ is a C1 to C6 chain hydrocarbon group optionally having one or more atoms or groups selected from group X, $OR^{14}$, $S(O)_m R^{11}$ or a hydrogen atom,
$R^{11}$ is a C1 to C6 alkyl group optionally having one or more halogen atoms,
$R^{14}$ is a C1 to C6 chain hydrocarbon group optionally having one or more halogen atoms, and
Q is an oxygen atom.
In the formula (1), compounds wherein
$R^1$ is a C1 to C6 alkyl group optionally having one or more atoms or groups selected from the group consisting of halogen atoms and C1 to C3 alkyl groups,
$R^2$ and $R^4$ are a hydrogen atom,
$R^3$ is a C1 to C6 alkyl group optionally having one or more halogen atoms or a hydrogen atom,
$R^5$ is a C1 to C6 alkyl group, a C3 to C6 cycloalkyl group or a hydrogen atom,
$G^1$ is a nitrogen atom or $CR^6$,
$G^2$ is a nitrogen atom or $CR^7$,
$G^3$ is a nitrogen atom or $CR^8$,
$G^4$ is a nitrogen atom or $CR^9$,
$G^5$ is a nitrogen atom or $CR^{10}$, $R^6$, $R^7$, $R^9$ and $R^{10}$ are the same or different and are a C1 to C6 alkyl group optionally having one or more halogen atoms or a hydrogen atom, $R^8$ is a C1 to C6 chain hydrocarbon group optionally having one or more atoms or groups selected from the group consisting of C1 to C6 alkoxy groups optionally having one or more halogen atoms and halogen atoms, $OR^{14}$, $S(O)_m R^{11}$ or a hydrogen atom, $R^{11}$ is a C1 to C6 alkyl group optionally having one or more halogen atoms, $R^{14}$ is a C1 to C6 chain hydrocarbon group optionally having one or more halogen atoms, and Q is an oxygen atom.

In the formula (1), compounds wherein
$R^1$ is a C1 to C6 alkyl group optionally having one or more atoms or groups selected from the group consisting of halogen atoms and C1 to C3 alkyl groups, $R^2$ and $R^4$ are a hydrogen atom, $R^3$ is a C1 to C6 alkyl group optionally having one or more halogen atoms or a hydrogen atom, $R^5$ is a C1 to C6 alkyl group, a C3 to C6 cycloalkyl group or a hydrogen atom, $G^1$ is $CR^6$,
$G^2$ is $CR^7$,
$G^3$ is $CR^8$,
$G^4$ is $CR^9$,
$G^5$ is $CR^{10}$, $R^6$, $R^7$, $R^9$ and $R^{10}$ are the same or different and are a C1 to C6 alkyl group optionally having one or more halogen atoms or a hydrogen atom, $R^8$ is a C1 to C6 chain hydrocarbon group optionally having one or more atoms or groups selected from the group consisting of C1 to C6 alkoxy groups optionally having one or more halogen atoms and halogen atoms, $OR^{14}$, $S(O)_m R^{11}$ or a hydrogen atom, $R^{11}$ is a C1 to C6 alkyl group optionally having one or more halogen atoms, $R^{14}$ is a C1 to C6 chain hydrocarbon group optionally having one or more halogen atoms, and Q is an oxygen atom.

In the formula (1), compounds wherein
$R^1$ is a C1 to C6 alkyl group optionally having one or more atoms or groups selected from the group consisting of halogen atoms and C1 to C3 alkyl groups, $R^2$ and $R^4$ are a hydrogen atom, $R^3$ is a C1 to C6 alkyl group optionally having one or more halogen atoms or a hydrogen atom, $R^5$ is a C1 to C6 alkyl group, a C3 to C6 cycloalkyl group or a hydrogen atom, $G^1$ is a nitrogen atom,
$G^2$ is $CR^7$,
$G^3$ is $CR^8$,
$G^4$ is $CR^9$,
$G^5$ is $CR^{10}$, $R^6$, $R^7$, $R^9$ and $R^{10}$ are the same or different and are a C1 to C6 alkyl group optionally having one or more halogen atoms or a hydrogen atom, $R^8$ is a C1 to C6 chain hydrocarbon group optionally having one or more atoms or groups selected from the group consisting of C1 to C6 alkoxy groups optionally having one or more halogen atoms and halogen atoms, $OR^{14}$, $S(O)_m R^{11}$ or a hydrogen atom, $R^{11}$ is a C1 to C6 alkyl group optionally having one or more halogen atoms, $R^{14}$ is a C1 to C6 chain hydrocarbon group optionally having one or more halogen atoms, and Q is an oxygen atom.

In the formula (1), compounds wherein
$R^1$ is a C1 to C6 alkyl group optionally having one or more atoms or groups selected from the group consisting of halogen atoms and C1 to C3 alkyl groups, $R^2$ and $R^4$ are a hydrogen atom, $R^3$ is a C1 to C6 alkyl group optionally having one or more halogen atoms or a hydrogen atom, $R^5$ is a C1 to C6 alkyl group, a C3 to C6 cycloalkyl group or a hydrogen atom, $G^1$ is $CR^6$,
$G^2$ is a nitrogen atom,
$G^3$ is $CR^8$,
$G^4$ is $CR^9$,
$G^5$ is $CR^{10}$, $R^6$, $R^7$, $R^9$ and $R^{10}$ are the same or different and are a C1 to C6 alkyl group optionally having one or more halogen atoms or a hydrogen atom, $R^8$ is a C1 to C6 chain hydrocarbon group optionally having one or more atoms or groups selected from the group consisting of C1 to C6 alkoxy groups optionally having one or more halogen atoms and halogen atoms, $OR^{14}$, $S(O)_m R^{11}$ or a hydrogen atom, $R^{11}$ is a C1 to C6 alkyl group optionally having one or more halogen atoms, $R^{14}$ is a C1 to C6 chain hydrocarbon group optionally having one or more halogen atoms, and Q is an oxygen atom.

In the formula (1), compounds wherein
$R^1$ is a C1 to C6 alkyl group optionally having one or more atoms or groups selected from the group consisting of halogen atoms and C1 to C3 alkyl groups, $R^2$ and $R^4$ are a hydrogen atom, $R^3$ is a C1 to C6 alkyl group optionally having one or more halogen atoms or a hydrogen atom, $R^5$ is a C1 to C6 alkyl group, a C3 to C6 cycloalkyl group or a hydrogen atom, $G^1$ is $CR^6$,
$G^2$ is $CR^7$,
$G^3$ is $CR^8$,
$G^4$ is $CR^9$,
$G^5$ is a nitrogen atom, $R^6$, $R^7$, $R^9$ and $R^{10}$ are the same or different and are a C1 to C6 alkyl group optionally having one or more halogen atoms or a hydrogen atom, $R^8$ is a C1 to C6 chain hydrocarbon group optionally having one or more atoms or groups selected from the group consisting of C1 to C6 alkoxy groups optionally having one or more halogen atoms and halogen atoms, $OR^{14}$, $S(O)_m R^{11}$ or a hydrogen atom, $R^{11}$ is a C1 to C6 alkyl group optionally having one or more halogen atoms, $R^{14}$ is a C1 to C6 chain hydrocarbon group optionally having one or more halogen atoms, and Q is an oxygen atom.

In the formula (1), compounds wherein
$R^1$ is a C1 to C6 chain hydrocarbon group optionally having one or more atoms or groups selected from group X, $R^2$, $R^3$ and $R^4$ are the same or different and are a C1 to C6 chain hydrocarbon group optionally having one or more atoms or groups selected from group X, a phenyl group optionally having one or more atoms or groups selected from group Z, a 5- or 6-membered heterocyclic group optionally having one or more atoms or groups selected from group Z, $S(O)_m R^{11}$, $NR^{11}R^{12}$, $NR^{15}C(O)R^{11}$, $NR^{15}C(O)OR^{11}$, $NR^{15}C(O)NR^{11}R^{12}$, $NR^{16}S(O)_2R^{13}$, $C(O)OR^{11}$, $C(O)NR^{11}R^{12}$, $C(O)NR^{11}NR^{15}R^{16}$, a halogen atom or a hydrogen atom, $R^5$ is a C1 to C6 chain hydrocarbon group optionally having one or more atoms or groups selected from group W, a C3 to C9 alicyclic hydrocarbon group optionally having one or more atoms or groups selected from group Y, a C1 to C6 chain hydrocarbon group having one phenyl group (wherein the phenyl group optionally has one or more atoms or groups selected from group Z), a C1 to C6 chain hydrocarbon group having one 5- or 6-membered heterocyclic group (wherein the 5- or 6-membered heterocyclic group optionally has one or more atoms or groups selected from group Z), $C(O)R^{11}$, $C(O)OR^{11}$, $C(O)NR^{11}R^{12}$ or a hydrogen atom, $G^1$ is a nitrogen atom or $CR^6$,
$G^2$ is a nitrogen atom or $CR^7$,
$G^3$ is $CR^8$,
$G^4$ is $CR^9$,
$G^5$ is $CR^{10}$, $R^6$ and $R^{10}$ are the same or different and are a C1 to C6 chain hydrocarbon group optionally having one or more atoms or groups selected from group X, a fluorine atom or a hydrogen atom, $R^7$, $R^8$ and $R^9$ are the same or different and are a C1 to C6 chain hydrocarbon group optionally having one or more atoms or groups selected from group X, a phenyl group optionally having one or more atoms or groups selected from group Z, $OR^{14}$, $S(O)_m R^{11}$, $C(O)OR^{11}$, a halogen atom or a hydrogen atom (wherein at least one of $R^7$, $R^8$ and $R^9$ represents a C1 to C6 chain hydrocarbon group optionally having one or more atoms or groups selected from group X, a phenyl group optionally having one or more atoms or groups selected from group Z, $OR^{14}$, $S(O)_m R^{11}$, $C(O)OR^{11}$, or a halogen atom), $R^{11}$ and $R^{12}$ are the same or different and are a C1 to C6 chain hydrocarbon group optionally having one or more atoms or groups selected from group V or a hydrogen atom, $R^{13}$ is a C1 to C6 chain hydrocarbon group optionally having one or more atoms or groups selected from group V, $R^{15}$ is a C1 to C6 chain hydrocarbon group optionally having one or more atoms or groups selected from group V or a hydrogen atom, $R^{16}$ is a C1 to C6 chain hydrocarbon group optionally having one or more atoms or groups selected from group V, $C(O)OR^{11}$ or $S(O)_2 R^{11}$, Q is an oxygen atom, or N-oxides thereof.

Next, the method for producing the compound of the present invention will be described.

The compound of the present invention and the intermediate compound can be produced, for example, according to the following (Production Method 1) to (Production Method 14).

(Production Method 1)

The compound of the present invention (1-n1) or the compound of the present invention (1-n2) in which n is 1 or 2 in the formula (1) can be produced by reacting the compound of the present invention (1-n0) in which n is 0 with an oxidizing agent:

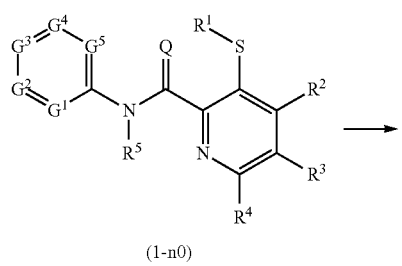

(1-n0)

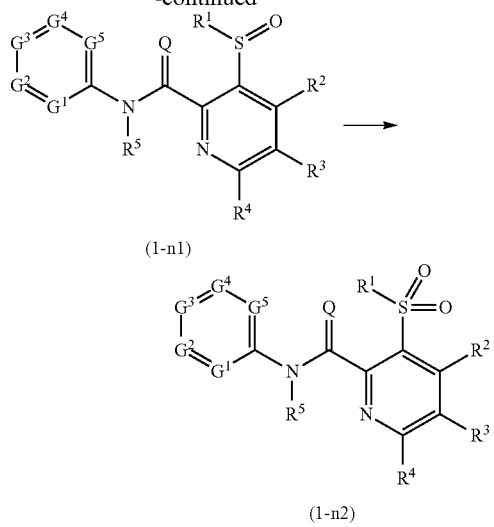

wherein symbols represent the same meaning as described above.

The compound of the present invention (1-n1) in which n is 1 in the formula (1) can be produced by reacting the compound of the present invention (1-n0) in which n is 0 with an oxidizing agent.

The reaction is usually carried out in the presence of a solvent. Examples of the solvent include aliphatic halogenated hydrocarbons such as dichloromethane and chloroform, alcohols such as methanol and ethanol, acetic acid, water, and mixtures thereof.

Examples of the oxidizing agent include sodium periodate and m-chloroperbenzoic acid.

In the reaction, the oxidizing agent is usually used in a ratio of 1 to 3 mol, based on 1 mol of the compound of the present invention (1-n0). Preferably, the oxidizing agent is used in a ratio of 1 to 1.2 mol, based on 1 mol of the compound of the present invention (1-n0).

The reaction temperature is usually within the range of −20 to 80° C. The reaction time is usually within the range of 0.1 to 12 hours.

After completion of the reaction, the reaction mixture is extracted with an organic solvent, and the organic layer is washed with an aqueous solution of a reducing agent (for example, sodium sulfite, sodium thiosulfate) and an aqueous solution of a base (for example, sodium bicarbonate) as necessary, and subjected to post-treatment operations such as drying and concentration, whereby the compound of the present invention (1-n1) can be isolated. The isolated compound of the present invention (1-n1) also can be further purified by chromatography, recrystallization, or the like. Alternatively, the compound of the present invention (1-n1) can be used to the next reaction as it is without isolation.

The compound of the present invention (1-n2) in which n is 2 in the formula (1) can be produced by reacting the compound of the present invention (1-n1) in which n is 1 with an oxidizing agent.

The reaction is usually carried out in the presence of a solvent. Examples of the solvent include aliphatic halogenated hydrocarbons such as dichloromethane and chloroform, alcohols such as methanol and ethanol, acetic acid, water, and mixtures thereof.

Examples of the oxidizing agent include m-chloroperbenzoic acid and aqueous hydrogen peroxide.

In the reaction, the oxidizing agent is usually used in a ratio of 1 to 4 mol, based on 1 mol of the compound of the present invention (1-n1). Preferably, the oxidizing agent is used in a ratio of 1 to 1.2 mol, based on 1 mol of the compound of the present invention (1-n1).

The reaction temperature is usually within the range of −20 to 120° C. The reaction time is usually within the range of 0.1 to 12 hours.

After completion of the reaction, the reaction mixture is extracted with an organic solvent, and the organic layer is washed with an aqueous solution of a reducing agent (for example, sodium sulfite, sodium thiosulfate) and an aqueous solution of a base (for example, sodium bicarbonate) as necessary, and subjected to post-treatment operations such as drying and concentration, whereby the compound of the present invention (1-n2) can be isolated. The compound of the present invention (1-n2) also can be further purified by chromatography, recrystallization, or the like.

The compound of the present invention (1-n2) in which n is 2 in the formula (1) can be produced by a one step reaction (one pot) by reacting the compound of the present invention (1-n0) in which n is 0 in the presence of an oxidizing agent.

The reaction is usually carried out in the presence of a solvent. Examples of the solvent include aliphatic halogenated hydrocarbons such as dichloromethane and chloroform, alcohols such as methanol and ethanol, acetic acid, water, and mixtures thereof.

Examples of the oxidizing agent include m-chloroperbenzoic acid or aqueous hydrogen peroxide.

The reaction can be also carried out, in the presence of a catalyst, as necessary. Examples of the catalyst include sodium tungstate.

In the reaction, the oxidizing agent is usually used in a ratio of 2 to 5 mol, and the catalyst is usually used in a ratio of 0.01 to 0.5 mol, based on 1 mol of the compound of the present invention (1-n0). Preferably, the oxidizing agent is used in a ratio of 2 to 2.2 mol, based on 1 mol of the compound of the present invention (1-n0).

The reaction temperature is usually within the range of 0 to 120° C. The reaction time is usually within the range of 0.1 to 12 hours.

After completion of the reaction, the reaction mixture is extracted with an organic solvent, and the organic layer is washed with an aqueous solution of a reducing agent (for example, sodium sulfite, sodium thiosulfate) and an aqueous solution of a base (for example, sodium bicarbonate) as necessary, and subjected to post-treatment operations such as drying and concentration, whereby the compound of the present invention (1-n2) can be isolated. The isolated compound of the present invention (1-n2) also can be further purified by chromatography, recrystallization, or the like.

(Production Method 2)

The compound of the present invention (P1) in which Q is an oxygen atom in the formula (1) can be produced by reacting the intermediate compound (M1) with the intermediate compound (M2):

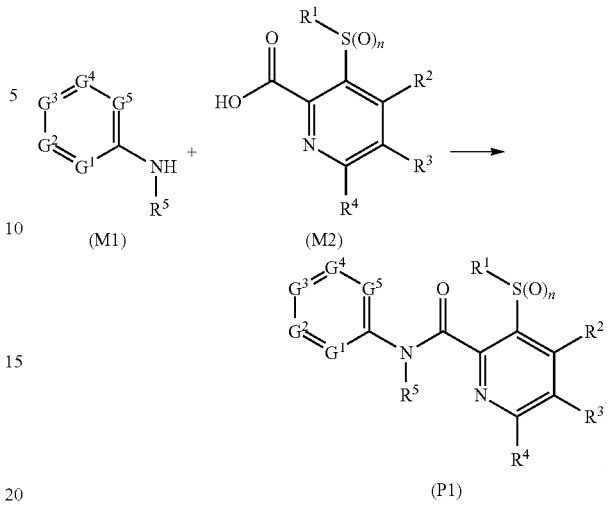

wherein symbols represent the same meaning as described above.

The compound of the present invention (P1) can be produced by reacting the intermediate compound (M1) with the intermediate compound (M2), in the presence of a condensing agent.

The reaction is usually carried out in the presence of a solvent. Examples of the solvent include ethers such as 1,4-dioxane, diethyl ether, tetrahydrofuran (hereinafter, referred to as THF) and tert-butyl methyl ether (hereinafter, referred to as MTBE), halogenated hydrocarbons such as dichloromethane, chloroform, carbon tetrachloride, 1,2-dichloroethane and chlorobenzene, aromatic hydrocarbons such as toluene, benzene and xylene, esters such as ethyl acetate and butyl acetate, nitriles such as acetonitrile, aprotic polar solvents such as N,N-dimethylformamide (hereinafter, referred to as DMF), N-methylpyrrolidone (hereinafter, referred to as NMP), 1,3-dimethyl-2-imidazolidinone and dimethyl sulfoxide (hereinafter, referred to as DMSO), nitrogen-containing aromatic compounds such as pyridine and quinoline, and mixtures thereof.

Examples of the condensing agent include carbodiimides such as 1-ethyl-3-(3-dimethylaminopropyl)carbodiimide hydrochloride (hereinafter, referred to as EDCI hydrochloride) and 1,3-dicyclohexylcarbodiimide.

The reaction can be also carried out by adding a catalyst, as necessary. Examples of the catalyst include 1-hydroxybenzotriazole (hereinafter, referred to as HOBt).

In the reaction, the intermediate compound (M2) is usually used in a ratio of 0.8 to 1.2 mol, the condensing agent is usually used in a ratio of 1 to 2 mol, and the catalyst is usually used in a ratio of 0.01 to 1 mol, based on 1 mol of the intermediate compound (M1).

The reaction temperature is usually within the range of 0 to 200° C. The reaction time is usually within the range of 0.1 to 24 hours.

After completion of the reaction, the compound of the present invention (P1) can be isolated by adding the reaction mixture to water, then extracting the mixture with an organic solvent, and concentrating the organic layer; collecting a solid generated by adding the reaction mixture to water by filtration; or collecting a solid generated in the reaction mixture by filtration. The isolated compound of the present invention (P1) also can be further purified by recrystallization, chromatography, or the like.

(Production Method 3)

The compound of the present invention (P1) in which Q is an oxygen atom in the formula (1) can be produced by reacting the intermediate compound (M1) with the intermediate compound (M3):

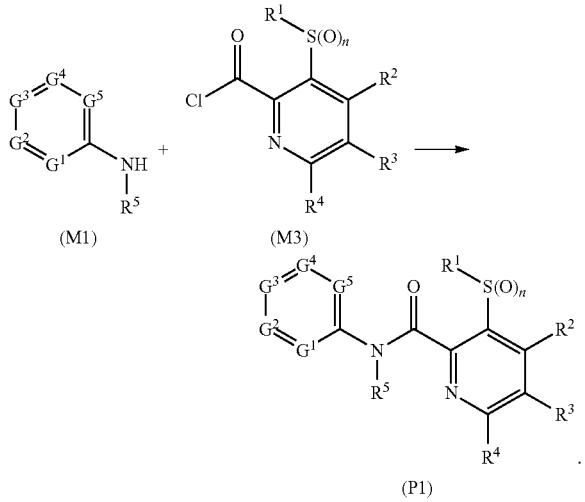

wherein symbols represent the same meaning as described above.

The compound of the present invention (P1) can be produced by reacting the intermediate compound (M1) with the intermediate compound (M3).

The reaction is usually carried out in the presence of a solvent. Examples of the solvent include ethers such as THF, ethylene glycol dimethyl ether, MTBE and 1,4-dioxane, aliphatic hydrocarbons such as hexane, heptane and octane, aromatic hydrocarbons such as toluene and xylene, halogenated hydrocarbons such as chlorobenzene, esters such as ethyl acetate and butyl acetate, nitriles such as acetonitrile, aprotic polar solvents such as DMF, NMP and DMSO, and mixtures thereof.

The reaction can be also carried out by adding a base, as necessary. Examples of the base include alkali metal carbonates such as sodium carbonate and potassium carbonate, tertiary amines such as triethylamine and N,N-diisopropylethylamine, and nitrogen-containing aromatic compounds such as pyridine, 4-dimethylaminopyridine, and the like.

In the reaction, the intermediate compound (M3) is usually used in a ratio of 0.8 to 1.2 mol, and the base is usually used in a ratio of 1 to 2 mol, based on 1 mol of the intermediate compound (M1).

The reaction temperature is usually within the range of −20 to 200° C. The reaction time is usually within the range of 0.1 to 24 hours.

After completion of the reaction, water is added to the reaction mixture, then the reaction mixture is extracted with an organic solvent, and the organic layer is subjected to post-treatment operations such as drying and concentration, whereby the compound of the present invention (P1) can be isolated. The isolated compound of the present invention (P1) also can be further purified by chromatography, recrystallization, or the like.

(Production Method 4)

The compound of the present invention (P1) in which Q is an oxygen atom in the formula (1) can be produced by reacting the intermediate compound (M4) with the intermediate compound (M5):

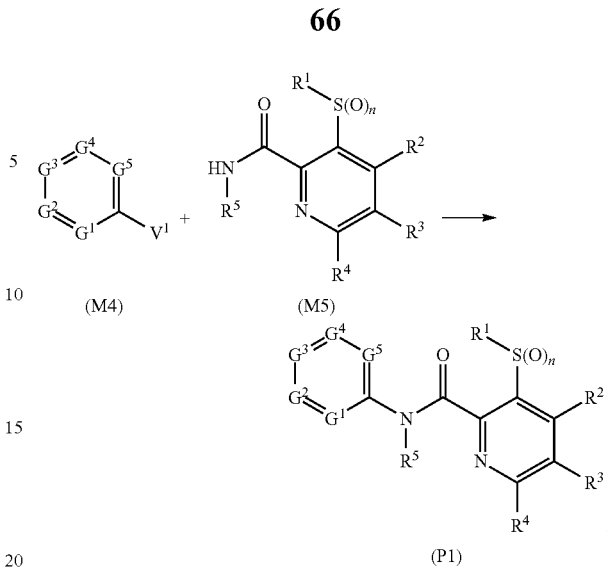

wherein $V^1$ represents a halogen atom, and other symbols represent the same meaning as described above.

When $V^1$ is a fluorine atom, the compound of the present invention (P1) can be produced by reacting the intermediate compound (M4) with the intermediate compound (M5), in the presence of a base.

The reaction is usually carried out in the presence of a solvent. Examples of the solvent include ethers such as THF, ethylene glycol dimethyl ether, MTBE and 1,4-dioxane, aromatic hydrocarbons such as toluene and xylene, nitriles such as acetonitrile, aprotic polar solvents such as DMF, NMP and DMSO, water, and mixtures thereof.

Examples of the base used in the reaction include alkali metal carbonates such as sodium carbonate, potassium carbonate and cesium carbonate, and alkali metal hydrides such as sodium hydride.

In the reaction, the intermediate compound (M5) is usually used in a ratio of 0.8 to 1.2 mol, and the base is usually used in a ratio of 1 to 2 mol, based on 1 mol of the intermediate compound (M4).

The reaction temperature is usually within the range of 0 to 200° C. The reaction time is usually within the range of 0.5 to 24 hours.

After completion of the reaction, the reaction mixture is extracted with an organic solvent, and the organic layer is subjected to post-treatment operations such as drying and concentration, whereby the compound of the present invention (P1) can be isolated. The isolated compound of the present invention (P1) also can be further purified by chromatography, recrystallization, or the like.

When $V^1$ is a chlorine atom, a bromine atom or an iodine atom, the compound of the present invention (P1) can be produced by reacting the intermediate compound (M4) with the intermediate compound (M5) and a base, in the presence of a copper catalyst or a palladium catalyst.

The reaction is usually carried out in the presence of a solvent. Examples of the solvent include ethers such as THF, ethylene glycol dimethyl ether, MTBE and 1,4-dioxane, aromatic hydrocarbons such as toluene and xylene, nitriles such as acetonitrile, aprotic polar solvents such as DMF, NMP and DMSO, water, and mixtures thereof.

Examples of the base include alkali metal carbonates such as sodium carbonate and potassium carbonate, phosphates such as trisodium phosphate and tripotassium phosphate, alkali metal hydrides such as sodium hydride, tertiary amines such as triethylamine and N,N-diisopropylethylamine, and cyclic amines such as 1,4-diazabicyclo[2.2.2]octane (hereinafter, referred to as DABCO) and diazabicycloundecene (hereinafter, referred to as DBU).

Examples of the copper catalyst include copper(I) iodide, copper(I) bromide, copper(I) chloride and copper(I) oxide, and examples of the palladium catalyst include palladium(II) acetate and tris(dibenzylideneacetone)dipalladium(0).

The reaction can be also carried out by adding a ligand as necessary. Examples of the ligand include acetylacetone, salen, phenanthroline, triphenylphosphine, and 4,5'-bis(diphenylphosphino)-9,9'-dimethylxanthene.

In the reaction, the intermediate compound (M5) is usually used in a ratio of 0.8 to 1.2 mol, the base is usually used in a ratio of 1 to 2 mol, the copper catalyst is usually used in a ratio of 0.01 to 0.5 mol, the palladium catalyst is usually used in a ratio of 0.01 to 0.2 mol, and the ligand is usually used in a ratio of 0.01 to 0.5 mol, based on 1 mol of the intermediate compound (M4).

The reaction temperature is usually within the range of 0 to 200° C. The reaction time is usually within the range of 0.5 to 24 hours.

After completion of the reaction, the reaction mixture is extracted with an organic solvent, and the organic layer is subjected to post-treatment operations such as drying and concentration, whereby the compound of the present invention (P1) can be isolated. The isolated compound of the present invention (P1) also can be further purified by chromatography, recrystallization, or the like.
(Production Method 5)

The compound of the present invention (1) can be produced by reacting the compound of the present invention (P4) with the intermediate compound (M7), in the presence of a base:

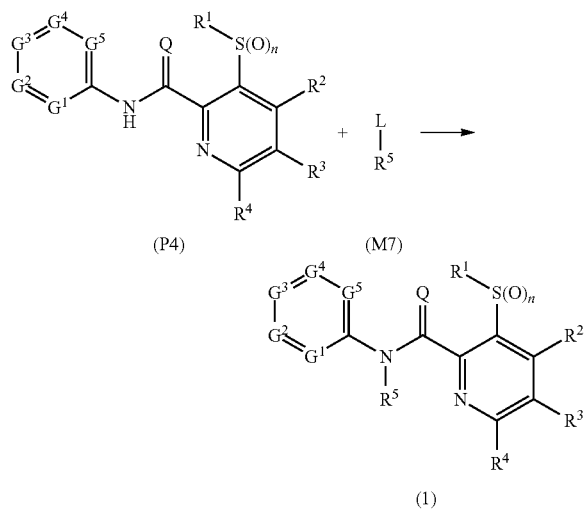

wherein L represents a leaving group such as a chlorine atom, a bromine atom, an iodine atom, a trifluoromethanesulfonyloxy group or a methanesulfonyloxy group, and other symbols represent the same meaning as described above.

The reaction is usually carried out in the presence of a solvent. Examples of the solvent include ethers such as THF, ethylene glycol dimethyl ether, MTBE and 1,4-dioxane, aromatic hydrocarbons such as toluene and xylene, nitriles such as acetonitrile, aprotic polar solvents such as DMF, NMP and DMSO, and mixtures thereof.

Examples of the base used in the reaction include hydrides of alkali metals or alkaline earth metals such as sodium hydride, potassium hydride and calcium hydride, inorganic bases such as sodium carbonate and potassium carbonate, organic bases such as triethylamine, and the like.

In the reaction, the intermediate compound (M7) is usually used in a ratio of 1 to 5 mol, and the base is usually used in a ratio of 1 to 2 mol, based on 1 mol of the compound of the present invention (P4).

The reaction temperature is usually within the range of 0 to 100° C. The reaction time is usually within the range of 0.1 to 24 hours.

After completion of the reaction, the reaction mixture is extracted with an organic solvent, and the organic layer is subjected to post-treatment operations such as drying and concentration, whereby the compound of the present invention (1) can be isolated. The isolated compound of the present invention (1) also can be further purified by chromatography, recrystallization, or the like.
(Production Method 6)

The compound of the present invention (1) can be produced by reacting the compound of the present invention (P4) with the intermediate compound (M8), in the presence of a condensing agent:

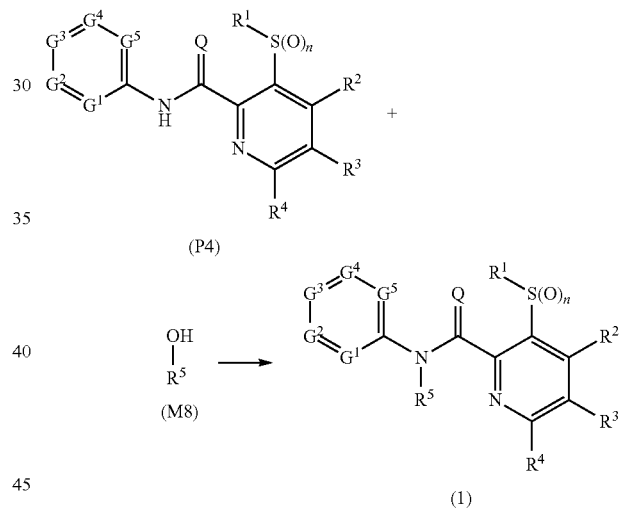

wherein symbols represent the same meaning as described above.

The reaction is usually carried out in the presence of a solvent. Examples of the solvent include ethers such as THF, ethylene glycol dimethyl ether, MTBE and 1,4-dioxane, aromatic hydrocarbons such as toluene and xylene, nitriles such as acetonitrile, aliphatic halogenated hydrocarbons such as dichloromethane and chloroform, aprotic polar solvents such as DMF, NMP and DMSO, and mixtures thereof.

Examples of the condensing agent include a mixture of diethyl azodicarboxylate and triphenylphosphine.

In the reaction, the intermediate compound (M8) is usually used in a ratio of 1 to 5 mol, and the condensing agent is usually used in a ratio of 1 to 2 mol, based on 1 mol of the compound of the present invention (P4).

The reaction temperature is usually within the range of 0 to 150° C. The reaction time is usually within the range of 0.1 to 24 hours.

After completion of the reaction, the reaction mixture is extracted with an organic solvent, and the organic layer is subjected to post-treatment operations such as drying and concentration, whereby the compound of the present invention (1) can be isolated. The isolated compound of the present invention (1) also can be further purified by chromatography, recrystallization, or the like.

(Production Method 7)

The compound of the present invention (P2) in which Q is an oxygen atom and n is 0 in the formula (1) can be produced by reacting the intermediate compound (M11) with the intermediate compound (M12), in the presence of a base:

After completion of the reaction, the reaction mixture is extracted with an organic solvent, and the organic layer is subjected to post-treatment operations such as drying and concentration, whereby the compound of the present invention (P2) can be isolated. The isolated compound of the present invention (P2) also can be further purified by chromatography, recrystallization, or the like.

In the reaction, $V^1$ is preferably a fluorine atom or a chlorine atom.

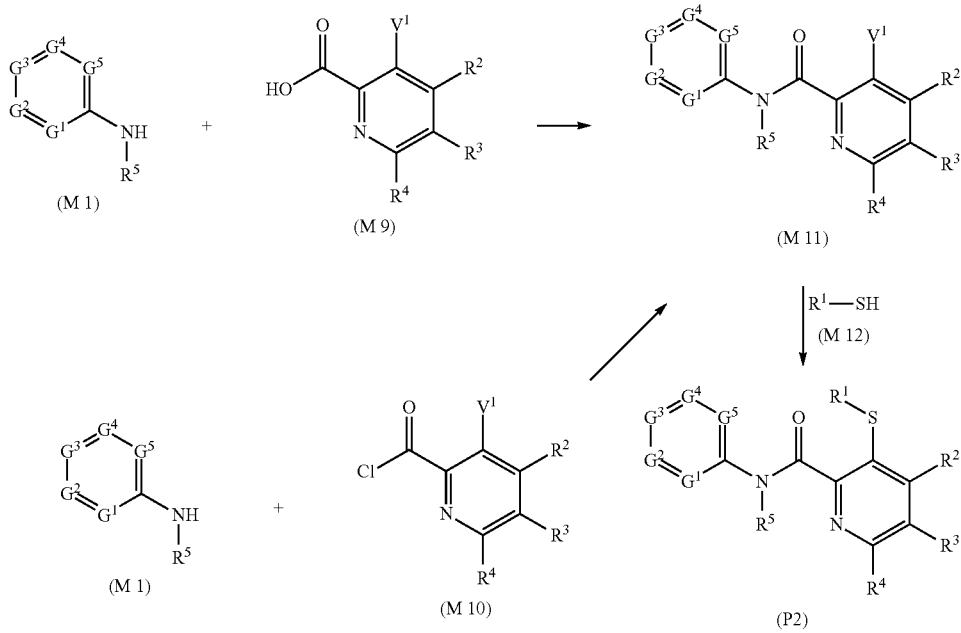

wherein symbols represent the same meaning as described above.

The intermediate compound (M11) can be produced, using the intermediate compound (M9) in place of the intermediate compound (M2), in accordance with the method of Production Method 2.

The intermediate compound (M11) can be produced, using the intermediate compound (M10) in place of the intermediate compound (M2), in accordance with the method of the step of Production Method 2.

The compound of the present invention (P2) in which Q is an oxygen atom and n is 0 in the formula (1) can be produced by reacting the intermediate compound (M11) with the intermediate compound (M12), in the presence of a base.

The reaction is usually carried out in the presence of a solvent. Examples of the solvent include ethers such as THF, ethylene glycol dimethyl ether, MTBE and 1,4-dioxane, aromatic hydrocarbons such as toluene and xylene, nitriles such as acetonitrile, aprotic polar solvents such as DMF, NMP and DMSO, water, and mixtures thereof.

Examples of the base include alkali metal carbonates such as sodium carbonate and potassium carbonate, and alkali metal hydrides such as sodium hydride.

In the reaction, the compound (M12) is usually used in a ratio of 0.8 to 1.2 mol, and the base is usually used in a ratio of 1 to 2 mol, based on 1 mol of the intermediate compound (M11).

The reaction temperature is usually within the range of 0 to 150° C. The reaction time is usually within the range of 0.5 to 24 hours.

(Production Method 8)

The intermediate compound (M13) can be produced by reacting the intermediate compound (M11) in the presence of a thiolating agent. Also, the compound of the present invention (P2) in which Q is an oxygen atom and n is 0 in the formula (1) can be produced by reacting the intermediate compound (M13) with the intermediate compound (M14), in the presence of a base:

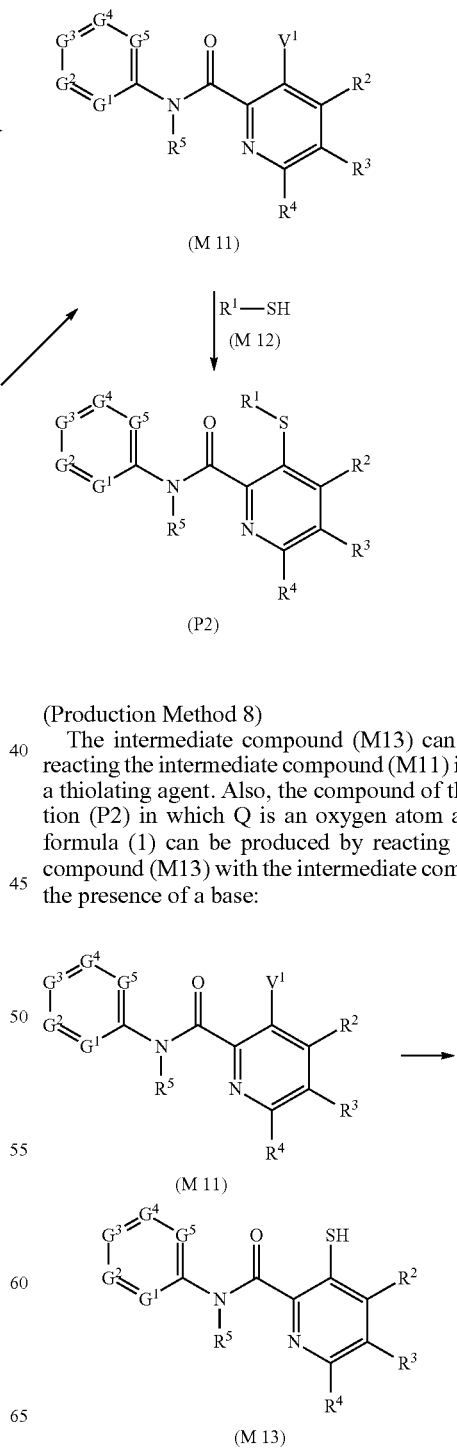

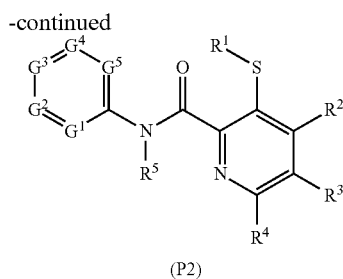

(P2)

wherein symbols represent the same meaning as described above.

The intermediate compound (M13) can be produced by reacting the intermediate compound (M11) in the presence of a thiolating agent.

The reaction is usually carried out in the presence of a solvent. Examples of the solvent include ethers such as THF, ethylene glycol dimethyl ether, MTBE and 1,4-dioxane, aromatic hydrocarbons such as toluene and xylene, nitriles such as acetonitrile, aprotic polar solvents such as DMF, NMP and DMSO, water, and mixtures thereof.

Examples of the thiolating agent include sodium sulfide and sodium sulfide nonahydrate.

In the reaction, the thiolating agent is usually used in a ratio of 1 to 2 mol, based on 1 mol of the intermediate compound (M11).

The reaction temperature is usually within the range of 0 to 150° C. The reaction time is usually within the range of 0.5 to 24 hours.

After completion of the reaction, the reaction mixture is extracted with an organic solvent, and the organic layer is subjected to post-treatment operations such as drying and concentration, whereby the intermediate compound (M13) can be isolated. The isolated intermediate compound (M13) also can be further purified by chromatography, recrystallization, or the like.

In the reaction, $V^1$ is preferably a fluorine atom or a chlorine atom.

The compound of the present invention (P2) can be produced by reacting the intermediate compound (M13) with the intermediate compound (M14), in the presence of a base.

The reaction is usually carried out in the presence of a solvent. Examples of the solvent include ethers such as THF, ethylene glycol dimethyl ether, MTBE and 1,4-dioxane, aromatic hydrocarbons such as toluene and xylene, nitriles such as acetonitrile, aprotic polar solvents such as DMF, NMP and DMSO, and mixtures thereof.

Examples of the base include hydrides of alkali metals or alkaline earth metals such as sodium hydride, potassium hydride and calcium hydride, inorganic bases such as sodium carbonate and potassium carbonate, organic bases such as triethylamine, and the like.

In the reaction, the intermediate compound (M14) is usually used in a ratio of 1 to 5 mol, and the base is usually used in a ratio of 1 to 2 mol, based on 1 mol of the intermediate compound (M13).

The reaction temperature is usually within the range of 0 to 100° C. The reaction time is usually within the range of 0.1 to 24 hours.

After completion of the reaction, the reaction mixture is extracted with an organic solvent, and the organic layer is subjected to post-treatment operations such as drying and concentration, whereby the compound of the present invention (P2) can be isolated. The isolated compound of the present invention (P2) also can be further purified by chromatography, recrystallization, or the like.

(Production Method 9)

The compound of the present invention (P3) in which Q is a sulfur atom in the formula (1) can be produced by reacting the compound of the present invention (P1) in which Q is an oxygen atom in the formula (1) with a sulfurizing agent:

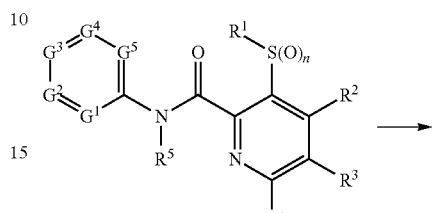

(P1)

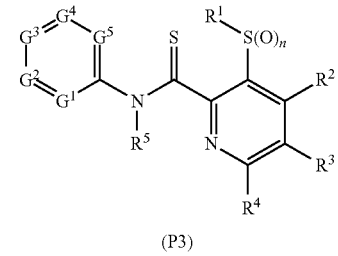

(P3)

wherein symbols represent the same meaning as described above.

The reaction is carried out in the presence of a solvent. Examples of the solvent include ethers such as 1,4-dioxane, diethyl ether, THF, MTBE and diglyme, halogenated hydrocarbons such as dichloromethane, chloroform, carbon tetrachloride, 1,2-dichloroethane and chlorobenzene, aromatic hydrocarbons such as toluene, benzene and xylene, nitriles such as acetonitrile, nitrogen-containing aromatic compounds such as pyridine, picoline, lutidine and quinoline, and mixtures thereof.

Examples of the sulfurizing agent used in the reaction include diphosphorus pentasulfide and Lawesson's reagent (2,4-bis-(4-methoxyphenyl)-1,3-dithia-2,4-diphosphetane-2,4-disulfide).

In the reaction, the sulfurizing agent is usually used in a ratio of 1 to 3 mol, based on 1 mol of the compound of the present invention (P1).

The reaction temperature is usually within the range of 0° C. to 200° C. The reaction time is usually within the range of 1 to 24 hours.

After completion of the reaction, the compound of the present invention (P3) can be isolated by adding the reaction mixture to water, then extracting the mixture with an organic solvent, and concentrating the organic layer; collecting a solid generated by adding the reaction mixture to water by filtration; or collecting a solid generated in the reaction mixture by filtration. The isolated compound of the present invention (P3) also can be further purified by recrystallization, chromatography, or the like.

(Production Method 10)

The intermediate compound (M2) can be produced by hydrolyzing the intermediate compound (M15). Also, the intermediate compound (M3) can be produced by reacting the intermediate compound (M2) with a chlorinating agent:

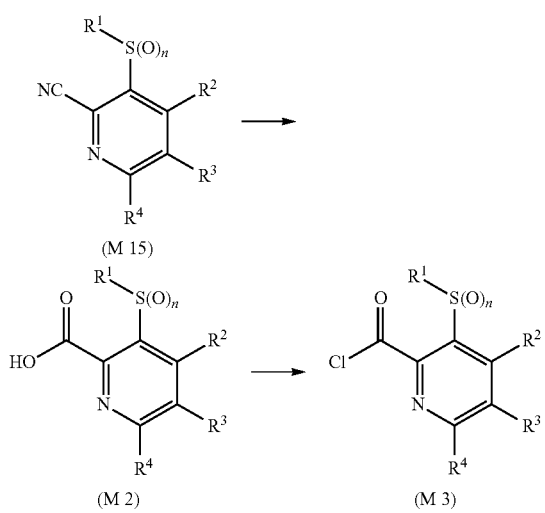

wherein symbols represent the same meaning as described above.

The intermediate compound (M2) can be produced by hydrolyzing the intermediate compound (M15).

When hydrolyzed by an acid, the reaction is usually carried out using an aqueous solution of an acid as a solvent. Examples of the acid include mineral acids such as hydrochloric acid, nitric acid, phosphoric acid and sulfuric acid, and carboxylic acids such as acetic acid and trifluoroacetic acid.

The reaction temperature is usually within the range of 0 to 150° C. The reaction time is usually within the range of 0.1 to 24 hours.

After completion of the reaction, the reaction mixture is extracted with an organic solvent, and the organic layer is subjected to post-treatment operations such as drying and concentration, whereby the intermediate compound (M2) can be isolated. The isolated intermediate compound (M2) also can be further purified by chromatography, recrystallization, or the like.

When hydrolyzed by a base, the reaction is usually carried out in the presence of a solvent. Examples of the solvent include ethers such as THF, ethylene glycol dimethyl ether, MTBE and 1,4-dioxane, alcohols such as methanol and ethanol, water, and mixtures thereof.

Examples of the base include alkali metal hydroxides such as sodium hydroxide and potassium hydroxide.

In the reaction, the base is usually used in a ratio of 1 to 10 mol, based on 1 mol of the intermediate compound (M15).

The reaction temperature is usually within the range of 0 to 120° C. The reaction time is usually within the range of 0.1 to 24 hours.

After completion of the reaction, the reaction solution is acidified, then the reaction mixture is extracted with an organic solvent, and the organic layer is subjected to post-treatment operations such as drying and concentration, whereby the intermediate compound (M2) can be isolated. The isolated intermediate compound (M2) also can be further purified by chromatography, recrystallization, or the like.

The intermediate compound (M3) can be produced by reacting the intermediate compound (M2) with a chlorinating agent.

The reaction is usually carried out in the presence of a solvent. Examples of the solvent include ethers such as THF, ethylene glycol dimethyl ether, MTBE and 1,4-dioxane, aromatic hydrocarbons such as toluene and xylene, aliphatic halogenated hydrocarbons such as dichloromethane and chloroform, and mixtures thereof.

Examples of the chlorinating agent include thionyl chloride, oxalyl dichloride and phosphorus oxychloride.

The reaction can be also carried out by adding DMF as necessary.

In the reaction, the chlorinating agent is usually used in a ratio of 1 to 5 mol, and DMF is usually used in a ratio of 0.001 to 0.1 mol, based on 1 mol of the intermediate compound (M2).

The reaction temperature is usually within the range of 0 to 100° C. The reaction time is usually within the range of 0.1 to 24 hours.

After completion of the reaction, the intermediate compound (M3) can be isolated by distilling the solvent.

Alternatively, the intermediate compound (M3) can be used to the next reaction as it is without isolation.

(Production Method 11)

The intermediate compound (M2) in which n is 0 can be produced by reacting the intermediate compound (M9) with the intermediate compound (M12), in the presence of a base. Also, the intermediate compound (M2-n1) in which n is 1 or intermediate compound (M2-n2) in which n is 2 can be produced by oxidizing the intermediate compound (M2-n0) in which n is 0:

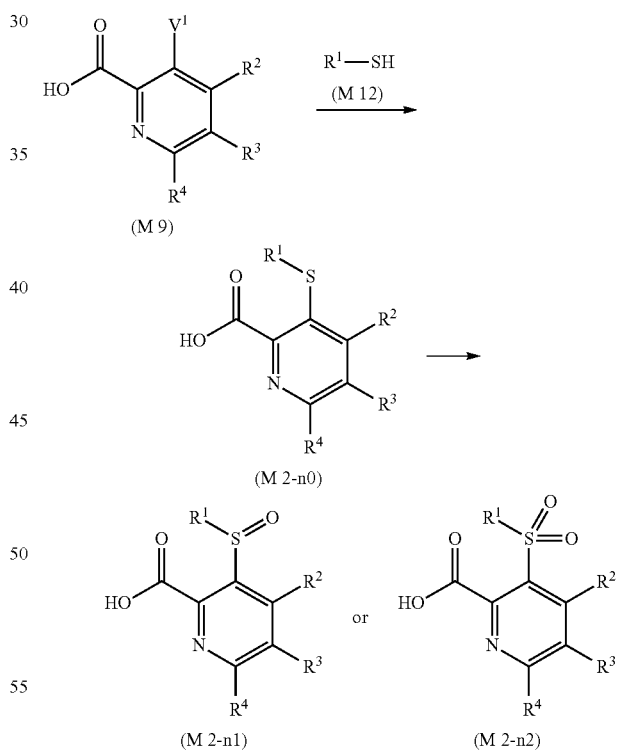

wherein symbols represent the same meaning as described above.

The intermediate compound (M2-n0) in which n is 0 can be produced, using the intermediate compound (M9) in place of the intermediate compound (M11), in accordance with the method of Production Method 7.

In the reaction, $V^1$ is preferably a fluorine atom or a chlorine atom.

The intermediate compound (M2-n1) or intermediate compound (M2-n2) in which n is 1 or 2 can be produced, using the intermediate compound (M2-n0) in which n is 0 in place of the compound of the present invention (1-n0) in which n is 0, in accordance with the method of Production Method 1.

(Production Method 12)

The compound of the present invention (P4-QO) in which Q is an oxygen atom in the compound of the present invention (P4) can be produced, using the intermediate compound (M16) in place of the intermediate compound (M1), in accordance with the method of Production Method 2. In addition, the intermediate compound (P4-QO) can be produced, using the intermediate compound (M16) in place of the intermediate compound (M1), in accordance with the method of Production Method 3.

The compound of the present invention (P4-QS) in which Q is a sulfur atom in the compound of the present invention (P4) can be produced, using the compound of the present invention (P4-QO) in which Q is an oxygen atom in place of the compound of the present invention (P1), in accordance with the method of Production Method 9.

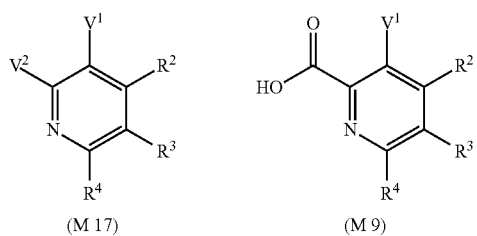

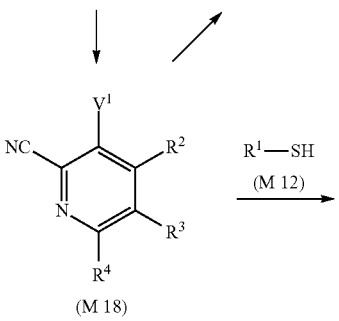

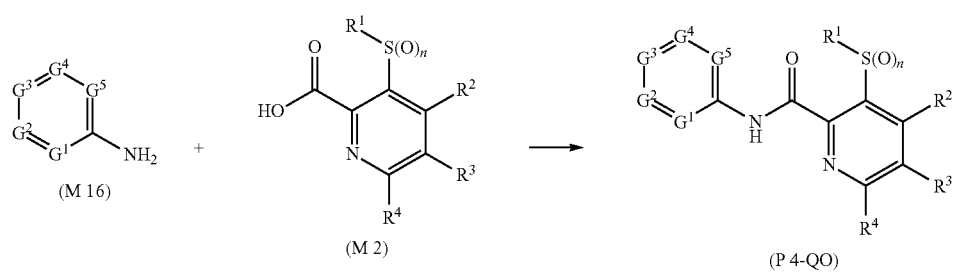

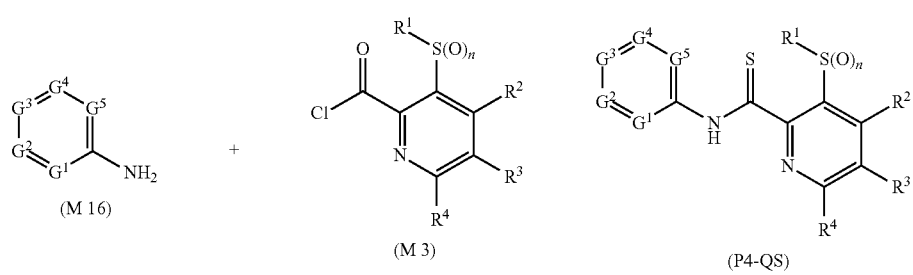

wherein symbols represent the same meaning as described above.

(Production Method 13)

The intermediate compound (M18) can be produced by reacting the intermediate compound (M17) with a cyanating agent, in the presence of a palladium compound. The intermediate compound (M9) can be produced by hydrolyzing the intermediate compound (M18) with an acid. The intermediate compound (M15-n0) in which n is 0 can be produced by reacting the intermediate compound (M18) with the intermediate compound (M12), in the presence of a base. Also, the intermediate compound (M15-n1) in which n is 1 or intermediate compound (M15-n2) in which n is 2 can be produced by reacting the intermediate compound (M15-n0) in which n is 0 with an oxidizing agent:

-continued

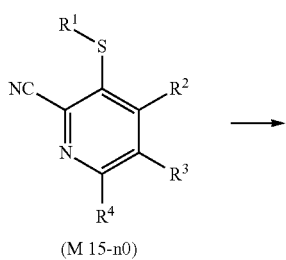

wherein $V^1$ represents a halogen atom, and the symbols represent the same meaning as described above.

The intermediate compound (M18) can be produced by reacting the intermediate compound (M17) with a cyanating agent, in the presence of a palladium compound.

The reaction is usually carried out in the presence of a solvent. Examples of the solvent include ethers such as THF, ethylene glycol dimethyl ether, tert-butyl methyl ether and 1,4-dioxane, aliphatic hydrocarbons such as hexane, heptane and octane, aromatic hydrocarbons such as toluene and xylene, alcohols such as methanol and ethanol, aprotic polar solvents such as DMF, NMP and DMSO, and mixtures thereof.

Examples of the cyanating agent include zinc cyanide and the like.

Examples of the palladium compound include tetrakis (triphenylphosphine)palladium and the like.

In the reaction, the cyanating agent is usually used in a ratio of 1 to 5 mol, and the palladium compound is usually used in a ratio of 0.01 to 0.5 mol, based on 1 mol of the intermediate compound (M17).

The reaction temperature is usually within the range of 50 to 200° C. The reaction time is usually within the range of 0.5 to 24 hours.

After completion of the reaction, the reaction mixture is extracted with an organic solvent, and the organic layer is subjected to post-treatment operations such as drying and concentration, whereby the intermediate compound (M18) can be isolated. The isolated intermediate compound (M18) also can be further purified by chromatography, recrystallization, or the like.

The intermediate compound (M9) can be produced by hydrolyzing the intermediate compound (M18) with an acid.

The reaction is usually carried out using an aqueous solution of an acid as a solvent. Examples of the acid include mineral acids such as hydrochloric acid, nitric acid, phosphoric acid and sulfuric acid, and carboxylic acids such as acetic acid and trifluoroacetic acid.

The reaction temperature is usually within the range of 0 to 150° C. The reaction time is usually within the range of 0.1 to 24 hours.

After completion of the reaction, the reaction mixture is extracted with an organic solvent, and the organic layer is subjected to post-treatment operations such as drying and concentration, whereby the intermediate compound (M9) can be isolated. The isolated intermediate compound (M9) also can be further purified by chromatography, recrystallization, or the like.

The intermediate compound (M15-n0) in which n is 0 can be produced, using the intermediate compound (M18) in place of the intermediate compound (M11), in accordance with the method of Production Method 7.

In the reaction, $V^1$ is preferably a fluorine atom or a chlorine atom.

The intermediate compound (M15-n1) or intermediate compound (M15-n2) in which n is 1 or 2 can be produced, using the intermediate compound (M15-n0) in which n is 0 in place of the compound of the present invention (1-n0) in which n is 0, in accordance with the method of Production Method 1.

(Production Method 14)

Among the compounds of the present invention and the above-described intermediate compounds, a compound having a nitrogen-containing heterocyclic group having a lone pair of electrons on the nitrogen atom is reacted with an oxidizing agent, whereby an N-oxide in which the nitrogen atom is oxidized can be manufactured in some cases.

Examples of the nitrogen-containing heterocyclic group include a pyridine ring.

The reaction can be carried out by a known method, and is carried out using an oxidizing agent such as m-chloroperbenzoic acid or hydrogen peroxide, in a solvent, for example, a halogenated hydrocarbon such as dichloromethane, chloroform or chlorobenzene, an alcohol such as methanol or ethanol, acetic acid, water, and mixtures thereof.

Next, specific examples of the compound of the present invention are shown below.

The compounds of the present invention, wherein, in the formula (1):

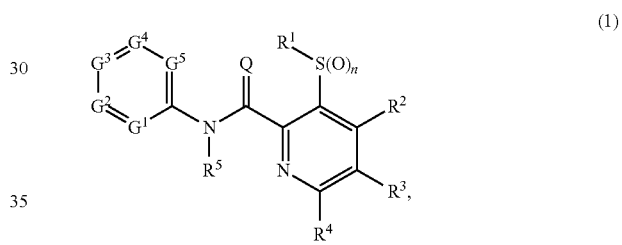

n is 0, $R^2$, $R^3$ and $R^4$ are a hydrogen atom, $G^1$, $G^2$, $G^4$ and $G^5$ are CH, Q is an oxygen atom, and $R^1$, $R^5$ and $G^3$ are the combinations shown in $R^1$, $R^5$ and $G^X$ in [Table 1] to [Table 15].

TABLE 1

| $R^1$ | $R^5$ | $G^X$ |
|---|---|---|
| Me | H | $C(CF_3)$ |
| Et | H | $C(CF_3)$ |
| Pr | H | $C(CF_3)$ |
| $CH_2C\!\!=\!\!CH$ | H | $C(CF_3)$ |
| CycPr | H | $C(CF_3)$ |
| $CH_2$CycPr | H | $C(CF_3)$ |
| Me | Me | $C(CF_3)$ |
| Et | Me | $C(CF_3)$ |
| Pr | Me | $C(CF_3)$ |
| $CH_2C\!\!=\!\!CH$ | Me | $C(CF_3)$ |
| CycPr | Me | $C(CF_3)$ |
| $CH_2$CycPr | Me | $C(CF_3)$ |
| Me | Et | $C(CF_3)$ |
| Et | Et | $C(CF_3)$ |
| Pr | Et | $C(CF_3)$ |
| $CH_2C\!\!=\!\!CH$ | Et | $C(CF_3)$ |
| CycPr | Et | $C(CF_3)$ |
| $CH_2$CycPr | Et | $C(CF_3)$ |
| Me | CycPr | $C(CF_3)$ |
| Et | CycPr | $C(CF_3)$ |
| Pr | CycPr | $C(CF_3)$ |
| $CH_2C\!\!=\!\!CH$ | CycPr | $C(CF_3)$ |
| CycPr | CycPr | $C(CF_3)$ |
| $CH_2$CycPr | CycPr | $C(CF_3)$ |

TABLE 2

| R¹ | R⁵ | G$^x$ |
|---|---|---|
| Me | CH₂CycPr | C(CF₃) |
| Et | CH₂CycPr | C(CF₃) |
| Pr | CH₂CycPr | C(CF₃) |
| CH₂C≡CH | CH₂CycPr | C(CF₃) |
| CycPr | CH₂CycPr | C(CF₃) |
| CH₂CycPr | CH₂CycPr | C(CF₃) |
| Me | CH₂C≡CH | C(CF₃) |
| Et | CH₂C≡CH | C(CF₃) |
| Pr | CH₂C≡CH | C(CF₃) |
| CH₂C≡CH | CH₂C≡CH | C(CF₃) |
| CycPr | CH₂C≡CH | C(CF₃) |
| CH₂CycPr | CH₂C≡CH | C(CF₃) |
| Me | CH₂CN | C(CF₃) |
| Et | CH₂CN | C(CF₃) |
| Pr | CH₂CN | C(CF₃) |
| CH₂C≡CH | CH₂CN | C(CF₃) |
| CycPr | CH₂CN | C(CF₃) |
| CH₂CycPr | CH₂CN | C(CF₃) |
| Me | CO₂CH₃ | C(CF₃) |
| Et | CO₂CH₃ | C(CF₃) |
| Pr | CO₂CH₃ | C(CF₃) |
| CH₂C≡CH | CO₂CH₃ | C(CF₃) |
| CycPr | CO₂CH₃ | C(CF₃) |
| CH₂CycPr | CO₂CH₃ | C(CF₃) |

TABLE 3

| R¹ | R⁵ | G$^x$ |
|---|---|---|
| Me | 6-Chloropyridin-3-ylmethyl | C(CF₃) |
| Et | 6-Chloropyridin-3-ylmethyl | C(CF₃) |
| Pr | 6-Chloropyridin-3-ylmethyl | C(CF₃) |
| CH₂C≡CH | 6-Chloropyridin-3-ylmethyl | C(CF₃) |
| CycPr | 6-Chloropyridin-3-ylmethyl | C(CF₃) |
| CH₂CycPr | 6-Chloropyridin-3-ylmethyl | C(CF₃) |
| Me | 2-Chlorothiazol-5-ylmethyl | C(CF₃) |
| Et | 2-Chlorothiazol-5-ylmethyl | C(CF₃) |
| Pr | 2-Chlorothiazol-5-ylmethyl | C(CF₃) |
| CH₂C≡CH | 2-Chlorothiazol-5-ylmethyl | C(CF₃) |
| CycPr | 2-Chlorothiazol-5-ylmethyl | C(CF₃) |
| CH₂CycPr | 2-Chlorothiazol-5-ylmethyl | C(CF₃) |
| Me | H | C(CF₂CF₃) |
| Et | H | C(CF₂CF₃) |
| Pr | H | C(CF₂CF₃) |
| CH₂C≡CH | H | C(CF₂CF₃) |
| CycPr | H | C(CF₂CF₃) |
| CH₂CycPr | H | C(CF₂CF₃) |
| Me | Me | C(CF₂CF₃) |
| Et | Me | C(CF₂CF₃) |
| Pr | Me | C(CF₂CF₃) |
| CH₂C≡CH | Me | C(CF₂CF₃) |
| CycPr | Me | C(CF₂CF₃) |
| CH₂CycPr | Me | C(CF₂CF₃) |

TABLE 4

| R¹ | R⁵ | G$^x$ |
|---|---|---|
| Me | Et | C(CF₂CF₃) |
| Et | Et | C(CF₂CF₃) |
| Pr | Et | C(CF₂CF₃) |
| CH₂C≡CH | Et | C(CF₂CF₃) |
| CycPr | Et | C(CF₂CF₃) |
| CH₂CycPr | Et | C(CF₂CF₃) |
| Me | CycPr | C(CF₂CF₃) |
| Et | CycPr | C(CF₂CF₃) |
| Pr | CycPr | C(CF₂CF₃) |
| CH₂C≡CH | CycPr | C(CF₂CF₃) |
| CycPr | CycPr | C(CF₂CF₃) |
| CH₂CycPr | CycPr | C(CF₂CF₃) |
| Me | CH₂CycPr | C(CF₂CF₃) |
| Et | CH₂CycPr | C(CF₂CF₃) |
| Pr | CH₂CycPr | C(CF₂CF₃) |
| CH₂C≡CH | CH₂CycPr | C(CF₂CF₃) |
| CycPr | CH₂CycPr | C(CF₂CF₃) |
| CH₂CycPr | CH₂CycPr | C(CF₂CF₃) |
| Me | CH₂C≡CH | C(CF₂CF₃) |
| Et | CH₂C≡CH | C(CF₂CF₃) |
| Pr | CH₂C≡CH | C(CF₂CF₃) |
| CH₂C≡CH | CH₂C≡CH | C(CF₂CF₃) |
| CycPr | CH₂C≡CH | C(CF₂CF₃) |
| CH₂CycPr | CH₂C≡CH | C(CF₂CF₃) |

TABLE 5

| R¹ | R⁵ | G$^x$ |
|---|---|---|
| Me | CH₂CN | C(CF₂CF₃) |
| Et | CH₂CN | C(CF₂CF₃) |
| Pr | CH₂CN | C(CF₂CF₃) |
| CH₂C≡CH | CH₂CN | C(CF₂CF₃) |
| CycPr | CH₂CN | C(CF₂CF₃) |
| CH₂CycPr | CH₂CN | C(CF₂CF₃) |
| Me | CO₂CH₃ | C(CF₂CF₃) |
| Et | CO₂CH₃ | C(CF₂CF₃) |
| Pr | CO₂CH₃ | C(CF₂CF₃) |
| CH₂C≡CH | CO₂CH₃ | C(CF₂CF₃) |
| CycPr | CO₂CH₃ | C(CF₂CF₃) |
| CH₂CycPr | CO₂CH₃ | C(CF₂CF₃) |
| Me | 6-Chloropyridin-3-ylmethyl | C(CF₂CF₃) |
| Et | 6-Chloropyridin-3-ylmethyl | C(CF₂CF₃) |
| Pr | 6-Chloropyridin-3-ylmethyl | C(CF₂CF₃) |
| CH₂C≡CH | 6-Chloropyridin-3-ylmethyl | C(CF₂CF₃) |
| CycPr | 6-Chloropyridin-3-ylmethyl | C(CF₂CF₃) |
| CH₂CycPr | 6-Chloropyridin-3-ylmethyl | C(CF₂CF₃) |
| Me | 2-Chlorothiazol-5-ylmethyl | C(CF₂CF₃) |
| Et | 2-Chlorothiazol-5-ylmethyl | C(CF₂CF₃) |
| Pr | 2-Chlorothiazol-5-ylmethyl | C(CF₂CF₃) |
| CH₂C≡CH | 2-Chlorothiazol-5-ylmethyl | C(CF₂CF₃) |
| CycPr | 2-Chlorothiazol-5-ylmethyl | C(CF₂CF₃) |
| CH₂CycPr | 2-Chlorothiazol-5-ylmethyl | C(CF₂CF₃) |

TABLE 6

| R¹ | R⁵ | G$^x$ |
|---|---|---|
| Me | H | C(OCF₃) |
| Et | H | C(OCF₃) |
| Pr | H | C(OCF₃) |
| CH₂C≡CH | H | C(OCF₃) |
| CycPr | H | C(OCF₃) |
| CH₂CycPr | H | C(OCF₃) |
| Me | Me | C(OCF₃) |
| Et | Me | C(OCF₃) |
| Pr | Me | C(OCF₃) |
| CH₂C≡CH | Me | C(OCF₃) |
| CycPr | Me | C(OCF₃) |
| CH₂CycPr | Me | C(OCF₃) |
| Me | Et | C(OCF₃) |
| Et | Et | C(OCF₃) |
| Pr | Et | C(OCF₃) |
| CH₂C≡CH | Et | C(OCF₃) |
| CycPr | Et | C(OCF₃) |
| CH₂CycPr | Et | C(OCF₃) |
| Me | CycPr | C(OCF₃) |
| Et | CycPr | C(OCF₃) |
| Pr | CycPr | C(OCF₃) |
| CH₂C≡CH | CycPr | C(OCF₃) |
| CycPr | CycPr | C(OCF₃) |
| CH₂CycPr | CycPr | C(OCF₃) |

TABLE 7

| R$^1$ | R$^5$ | G$^x$ |
|---|---|---|
| Me | CH$_2$CycPr | C(OCF$_3$) |
| Et | CH$_2$CycPr | C(OCF$_3$) |
| Pr | CH$_2$CycPr | C(OCF$_3$) |
| CH$_2$C≡CH | CH$_2$CycPr | C(OCF$_3$) |
| CycPr | CH$_2$CycPr | C(OCF$_3$) |
| CH$_2$CycPr | CH$_2$CycPr | C(OCF$_3$) |
| Me | CH$_2$C≡CH | C(OCF$_3$) |
| Et | CH$_2$C≡CH | C(OCF$_3$) |
| Pr | CH$_2$C≡CH | C(OCF$_3$) |
| CH$_2$C≡CH | CH$_2$C≡CH | C(OCF$_3$) |
| CycPr | CH$_2$C≡CH | C(OCF$_3$) |
| CH$_2$CycPr | CH$_2$C≡CH | C(OCF$_3$) |
| Me | CH$_2$CN | C(OCF$_3$) |
| Et | CH$_2$CN | C(OCF$_3$) |
| Pr | CH$_2$CN | C(OCF$_3$) |
| CH$_2$C≡CH | CH$_2$CN | C(OCF$_3$) |
| CycPr | CH$_2$CN | C(OCF$_3$) |
| CH$_2$CycPr | CH$_2$CN | C(OCF$_3$) |
| Me | CO$_2$CH$_3$ | C(OCF$_3$) |
| Et | CO$_2$CH$_3$ | C(OCF$_3$) |
| Pr | CO$_2$CH$_3$ | C(OCF$_3$) |
| CH$_2$C≡CH | CO$_2$CH$_3$ | C(OCF$_3$) |
| CycPr | CO$_2$CH$_3$ | C(OCF$_3$) |
| CH$_2$CycPr | CO$_2$CH$_3$ | C(OCF$_3$) |

TABLE 8

| R$^1$ | R$^5$ | G$^x$ |
|---|---|---|
| Me | 6-Chloropyridin-3-ylmethyl | C(OCF$_3$) |
| Et | 6-Chloropyridin-3-ylmethyl | C(OCF$_3$) |
| Pr | 6-Chloropyridin-3-ylmethyl | C(OCF$_3$) |
| CH$_2$C≡CH | 6-Chloropyridin-3-ylmethyl | C(OCF$_3$) |
| CycPr | 6-Chloropyridin-3-ylmethyl | C(OCF$_3$) |
| CH$_2$CycPr | 6-Chloropyridin-3-ylmethyl | C(OCF$_3$) |
| Me | 2-Chlorothiazol-5-ylmethyl | C(OCF$_3$) |
| Et | 2-Chlorothiazol-5-ylmethyl | C(OCF$_3$) |
| Pr | 2-Chlorothiazol-5-ylmethyl | C(OCF$_3$) |
| CH$_2$C≡CH | 2-Chlorothiazol-5-ylmethyl | C(OCF$_3$) |
| CycPr | 2-Chlorothiazol-5-ylmethyl | C(OCF$_3$) |
| CH$_2$CycPr | 2-Chlorothiazol-5-ylmethyl | C(OCF$_3$) |
| Me | H | C(SCF$_3$) |
| Et | H | C(SCF$_3$) |
| Pr | H | C(SCF$_3$) |
| CH$_2$C≡CH | H | C(SCF$_3$) |
| CycPr | H | C(SCF$_3$) |
| CH$_2$CycPr | H | C(SCF$_3$) |
| Me | Me | C(SCF$_3$) |
| Et | Me | C(SCF$_3$) |
| Pr | Me | C(SCF$_3$) |
| CH$_2$C≡CH | Me | C(SCF$_3$) |
| CycPr | Me | C(SCF$_3$) |
| CH$_2$CycPr | Me | C(SCF$_3$) |

TABLE 9

| R$^1$ | R$^5$ | G$^x$ |
|---|---|---|
| Me | Et | C(SCF$_3$) |
| Et | Et | C(SCF$_3$) |
| Pr | Et | C(SCF$_3$) |
| CH$_2$C≡CH | Et | C(SCF$_3$) |
| CycPr | Et | C(SCF$_3$) |
| CH$_2$CycPr | Et | C(SCF$_3$) |
| Me | CycPr | C(SCF$_3$) |
| Et | CycPr | C(SCF$_3$) |
| Pr | CycPr | C(SCF$_3$) |
| CH$_2$C≡CH | CycPr | C(SCF$_3$) |
| CycPr | CycPr | C(SCF$_3$) |
| CH$_2$CycPr | CycPr | C(SCF$_3$) |
| Me | CH$_2$CycPr | C(SCF$_3$) |
| Et | CH$_2$CycPr | C(SCF$_3$) |
| Pr | CH$_2$CycPr | C(SCF$_3$) |
| CH$_2$C≡CH | CH$_2$CycPr | C(SCF$_3$) |
| CycPr | CH$_2$CycPr | C(SCF$_3$) |
| CH$_2$CycPr | CH$_2$CycPr | C(SCF$_3$) |
| Me | CH$_2$C≡CH | C(SCF$_3$) |
| Et | CH$_2$C≡CH | C(SCF$_3$) |
| Pr | CH$_2$C≡CH | C(SCF$_3$) |
| CH$_2$C≡CH | CH$_2$C≡CH | C(SCF$_3$) |
| CycPr | CH$_2$C≡CH | C(SCF$_3$) |
| CH$_2$CycPr | CH$_2$C≡CH | C(SCF$_3$) |

TABLE 10

| R$^1$ | R$^5$ | G$^x$ |
|---|---|---|
| Me | CH$_2$CN | C(SCF$_3$) |
| Et | CH$_2$CN | C(SCF$_3$) |
| Pr | CH$_2$CN | C(SCF$_3$) |
| CH$_2$C≡CH | CH$_2$CN | C(SCF$_3$) |
| CycPr | CH$_2$CN | C(SCF$_3$) |
| CH$_2$CycPr | CH$_2$CN | C(SCF$_3$) |
| Me | CO$_2$CH$_3$ | C(SCF$_3$) |
| Et | CO$_2$CH$_3$ | C(SCF$_3$) |
| Pr | CO$_2$CH$_3$ | C(SCF$_3$) |
| CH$_2$C≡CH | CO$_2$CH$_3$ | C(SCF$_3$) |
| CycPr | CO$_2$CH$_3$ | C(SCF$_3$) |
| CH$_2$CycPr | CO$_2$CH$_3$ | C(SCF$_3$) |
| Me | 6-Chloropyridin-3-ylmethyl | C(SCF$_3$) |
| Et | 6-Chloropyridin-3-ylmethyl | C(SCF$_3$) |
| Pr | 6-Chloropyridin-3-ylmethyl | C(SCF$_3$) |
| CH$_2$C≡CH | 6-Chloropyridin-3-ylmethyl | C(SCF$_3$) |
| CycPr | 6-Chloropyridin-3-ylmethyl | C(SCF$_3$) |
| CH$_2$CycPr | 6-Chloropyridin-3-ylmethyl | C(SCF$_3$) |
| Me | 2-Chlorothiazol-5-ylmethyl | C(SCF$_3$) |
| Et | 2-Chlorothiazol-5-ylmethyl | C(SCF$_3$) |
| Pr | 2-Chlorothiazol-5-ylmethyl | C(SCF$_3$) |
| CH$_2$C≡CH | 2-Chlorothiazol-5-ylmethyl | C(SCF$_3$) |
| CycPr | 2-Chlorothiazol-5-ylmethyl | C(SCF$_3$) |
| CH$_2$CycPr | 2-Chlorothiazol-5-ylmethyl | C(SCF$_3$) |

TABLE 11

| R$^1$ | R$^5$ | G$^x$ |
|---|---|---|
| Me | H | C[S(O)CF$_3$] |
| Et | H | C[S(O)CF$_3$] |
| Pr | H | C[S(O)CF$_3$] |
| CH$_2$C≡CH | H | C[S(O)CF$_3$] |
| CycPr | H | C[S(O)CF$_3$] |
| CH$_2$CycPr | H | C[S(O)CF$_3$] |
| Me | Me | C[S(O)CF$_3$] |
| Et | Me | C[S(O)CF$_3$] |
| Pr | Me | C[S(O)CF$_3$] |
| CH$_2$C≡CH | Me | C[S(O)CF$_3$] |
| CycPr | Me | C[S(O)CF$_3$] |
| CH$_2$CycPr | Me | C[S(O)CF$_3$] |
| Me | Et | C[S(O)CF$_3$] |
| Et | Et | C[S(O)CF$_3$] |
| Pr | Et | C[S(O)CF$_3$] |
| CH$_2$C≡CH | Et | C[S(O)CF$_3$] |
| CycPr | Et | C[S(O)CF$_3$] |
| CH$_2$CycPr | Et | C[S(O)CF$_3$] |
| Me | CycPr | C[S(O)CF$_3$] |
| Et | CycPr | C[S(O)CF$_3$] |
| Pr | CycPr | C[S(O)CF$_3$] |
| CH$_2$C≡CH | CycPr | C[S(O)CF$_3$] |
| CycPr | CycPr | C[S(O)CF$_3$] |
| CH$_2$CycPr | CycPr | C[S(O)CF$_3$] |

TABLE 12

| $R^1$ | $R^5$ | $G^x$ |
|---|---|---|
| Me | $CH_2CycPr$ | $C[S(O)CF_3]$ |
| Et | $CH_2CycPr$ | $C[S(O)CF_3]$ |
| Pr | $CH_2CycPr$ | $C[S(O)CF_3]$ |
| $CH_2C\equiv CH$ | $CH_2CycPr$ | $C[S(O)CF_3]$ |
| CycPr | $CH_2CycPr$ | $C[S(O)CF_3]$ |
| $CH_2CycPr$ | $CH_2CycPr$ | $C[S(O)CF_3]$ |
| Me | $CH_2C\equiv CH$ | $C[S(O)CF_3]$ |
| Et | $CH_2C\equiv CH$ | $C[S(O)CF_3]$ |
| Pr | $CH_2C\equiv CH$ | $C[S(O)CF_3]$ |
| $CH_2C\equiv CH$ | $CH_2C\equiv CH$ | $C[S(O)CF_3]$ |
| CycPr | $CH_2C\equiv CH$ | $C[S(O)CF_3]$ |
| $CH_2CycPr$ | $CH_2C\equiv CH$ | $C[S(O)CF_3]$ |
| Me | $CH_2CN$ | $C[S(O)CF_3]$ |
| Et | $CH_2CN$ | $C[S(O)CF_3]$ |
| Pr | $CH_2CN$ | $C[S(O)CF_3]$ |
| $CH_2C\equiv CH$ | $CH_2CN$ | $C[S(O)CF_3]$ |
| CycPr | $CH_2CN$ | $C[S(O)CF_3]$ |
| $CH_2CycPr$ | $CH_2CN$ | $C[S(O)CF_3]$ |
| Me | $CO_2CH_3$ | $C[S(O)CF_3]$ |
| Et | $CO_2CH_3$ | $C[S(O)CF_3]$ |
| Pr | $CO_2CH_3$ | $C[S(O)CF_3]$ |
| $CH_2C\equiv CH$ | $CO_2CH_3$ | $C[S(O)CF_3]$ |
| CycPr | $CO_2CH_3$ | $C[S(O)CF_3]$ |
| $CH_2CycPr$ | $CO_2CH_3$ | $C[S(O)CF_3]$ |

TABLE 13

| $R^1$ | $R^5$ | $G^x$ |
|---|---|---|
| Me | 6-Chloropyridin-3-ylmethyl | $C[S(O)CF_3]$ |
| Et | 6-Chloropyridin-3-ylmethyl | $C[S(O)CF_3]$ |
| Pr | 6-Chloropyridin-3-ylmethyl | $C[S(O)CF_3]$ |
| $CH_2C\equiv CH$ | 6-Chloropyridin-3-ylmethyl | $C[S(O)CF_3]$ |
| CycPr | 6-Chloropyridin-3-ylmethyl | $C[S(O)CF_3]$ |
| $CH_2CycPr$ | 6-Chloropyridin-3-ylmethyl | $C[S(O)CF_3]$ |
| Me | 2-Chlorothiazol-5-ylmethyl | $C[S(O)CF_3]$ |
| Et | 2-Chlorothiazol-5-ylmethyl | $C[S(O)CF_3]$ |
| Pr | 2-Chlorothiazol-5-ylmethyl | $C[S(O)CF_3]$ |
| $CH_2C\equiv CH$ | 2-Chlorothiazol-5-ylmethyl | $C[S(O)CF_3]$ |
| CycPr | 2-Chlorothiazol-5-ylmethyl | $C[S(O)CF_3]$ |
| $CH_2CycPr$ | 2-Chlorothiazol-5-ylmethyl | $C[S(O)CF_3]$ |
| Me | H | $C[S(O)_2CF_3]$ |
| Et | H | $C[S(O)_2CF_3]$ |
| Pr | H | $C[S(O)_2CF_3]$ |
| $CH_2C\equiv CH$ | H | $C[S(O)_2CF_3]$ |
| CycPr | H | $C[S(O)_2CF_3]$ |
| $CH_2CycPr$ | H | $C[S(O)_2CF_3]$ |
| Me | Me | $C[S(O)_2CF_3]$ |
| Et | Me | $C[S(O)_2CF_3]$ |
| Pr | Me | $C[S(O)_2CF_3]$ |
| $CH_2C\equiv CH$ | Me | $C[S(O)_2CF_3]$ |
| CycPr | Me | $C[S(O)_2CF_3]$ |
| $CH_2CycPr$ | Me | $C[S(O)_2CF_3]$ |

TABLE 14

| $R^1$ | $R^5$ | $G^x$ |
|---|---|---|
| Me | Et | $C[S(O)_2CF_3]$ |
| Et | Et | $C[S(O)_2CF_3]$ |
| Pr | Et | $C[S(O)_2CF_3]$ |
| $CH_2C\equiv CH$ | Et | $C[S(O)_2CF_3]$ |
| CycPr | Et | $C[S(O)_2CF_3]$ |
| $CH_2CycPr$ | Et | $C[S(O)_2CF_3]$ |
| Me | CycPr | $C[S(O)_2CF_3]$ |
| Et | CycPr | $C[S(O)_2CF_3]$ |
| Pr | CycPr | $C[S(O)_2CF_3]$ |
| $CH_2C\equiv CH$ | CycPr | $C[S(O)_2CF_3]$ |
| CycPr | CycPr | $C[S(O)_2CF_3]$ |
| $CH_2CycPr$ | CycPr | $C[S(O)_2CF_3]$ |
| Me | $CH_2CycPr$ | $C[S(O)_2CF_3]$ |
| Et | $CH_2CycPr$ | $C[S(O)_2CF_3]$ |
| Pr | $CH_2CycPr$ | $C[S(O)_2CF_3]$ |
| $CH_2C\equiv CH$ | $CH_2CycPr$ | $C[S(O)_2CF_3]$ |
| CycPr | $CH_2CycPr$ | $C[S(O)_2CF_3]$ |
| $CH_2CycPr$ | $CH_2CycPr$ | $C[S(O)_2CF_3]$ |
| Me | $CH_2C\equiv CH$ | $C[S(O)_2CF_3]$ |
| Et | $CH_2C\equiv CH$ | $C[S(O)_2CF_3]$ |
| Pr | $CH_2C\equiv CH$ | $C[S(O)_2CF_3]$ |
| $CH_2C\equiv CH$ | $CH_2C\equiv CH$ | $C[S(O)_2CF_3]$ |
| CycPr | $CH_2C\equiv CH$ | $C[S(O)_2CF_3]$ |
| $CH_2CycPr$ | $CH_2C\equiv CH$ | $C[S(O)_2CF_3]$ |

TABLE 15

| $R^1$ | $R^5$ | $G^x$ |
|---|---|---|
| Me | $CH_2CN$ | $C[S(O)_2CF_3]$ |
| Et | $CH_2CN$ | $C[S(O)_2CF_3]$ |
| Pr | $CH_2CN$ | $C[S(O)_2CF_3]$ |
| $CH_2C\equiv CH$ | $CH_2CN$ | $C[S(O)_2CF_3]$ |
| CycPr | $CH_2CN$ | $C[S(O)_2CF_3]$ |
| $CH_2CycPr$ | $CH_2CN$ | $C[S(O)_2CF_3]$ |
| Me | $CO_2CH_3$ | $C[S(O)_2CF_3]$ |
| Et | $CO_2CH_3$ | $C[S(O)_2CF_3]$ |
| Pr | $CO_2CH_3$ | $C[S(O)_2CF_3]$ |
| $CH_2C\equiv CH$ | $CO_2CH_3$ | $C[S(O)_2CF_3]$ |
| CycPr | $CO_2CH_3$ | $C[S(O)_2CF_3]$ |
| $CH_2CycPr$ | $CO_2CH_3$ | $C[S(O)_2CF_3]$ |
| Me | 6-Chloropyridin-3-ylmethyl | $C[S(O)_2CF_3]$ |
| Et | 6-Chloropyridin-3-ylmethyl | $C[S(O)_2CF_3]$ |
| Pr | 6-Chloropyridin-3-ylmethyl | $C[S(O)_2CF_3]$ |
| $CH_2C\equiv CH$ | 6-Chloropyridin-3-ylmethyl | $C[S(O)_2CF_3]$ |
| CycPr | 6-Chloropyridin-3-ylmethyl | $C[S(O)_2CF_3]$ |
| $CH_2CycPr$ | 6-Chloropyridin-3-ylmethyl | $C[S(O)_2CF_3]$ |
| Me | 2-Chlorothiazol-5-ylmethyl | $C[S(O)_2CF_3]$ |
| Et | 2-Chlorothiazol-5-ylmethyl | $C[S(O)_2CF_3]$ |
| Pr | 2-Chlorothiazol-5-ylmethyl | $C[S(O)_2CF_3]$ |
| $CH_2C\equiv CH$ | 2-Chlorothiazol-5-ylmethyl | $C[S(O)_2CF_3]$ |
| CycPr | 2-Chlorothiazol-5-ylmethyl | $C[S(O)_2CF_3]$ |
| $CH_2CycPr$ | 2-Chlorothiazol-5-ylmethyl | $C[S(O)_2CF_3]$ |

(In [Table 1] to [Table 15] above, Me represents a methyl group, Et represents an ethyl group, Pr represents a n-propyl group, and CycPr represents a cyclopropyl group.)

In the formula (1), n is 1, $R^2$, $R^3$ and $R^4$ are a hydrogen atom, $G^1$, $G^2$, $G^4$ and $G^5$ are CH, Q is an oxygen atom, and $R^1$, $R^5$ and $G^3$ are the combinations shown in $R^1$, $R^5$ and $G^X$ in [Table 1] to [Table 15].

In the formula (1), n is 2, $R^2$, $R^3$ and $R^4$ are a hydrogen atom, $G^1$, $G^2$, $G^4$ and $G^5$ are CH, Q is an oxygen atom, and $R^1$, $R^5$ and $G^3$ are the combinations shown in $R^1$, $R^5$ and $G^X$ in [Table 1] to [Table 15].

In the formula (1), n is 0, $R^2$, $R^3$ and $R^4$ are a hydrogen atom, $G^1$, $G^2$, $G^4$ and $G^5$ are CH, Q is a sulfur atom, and $R^1$, $R^5$ and $G^3$ are the combinations shown in $R^1$, $R^5$ and $G^X$ in [Table 1] to [Table 15].

In the formula (1), n is 1, $R^2$, $R^3$ and $R^4$ are a hydrogen atom, $G^1$, $G^2$, $G^4$ and $G^5$ are CH, Q is a sulfur atom, and $R^1$, $R^5$ and $G^3$ are the combinations shown in $R^1$, $R^5$ and $G^X$ in [Table 1] to [Table 15].

In the formula (1), n is 2, $R^2$, $R^3$ and $R^4$ are a hydrogen atom, $G^1$, $G^2$, $G^4$ and $G^5$ are CH, Q is a sulfur atom, and $R^1$, $R^5$ and $G^3$ are the combinations shown in $R^1$, $R^5$ and $G^X$ in [Table 1] to [Table 15].

In the formula (1), n is 0, $R^2$ and $R^4$ are a hydrogen atom, $R^3$ is a trifluoromethyl group, $G^1$, $G^2$, $G^4$ and $G^5$ are CH, Q is an oxygen atom, and $R^1$, $R^5$ and $G^3$ are the combinations shown in $R^1$, $R^5$ and $G^X$ in [Table 1] to [Table 15].

In the formula (1), n is 1, $R^2$ and $R^4$ are a hydrogen atom, $R^3$ is a trifluoromethyl group, $G^1$, $G^2$, $G^4$ and $G^5$ are CH, Q is an oxygen atom, and $R^1$, $R^5$ and $G^3$ are the combinations shown in $R^1$, $R^5$ and $G^X$ in [Table 1] to [Table 15].

In the formula (1), n is 2, $R^2$ and $R^4$ are a hydrogen atom, $R^3$ is a trifluoromethyl group, $G^1$, $G^2$, $G^4$ and $G^5$ are CH, Q is an oxygen atom, and $R^1$, $R^5$ and $G^3$ are the combinations shown in $R^1$, $R^5$ and $G^X$ in [Table 1] to [Table 15].

In the formula (1), n is 0, $R^2$ and $R^4$ are a hydrogen atom, $R^3$ is a chlorine atom, $G^1$, $G^2$, $G^4$ and $G^5$ are CH, Q is an oxygen atom, and $R^1$, $R^5$ and $G^3$ are the combinations shown in $R^1$, $R^5$ and $G^X$ in [Table 1] to [Table 15].

In the formula (1), n is 1, $R^2$ and $R^4$ are a hydrogen atom, $R^3$ is a chlorine atom, $G^1$, $G^2$, $G^4$ and $G^5$ are CH, Q is an oxygen atom, and $R^1$, $R^5$ and $G^3$ are the combinations shown in $R^1$, $R^5$ and $G^X$ in [Table 1] to [Table 15].

In the formula (1), n is 2, $R^2$ and $R^4$ are a hydrogen atom, $R^3$ is a chlorine atom, $G^1$, $G^2$, $G^4$ and $G^5$ are CH, Q is an oxygen atom, and $R^1$, $R^5$ and $G^3$ are the combinations shown in $R^1$, $R^5$ and $G^X$ in [Table 1] to [Table 15].

In the formula (1), n is 0, $R^2$ and $R^4$ are a hydrogen atom, $R^3$ is an ethoxycarbonyl group, $G^1$, $G^2$, $G^4$ and $G^5$ are CH, Q is an oxygen atom, and $R^1$, $R^5$ and $G^3$ are the combinations shown in $R^1$, $R^5$ and $G^X$ in [Table 1] to [Table 15].

In the formula (1), n is 1, $R^2$ and $R^4$ are a hydrogen atom, $R^3$ is an ethoxycarbonyl group, $G^1$, $G^2$, $G^4$ and $G^5$ are CH, Q is an oxygen atom, and $R^1$, $R^5$ and $G^3$ are the combinations shown in $R^1$, $R^5$ and $G^X$ in [Table 1] to [Table 15].

In the formula (1), n is 2, $R^2$ and $R^4$ are a hydrogen atom, $R^3$ is an ethoxycarbonyl group, $G^1$, $G^2$, $G^4$ and $G^5$ are CH, Q is an oxygen atom, and $R^1$, $R^5$ and $G^3$ are the combinations shown in $R^1$, $R^5$ and $G^X$ in [Table 1] to [Table 15].

In the formula (1), n is 0, $R^2$ and $R^4$ are a hydrogen atom, $R^3$ is a methoxycarbonylamino group, $G^1$, $G^2$, $G^4$ and $G^5$ are CH, Q is an oxygen atom, and $R^1$, $R^5$ and $G^3$ are the combinations shown in $R^1$, $R^5$ and $G^X$ in [Table 1] to [Table 15].

In the formula (1), n is 1, $R^2$ and $R^4$ are a hydrogen atom, $R^3$ is a methoxycarbonylamino group, $G^1$, $G^2$, $G^4$ and $G^5$ are CH, Q is an oxygen atom, and $R^1$, $R^5$ and $G^3$ are the combinations shown in $R^1$, $R^5$ and $G^X$ in [Table 1] to [Table 15].

In the formula (1), n is 2, $R^2$ and $R^4$ are a hydrogen atom, $R^3$ is a methoxycarbonylamino group, $G^1$, $G^2$, $G^4$ and $G^5$ are CH, Q is an oxygen atom, and $R^1$, $R^5$ and $G^3$ are the combinations shown in $R^1$, $R^5$ and $G^X$ in [Table 1] to [Table 15].

In the formula (1), n is 0, $R^2$ and $R^4$ are a hydrogen atom, $R^3$ is a phenyl group, $G^1$, $G^2$, $G^4$ and $G^5$ are CH, Q is an oxygen atom, and $R^1$, $R^5$ and $G^3$ are the combinations shown in $R^1$, $R^5$ and $G^X$ in [Table 1] to [Table 15].

In the formula (1), n is 1, $R^2$ and $R^4$ are a hydrogen atom, $R^3$ is a phenyl group, $G^1$, $G^2$, $G^4$ and $G^5$ are CH, Q is an oxygen atom, and $R^1$, $R^5$ and $G^3$ are the combinations shown in $R^1$, $R^5$ and $G^X$ in [Table 1] to [Table 15].

In the formula (1), n is 2, $R^2$ and $R^4$ are a hydrogen atom, $R^3$ is a phenyl group, $G^1$, $G^2$, $G^4$ and $G^5$ are CH, Q is an oxygen atom, and $R^1$, $R^5$ and $G^3$ are the combinations shown in $R^1$, $R^5$ and $G^X$ in [Table 1] to [Table 15].

In the formula (1), n is 0, $R^2$, $R^3$ and $R^4$ are a hydrogen atom, $G^1$ is a nitrogen atom, $G^2$, $G^4$ and $G^5$ are CH, Q is an oxygen atom, and $R^1$, $R^5$ and $G^3$ are the combinations shown in $R^1$, $R^5$ and $G^X$ in [Table 1] to [Table 15].

In the formula (1), n is 1, $R^2$, $R^3$ and $R^4$ are a hydrogen atom, $G^1$ is a nitrogen atom, $G^2$, $G^4$ and $G^5$ are CH, Q is an oxygen atom, and $R^1$, $R^5$ and $G^3$ are the combinations shown in $R^1$, $R^5$ and $G^X$ in [Table 1] to [Table 15].

In the formula (1), n is 2, $R^2$, $R^3$ and $R^4$ are a hydrogen atom, $G^1$ is a nitrogen atom, $G^2$, $G^4$ and $G^5$ are CH, Q is an oxygen atom, and $R^1$, $R^5$ and $G^3$ are the combinations shown in $R^1$, $R^5$ and $G^X$ in [Table 1] to [Table 15].

In the formula (1), n is 0, $R^2$, $R^3$ and $R^4$ are a hydrogen atom, $G^1$ is a nitrogen atom, $G^2$, $G^4$ and $G^5$ are CH, Q is a sulfur atom, and $R^1$, $R^5$ and $G^3$ are the combinations shown in $R^1$, $R^5$ and $G^X$ in [Table 1] to [Table 15].

In the formula (1), n is 1, $R^2$, $R^3$ and $R^4$ are a hydrogen atom, $G^1$ is a nitrogen atom, $G^2$, $G^4$ and $G^5$ are CH, Q is a sulfur atom, and $R^1$, $R^5$ and $G^3$ are the combinations shown in $R^1$, $R^5$ and $G^X$ in [Table 1] to [Table 15].

In the formula (1), n is 2, $R^2$, $R^3$ and $R^4$ are a hydrogen atom, $G^1$ is a nitrogen atom, $G^2$, $G^4$ and $G^5$ are CH, Q is a sulfur atom, and $R^1$, $R^5$ and $G^3$ are the combinations shown in $R^1$, $R^5$ and $G^X$ in [Table 1] to [Table 15].

In the formula (1), n is 0, $R^2$ and $R^4$ are a hydrogen atom, $R^3$ is a trifluoromethyl group, $G^1$ is a nitrogen atom, $G^2$, $G^4$ and $G^5$ are CH, Q is an oxygen atom, and $R^1$, $R^5$ and $G^3$ are the combinations shown in $R^1$, $R^5$ and $G^X$ in [Table 1] to [Table 15].

In the formula (1), n is 1, $R^2$ and $R^4$ are a hydrogen atom, $R^3$ is a trifluoromethyl group, $G^1$ is a nitrogen atom, $G^2$, $G^4$ and $G^5$ are CH, Q is an oxygen atom, and $R^1$, $R^5$ and $G^3$ are the combinations shown in $R^1$, $R^5$ and $G^X$ in [Table 1] to [Table 15].

In the formula (1), n is 2, $R^2$ and $R^4$ are a hydrogen atom, $R^3$ is a trifluoromethyl group, $G^1$ is a nitrogen atom, $G^2$, $G^4$ and $G^5$ are CH, Q is an oxygen atom, and $R^1$, $R^5$ and $G^3$ are the combinations shown in $R^1$, $R^5$ and $G^X$ in [Table 1] to [Table 15].

In the formula (1), n is 0, $R^2$ and $R^4$ are a hydrogen atom, $R^3$ is a chlorine atom, $G^1$ is a nitrogen atom, $G^2$, $G^4$ and $G^5$ are CH, Q is an oxygen atom, and $R^1$, $R^5$ and $G^3$ are the combinations shown in $R^1$, $R^5$ and $G^X$ in [Table 1] to [Table 15].

In the formula (1), n is 1, $R^2$ and $R^4$ are a hydrogen atom, $R^3$ is a chlorine atom, $G^1$ is a nitrogen atom, $G^2$, $G^4$ and $G^5$ are CH, Q is an oxygen atom, and $R^1$, $R^5$ and $G^3$ are the combinations shown in $R^1$, $R^5$ and $G^X$ in [Table 1] to [Table 15].

In the formula (1), n is 2, $R^2$ and $R^4$ are a hydrogen atom, $R^3$ is a chlorine atom, $G^1$ is a nitrogen atom, $G^2$, $G^4$ and $G^5$ are CH, Q is an oxygen atom, and $R^1$, $R^5$ and $G^3$ are the combinations shown in $R^1$, $R^5$ and $G^X$ in [Table 1] to [Table 15].

In the formula (1), n is 0, $R^2$ and $R^4$ are a hydrogen atom, $R^3$ is an ethoxycarbonyl group, $G^1$ is a nitrogen atom, $G^2$, $G^4$ and $G^5$ are CH, Q is an oxygen atom, and $R^1$, $R^5$ and $G^3$ are the combinations shown in $R^1$, $R^5$ and $G^X$ in [Table 1] to [Table 15].

In the formula (1), n is 1, $R^2$ and $R^4$ are a hydrogen atom, $R^3$ is an ethoxycarbonyl group, $G^1$ is a nitrogen atom, $G^2$, $G^4$ and $G^5$ are CH, Q is an oxygen atom, and $R^1$, $R^5$ and $G^3$ are the combinations shown in $R^1$, $R^5$ and $G^X$ in [Table 1] to [Table 15].

In the formula (1), n is 2, $R^2$ and $R^4$ are a hydrogen atom, $R^3$ is an ethoxycarbonyl group, $G^1$ is a nitrogen atom, $G^2$, $G^4$ and $G^5$ are CH, Q is an oxygen atom, and $R^1$, $R^5$ and $G^3$ are the combinations shown in $R^1$, $R^5$ and $G^X$ in [Table 1] to [Table 15].

In the formula (1), n is 0, $R^2$ and $R^4$ are a hydrogen atom, $R^3$ is a methoxycarbonylamino group, $G^1$ is a nitrogen atom, $G^2$, $G^4$ and $G^5$ are CH, Q is an oxygen atom, and $R^1$, $R^5$ and $G^3$ are the combinations shown in $R^1$, $R^5$ and $G^X$ in [Table 1] to [Table 15].

In the formula (1), n is 1, $R^2$ and $R^4$ are a hydrogen atom, $R^3$ is a methoxycarbonylamino group, $G^1$ is a nitrogen atom, $G^2$, $G^4$ and $G^5$ are CH, Q is an oxygen atom, and $R^1$, $R^5$ and $G^3$ are the combinations shown in $R^1$, $R^5$ and $G^X$ in [Table 1] to [Table 15].

In the formula (1), n is 2, $R^2$ and $R^4$ are a hydrogen atom, $R^3$ is a methoxycarbonylamino group, $G^1$ is a nitrogen atom, $G^2$, $G^4$ and $G^5$ are CH, Q is an oxygen atom, and $R^1$, $R^5$ and $G^3$ are the combinations shown in $R^1$, $R^5$ and $G^X$ in [Table 1] to [Table 15].

In the formula (1), n is 0, $R^2$ and $R^4$ are a hydrogen atom, $R^3$ is a phenyl group, $G^1$ is a nitrogen atom, $G^2$, $G^4$ and $G^5$ are CH, Q is an oxygen atom, and $R^1$, $R^5$ and $G^3$ are the combinations shown in $R^1$, $R^5$ and $G^X$ in [Table 1] to [Table 15].

In the formula (1), n is 1, $R^2$ and $R^4$ are a hydrogen atom, $R^3$ is a phenyl group, $G^1$ is a nitrogen atom, $G^2$, $G^4$ and $G^5$ are CH, Q is an oxygen atom, and $R^1$, $R^5$ and $G^3$ are the combinations shown in $R^1$, $R^5$ and $G^X$ in [Table 1] to [Table 15].

In the formula (1), n is 2, $R^2$ and $R^4$ are a hydrogen atom, $R^3$ is a phenyl group, $G^1$ is a nitrogen atom, $G^2$, $G^4$ and $G^5$ are CH, Q is an oxygen atom, and $R^1$, $R^5$ and $G^3$ are the combinations shown in $R^1$, $R^5$ and $G^X$ in [Table 1] to [Table 15].

In the formula (1), n is 0, $R^2$, $R^3$ and $R^4$ are a hydrogen atom, $G^2$ is a nitrogen atom, $G^1$, $G^4$ and $G^5$ are CH, Q is an oxygen atom, and $R^1$, $R^5$ and $G^3$ are the combinations shown in $R^1$, $R^5$ and $G^X$ in [Table 1] to [Table 15].

In the formula (1), n is 1, $R^2$, $R^3$ and $R^4$ are a hydrogen atom, $G^2$ is a nitrogen atom, $G^1$, $G^4$ and $G^5$ are CH, Q is an oxygen atom, and $R^1$, $R^5$ and $G^3$ are the combinations shown in $R^1$, $R^5$ and $G^X$ in [Table 1] to [Table 15].

In the formula (1), n is 2, $R^2$, $R^3$ and $R^4$ are a hydrogen atom, $G^2$ is a nitrogen atom, $G^1$, $G^4$ and $G^5$ are CH, Q is an oxygen atom, and $R^1$, $R^5$ and $G^3$ are the combinations shown in $R^1$, $R^5$ and $G^X$ in [Table 1] to [Table 15].

In the formula (1), n is 0, $R^2$, $R^3$ and $R^4$ are a hydrogen atom, $G^2$ is a nitrogen atom, $G^1$, $G^4$ and $G^5$ are CH, Q is a sulfur atom, and $R^1$, $R^5$ and $G^3$ are the combinations shown in $R^1$, $R^5$ and $G^X$ in [Table 1] to [Table 15].

In the formula (1), n is 1, $R^2$, $R^3$ and $R^4$ are a hydrogen atom, $G^2$ is a nitrogen atom, $G^1$, $G^4$ and $G^5$ are CH, Q is a sulfur atom, and $R^1$, $R^5$ and $G^3$ are the combinations shown in $R^1$, $R^5$ and $G^X$ in [Table 1] to [Table 15].

In the formula (1), n is 2, $R^2$, $R^3$ and $R^4$ are a hydrogen atom, $G^2$ is a nitrogen atom, $G^1$, $G^4$ and $G^5$ are CH, Q is a sulfur atom, and $R^1$, $R^5$ and $G^3$ are the combinations shown in $R^1$, $R^5$ and $G^X$ in [Table 1] to [Table 15].

In the formula (1), n is 0, $R^2$ and $R^4$ are a hydrogen atom, $R^3$ is a trifluoromethyl group, $G^2$ is a nitrogen atom, $G^1$, $G^4$ and $G^5$ are CH, Q is an oxygen atom, and $R^1$, $R^5$ and $G^3$ are the combinations shown in $R^1$, $R^5$ and $G^X$ in [Table 1] to [Table 15].

In the formula (1), n is 1, $R^2$ and $R^4$ are a hydrogen atom, $R^3$ is a trifluoromethyl group, $G^2$ is a nitrogen atom, $G^1$, $G^4$ and $G^5$ are CH, Q is an oxygen atom, and $R^1$, $R^5$ and $G^3$ are the combinations shown in $R^1$, $R^5$ and $G^X$ in [Table 1] to [Table 15].

In the formula (1), n is 2, $R^2$ and $R^4$ are a hydrogen atom, $R^3$ is a trifluoromethyl group, $G^2$ is a nitrogen atom, $G^1$, $G^4$ and $G^5$ are CH, Q is an oxygen atom, and $R^1$, $R^5$ and $G^3$ are the combinations shown in $R^1$, $R^5$ and $G^X$ in [Table 1] to [Table 15].

In the formula (1), n is 0, $R^2$, $R^3$ and $R^4$ are a hydrogen atom, $G^1$, $G^3$ and $G^5$ are CH, Q is an oxygen atom, and $R^1$, $R^5$, $G^2$ and $G^4$ are the combinations shown in $R^1$, $R^5$ and $G^X$ in [Table 1] to [Table 15](wherein $G^2$ and $G^4$ represent the combinations shown in $G^X$ at the same time).

In the formula (1), n is 1, $R^2$, $R^3$ and $R^4$ are a hydrogen atom, $G^1$, $G^3$ and $G^5$ are CH, Q is an oxygen atom, and $R^1$, $R^5$, $G^2$ and $G^4$ are the combinations shown in $R^1$, $R^5$ and $G^X$ in [Table 1] to [Table 15](wherein $G^2$ and $G^4$ represent the combinations shown in $G^X$ at the same time).

In the formula (1), n is 2, $R^2$, $R^3$ and $R^4$ are a hydrogen atom, $G^1$, $G^3$ and $G^5$ are CH, Q is an oxygen atom, and $R^1$, $R^5$, $G^2$ and $G^4$ are the combinations shown in $R^1$, $R^5$ and $G^X$ in [Table 1] to [Table 15](wherein $G^2$ and $G^4$ represent the combinations shown in $G^X$ at the same time).

In the formula (1), n is 0, $R^2$ and $R^4$ are a hydrogen atom, $R^3$ is a trifluoromethyl group, $G^1$, $G^3$ and $G^5$ are CH, Q is an oxygen atom, and $R^1$, $R^5$, $G^2$ and $G^4$ are the combinations shown in $R^1$, $R^5$ and $G^X$ in [Table 1] to [Table 15](wherein $G^2$ and $G^4$ represent the combinations shown in $G^X$ at the same time).

In the formula (1), n is 1, $R^2$ and $R^4$ are a hydrogen atom, $R^3$ is a trifluoromethyl group, $G^1$, $G^3$ and $G^5$ are CH, Q is an oxygen atom, and $R^1$, $R^5$, $G^2$ and $G^4$ are the combinations shown in $R^1$, $R^5$ and $G^X$ in [Table 1] to [Table 15](wherein $G^2$ and $G^4$ represent the combinations shown in $G^X$ at the same time).

In the formula (1), n is 2, $R^2$ and $R^4$ are a hydrogen atom, $R^3$ is a trifluoromethyl group, $G^1$, $G^3$ and $G^5$ are CH, Q is an oxygen atom, and $R^1$, $R^5$, $G^2$ and $G^4$ are the combinations shown in $R^1$, $R^5$ and $G^X$ in [Table 1] to [Table 15](wherein $G^2$ and $G^4$ represent the combinations shown in $G^X$ at the same time).

Examples of the pest on which the compound of the present invention has an effect include arthropod pests such as pest insects and pest mites and nematoda. Specifically, examples of the pests include those shown below.

Hemiptera: Delphacidae such as *Laodelphax striatellus*, *Nilaparvata lugens*, and *Sogatella furcifera*, Deltocephalidae such as *Nephotettix cincticeps*, *Nephotettix virescens*, and *Empoasca onukii*, Aphididae such as *Aphis gossypii*, *Myzus persicae*, *Brevicoryne brassicae*, *Aphis spiraecola*, *Macrosiphum euphorbiae*, *Aulacorthum solani*, *Rhopalosiphum padi*, *Toxoptera citricidus*, and *Hyalopterus pruni*, Pentatomidae such as *Nezara antennata*, *Eysarcoris parvus*, and *Halyomorpha mista*, Alydidae such as *Riptortus clavetus* and *Leptocorisa chinensis*, Miridae such as *Trigonotylus caelestialium* and *Stenotus rubrovittatus*, Aleyrodidae such as *Trialeurodes vaporariorum*, *Bemisia tabaci*, *Dialeurodes citri*, and *Aleurocanthus spiniferus*, Coccidae such as *Aonidiella aurantii*, *Comstockaspis perniciosa*, *Unaspis citri*, *Ceroplastes rubens*, *Icerya purchasi*, *Planococcus kraunhiae*, *Pseudococcus longispinis*, and *Pseudaulacaspis pentagona*, Psyllidae such as *Diaphorina citri*, *Psylla pyrisuga* and *Bactericerca cockerelli*, Tingidae such as *Stephanitis nasi*, and Cimicoidea such as *Cimex lectularius*.

Lepidoptera: Pyralidae such as *Chilo suppressalis*, *Tryporyza incertulas*, *Cnaphalocrocis medinalis*, *Notarcha derogata*, *Plodia interpunctella*, *Ostrinia furnacalis*, *Hellula undalis*, and *Pediasia teterrellus*, Noctuidae such as *Spodoptera litura*, *Spodoptera exigua*, *Pseudaletia separata*, *Mamestra brassicae*, *Agrotis ipsilon*, *Plusia nigrisigna*, *Trichoplusia* spp., *Heliothis* spp., and *Helicoverpa* spp., Pieridae such as *Pieris rapae*, *Adoxophyes* spp., Tortricidae such as *Grapholita molesta*, *Leguminivora glycinivorella*, *Matsumuraeses azukivora*, *Adoxophyes orana fasciata*, *Adoxophyes honmai.*, *Homona magnanima*, *Archips fuscocupreanus*, and *Cydia pomonella*, Gracillariidae such as *Caloptilia theivora* and *Phyllonorycter ringoneella*, Carposimidae such as *Carposina niponensis*, Lyonetiidae such as *Lyonetia* spp., Lymantriidae such as *Lymantria* spp. and *Euproctis* spp., Yponomeutidae such as *Plutella xylostella*, Gelechiidae such as *Pectinophora gossypiella* and *Phthorimaea operculella*, Arctiidae such as *Hyphantria cunea*, and Tineidae such as *Tinea translucens* and *Tineola bisselliella*.

Thysanoptera: Thripidae such as *Frankliniella occidentalis*, *Thrips parmi*, *Scirtothrips dorsalis*, *Thrips tabaci*, and *Frankliniella intonsa*.

Diptera: Culex such as *Culex pipiens pallens*, *Culex tritaeniorhynchus*, and *Culex quinquefasciatus*, *Aedes* spp. such as

*Aedes aegypti* and *Aedes albopictus*, *Anopheles* spp. such as *Anopheles sinensis*, Chironomidae, Muscidae such as *Musca domestica* and *Muscina stabulans*, Calliphoridae, Sarcophagidae, Fanniidae, Anthomyiidae such as *Delia platura* and *Delia antiqua*, Agromyzidae such as *Agromyza oryzae*, *Hydrellia griseola*, *Liriomyza sativae*, *Liriomyza trifolii*, and *Chromatomyia horticola*, Chloropidae such as *Chlorops oryzae*, Tephritidae such as *Dacus cucurbitae* and *Ceratitis capitata*, Drosophilidae, Phoridae such as *Megaselia spiracularis*, Psychodidae such as *Clogmia albipunctata*, Sciaridae, Simuliidae, Tabanidae such as *Tabanus trigonus*, Stomoxys, and Stomoxyidae.

Coleoptera: *Diabrotica virgifera virgifera* and *Diabrotica undecimpunctata howardi*, Chrysomelidae such as *Oulema oryzae*, *Aulacophora femoralis*, *Phyllotreta striolata*, and *Leptinotarsa decemlineata*, Scarabaeidae such as *Anomala cuprea*, *Anomala rufocuprea*, and *Popillia japonica*, Echinocnemus squameus such as *Sitophilus zeamais*, *Echinocnemus squameus*, *Lissorhoptrus oryzophilus*, and *Sphenophorus venatus*, Curculionidae such as *Anthonomus grandis*, Bruchidae such as *Callosobruchuys chienensis*, Tenebrionidae such as *Tenebrio molitor* and *Tribolium castaneum*, Dermestidae such as *Anthrenus verbasci* and *Dermestes maculates*, Anobiidae such as *Lasioderma serricorne*, Epilachna such as *Epilachna vigintioctopunctata*, Lyctidae such as *Lyctus brunneus* and *Tomicus piniperda*, Bostrychidae, Ptinidae, Cerambycidae such as *Anoplophora malasiaca*, *Agriotes* spp. such as *Agriotes ogurae fuscicollis*, and Staphylimidae such as *Paederus fuscipes*.

Orthoptera: *Locusta migratoria*, *Gryllotalpa africana*, *Oxya yezoensis*, *Oxya japonica*, and *Grylloidea*.

Siphonaptera: *Ctenocephalides felis*, *Ctenocephalides canis*, *Pulex irritans*, *Xenopsylla cheopis*, and the like.

Anoplura: *Pediculus humanus corporis*, *Pediculus humanus humanus*, *Phthirus pubis*, *Haematopinus eurysternus*, *Dalmalinia ovis*, *Haematopinus suis*, *Linognathus setosus*, and the like.

Mallophaga: *Dalmalinia ovis*, *Dalmalinia bovis*, *Menopon gallinae*, *Trichodectes canis*, *Felicola subrostrata*, and the like.

Hymenoptera: Formicidae such as *Monomorium pharaosis*, *Formica fusca japonica*, *Ochetellus glaber*, *Pristomyrmex pungens*, *Pheidole noda*, *Acromyrmex* spp., *Solenopsis* spp., and *Linepithema humile*, Vespidae, Bethylidae, and Tenthredimidae such as *Athalia rosae* and *Athalia japonica*.

Nematoda: *Aphelenchoides besseyi*, *Nothotylenchus acris*, *Meloidogyne incognita*, *Meloidogyne hapla*, *Meloidogyne javanica*, *Heterodera glycines*, *Globodera rostochiensis*, *Pratylenchus coffeae*, *Pratylenchus neglectus*, and the like.

Blattodea: *Blattella germanica*, *Periplaneta fuliginosa*, *Periplaneta americana*, *Periplaneta brunnea*, *Blatta orientalis*, and the like.

Isoptera: *Reticulitermes speratus*, *Coptotermes formosanus*, *Incisitermes minor*, *Cryptotermes domesticus*, *Odontotermes formosanus*, *Neotermes koshunensis*, *Glyptotermes satsumensis*, *Glyptotermes nakajimai*, *Glyptotermes fuscus*, *Glyptotermes kodamai*, *Glyptotermes kushimensis*, *Hodotermopsis japonica*, *Coptotermes guangzhoensis*, *Reticulitermes miyatakei*, *Reticulitermes flaviceps amamianus*, *Reticulitermes* sp., *Nasutitermes takasagoensis*, *Pericapritermes nitobei*, *Sinocapritermes mushae*, and the like.

Acarina: Tetranychidae such as *Tetranychus urticae*, *Tetranychus kanzawai*, *Panonychus citri*, *Panonychus ulmi*, and *Oligonychus* spp., Eriophyidae such as *Aculops pelekassi*, *Phyllocoptruta citri*, *Aculops lycopersici*, *Calacarus carinatus*, *Acaphylla theavagrans*, *Eriophyes chibaensis*, and *Aculus schlechtendali*, Tarsonemidae such as *Polyphagotarsonemus latus*, Tenuipalpidae such as *Brevipalpus phoenicis*, Tuckerellidae, Metastigmata such as *Haemaphysalis longicornis*, *Haemaphysalis flava*, *Dermacentor taiwanicus*, *Dermacentor variabilis*, *Ixodes ovatus*, *Ixodes persulcatus*, *Ixodes scapularis*, *Amblyomma americanum*, *Boophilus microplus*, and *Rhipicephalus sanguineus*, Acaridae such as *Tyrophagus putrescentiae* and *Tyrophagus similis*, Pyroglyphidae such as *Dermatophagoides farinae* and *Dermatophagoides ptrenyssnus*, Cheyletidae such as *Cheyletus eruditus*, *Cheyletus malaccensis*, *Cheyletus moorei*, and *Cheyletiella yasguri*, Sarcoptidae such as *Octodectes cynotis* and *Sacroptes scabiei*, Demodicidae such as *Demodex canis*, Listrophoridae, Oribatei, Dermanyssidae such as *Ornithonyssus bacoti*, *Ornithonyssus sylvairum*, and *Dermanyssus gallinae*, Trombiculidae such as *Leptotrombidium akamushi*, Arachnida such as *Chiracanthium japonicum* and *Latrodectus hasseltii*, and the like.

Chilopoda: *Thereuonema hilgendorfi*, *Scolopendra subspinipes*, and the like.

Diplopoda: *Oxidus gracilis*, *Nedyopus tambanus*, and the like.

Isopoda: *Armadillidium vulgare*, and the like.

Gastropoda: *Limax marginatus*, *Limax flavus*, and the like.

The pest control agent of the present invention contains the compound of the present invention and an inert carrier. The pest control agent of the present invention is usually obtained by mixing the compound of the present invention and an inert carrier such as a solid carrier, a liquid carrier or a gaseous carrier, and adding a surfactant or other auxiliaries for formulation as necessary, to be formulated into emulsifiable concentrates, oil formulations, dust formulations, granules, wettable powders, flowables, microcapsule formulations, aerosols, smoking agents, poisonous baits, resin formulations, shampoo agents, paste formulations, foam agents, carbon dioxide preparations, tablets, and the like. These formulations may be processed into mosquito repellent coils, electric mosquito repellent mats, mosquito repellent liquid formulations, smoking agents, fumigants, sheet formulations, spot-on agents, or oral treatment agents, and used.

The pest control agent of the present invention usually contains the compound of the present invention in an amount of 0.01 to 95% by weight.

Examples of the solid carrier which is used in the formulation include fine powder and granules of clays (kaolin clay, diatomaceous earth, bentonite, Fubasami clay, acid clay, etc.), synthetic hydrated silicon oxide, talc, ceramics, other inorganic minerals (sericite, quartz, sulfur, activated carbon, calcium carbonate, hydrated silica, etc.), fine powder and granulated substances of chemical fertilizers (ammonium sulfate, ammonium phosphate, ammonium nitrate, urea, ammonium chloride, etc.) and the like, and synthetic resins (polyester resins such as polypropylene, polyacrylonitrile, polymethylmethacrylate and polyethylene terephthalate, nylon resins such as nylon-6, nylon-11 and nylon-66, polyamide resin, polyvinyl chloride, polyvinylidene chloride, vinyl chloride-propylene copolymer, and the like).

Examples of the liquid carrier include water, alcohols (methanol, ethanol, isopropyl alcohol, butanol, hexanol, benzyl alcohol, ethylene glycol, propylene glycol, phenoxyethanol, etc.), ketones (acetone, methyl ethyl ketone, cyclohexanone, etc.), aromatic hydrocarbons (toluene, xylene, ethylbenzene, dodecylbenzene, phenylxylylethane, methylnaphthalene, etc.), aliphatic hydrocarbons (hexane, cyclohexane, kerosene, light oil, etc.), esters (ethyl acetate, butyl acetate, isopropyl myristate, ethyl oleate, diisopropyl adipate, diisobutyl adipate, propylene glycol monomethyl ether acetate, etc.), nitriles (acetonitrile, isobutyronitrile, etc.), ethers (diisopropyl ether, 1,4-dioxane, ethylene glycol dimethyl ether, diethylene glycol dimethyl ether, diethylene glycol monomethyl ether, propylene glycol monomethyl ether, dipropylene glycol monomethyl ether, 3-methoxy-3-methyl-1-butanol, etc.), acid amides (N,N-dimethylformamide, N,N-dimethylacetamide, etc.), halogenated hydrocarbons (dichloromethane, trichloroethane, carbon tetrachloride, etc.), sulfoxides (dimethyl sulfoxide, etc.), and propylene carbonate and vegetable oils (soybean oil, cottonseed oil, etc.).

Examples of the gaseous carrier include fluorocarbon, butane gas, LPG (liquefied petroleum gas), dimethyl ether, and carbon dioxide.

Examples of the surfactant include nonionic surfactants such as polyoxyethylene alkyl ether, polyoxyethylene alkylaryl ether and polyethylene glycol fatty acid ester, and anionic surfactants such as alkyl sulfonates, alkylbenzene sulfonates and alkylsulfates.

The other auxiliaries for formulation include such as fixing agents, dispersants, colorants and stabilizers, specifically, for example, casein, gelatin, polysaccharides (starch, arabic gum, cellulose derivatives, alginic acid, etc.), lignin derivatives, bentonite, synthetic water-soluble polymers (polyvinyl alcohol, polyvinyl pyrrolidone, polyacrylic acid, etc.), PAP (isopropyl acid phosphate), BHT (2,6-di-tert-butyl-4-methylphenol) and BHA (mixtures of 2-tert-butyl-4-methoxyphenol and 3-tert-butyl-4-methoxyphenol).

Examples of a base material of the resin formulation include vinyl chloride polymer, polyurethane and the like, and a plasticizer such as ester phthalates (dimethyl phthalate, dioctyl phthalate, etc.), ester adipates or stearic acid may be added to these base materials as necessary. The resin formulation is obtained by kneading a compound into the base material using an ordinary kneading apparatus, and then molding it by injection molding, extrusion molding, press molding or the like, and can be processed into a plate, film, taped, reticular or string resin formulation by further undergoing molding or cutting step as necessary. These resin formulation is processed into, for example, a collar for animal, an ear tag for animal, a sheet formulation, an induction cord, and a gardening pole.

Examples of a base material of the poisonous bait include grain powder, vegetable oil, sugar, crystalline cellulose and the like, and further, an antioxidant such as dibutylhydroxytoluene and nordihydroguaiaretic acid, a preservative such as dehydroacetic acid, a substance for preventing accidental ingestion by children and pets such as red pepper powder, a pest attractant such as cheese flavor, onion flavor and peanut oil or the like are added as necessary.

The method for controlling pests of the present invention is carried out by applying an effective amount of the compound of the present invention to a pest directly and/or a pest-infested area (plants, soil, in-house, animal body, etc.). In the method for controlling pests of the present invention, the compound is usually used in the form of the pest control agent of the present invention.

When the pest control agent of the present invention is used in pest controlling in the agricultural field, the application amount is usually 1 to 10000 g in the amount of the compound of the present invention per 10000 m². When the pest control agent of the present invention is formulated into an emulsifiable concentrate, a wettable powder, a flowable or the like, the pest control agent is usually diluted with water for an application so as to have a concentration of the active ingredient of 0.01 to 10000 ppm, and dust formulations, granules and the like are usually applied as they are.

These formulations and formulation solutions diluted with water may be directly applied by being sprayed on a pest or a plant such as crops which should be protected from pests, and also may be applied on a soil in order to control a pest that infests in the soil of cultivated land.

Also, the resin formulation processed into a sheet or string can be also applied by a method such as winding it around crops, spreading it in the vicinity of crops, or spreading it to the soil around crop roots.

When the pest control agent of the present invention is used in controlling the pest that inhabits in the house, the application amount is usually 0.01 to 1000 mg in an amount of the compound of the present invention per 1 m² of an area to be treated, in the case of using it on a planar area, and is usually 0.01 to 500 mg in an amount of the compound of the present invention per 1 m³ of a space to be treated, in the case of using it in a space. When the pest control agent of the present invention is formulated into an emulsifiable concentrate, a wettable powder, a flowable or the like, the pest control agent is usually diluted with water for an application so as to have a concentration of the active ingredient of 0.1 to 10000 ppm, and oil formulations, aerosols, smoking agents, poisonous baits and the like are applied as they are.

When the arthropod pest control agent of the present invention is used in the control of external parasites on livestock such as cows, horses, pigs, sheep, goats and chickens, and small animals such as dogs, cats, rats and mice, veterinary known methods can be applied to the animals. As specific methods, the formulation is administered, for example, by way of a tablet, mixing in feed, a suppository and injection (intramuscular, subcutaneous, intravenous, intraperitoneal injections, etc.), when systemic control is intended, and the formulation is used, for example, by way of spraying an oil solution or aqueous solution, pour-on or spot-on treatment, washing an animal with a shampoo formulation, or putting a collar or ear tag made of a resin formulation on to an animal, when non-systemic control is intended. The amount of the compound of the present invention when administered to an animal body is usually in the range from 0.1 to 1000 mg per 1 kg of the weight of an animal.

The pest control agent of the present invention can be used in the farmland where the following "crops" are grown.

Crops: corn, rice, wheat, barley, rye, oat, sorghum, cotton, soybean, peanut, sarrazin, sugar beet, rapeseed, sunflower, sugar cane, tobacco, etc.

Vegetables: Solanaceae vegetables (eggplant, tomato, green pepper, hot pepper, potato, etc.), Cucurbitaceae vegetables (cucumber, pumpkin, zucchini, watermelon, melon, etc.), Cruciferae vegetables (Japanese radish, turnip, horseradish, kohlrabi, Chinese cabbage, cabbage, brown mustard, broccoli, cauliflower, etc.), Compositae vegetables (burdock, garland chrysanthemum, artichoke, lettuce, etc.), Liliaceae vegetables (Welsh onion, onion, garlic, asparagus, etc.), Umbelliferae vegetables (carrot, parsley, celery, parsnip, etc.), Chenopodiaceae vegetables (spinach, Swiss chard, etc.), Labiatae vegetables (Japanese mint, mint, basil, etc.), strawberry, sweat potato, yam, aroid, etc.

Fruit trees: pomaceous fruits (apple, common pear, Japanese pear, Chinese quince, quince, etc.), stone fleshy fruits (peach, plum, nectarine, Japanese plum, cherry, apricot, prune, etc.), citrus plants (Satsuma mandarin, orange, lemon, lime, grapefruits, etc.), nuts (chestnut, walnut, hazel nut, almond, pistachio, cashew nut, macadamia nut, etc.), berry fruits (blueberry, cranberry, blackberry, raspberry, etc.), grape, persimmon, olive, loquat, banana, coffee, date, coconut, oil palm, etc.

Trees other than fruit trees: tea, mulberry, flowering trees and shrubs (azalea, camellia, hydrangea, sasanqua, *Illicium religiosum*, cherry tree, tulip tree, crape myrtle, fragrant olive, etc.), street trees (ash tree, birch, dogwood, eucalyptus, ginkgo, lilac, maple tree, oak, poplar, cercis, Chinese sweet gum, plane tree, zelkova, Japanese arborvitae, fir tree, Japanese hemlock, needle juniper, pine, spruce, yew, elm, horse-chestnut, etc.), sweet viburnum, *Podocarpus macrophyllus*, Japanese cedar, Japanese cypress, croton, spindle tree, Chainese howthorn, etc.

Lawn: zoysia (Japanese lawn grass, mascarene grass, etc.), Bermuda grass (*Cynodon dactylon*, etc.), bent grass (creeping bent grass, *Agrostis stolonifera, Agrostis tenuis*, etc.), bluegrass (Kentucky bluegrass, rough bluegrass, etc.), fescue (tall fescue, chewing fescue, creeping fescue, etc.), ryegrass (darnel, perennial ryegrass, etc.), cocksfoot, timothy grass, etc.

Others: flowers (rose, carnation, chrysanthemum, *Eustoma grandiflorum* Shinners (prairie gentian), gypsophila, gerbera, pot marigold, salvia, petunia, verbena, tulip, aster, gentian, lily, pansy, cyclamen, orchid, lily of the valley, lavender, stock, ornamental kale, primula, poinsttia, gladiolus, cattleya, daisy, cymbidium, begonia, etc.), bio-fuel plants (*Jatropha*, curcas, safflower, *Camelina alyssum*, switchgrass, miscanthus, reed canary grass, *Arundo donax*, kenaf, cassava, willow, algae, etc.), foliage plants, etc.

The "crops" also contains genetically modified crops.

The pest control agent of the present invention can be used as a mixture with or in combination with other insecticide, miticide, nematicide, fungicide, plant growth regulator, herbicide or synergist. Examples of the active ingredient of said insecticide, miticide, nematicide, fungicide, herbicide and synergist are shown below.

Active Ingredients of Insecticide
(1) Organic Phosphorus Compounds
acephate, Aluminium phosphide, butathiofos, cadusafos, chlorethoxyfos, chlorfenvinphos, chlorpyrifos, chlorpyrifos-methyl, cyanophos: CYAP, diazinon, DCIP (dichlorodiisopropylether), dichlofenthion: ECP, dichlorvos: DDVP, dimethoate, dimethylvinphos, disulfoton, EPN, ethion, ethoprophos, etrimfos, fenthion: MPP, fenitrothion: MEP, fosthiazate, formothion, Hydrogenphosphide, isofenphos, isoxathion, malathion, mesulfenfos, methidathion: DMTP, monocrotophos, naled: BRP, oxydeprofos: ESP, parathion, phosalone, phosmet: PMP, pirimiphos-methyl, pyridafenthion, quinalphos, phenthoate: PAP, profenofos, propaphos, prothiofos, pyraclorfos, salithion, sulprofos, tebupirimfos, temephos, tetrachlorvinphos, terbufos, thiometon, trichlorphon: DEP, vamidothion, and phorate.

(2) Carbamate Compounds
alanycarb, bendiocarb, benfuracarb, BPMC, carbaryl, carbofuran, carbosulfan, cloethocarb, ethiofencarb, fenobucarb, fenothiocarb, fenoxycarb, furathiocarb, isoprocarb: MIPC, metolcarb, methomyl, methiocarb, NAC, oxamyl, pirimicarb, propoxur: PHC, XMC, thiodicarb, xylylcarb, and aldicarb.

(3) Pyrethroid Compounds
acrinathrin, allethrin, benfluthrin, beta-cyfluthrin, bifenthrin, cycloprothrin, cyfluthrin, cyhalothrin, cypermethrin, deltamethrin, esfenvalerate, ethofenprox, fenpropathrin, fenvalerate, flucythrinate, flufenoprox, flumethrin, fluvalinate, halfenprox, imiprothrin, permethrin, prallethrin, pyrethrins, resmethrin, sigma-cypermethrin, silafluofen, tefluthrin, tralomethrin, transfluthrin, tetramethrin, phenothrin, cyphenothrin, alpha-cypermethrin, zeta-cypermethrin, lambda-cyhalothrin, gamma-cyhalothrin, furamethrin, tau-fluvalinate, metofluthrin, profluthrin, dimefluthrin, 2,3,5,6-tetrafluoro-4-(methoxymethyl)benzyl (EZ)-(1RS, 3RS; 1RS, 3SR)-2,2-dimethyl-3-prop-1-enylcyclopropanecarboxylate, 2,3,5,6-tetrafluoro-4-methylbenzyl (EZ)-(1RS, 3RS; 1RS, 3SR)-2,2-dimethyl-3-prop-1-enylcyclopropanecarboxylate, and 2,3,5,6-tetrafluoro-4-(methoxymethyl)benzyl (1RS, 3RS; 1RS, 3SR)-2,2-dimethyl-3-(2-methyl-1-propenyl)cyclopropanecarboxylate, 2,3,5,6-tetrafluoro-4-(methoxymethyl)benzyl(EZ)-(1RS, 3RS; 1RS, 3SR)-2,2-dimethyl-3-(2-cyano-1-propenyl)cyclopropanecarboxylate.

(4) Nereistoxin Compounds
cartap, bensultap, thiocyclam, monosultap, and bisultap.

(5) Neonicotinoid Compounds
imidacloprid, nitenpyram, acetamiprid, thiamethoxam, thiacloprid, dinotefuran, and clothianidin.

(6) Benzoyl Urea Compounds
chlorfluazuron, bistrifluoron, diafenthiuron, diflubenzuron, fluazuron, flucycloxuron, flufenoxuron, hexaflumuron, lufenuron, novaluron, noviflumuron, teflubenzuron, triflumuron, and triazuron.

(7) Phenylpyrazole-Based Compounds
acetoprole, ethiprole, fipronil, vaniliprole, pyriprole, and pyrafluprole.

(8) Bt Toxins
Living spores derived from *Bacillus thuringiensis* and produced crystalline toxins and mixtures thereof;

(9) Hydrazine Compounds
chromafenozide, halofenozide, methoxyfenozide, and tebufenozide.

(10) Organic Chlorine Compounds
aldrin, dieldrin, dienochlor, endosulfan, and methoxychlor.

(11) Other Active Ingredients of Insecticide
machine oil, nicotine-sulfate; avermectin-B, bromopropylate, buprofezin, chlorphenapyr, cyromazine, D-D(1,3-Dichloropropene), emamectin-benzoate, fenazaquin, flupyrazofos, hydroprene, methoprene, indoxacarb, metoxadiazone, milbemycin-A, pymetrozine, pyridalyl, pyriproxyfen, spinosad, sulfluramid, tolfenpyrad, triazamate, lepimectin, Arsenic acid, benclothiaz, Calcium cyanamide, Calcium polysulfide, chlordane, DDT, DSP, flufenerim, flonicamid, flurimfen, formetanate, metam-ammonium, metam-sodium, Methyl bromide, Potassium oleate, protrifenbute, spiromesifen, sulfoxaflor, Sulfur, metaflumizone, spirotetramat, pyrifluquinazone, spinetoram, tralopyril, flupyradifurone, chlorantraniliprole, cyantraniliprole, flubendiamide,
compounds represented by the following formula (K):

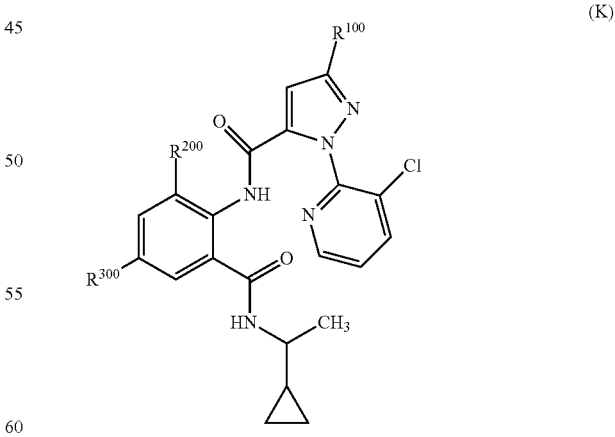

wherein
$R^{100}$ represents chlorine, bromine or a trifluoromethyl group,
$R^{200}$ represents chlorine, bromine or a methyl group, and
$R^{300}$ represents chlorine, bromine or a cyano group, and compounds represented by the following formula (L):

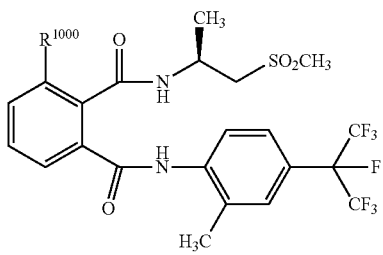
(L)

wherein
R[1000] represents chlorine, bromine or iodine.

Active Ingredients of Miticide
acequinocyl, amitraz, benzoximate, bifenaate, bromopropylate, chinomethionat, chlorobenzilate, CPCBS (chlorfenson), clofentezine, cyflumetofen, kelthane (dicofol), etoxazole, fenbutatin oxide, fenothiocarb, fenpyroximate, fluacrypyrim, fluproxyfen, hexythiazox, propargite: BPPS, polynactins, pyridaben, Pyrimidifen, tebufenpyrad, tetradifon, spirodiclofen, spiromesifen, spirotetramat, amidoflumet, and cyenopyrafen.

Active Ingredients of Nematicide
DCIP, fosthiazate, levamisol, methylsothiocyanate, morantel tartarate, and imicyafos.

Active Ingredients of Fungicide
(1) Azole Compounds
triforine, imazalil, pefurazoate, prochloraz, triflumizole, bitertanol, bromuconazole, cyproconazole, difenoconazole, diniconazole-M, epoxiconazole, fenbuconazole, fluquinconazole, flusilazole, flutriafol, hexaconazole, ipconazole, metconazole, myclobutanil, penconazole, propiconazole, prothioconazole, tebuconazole, tetraconazole, triadimenol, triticonazole, etc.;
(2) Strobilurin Compounds
azoxystrobin, kresoxim-methyl, metominostrobin, trifloxystrobin, picoxystrobin, pyraclostrobin, enestrobin, dimoxystrobin, orysastrobin, fluoxastrobin, famoxadone, fenamidone, pyribencarb, etc.;
(3) Other Active Ingredients of Fungicide
carbendezim, benomyl, thiabendazole, thiophanate-methyl, zoxamide, diethofencarb, pencycuron, fluopicolide, carboxin, frutolanil, frametpyr, thifluzamide, boscalid, penthiopyrad, fluopyram, bixafen, isopyrazam, penflufen, sedaxan, fluxapyroxad, fluazinam, ferimzone, silthiofam, procymidone, iprodione, vinclozolin, metalaxyl, benalaxyl, pyrimethanil, mepanipyrim, cyprodinil, quinoxyfen, proquinazid, fenpiclonil, fludioxonil, fenhexamid, fenpropimorph, tridemorph, fenpropidin, spiroxamine, thiuram, ziram, mancozeb, chlorothalonil, dichlofluanid, captan, folpet, iminoctadine, ethaboxam, metrafenone, dodine, fthalide, tricyclazole, pyroquilon, carpropamid, diclocymet, fenoxanil, dimethomorph, iprovalicarb, benthiavalicarb, mandipropamid, tolclofos-methyl, quintozene, cyazofamid, amisulbrom, ametoctradin, cyflufenamid, validamycin A, polyoxin B, blasticidin-S, kasugamycin, oxolinic acid, etc.;
(4) Resistance Inducing Compounds
acibenzolar-5-methyl, probenazole, isotianil, and tiadinil.

Active Ingredients of Herbicide
(1) Phenoxy Fatty Acid Herbicidal Compounds
2,4-PA, MCP, MCPB, phenothiol, mecoprop, fluoroxypyr, triclopyr, clomeprop, and naproanilide.
(2) Benzoate Herbicidal Compounds
2,3,6-TBA, dicamba, clopyralid, picloram, aminopyralid, quinclorac, and quinmerac.
(3) Urea Herbicidal Compounds
diuron, linuron, chlortoluron, isoproturon, fluometuron, isouron, tebuthiuron, methabenzthiazuron, cumyluron, daimuron, and methyl-daimuron.
(4) Triazine Herbicidal Compounds
atrazine, ametoryn, cyanazine, simazine, propazine, simetryn, dimethametryn, prometryn, metribuzin, triaziflam, and indaziflam.
(5) Bipyridinium Herbicidal Compounds
paraquat, and diquat.
(6) Hydroxybenzonitrile Herbicidal Compounds
bromoxynil, and ioxynil.
(7) Dinitroaniline Herbicidal Compounds
pendimethalin, prodiamine, and trifluralin.
(8) Organophosphorus Herbicidal Compounds
amiprofos-methyl, butamifos, bensulide, piperophos, anilofos, glyphosate, glufosinate, glufosinate-P, and bialaphos.
(9) Carbamate Herbicidal Compounds
di-allate, tri-allate, EPTC, butylate, benthiocarb, esprocarb, molinate, dimepiperate, swep, chlorpropham, phenmedipham, phenisopham, pyributicarb, and asulam.
(10) Acid Amide Herbicidal Compounds
propanil, propyzamide, bromobutide, and etobenzanid.
(11) Chloroacetanilide Herbicidal Compounds
acetochlor, alachlor, butachlor, dimethenamid, propachlor, metazachlor, metolachlor, pretilachlor, thenylchlor, and pethoxamid.
(12) Diphenyl Ether Herbicidal Compounds
acifluorfen-sodium, bifenox, oxyfluorfen, lactofen, fomesafen, chlomethoxynil, and aclonifen.
(13) Cyclic Imide Herbicidal Compounds
oxadiazon, cinidon-ethyl, carfentrazone-ethyl, surfentrazone, flumiclorac-pentyl, flumioxazin, pyraflufen-ethyl, oxadiargyl, pentoxazone, fluthiacet-methyl, butafenacil, benzfendizone, bencarbazone, and saflufenacil.
(14) Pyrazole Herbicidal Compounds
benzofenap, pyrazolate, pyrazoxyfen, topramezone, and pyrasulfotole.
(15) Triketone Herbicidal Compounds
isoxaflutole, benzobicyclon, sulcotrione, mesotrione, tembotrione, and tefuryltrione.
(16) Aryloxyphenoxypropionate Herbicidal Compounds
clodinafop-propargyl, cyhalofop-butyl, diclofop-methyl, fenoxaprop-ethyl, fluazifop-butyl, haloxyfop-methyl, and quizalofop-ethyl, metamifop.
(17) Trione Oxime Herbicidal Compounds
alloxydim-sodium, sethoxydim, butroxydim, clethodim, cloproxydim, cycloxydim, tepraloxydim, tralkoxydim, and profoxydim.
(18) Sulfonyl Urea Herbicidal Compounds
chlorsulfuron, sulfometuron-methyl, metsulfuron-methyl, chlorimuron-ethyl, tribenuron-methyl, triasulfuron, bensulfuron-methyl, thifensulfuron-methyl, pyrazosulfuron-ethyl, primisulfuron-methyl, nicosulfuron, amidosulfuron, cinosulfuron, imazosulfuron, rimsulfuron, halosulfuron-methyl, prosulfuron, ethametsulfuron-methyl, triflusulfuron-methyl, flazasulfuron, cyclosulfamuron, flupyrsulfuron, sulfosulfuron, azimsulfuron, ethoxysulfuron, oxasulfuron, iodosulfuron-methyl-sodium, foramsulfuron, mesosulfuron-methyl, trifloxysulfuron, tritosulfuron, orthosulfamuron, flucetosulfuron, and propyrisulfuron.
(19) Imidazolinone Herbicidal Compounds
imazamethabenz-methyl, imazamethapyr, imazamox, imazapyr, imazaquin, and imazethapyr.

(20) Sulfonamide Herbicidal Compounds flumetsulam, metosulam, diclosulam, florasulam, cloransulam-methyl, penoxsulam, and pyroxsulam.

(21) Pyrimidinyloxybenzoate Herbicidal Compounds pyrithiobac-sodium, bispyribac-sodium, pyriminobac-methyl, pyribenzoxim, pyriftalid, and pyrimisulfan.

(22) Other Herbicidal Compounds bentazon, bromacil, terbacil, chlorthiamid, isoxaben, dinoseb, amitrole, cinmethylin, tridiphane, dalapon, diflufenzopyr-sodium, dithiopyr, thiazopyr, flucarbazone-sodium, propoxycarbazone-sodium, mefenacet, flufenacet, fentrazamide, cafenstrole, indanofan, oxaziclomefone, benfuresate, ACN, pyridate, chloridazon, norflurazon, flurtamone, diflufenican, picolinafen, beflubutamid, clomazone, amicarbazone, pinoxaden, pyraclonil, pyroxasulfone, thiencarbazone-methyl, aminocyclopyrachlor, ipfencarbazone, and methiozolin.

Active Ingredients of Synergist piperonyl butoxide, sesamex, sulfoxide, N-(2-ethylhexyl)-8,9,10-trinorborn-5-ene-2,3-dicarboximide (MGK 264), N-declyimidazole), WARF-antiresistant, TBPT, TPP, IBP, PSCP, CH$_3$I, t-phenylbutenone, diethylmaleate, DMC, FDMC, ETP, and ETN.

EXAMPLES

Hereinbelow, the present invention will be further described in detail by production examples, formulation examples, test examples, and the like. However, the present invention is not limited to these examples.

First, the production examples for the production of the compounds of the present invention are shown below.

Production Example 1 (1)

A mixture of 0.81 g of 2-amino-5-trifluoromethylpyridine, 1.13 g of 3-chloro-5-trifluoromethylpicolinic acid, 1.15 g of EDCI hydrochloride, 0.06 g of HOBt and 10 mL of pyridine was stirred at 60° C. for 2 hours. A saturated aqueous sodium bicarbonate solution was poured to the cooled reaction mixture, and the mixture was extracted with ethyl acetate. The organic layer was dried over anhydrous sodium sulfate and then concentrated under reduced pressure, and the resulting residue was applied to a silica gel column chromatography to obtain 1.35 g of 3-chloro-5-trifluoromethyl-N-(5-trifluoromethylpyridin-2-yl)picolinamide.

3-Chloro-5-trifluoromethyl-N-(5-trifluoromethylpyridin-2-yl)picolinamide

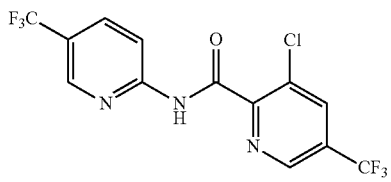

$^1$H-NMR (CDCl$_3$)δ: 10.51 (1H, brs), 8.83 (1H, brs), 8.64 (1H, brs), 8.56 (1H, d), 8.17 (1H, d), 8.02 (1H, dd).

Production Example 1 (2)

0.37 g of 60% sodium hydride (oil-based) was added to a mixture of 0.34 g of ethyl mercaptan and 3 mL of DMF under ice cooling, and the mixture was stirred at room temperature for 10 minutes. 1.35 g of 3-chloro-5-trifluoromethyl-N-(5-trifluoromethylpyridin-2-yl)picolinamide was added to the reaction mixture, and the mixture was stirred at room temperature for 3 hours. Water was poured to the reaction mixture, and the precipitated solid was taken by filtration and dried under reduced pressure to obtain 1.55 g of 3-ethylsulfanyl-5-trifluoromethyl-N-(5-trifluoromethylpyridin-2-yl)picolinamide (hereinafter, referred to as Compound of Present Invention 1).

Compound of Present Invention 1

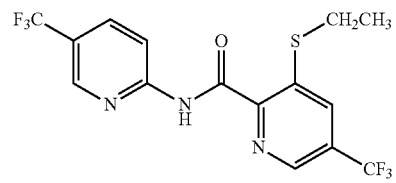

$^1$H-NMR (CDCl$_3$)δ: 10.72 (1H, brs), 8.68-8.53 (3H, m), 7.98 (1H, d), 7.92 (1H, s), 3.01 (2H, q), 1.48 (3H, t).

Production Example 2 (1)

A mixture of 0.81 g of 2-amino-5-trifluoromethylpyridine, 0.78 g of 3-chloropicolinic acid, 1.15 g of EDCI hydrochloride, 0.06 g of HOBt and 10 mL of pyridine was stirred at 60° C. for 2 hours. A saturated aqueous sodium bicarbonate solution was poured to the cooled reaction mixture, and the mixture was extracted with ethyl acetate. The organic layer was dried over anhydrous sodium sulfate and then concentrated under reduced pressure, and the resulting residue was applied to a silica gel column chromatography to obtain 0.51 g of 3-chloro-N-(5-trifluoromethylpyridin-2-yl)picolinamide.

3-Chloro-N-(5-trifluoromethylpyridin-2-yl)picolinamide

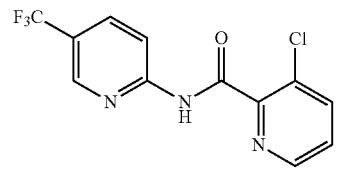 [SMILES: O=C(Nc1ccc(C(F)(F)F)cn1)c1ncccc1Cl]

$^1$H-NMR (CDCl$_3$)δ: 10.69 (1H, brs), 8.62 (1H, s), 8.60-8.55 (2H, m), 7.99 (1H, dd), 7.92 (1H, dd), 7.49 (1H, dd).

Production Example 2 (2)

0.33 g of sodium ethanethiolate was added to a mixture of 0.45 g of 3-chloro-N-(5-trifluoromethylpyridin-2-yl)picolinamide and 3 mL of DMF, and the mixture was stirred at 60° C. for 2 hours. Water was poured to the reaction mixture cooled to room temperature, and the precipitated solid was taken by filtration and dried under reduced pressure to obtain 0.42 g of 3-ethylsulfanyl-N-(5-trifluoromethylpyridin-2-yl)picolinamide (hereinafter, referred to as Compound of Present Invention 2).

Compound of Present Invention 2

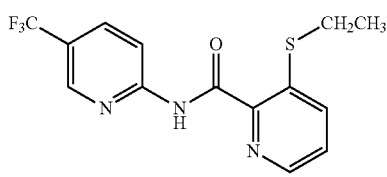 [SMILES: CCSc1cccnc1C(=O)Nc1ccc(C(F)(F)F)cn1]

$^1$H-NMR (CDCl$_3$)δ: 10.86-10.86 (1H, brm), 8.67-8.56 (2H, m), 8.42-8.32 (1H, m), 7.96 (1H, d), 7.74 (1H, d), 7.49-7.40 (1H, m), 2.98 (2H, d), 1.45 (3H, t).

Production Example 3

0.30 g of m-chloroperbenzoic acid (purity of 68%) was added to a mixture of 0.20 g of 3-ethylsulfanyl-N-(5-trifluoromethylpyridin-2-yl)picolinamide (Compound of Present Invention 2) and 3 mL of chloroform under ice cooling, and the mixture was stirred at room temperature for 2 hours. A saturated aqueous sodium bicarbonate solution and a saturated aqueous sodium thiosulfate solution were poured to the reaction mixture, and the mixture was extracted with ethyl acetate. The organic layer was dried over anhydrous sodium sulfate and concentrated under reduced pressure to obtain 0.11 g of 3-ethylsulfonyl-N-(5-trifluoromethylpyridin-2-yl)picolinamide (hereinafter, referred to as Compound of Present Invention 3).

Compound of Present Invention 3

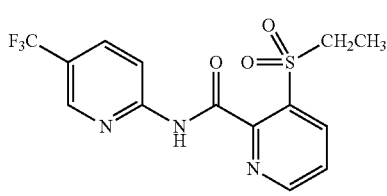 [SMILES: CCS(=O)(=O)c1cccnc1C(=O)Nc1ccc(C(F)(F)F)cn1]

$^1$H-NMR (CDCl$_3$)δ: 10.27 (1H, brs), 8.87 (1H, d), 8.71-8.61 (2H, m), 8.53 (1H, d), 8.00 (1H, d), 7.81-7.71 (1H, m), 3.96 (2H, q), 1.38 (3H, t).

Production Example 4

0.36 g of m-chloroperbenzoic acid (purity of 68%) was added to a mixture of 0.20 g of 3-ethylsulfanyl-5-trifluoromethyl-N-(5-trifluoromethylpyridin-2-yl)picolinamide (Compound of Present Invention 1) and 3 mL of chloroform under ice cooling, and the mixture was stirred at room temperature for 2 hours. A saturated aqueous sodium bicarbonate solution and a saturated aqueous sodium thiosulfate solution were poured to the reaction mixture, and the mixture was extracted with ethyl acetate. The organic layer was dried over anhydrous sodium sulfate and then concentrated under reduced pressure, and the resulting residue was applied to a silica gel column chromatography to obtain 0.06 g of 3-ethylsulfonyl-5-trifluoromethyl-N-(5-trifluoromethylpyridin-2-yl)picolinamide (hereinafter, referred to as Compound of Present Invention 4) and 0.13 g of 3-ethylsulfinyl-5-trifluoromethyl-N-(5-trifluoromethylpyridin-2-yl)picolinamide (hereinafter, referred to as Compound of Present Invention 5).

Compound of Present Invention 4

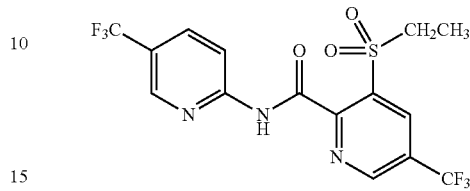

$^1$H-NMR (CDCl$_3$)δ: 10.09 (1H, brs), 9.11 (1H, d), 8.88 (1H, d), 8.65 (1H, s), 8.51 (1H, d), 8.02 (1H, d), 3.98 (2H, q), 1.42 (3H, t).

Compound of Present Invention 5

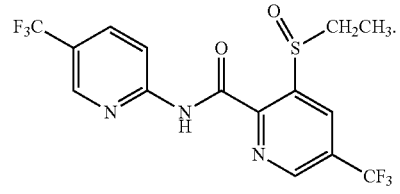

$^1$H-NMR (CDCl$_3$)δ: 11.95 (1H, brs), 9.20 (1H, s), 8.89 (1H, s), 8.72 (1H, d), 8.62 (1H, s), 7.61 (1H, d), 3.94 (2H, q), 1.43 (3H, t).

Production Example 5

0.39 g of m-chloroperbenzoic acid (purity of 68%) was added to a mixture of 0.21 g of 3-ethylsulfanyl-N-(5-trifluoromethylpyridin-2-yl)picolinamide (Compound of Present Invention 2) and 3 mL of chloroform under ice cooling, and the mixture was stirred at room temperature for 3 hours. A saturated aqueous sodium bicarbonate solution and a saturated aqueous sodium thiosulfate solution were poured to the reaction mixture, and the mixture was extracted with ethyl acetate. The organic layer was dried over anhydrous sodium sulfate and then concentrated under reduced pressure, and the resulting residue was applied to a silica gel column chromatography to obtain 0.10 g of 3-ethylsulfonyl-N-(1-oxy-5-trifluoromethylpyridin-2-yl)picolinamide (hereinafter, referred to as Compound of Present Invention 6).

Compound of Present Invention 6

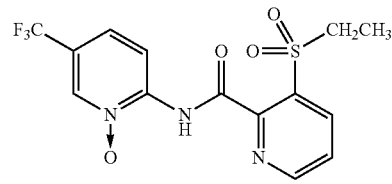 [SMILES: CCS(=O)(=O)c1cccnc1C(=O)Nc1ccc(C(F)(F)F)c[n+]1[O-]]

¹H-NMR (CDCl₃)δ: 12.05 (1H, brs), 8.95 (1H, dd), 8.73 (1H, d), 8.67 (1H, dd), 8.61 (1H, s), 7.79 (1H, dd), 7.58 (1H, d), 3.91 (2H, q), 1.38 (3H, t).

Production Example 6 (1)

A mixture of 0.81 g of 2-amino-6-trifluoromethylpyridine, 0.78 g of 3-chloropicolinic acid, 1.15 g of EDCI hydrochloride, 0.06 g of HOBt and 10 mL of pyridine was stirred at 70° C. for 2 hours. A saturated aqueous sodium bicarbonate solution was poured to the cooled reaction mixture, and the mixture was extracted with ethyl acetate. The organic layer was dried over anhydrous sodium sulfate and then concentrated under reduced pressure, and the resulting solid was washed with hexane and dried to obtain 1.33 g of 3-chloro-N-(6-trifluoromethylpyridin-2-yl)picolinamide.

3-Chloro-N-(6-trifluoromethylpyridin-2-yl)picolinamide

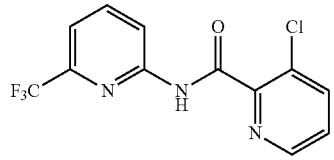 [SMILES: O=C(Nc1cccc(C(F)(F)F)n1)c1ncccc1Cl]

¹H-NMR (CDCl₃)δ: 10.60 (1H, brs), 8.66 (1H, d), 8.58 (1H, d), 7.97-7.87 (2H, m), 7.53-7.43 (2H, m).

Production Example 6 (2)

0.86 g of sodium ethanethiolate was added to a mixture of 1.23 g of 3-chloro-N-(6-trifluoromethylpyridin-2-yl)picolinamide and 3 mL of DMF, and the mixture was stirred at 60° C. for 2 hours. The reaction mixture cooled to room temperature was poured to water, and the precipitated solid was taken by filtration. The resulting solid was dissolved in ethyl acetate, and the mixture was extracted with water and ethyl acetate. The organic layer was dried over anhydrous sodium sulfate and then concentrated under reduced pressure to obtain 1.30 g of 3-ethylsulfanyl-N-(6-trifluoromethylpyridin-2-yl)picolinamide (hereinafter, referred to as Compound of Present Invention 7).

Compound of Present Invention 7

¹H-NMR (CDCl₃)δ: 10.78 (1H, brs), 8.69 (1H, d), 8.37 (1H, d), 7.90 (1H, dd), 7.74 (1H, d), 7.46-7.38 (2H, m), 2.97 (2H, q), 1.45 (3H, t).

Production Example 7 (1)

A mixture of 0.81 g of 2-amino-4-trifluoromethylpyridine, 0.78 g of 3-chloropicolinic acid, 1.15 g of EDCI hydrochloride, 0.06 g of HOBt and 10 mL of pyridine was stirred at 70° C. for 2 hours. A saturated aqueous sodium bicarbonate solution was poured to the cooled reaction mixture, and the mixture was extracted with ethyl acetate. The organic layer was dried over anhydrous sodium sulfate and then concentrated under reduced pressure, and the resulting solid was washed with hexane and dried to obtain 1.33 g of 3-chloro-N-(4-trifluoromethylpyridin-2-yl)picolinamide.

3-Chloro-N-(4-trifluoromethylpyridin-2-yl)picolinamide

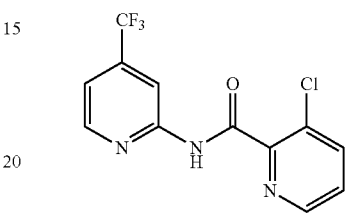

¹H-NMR (CDCl₃)δ: 10.69 (1H, brs), 8.75 (1H, s), 8.57 (1H, d), 8.52 (1H, d), 7.92 (1H, d), 7.49 (1H, dd), 7.30 (1H, d).

Production Example 7 (2)

0.86 g of sodium ethanethiolate was added to a mixture of 1.23 g of 3-chloro-N-(4-trifluoromethylpyridin-2-yl)picolinamide and 3 mL of DMF, and the mixture was stirred at 60° C. for 2 hours. The reaction mixture cooled to room temperature was poured to water, and the precipitated solid was taken by filtration. The resulting solid was dissolved in ethyl acetate, and the mixture was extracted with water and ethyl acetate. The organic layer was dried over anhydrous sodium sulfate and then concentrated under reduced pressure to obtain 1.23 g of 3-ethylsulfanyl-N-(4-trifluoromethylpyridin-2-yl)picolinamide (hereinafter, referred to as Compound of Present Invention 8).

Compound of Present Invention 8

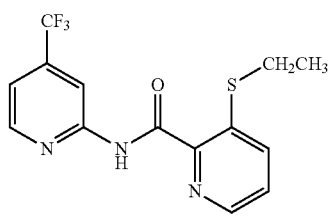 [SMILES: CCSc1cccnc1C(=O)Nc1cc(C(F)(F)F)ccn1]

¹H-NMR (CDCl₃)δ: 10.86 (1H, brs), 8.78 (1H, s), 8.51 (1H, d), 8.37 (1H, dd), 7.75 (1H, dd), 7.44 (1H, dd), 7.29-7.26 (1H, m), 2.98 (2H, q), 1.46 (3H, t).

Production Example 8 (1)

A mixture of 0.80 g of 4-trifluoromethylaniline, 0.78 g of 3-chloropicolinic acid, 1.15 g of EDCI hydrochloride, 0.06 g of HOBt and 10 mL of pyridine was stirred at room temperature for 2 hours. A saturated aqueous sodium bicarbonate solution was poured to the reaction mixture, and the mixture was extracted with ethyl acetate. The organic layer was dried over anhydrous sodium sulfate and then concentrated under reduced pressure, and the resulting solid was washed with hexane and dried to obtain 1.34 g of 3-chloro-N-(4-trifluoromethylphenyl)picolinamide.

3-Chloro-N-(4-trifluoromethylphenyl)picolinamide

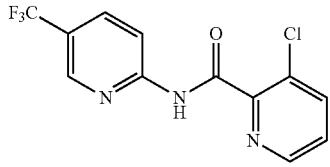 [SMILES: O=C(Nc1ccc(C(F)(F)F)cn1)c1ncccc1Cl]

$^1$H-NMR (CDCl$_3$)δ: 10.16 (1H, s), 8.55 (1H, d), 7.95-7.87 (3H, m), 7.64 (2H, d), 7.47 (1H, dd).

Production Example 8 (2)

0.91 g of sodium ethanethiolate was added to a mixture of 1.29 g of 3-chloro-N-(4-trifluoromethylphenyl)picolinamide and 3 mL of DMF, and the mixture was stirred at 60° C. for 2 hours. The reaction mixture cooled to room temperature was poured to water, and the precipitated solid was taken by filtration. The resulting solid was dissolved in ethyl acetate, and the mixture was extracted with water and ethyl acetate. The organic layer was dried over anhydrous sodium sulfate and then concentrated under reduced pressure to obtain 1.37 g of 3-ethylsulfanyl-N-(4-trifluoromethylphenyl)picolinamide (hereinafter, referred to as Compound of Present Invention 9).

Compound of Present Invention 9

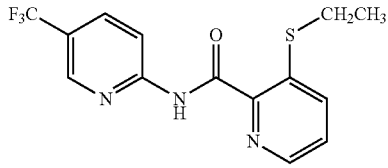 [SMILES: CCSc1cccnc1C(=O)Nc1ccc(C(F)(F)F)cn1]

$^1$H-NMR (CDCl$_3$)δ: 10.33 (1H, brs), 8.34 (1H, dd), 7.92 (2H, d), 7.74 (1H, t), 7.62 (2H, d), 7.43 (1H, dd), 2.96 (2H, q), 1.45 (3H, t).

Production Example 9 (1)

A mixture of 1.15 g of 3,5-bistrifluoromethylaniline, 0.78 g of 3-chloropicolinic acid, 1.15 g of EDCI hydrochloride, 0.06 g of HOBt and 10 mL of pyridine was stirred at room temperature for 2 hours. A saturated aqueous sodium bicarbonate solution was poured to the reaction mixture, and the mixture was extracted with ethyl acetate. The organic layer was dried over anhydrous sodium sulfate and then concentrated under reduced pressure, and the resulting solid was washed with hexane and dried to obtain 1.67 g of 3-chloro-N-(3,5-bistrifluoromethylphenyl)picolinamide.

3-Chloro-N-(3,5-bistrifluoromethylphenyl)picolinamide

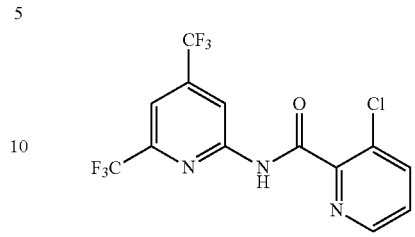

$^1$H-NMR (CDCl$_3$)δ: 10.38 (1H, brs), 8.57 (1H, d), 8.30 (2H, s), 7.94 (1H, d), 7.65 (1H, s), 7.51 (1H, dd).

Production Example 9 (2)

0.89 g of sodium ethanethiolate was added to a mixture of 1.56 g of 3-chloro-N-(3,5-bistrifluoromethylphenyl)picolinamide and 3 mL of DMF, and the mixture was stirred at 60° C. for 2 hours. The reaction mixture cooled to room temperature was poured to water, and the precipitated solid was taken by filtration. The resulting solid was dissolved in ethyl acetate, and the mixture was extracted with water and ethyl acetate. The organic layer was dried over anhydrous sodium sulfate and then concentrated under reduced pressure to obtain 1.64 g of 3-ethylsulfanyl-N-(3,5-bistrifluoromethylphenyl)picolinamide (hereinafter, referred to as Compound of Present Invention 10).

Compound of Present Invention 10

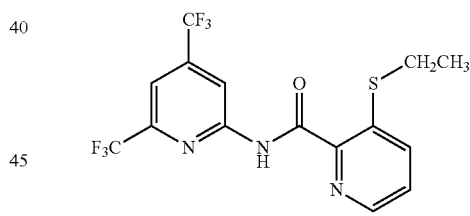

$^1$H-NMR (CDCl$_3$)δ: 10.51 (1H, s), 8.35 (1H, dd), 8.31 (2H, s), 7.76 (1H, dd), 7.62 (1H, s), 7.45 (1H, dd), 2.98 (2H, q), 1.46 (3H, t).

Production Example 10

1.15 g of m-chloroperbenzoic acid (purity of 68%) was added to a mixture of 0.78 g of 3-ethylsulfanyl-N-(3,5-bistrifluoromethylphenyl)picolinamide (Compound of Present Invention 10) and 10 mL of chloroform under ice cooling, and the mixture was stirred at room temperature for 2 hours. A saturated aqueous sodium bicarbonate solution and a saturated aqueous sodium thiosulfate solution were poured to the reaction mixture, and the mixture was extracted with ethyl acetate. The organic layer was dried over anhydrous sodium sulfate and then concentrated under reduced pressure, and the resulting solid was washed with MTBE and dried to obtain 0.78 g of 3-ethylsulfonyl-N-(3,5-bistrifluoromethylphenyl) picolinamide (hereinafter, referred to as Compound of Present Invention 14).

Compound of Present Invention 14

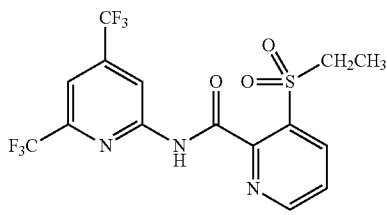 [SMILES: CCS(=O)(=O)c1cccnc1C(=O)Nc1cc(C(F)(F)F)cc(C(F)(F)F)n1]

¹H-NMR (CDCl₃)δ: 9.88 (1H, brs), 8.85 (1H, d), 8.68 (1H, d), 8.25 (2H, s), 7.76 (1H, dd), 7.68 (1H, s), 3.99 (2H, q), 1.38 (3H, t).

Production Example 11

0.9 g of 60% sodium hydride (oil-based) was added to a mixture of 0.65 g of 3-ethylsulfanyl-N-(5-trifluoromethylpyridin-2-yl)picolinamide (Compound of Present Invention 2) and 4 mL of THF under ice cooling, and the mixture was stirred at room temperature for 10 minutes. The reaction mixture was ice-cooled, 1.0 g of methyl iodide was added thereto, and then the mixture was stirred at 30° C. for 2 hours. Water and a saturated aqueous sodium bicarbonate solution were poured to the reaction mixture cooled to room temperature, and the mixture was extracted with ethyl acetate. The organic layer was dried over anhydrous sodium sulfate and then concentrated under reduced pressure, and the resulting residue was applied to a silica gel column chromatography to obtain 0.27 g of 3-ethylsulfanyl-N-methyl-N-(5-trifluoromethyl-pyridin-2-yl) picolinamide (hereinafter, referred to as Compound of Present Invention 16).

Compound of Present Invention 16

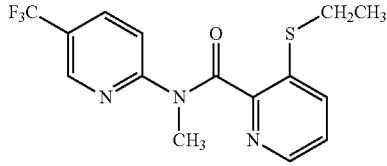 [SMILES: CCSc1cccnc1C(=O)N(C)c1ccc(C(F)(F)F)cn1]

¹H-NMR (CDCl₃)δ: 8.59 (1H, s), 8.31 (1H, d), 7.78 (1H, d), 7.71 (1H, d), 7.64-7.54 (1H, m), 7.30-7.22 (1H, m), 3.54 (3H, s), 2.96 (2H, q), 1.30 (3H, t).

Production Example 12

0.33 g of m-chloroperbenzoic acid (purity of 68%) was added to a mixture of 0.20 g of 3-ethylsulfanyl-N-methyl-N-(5-trifluoromethylpyridin-2-yl)picolinamide (Compound of Present Invention 16) and 3 mL of chloroform under ice cooling, and the mixture was stirred at room temperature for 2 hours. A saturated aqueous sodium bicarbonate solution and a saturated aqueous sodium thiosulfate solution were poured to the reaction mixture, and the mixture was extracted with ethyl acetate. The organic layer was dried over anhydrous sodium sulfate and then concentrated under reduced pressure, and the resulting residue was applied to a silica gel column chromatography to obtain 0.17 g of 3-ethylsulfonyl-N-methyl-N-(5-trifluoromethylpyridin-2-yl)picolinamide (hereinafter, referred to as Compound of Present Invention 17).

Compound of Present Invention 17

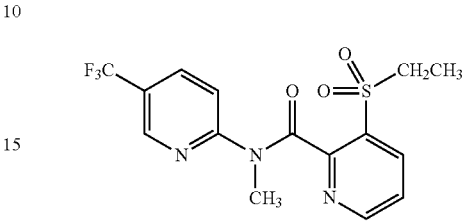

¹H-NMR (DMSO-D₆, 80° C.)δ: 8.77-8.71 (1H, m), 8.66 (1H, s), 8.38 (1H, dd), 8.12 (1H, dd), 7.79-7.64 (2H, m), 3.49 (2H, q), 3.42 (3H, s), 1.20 (3H, t).

Production Example 13 (1)

A mixture of 29.6 g of 2,3-dichloropyridine, 46.97 g of zinc cyanide, 11.56 g of tetratris(triphenylphosphine)palladium (0) and 150 mL of NMP was stirred at 100° C. for 2 hours. Water was added to the reaction mixture cooled to room temperature, and the mixture was extracted with ethyl acetate. The organic layer was dried over anhydrous sodium sulfate and then concentrated under reduced pressure, and the resulting residue was applied to a silica gel column chromatography to obtain 9.08 g of 3-chloropyridine-2-carbonitrile.

3-Chloropyridine-2-carbonitrile

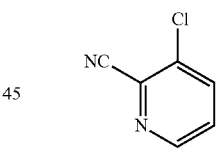

¹H-NMR (CDCl₃)δ: 8.63 (1H, dd), 7.88 (1H, dd), 7.50 (1H, ddd).

Production Example 13 (2)

0.9 mL of ethanethiol was added to a mixture of 1.39 g of 3-chloropyridine-2-carbonitrile and 10 mL of DMF, 0.52 g of 60% sodium hydride (oil-based) was added to the reaction mixture under ice cooling, and then the mixture was stirred at room temperature for 1 hour. The reaction mixture was poured to water, and the mixture was extracted with ethyl acetate. The organic layer was dried over anhydrous sodium sulfate and then concentrated under reduced pressure, and the resulting residue was applied to a silica gel column chromatography to obtain 1.52 g of 3-ethylsulfanylpyridine-2-carbonitrile.

3-Ethylsulfanylpyridine-2-carbonitrile

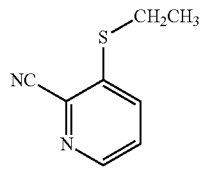 [SMILES: CCSc1cccnc1C#N]

¹H-NMR (CDCl₃)δ: 8.49 (1H, dd), 7.75 (1H, dd), 7.43 (1H, dd), 3.06 (2H, q), 1.38 (3H, t).

Production Example 13 (3)

A mixture of 1.4 g of 3-ethylsulfanylpyridine-2-carbonitrile, 15 mL of concentrated sulfuric acid and 5 mL of water was stirred at 130° C. for 2 hours. Water was poured to the reaction mixture cooled to room temperature, sodium hydroxide was added thereto, and the mixture was extracted with ethyl acetate. Concentrated hydrochloric acid was added to the aqueous layer, and the mixture was extracted with chloroform. The organic layer was dried over anhydrous sodium sulfate and then concentrated under reduced pressure to obtain 1.15 g of 3-ethylsulfanylpicolinic acid.

3-Ethylsulfanylpicolinic acid

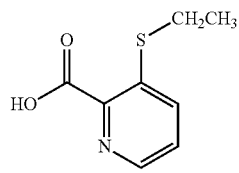 [SMILES: CCSc1cccnc1C(=O)O]

¹H-NMR (CDCl₃)δ: 8.31 (1H, d), 7.75 (1H, d), 7.49 (1H, dd), 2.97 (2H, q), 1.44 (3H, t).

Production Example 13 (4)

A mixture of 0.35 g of 4-trifluoromethoxyaniline, 0.36 g of 3-ethylsulfanylpicolinic acid, 0.46 g of EDCI hydrochloride, 0.02 g of HOBt and 3 mL of pyridine was stirred at room temperature overnight. A saturated aqueous sodium bicarbonate solution was poured to the reaction mixture, and the mixture was extracted with ethyl acetate. The organic layer was dried over anhydrous sodium sulfate and then concentrated under reduced pressure, and the resulting solid was washed with hexane and dried to obtain 0.60 g of 3-ethylsulfanyl-N-(4-trifluoromethoxyphenyl)picolinamide (hereinafter, referred to as Compound of Present Invention 18).

Compound of Present Invention 18

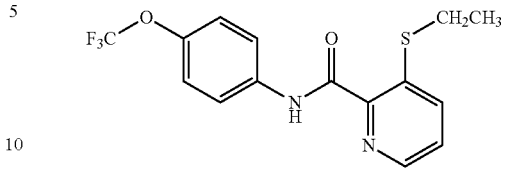

¹H-NMR (CDCl₃)δ: 10.19 (1H, brs), 8.33 (1H, d), 7.82 (2H, d), 7.73 (1H, d), 7.41 (1H, dd), 7.21 (2H, d), 2.95 (2H, q), 1.44 (3H, t).

Production Example 14

0.84 g of m-chloroperbenzoic acid (purity of 68%) was added to a mixture of 0.50 g of 3-ethylsulfanyl-N-(4-trifluoromethoxyphenyl)picolinamide (Compound of Present Invention 18) and 5 mL of chloroform under ice cooling, and the mixture was stirred at room temperature for 3 hours. A saturated aqueous sodium bicarbonate solution and a saturated aqueous sodium thiosulfate solution were poured to the reaction mixture, and the mixture was extracted with ethyl acetate. The organic layer was dried over anhydrous sodium sulfate and then concentrated under reduced pressure, and the resulting residue was applied to a silica gel column chromatography to obtain 0.50 g of 3-ethylsulfonyl-N-(4-trifluoromethoxyphenyl)picolinamide (hereinafter, referred to as Compound of Present Invention 21).

Compound of Present Invention 21

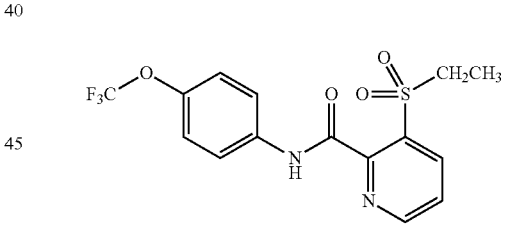

¹H-NMR (CDCl₃)δ: 9.54 (1H, brs), 8.83 (1H, d), 8.65 (1H, d), 7.76 (2H, d), 7.74-7.69 (1H, m), 7.28-7.22 (2H, m), 3.97 (2H, q), 1.36 (3H, t).

Production Example 15

A mixture of 0.35 g of 2-methylamino-5-trifluoromethylpyridine, 0.50 g of 3-ethylsulfanyl-5-trifluoromethylpicolinic acid, 0.46 g of EDCI hydrochloride, 0.02 g of HOBt and 3 mL of pyridine was stirred at room temperature for 3 hours. A saturated aqueous sodium bicarbonate solution was poured to the reaction mixture, and the mixture was extracted with ethyl acetate. The organic layer was dried over anhydrous sodium sulfate and then concentrated under reduced pressure, and the resulting residue was applied to a silica gel column chromatography to obtain 0.18 g of 3-ethylsulfanyl- N-methyl-5-trifluoromethyl-N-(5-trifluoromethylpyridin-2-yl)picolinamide (hereinafter, referred to as Compound of Present Invention 24).

Compound of Present Invention 24

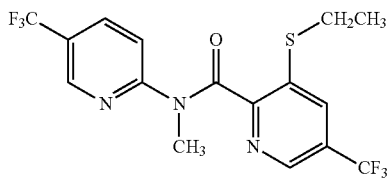 [SMILES: CCSc1cc(C(F)(F)F)cnc1C(=O)N(C)c1ccc(C(F)(F)F)cn1]

¹H-NMR (CDCl₃)δ: 8.54-8.47 (2H, m), 7.89-7.81 (2H, m), 7.61 (1H, s), 3.55 (3H, s), 3.02 (2H, q), 1.35 (3H, t).

Production Example 16

0.23 g of m-chloroperbenzoic acid (purity of 68%) was added to a mixture of 0.10 g of 3-ethylsulfanyl-N-methyl-5-trifluoromethyl-N-(5-trifluoromethylpyridin-2-yl)picolinamide (Compound of Present Invention 24) and 5 mL of chloroform under ice cooling, and the mixture was stirred at room temperature for 3 hours. A saturated aqueous sodium bicarbonate solution and a saturated aqueous sodium thiosulfate solution were poured to the reaction mixture, and the mixture was extracted with ethyl acetate. The organic layer was dried over anhydrous sodium sulfate and then concentrated under reduced pressure, and the resulting residue was applied to a silica gel column chromatography to obtain 0.10 g of 3-ethylsulfonyl-N-methyl-5-trifluoromethyl-N-(5-trifluoromethylpyridin-2-yl)picolinamide (hereinafter, referred to as Compound of Present Invention 25).

Compound of Present Invention 25

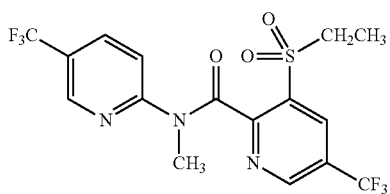 [SMILES: CCS(=O)(=O)c1cc(C(F)(F)F)cnc1C(=O)N(C)c1ccc(C(F)(F)F)cn1]

¹H-NMR (DMSO-D₆, 80° C.)δ: 9.16 (1H, s), 8.64 (1H, s), 8.60-8.52 (1H, m), 8.17 (1H, d), 7.92-7.44 (1H, m), 3.56 (2H, q), 3.46 (3H, s), 1.23 (3H, t).

Production Example 17

0.78 g of ethyl iodide was added to a mixture of 0.32 g of 3-ethylsulfanyl-N-(5-trifluoromethylpyridin-2-yl)picolinamide (Compound of Present Invention 2), 0.21 g of potassium carbonate and 3 mL of acetone, and the mixture was stirred at room temperature for 1 hour. 3 mL of DMF was added to the reaction mixture, the mixture was stirred at 60° C. for 1 hour and then cooled to room temperature, and 1.0 g of ethyl iodide was added and then the mixture was stirred at 60° C. for 2 hours. Water and a saturated aqueous sodium bicarbonate solution were poured to the reaction mixture cooled to room temperature, and the mixture was extracted with ethyl acetate. The organic layer was dried over anhydrous sodium sulfate and then concentrated under reduced pressure, and the resulting residue was applied to a silica gel column chromatography to obtain 0.17 g of N-ethyl-3-ethylsulfanyl-N-(5-trifluoromethylpyridin-2-yl)picolinamide (hereinafter, referred to as Compound of Present Invention 26).

Compound of Present Invention 26

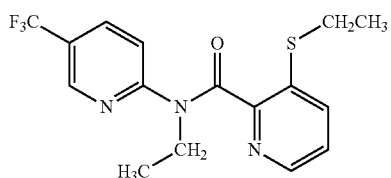

¹H-NMR (CDCl₃)δ: 8.60 (1H, s), 8.27 (1H, d), 7.74 (1H, d), 7.67 (H, d), 7.48-7.36 (1H, m), 7.22 (1H, dd), 4.14 (2H, q), 2.95 (2H, q), 1.35-1.26 (6H, m).

Production Example 18

0.21 g of m-chloroperbenzoic acid (purity of 68%) was added to a mixture of 0.13 g of N-ethyl-3-ethylsulfanyl-N-(5-trifluoromethylpyridin-2-yl)picolinamide (Compound of Present Invention 26) and 4 mL of chloroform under ice cooling, and the mixture was stirred at room temperature for 3 hours. A saturated aqueous sodium bicarbonate solution and a saturated aqueous sodium thiosulfate solution were poured to the reaction mixture, and the mixture was extracted with ethyl acetate. The organic layer was dried over anhydrous sodium sulfate and then concentrated under reduced pressure, and the resulting residue was applied to a silica gel column chromatography to obtain 0.13 g of N-ethyl-3-ethylsulfonyl-N-(5-trifluoromethylpyridin-2-yl)picolinamide (hereinafter, referred to as Compound of Present Invention 27).

Compound of Present Invention 27

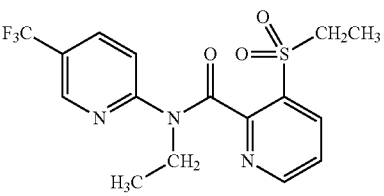 [SMILES: CCN(C(=O)c1ncccc1S(=O)(=O)CC)c1ccc(C(F)(F)F)cn1]

¹H-NMR (DMSO-D₆, 80° C.)δ: 8.72-8.63 (2H, m), 8.37 (1H, dd), 8.08 (1H, d), 7.69 (1H, dd), 7.61-7.46 (1H, m), 4.04 (2H, q), 3.53 (2H, q), 1.24-1.16 (6H, m).

Production Example 19

0.23 g of oxalyl chloride was added to a mixture of 0.22 g of 3-ethylsulfanylpicolinic acid, 10 mL of chloroform and 0.1 mL of DMF under ice cooling, and the mixture was stirred at room temperature for 2 hours. The reaction mixture was concentrated under reduced pressure, and 1 mL of toluene was added. The reaction mixture was added to a mixture of 0.22 g of 2-methylamino-5-pentafluoroethylpyridine and 1 mL of toluene, and the mixture was stirred at 100° C. for 2 hours. Water and a saturated aqueous sodium bicarbonate solution were poured to the reaction mixture cooled to room temperature, and the mixture was extracted with ethyl acetate. The organic layer was dried over anhydrous sodium sulfate and then concentrated under reduced pressure, and the resulting residue was applied to a silica gel column chromatography to obtain 0.35 g of 3-ethylsulfanyl-N-methyl-N-(5-pentafluoroethylpyridin-2-yl)picolinamide (hereinafter, referred to as Compound of Present Invention 31).

Compound of Present Invention 31

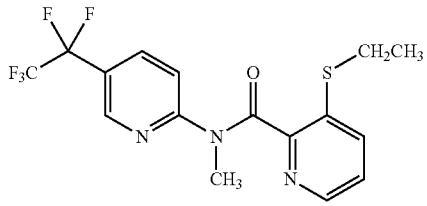 [SMILES: CCSc1cccnc1C(=O)N(C)c1ccc(C(F)(F)C(F)(F)F)cn1]

$^1$H-NMR (CDCl$_3$)δ: 8.55 (1H, s), 8.31 (1H, dd), 7.77 (1H, dd), 7.71 (1H, dd), 7.69-7.62 (1H, m), 7.29-7.23 (1H, m), 3.54 (3H, S) 2.95 (2H, q), 1.30 (3H, t).

Production Example 20

0.18 g of m-chloroperbenzoic acid (purity of 68%) was added to a mixture of 0.12 g of 3-ethylsulfanyl-N-methyl-N-(5-pentafluoroethylpyridin-2-yl)picolinamide (Compound of Present Invention 31) and 5 mL of chloroform under ice cooling, and the mixture was stirred at room temperature for 3 hours. A saturated aqueous sodium bicarbonate solution and a saturated aqueous sodium thiosulfate solution were poured to the reaction mixture, and the mixture was extracted with ethyl acetate. The organic layer was dried over anhydrous sodium sulfate and then concentrated under reduced pressure, and the resulting residue was applied to a silica gel column chromatography to obtain 0.13 g of 3-ethylsulfonyl-N-methyl-N-(5-pentafluoroethylpyridin-2-yl) picolinamide (hereinafter, referred to as Compound of Present Invention 30).

Compound of Present Invention 30

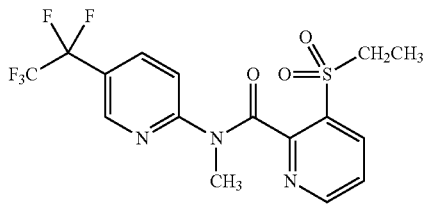 [SMILES: CCS(=O)(=O)c1cccnc1C(=O)N(C)c1ccc(C(F)(F)C(F)(F)F)cn1]

$^1$H-NMR (DMSO-D$_6$, 80° C.)δ: 8.74 (1H, d), 8.61 (1H, brs), 8.38 (1H, dd), 8.09 (1H, dd), 7.82-7.67 (2H, m), 3.49 (2H, q), 3.42 (3H, s), 1.20 (3H, t).

Production Example 21

0.38 g of oxalyl chloride was added to a mixture of 0.40 g of 3-ethylsulfanylpicolinic acid, 10 mL of chloroform and 0.1 mL of DMF under ice cooling, and the mixture was stirred at room temperature for 2 hours. The reaction mixture was concentrated under reduced pressure, and 1 mL of toluene was added. The reaction mixture was added to a mixture of 0.41 g of 2-methylamino-5-trifluoromethylsulfanylpyridine and 1 mL of toluene, and the mixture was stirred at 100° C. for 1 hour. Water and a saturated aqueous sodium bicarbonate solution were poured to the reaction mixture cooled to room temperature, and the mixture was extracted with ethyl acetate. The organic layer was dried over anhydrous sodium sulfate and then concentrated under reduced pressure, and the resulting residue was applied to a silica gel column chromatography to obtain 0.29 g of 3-ethylsulfanyl-N-methyl-N-(5-trifluoromethylsulfanylpyridin-2-yl)picolinamide (hereinafter, referred to as Compound of Present Invention 32).

Compound of Present Invention 32

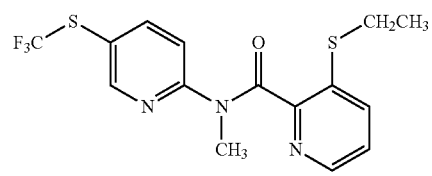 [SMILES: CCSc1cccnc1C(=O)N(C)c1ccc(SC(F)(F)F)cn1]

$^1$H-NMR (CDCl$_3$)δ: 8.52 (1H, d), 8.29 (1H, d), 7.82 (1H, d), 7.70 (1H, d), 7.61-7.47 (1H, m), 7.28-7.20 (1H, m), 3.53 (3H, s), 2.95 (2H, q), 1.30 (3H, t).

Production Example 22

0.37 g of m-chloroperbenzoic acid (purity of 68%) was added to a mixture of 0.23 g of 3-ethylsulfanyl-N-methyl-N-(5-trifluoromethylsulfanylpyridin-2-yl)picolinamide (Compound of Present Invention 32) and 5 mL of chloroform under ice cooling, and the mixture was stirred at 0° C. for 2 hours. A saturated aqueous sodium bicarbonate solution and a saturated aqueous sodium thiosulfate solution were poured to the reaction mixture, and the mixture was extracted with ethyl acetate. The organic layer was dried over anhydrous sodium sulfate and then concentrated under reduced pressure, and the resulting residue was applied to a silica gel column chromatography to obtain 0.20 g of 3-ethylsulfonyl-N-methyl-N-(5-trifluoromethylsulfanylpyridin-2-yl)picolinamide (hereinafter, referred to as Compound of Present Invention 33).

Compound of Present Invention 33

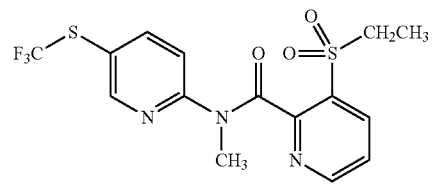 [SMILES: CCS(=O)(=O)c1cccnc1C(=O)N(C)c1ccc(SC(F)(F)F)cn1]

$^1$H-NMR (DMSO-D$_6$, 80° C.)δ: 8.77-8.68 (1H, m), 8.56-8.50 (1H, m), 8.37 (1H, d), 8.08 (1H, d), 7.72 (1H, dd), 7.68-7.59 (1H, m), 3.48 (2H, q), 3.40 (3H, s), 1.20 (3H, t).

Production Example 23

0.50 g of methyl iodide was added to a mixture of 0.20 g of 3-ethylsulfonyl-N-(3,5-bistrifluoromethylphenyl)picolinamide (Compound of Present Invention 14), 0.12 g of potassium carbonate and 3 mL of acetone, and the mixture was stirred at room temperature for 1 hour. 1 mL of DMF was added to the reaction mixture, and the mixture was stirred at 60° C. for 2 hours. Water was added to the reaction mixture cooled to room temperature, and the mixture was extracted with ethyl acetate. The organic layer was dried over anhydrous sodium sulfate and then concentrated under reduced pressure, and the resulting residue was applied to a silica gel column chromatography to obtain 0.18 g of 3-ethylsulfonyl-N-methyl-N-(3,5-bistrifluoromethylphenyl)picolinamide (hereinafter, referred to as Compound of Present Invention 38).

Compound of Present Invention 38

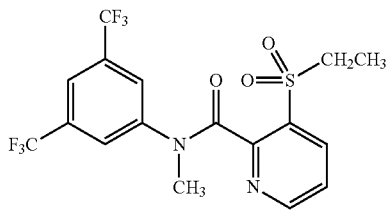 [SMILES: CCS(=O)(=O)c1cccnc1C(=O)N(C)c1cc(C(F)(F)F)cc(C(F)(F)F)c1]

$^1$H-NMR (CDCl$_3$, 22° C.)δ: 8.92 (0.3H, dd), 8.50 (0.7H, dd), 8.39 (0.3H, dd), 8.22 (0.7H, dd), 7.99 (0.7H, s), 7.85 (1.3H, s), 7.83 (0.3H, s), 7.64 (0.3H, dd), 7.60 (0.7H, s), 7.37 (0.7H, dd), 3.65-3.54 (3.3H, m), 3.45 (0.7H, q), 3.26 (1.0H, s), 1.39-1.28 (3H, m).

Production Example 24

0.50 g of methyl iodide was added to a mixture of 0.20 g of 3-ethylsulfonyl-N-(4-trifluoromethoxyphenyl)picolinamide (Compound of Present Invention 21), 0.12 g of potassium carbonate and 3 mL of acetone, and the mixture was stirred at room temperature for 1 hour. 1 mL of DMF was added to the reaction mixture, and the mixture was stirred at 60° C. for 2 hours. Water was poured to the reaction mixture cooled to room temperature, and the mixture was extracted with ethyl acetate. The organic layer was dried over anhydrous sodium sulfate and then concentrated under reduced pressure, and the resulting residue was applied to a silica gel column chromatography to obtain 0.19 g of 3-ethylsulfonyl-N-methyl-N-(4-trifluoromethoxyphenyl)picolinamide (hereinafter, referred to as Compound of Present Invention 39).

Compound of Present Invention 39

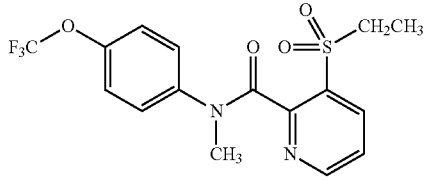 [SMILES: CCS(=O)(=O)c1cccnc1C(=O)N(C)c1ccc(OC(F)(F)F)cc1]

$^1$H-NMR (CDCl$_3$, 22° C.)δ: 8.91 (0.2H, dd), 8.48 (0.8H, dd), 8.37 (0.2H, dd), 8.20 (0.8H, dd), 7.61 (0.2H, dd), 7.54 (0.4H, dd), 7.40 (1.6H, d), 7.35-7.29 (1.2H, m), 7.01 (1.6H, d), 3.62 (1.6H, q), 3.52 (2.4H, s), 3.47 (0.4H, q), 3.20 (0.6H, s), 1.32 (3H, t).

Production Example 25 (1)

0.40 g of sodium hydroxide was added to a mixture of 0.30 g of N-(4-pentafluoroethylphenyl)acetamide, 9 mL of methanol and 6 mL of water, and the mixture was stirred at room temperature for 1 hour, stirred at 70° C. for 2.5 hours, and stirred under heating and refluxing for 3 hours. A saturated aqueous sodium chloride solution was added to the reaction mixture cooled to room temperature, and the mixture was extracted with ethyl acetate. The organic layer was dried over anhydrous sodium sulfate and then concentrated under reduced pressure, and the resulting residue was applied to a silica gel column chromatography to obtain 0.38 g of 4-(2,2,2-trifluoro-1,1-dimethoxyethyl)aniline.

4-(2,2,2-Trifluoro-1,1-dimethoxyethyl)aniline

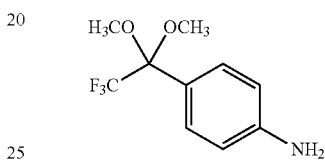

$^1$H-NMR (CDCl$_3$)δ: 7.35 (2H, d), 6.68 (2H, d), 3.78 (2H, brs), 3.37 (6H, s).

Production Example 25 (2)

A mixture of 0.38 g of 4-(2,2,2-trifluoro-1,1-dimethoxyethyl)aniline, 0.22 g of 3-ethylsulfanylpicolinic acid, 0.29 g of EDCI hydrochloride, 0.01 g of HOBt and 5 mL of pyridine was stirred at room temperature for 2 hours. A saturated aqueous sodium bicarbonate solution was poured to the reaction mixture, and the mixture was extracted with ethyl acetate. The organic layer was dried over anhydrous sodium sulfate and then concentrated under reduced pressure, and the resulting residue was applied to a silica gel column chromatography to obtain 0.43 g of 3-ethylsulfanyl-N-[4-(2,2,2-trifluoro-1,1-dimethoxyethyl)phenyl]picolinamide (Compound of Present Invention 58).

Compound of Present Invention 58

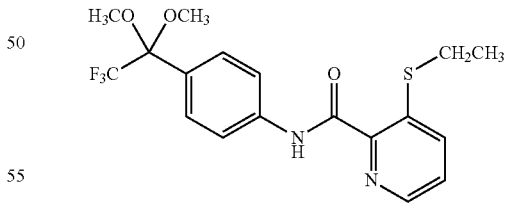

$^1$H-NMR (CDCl$_3$)δ: 10.21 (1H, brs), 8.33 (1H, d), 7.83 (2H, d), 7.72 (1H, d), 7.58 (2H, d), 7.40 (1H, dd), 3.40 (6H, s), 2.95 (2H, q), 1.44 (3H, t).

Production Example 25 (3)

0.55 g of m-chloroperbenzoic acid (purity of 68%) was added to a mixture of 0.43 g of 3-ethylsulfanyl-N-[4-(2,2,2-trifluoro-1,1-dimethoxyethyl)phenyl]picolinamide (Compound of Present Invention 58) and 5 mL of chloroform under ice cooling, and the mixture was stirred at room temperature for 2 hours. A saturated aqueous sodium bicarbonate solution and a saturated aqueous sodium thiosulfate solution were poured to the reaction mixture, and the mixture was extracted with ethyl acetate. The organic layer was dried over anhydrous sodium sulfate and then concentrated under reduced pressure to obtain 0.43 g of 3-ethylsulfonyl-N-[4-(2,2,2-trifluoro-1,1-dimethoxyethyl)phenyl]picolinamide (hereinafter, referred to as Compound of Present Invention 42).

Compound of Present Invention 42

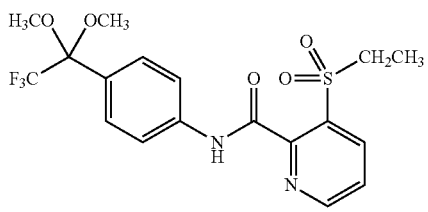 [SMILES: CCS(=O)(=O)c1cccnc1C(=O)Nc1ccc(C(OC)(OC)C(F)(F)F)cc1]

$^1$H-NMR (CDCl$_3$)δ: 9.56 (1H, brs), 8.83 (1H, d), 8.65 (1H, d), 7.77 (2H, d), 7.74-7.68 (1H, m), 7.61 (2H, d), 3.99 (2H, q), 3.40 (6H, s), 1.36 (3H, t).

Production Example 26

1.0 g of methyl iodide was added to a mixture of 0.12 g of 3-ethylsulfonyl-N-[4-(2,2,2-trifluoro-1,1-dimethoxyethyl) phenyl]picolinamide (Compound of Present Invention 42), 0.15 g of potassium carbonate, 2 mL of acetone and 2 mL of DMF, and the mixture was stirred at 80° C. for 3 hours. Water was added to the reaction mixture cooled to room temperature, and the mixture was extracted with ethyl acetate. The organic layer was dried over anhydrous sodium sulfate and then concentrated under reduced pressure, and the resulting residue was applied to a silica gel column chromatography to obtain 0.13 g of 3-ethylsulfonyl-N-methyl-N-[4-(2,2,2-trifluoro-1,1-dimethoxyethyl)phenyl]picolinamide (hereinafter, referred to as Compound of Present Invention 43).

Compound of Present Invention 43

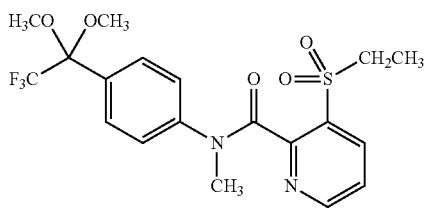 [SMILES: CCS(=O)(=O)c1cccnc1C(=O)N(C)c1ccc(C(OC)(OC)C(F)(F)F)cc1]

$^1$H-NMR (CDCl$_3$, 22° C.)δ: 8.90 (0.2H, dd), 8.40 (0.8H, dd), 8.38 (0.2H, dd), 8.20 (0.8H, dd), 7.75-7.25 (5H, m), 3.63 (1.5H, q), 3.55 (2.3H, s), 3.49 (0.5H, q), 3.42 (1.2H, s), 3.29 (4.8H, s), 3.21 (0.7H, s), 1.37-1.26 (3H, m).

Production Example 27

4 mL of a 30% aqueous hydrogen peroxide was added to a mixture of 0.23 g of 3-ethylsulfonyl-N-methyl-N-(5-trifluoromethylsulfanylpyridin-2-yl)picolinamide (Compound of Present Invention 33), 0.01 g of sodium tungstate dihydrate and 2 mL of acetonitrile, and the mixture was stirred at 60° C. for 2 hours. Water was added to the reaction mixture cooled to room temperature, then a saturated aqueous sodium thiosulfate solution was poured, and the mixture was extracted with ethyl acetate. The organic layer was dried over anhydrous sodium sulfate and then concentrated under reduced pressure, and the resulting residue was applied to a silica gel column chromatography to obtain 0.21 g of 3-ethylsulfonyl-N-methyl-N-(5-trifluoromethylsulfonylpyridin-2-yl)picolinamide (hereinafter, referred to as Compound of Present Invention 44).

Compound of Present Invention 44

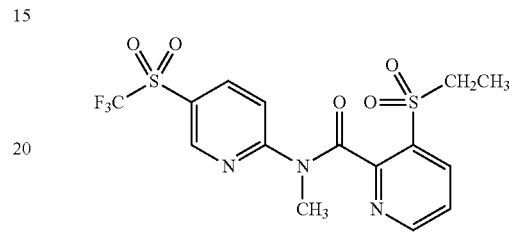

$^1$H-NMR (DMSO-D$_6$, 80° C.)δ: 8.87 (1H, d), 8.78 (1H, dd), 8.45 (1H, dd), 8.41 (1H, dd), 7.98 (1H, d), 7.77 (1H, dd), 3.52-3.43 (5H, m), 1.20 (3H, t).

Production Example 28 (1)

2.6 g of sodium azide was added to a mixture of 4.6 g of 2-chloro-5-pentafluoroethylpyridine and 20 mL of DMF, and the mixture was stirred at room temperature for 5 hours, and stirred at 80° C. for 4 hours and at 90° C. for 3 hours. Water was added to the reaction mixture cooled to room temperature, and the mixture was extracted with MTBE. The organic layer was dried over anhydrous sodium sulfate and then concentrated under reduced pressure. 3 mL of water, 30 mL of THF and 6.30 g of triphenylphosphine were added to the resulting residue, and the mixture was stirred at room temperature overnight. Water was poured to the reaction mixture, and the mixture was extracted with ethyl acetate. The organic layer was dried over anhydrous sodium sulfate and then concentrated under reduced pressure.

30 mL of 2N hydrochloric acid and 10 mL of ethanol were added to the resulting residue, and the mixture was stirred at 80° C. for 2 hours. Water was poured to the reaction mixture cooled to room temperature, then a saturated aqueous sodium bicarbonate solution was added, and the mixture was extracted with MTBE. The organic layer was dried over anhydrous sodium sulfate and then concentrated under reduced pressure, and the resulting residue was applied to a silica gel column chromatography to obtain 1.31 g of 2-amino-5-pentafluoroethylpyridine.

2-Amino-5-pentafluoroethylpyridine

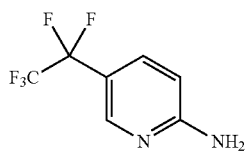 [SMILES: Nc1ccc(C(F)(F)C(F)(F)F)cn1]

$^1$H-NMR (CDCl$_3$)δ: 8.27 (1H, s), 7.57 (1H, d), 6.54 (1H, d), 4.83 (2H, brs).

Production Example 28 (2)

A mixture of 0.63 g of 2-amino-5-pentafluoroethylpyridine, 0.55 g of 3-ethylsulfanylpicolinic acid, 1.0 g of EDCI hydrochloride, 0.04 g of HOBt and 5 mL of pyridine was stirred at room temperature overnight. A saturated aqueous sodium bicarbonate solution was poured to the reaction mixture, and the mixture was extracted with ethyl acetate. The organic layer was dried over anhydrous sodium sulfate and then concentrated under reduced pressure, and the resulting residue was applied to a silica gel column chromatography to obtain 0.33 g of 3-ethylsulfanyl-N-(5-pentafluoroethylpyridin-2-yl)picolinamide (hereinafter, referred to as Compound of Present Invention 46).

Compound of Present Invention 46

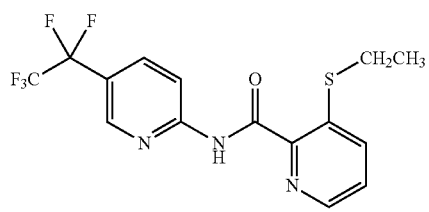 [SMILES: CCSc1cccnc1C(=O)Nc1ccc(C(F)(F)C(F)(F)F)cn1]

$^1$H-NMR (CDCl$_3$)δ: 10.87 (1H, brs), 8.62 (1H, d), 8.56 (1H, brs), 8.38 (1H, d), 7.93 (1H, d), 7.75 (1H, d), 7.44 (1H, dd), 2.98 (2H, q), 1.45 (3H, t).

Production Example 29

0.25 g of m-chloroperbenzoic acid (purity of 68%) was added to a mixture of 0.18 g of 3-ethylsulfanyl-N-(5-pentafluoroethylpyridin-2-yl)picolinamide (Compound of Present Invention 46) and 5 mL of chloroform under ice cooling, and the mixture was stirred at room temperature for 2 hours. A saturated aqueous sodium bicarbonate solution and a saturated aqueous sodium thiosulfate solution were poured to the reaction mixture, and the mixture was extracted with ethyl acetate. The organic layer was dried over anhydrous sodium sulfate and then concentrated under reduced pressure, and the resulting residue was applied to a silica gel column chromatography to obtain 0.15 g of 3-ethylsulfonyl-N-(5-pentafluoroethylpyridin-2-yl)picolinamide (hereinafter, referred to as Compound of Present Invention 47).

Compound of Present Invention 47

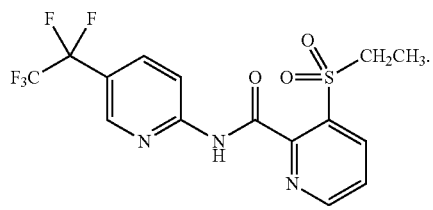 [SMILES: CCS(=O)(=O)c1cccnc1C(=O)Nc1ccc(C(F)(F)C(F)(F)F)cn1]

$^1$H-NMR (CDCl$_3$)δ: 10.25 (1H, brs), 8.87 (1H, dd), 8.67 (1H, dd), 8.59 (1H, brs), 8.55 (1H, d), 7.97 (1H, d), 7.76 (1H, dd), 3.95 (2H, q), 1.38 (3H, t).

Production Example 30

A mixture of 0.64 g of 2-chloro-5-trifluoromethylsulfanylpyridine, 0.54 g of 3-ethylsulfanylpicolinic acid amide, 1.96 g of cesium carbonate, 0.33 g of DABCO and 5 mL of DMSO was stirred at 70° C. for 1 hour. Water was added to the reaction mixture cooled to room temperature, and the mixture was extracted with ethyl acetate. The organic layer was dried over anhydrous sodium sulfate and then concentrated under reduced pressure, and the resulting residue was applied to a silica gel column chromatography to obtain 0.40 g of 3-ethylsulfanyl-N-(5-trifluoromethylsulfanylpyridin-2-yl)picolinamide (hereinafter, referred to as Compound of Present Invention 48).

Compound of Present Invention 48

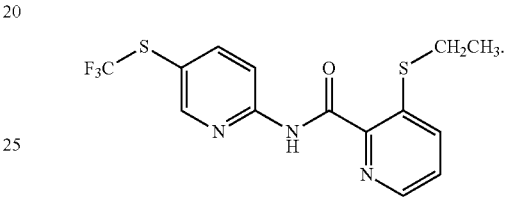

$^1$H-NMR (CDCl$_3$)δ: 10.82 (1H, brs), 8.59-8.52 (2H, m), 8.36 (1H, dd), 8.00 (1H, dd), 7.74 (1H, d), 7.43 (1H, dd), 2.97 (2H, q), 1.45 (3H, t).

Production Example 31

0.24 g of m-chloroperbenzoic acid (purity of 68%) was added to a mixture of 0.18 g of 3-ethylsulfanyl-N-(5-trifluoromethylsulfanylpyridin-2-yl)picolinamide (Compound of Present Invention 48) and 5 mL of chloroform under ice cooling, and the mixture was stirred at room temperature for 2 hours. A saturated aqueous sodium bicarbonate solution and a saturated aqueous sodium thiosulfate solution were poured to the reaction mixture, and the mixture was extracted with ethyl acetate. The organic layer was dried over anhydrous sodium sulfate and then concentrated under reduced pressure, and the resulting residue was applied to a silica gel column chromatography to obtain 0.17 g of 3-ethylsulfonyl-N-(5-trifluoromethylsulfanylpyridin-2-yl)picolinamide (hereinafter, referred to as Compound of Present Invention 49).

Compound of Present Invention 49

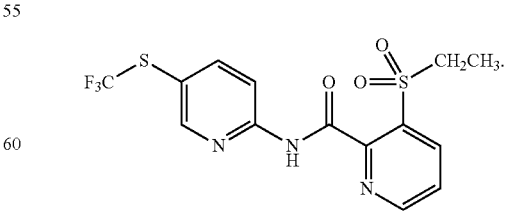

$^1$H-NMR (CDCl$_3$)δ: 10.21 (1H, brs), 8.87 (1H, dd), 8.66 (1H, dd), 8.58 (1H, d), 8.49 (1H, d), 8.04 (1H, dd), 7.75 (1H, dd), 3.95 (2H, q), 1.38 (3H, t).

Production Example 32 (1)

5.53 ml of thionyl chloride was added to a mixture of 4.7 g of 3,5-dichloropicolinic acid, 49 ml of toluene and 0.1 ml of DMF, and the mixture was stirred at 80° C. for 2 hours. The cooled reaction mixture was concentrated under reduced pressure, and 49 ml of toluene, 4.84 g of N-methyl-4-trifluoromethylsulfanylaniline and 8.05 ml of diisopropylethylamine were added, and the mixture was stirred at 80° C. for 2 hours. The cooled reaction mixture was poured to a saturated aqueous sodium bicarbonate solution, and the mixture was extracted with ethyl acetate. The organic layer was dried over anhydrous sodium sulfate and then concentrated under reduced pressure, and the resulting residue was applied to a silica gel column chromatography to obtain 8.92 g of 3,5-dichloro-N-methyl-N-(4-trifluoromethylsulfanylphenyl)picolinamide.

3,5-Dichloro-N-methyl-N-(4-trifluoromethylsulfanylphenyl)picolinamide

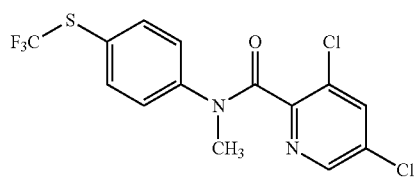 [SMILES: CN(C(=O)c1ncc(Cl)cc1Cl)c1ccc(SC(F)(F)F)cc1]

$^1$H-NMR (CDCl$_3$)δ: 8.28 (1H, d), 7.58 (1H, d), 7.50 (2H, d), 7.19 (2H, d), 3.54 (3H, s).

Production Example 32 (2)

1.03 g of 60% sodium hydride (oil-based) was added to a mixture of 1.82 mL of ethanethiol and 59 ml of THF under ice cooling, and the mixture was stirred for 1 hour under ice cooling. A mixture of 8.92 g of 3,5-dichloro-N-methyl-N-(4-trifluoromethylsulfanylphenyl)picolinamide and 59 ml of THF was added to the reaction mixture under ice cooling, and the mixture was stirred at room temperature for 7 hours. Water was poured to the reaction mixture, and the mixture was extracted with ethyl acetate. The organic layer was dried over anhydrous sodium sulfate and then concentrated under reduced pressure, and the resulting residue was applied to a silica gel column chromatography to obtain 9.02 g of 5-chloro-3-ethylsulfanyl-N-methyl-N-(4-trifluoromethylsulfanylphenyl)picolinamide (hereinafter, referred to as Compound of Present Invention 158).

Compound of Present Invention 158

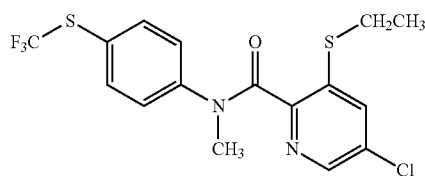 [SMILES: CCSc1cc(Cl)cnc1C(=O)N(C)c1ccc(SC(F)(F)F)cc1]

$^1$H-NMR (CDCl$_3$)δ: 8.17-8.10 (1H, m), 7.56-7.44 (3H, m), 7.24-7.17 (2H, m), 3.50 (3H, s), 2.92 (2H, q), 1.32 (3H, t).

Production Example 33

10.2 g of m-chloroperbenzoic acid (purity of 68%) was added to a mixture of 9.07 g of 5-chloro-3-ethylsulfanyl-N-methyl-N-(4-trifluoromethylsulfanylphenyl)picolinamide (Compound of Present Invention 158) and 223 ml of chloroform under ice cooling, and the mixture was stirred at room temperature for 5 hours. A saturated aqueous sodium bicarbonate solution and a saturated aqueous sodium thiosulfate solution were poured to the reaction mixture, and the mixture was extracted with ethyl acetate. The organic layer was dried over anhydrous sodium sulfate and then concentrated under reduced pressure, and the resulting residue was applied to a silica gel column chromatography to obtain 7.0 g of 5-chloro-3-ethylsulfonyl-N-methyl-N-(4-trifluoromethylsulfanylphenyl)picolinamide (hereinafter, referred to as Compound of Present Invention 118) and 2.04 g of 5-chloro-3-ethylsulfonyl-N-methyl-N-(4-trifluoromethylsulfinylphenyl)picolinamide (hereinafter, referred to as Compound of Present Invention 117).

Compound of Present Invention 118

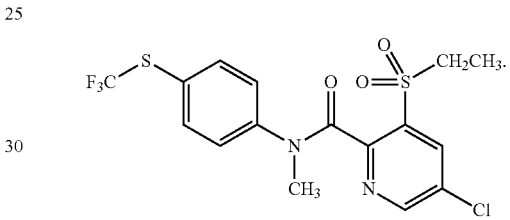

$^1$H-NMR (CDCl$_3$)δ: 8.84 (0.2H, d), 8.38 (0.8H, d), 8.35 (0.2H, d), 8.20 (0.8H, d), 7.75 (0.4H, d), 7.56 (0.4H, d), 7.48 (1.6H, d), 7.37 (1.6H, d), 3.66 (1.6H, q), 3.54 (2.5H, s), 3.49 (0.4H, q), 3.22 (0.5H, s), 1.34 (3.0H, t).

Compound of Present Invention 117

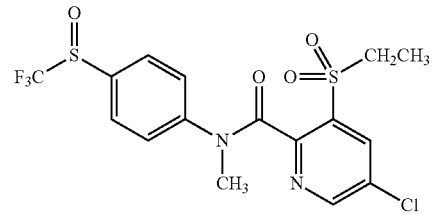 [SMILES: CCS(=O)(=O)c1cc(Cl)cnc1C(=O)N(C)c1ccc(S(=O)C(F)(F)F)cc1]

$^1$H-NMR (CDCl$_3$)δ: 8.36 (1.0H, d), 8.21 (1.0H, d), 7.90 (0.5H, d), 7.77 (0.5H, d), 7.64 (1.5H, d), 7.57 (1.5H, d), 3.67 (1.5H, q), 3.58 (2.3H, s), 3.52-3.46 (0.5H, m), 3.27 (0.7H, s), 1.36 (3.0H, t).

Production Example 34

Carbon monoxide at 10 atm was introduced to a mixture of 1.07 g of 5-chloro-3-ethylsulfonyl-N-methyl-N-(4-trifluoromethylsulfanylphenyl)picolinamide (Compound of Present Invention 118), 6 mg of palladium(II) acetate, 80 mg of 1,1'-bis(diphenylphosphino)ferrocene, 410 mg of sodium acetate and 20 ml of ethanol, and the mixture was stirred at 110° C. for 3 hours. 6 mg of palladium(II) acetate and 80 mg of 1,1'-bis(diphenylphosphino)ferrocene were added to the cooled reaction mixture, then carbon monoxide at 10 atm was introduced, and the mixture was stirred at 130° C. for 3 hours. The cooled reaction mixture was poured to water, and the mixture was extracted with ethyl acetate. The organic layer was dried over anhydrous sodium sulfate and then concentrated under reduced pressure, and the resulting residue was applied to a silica gel column chromatography to obtain 0.96 g of ethyl 5-ethylsulfonyl-6-[methyl-(4-trifluoromethylsulfanylphenyl) carbamoyl]nicotinate (hereinafter, referred to as Compound of Present Invention 125).

Compound of Present Invention 125

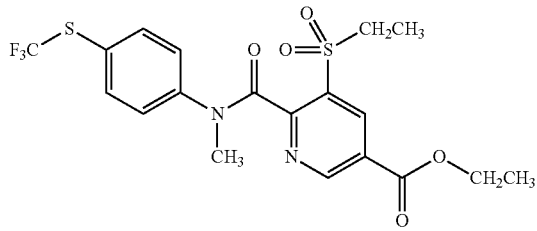 [SMILES: CCOC(=O)c1cnc(C(=O)N(C)c2ccc(SC(F)(F)F)cc2)c(S(=O)(=O)CC)c1]

$^1$H-NMR (CDCl$_3$)δ: 9.45 (0.2H, d), 9.00 (0.8H, d), 8.91 (0.2H, d), 8.75 (0.8H, d), 7.76 (0.4H, d), 7.58 (0.4H, d), 7.47 (1.6H, d), 7.40 (1.6H, d), 4.51 (0.4H, q), 4.41 (1.6H, q), 3.65 (1.6H, q), 3.56 (2.4H, s), 3.48 (0.4H, q), 3.22 (0.6H, s), 1.49-1.19 (6.0H, m).

Production Example 35

A mixture of 250 mg of 5-chloro-3-ethylsulfonyl-N-methyl-N-(4-trifluoromethylsulfanylphenyl)picolinamide (Compound of Present Invention 118), 104 mg of phenylboronic acid, 10 mg of tris(dibenzylideneacetone)dipalladium (0), 25 mg of 2-dicyclohexylphosphino-2'-4'-6'-triisopropylphenyl, 242 mg of tripotassium phosphate and 3 ml of dimethoxyethane was stirred at 70° C. for 3 hours. Water was poured to the reaction mixture, and the mixture was extracted with ethyl acetate. The organic layer was dried over anhydrous sodium sulfate and then concentrated under reduced pressure, and the resulting residue was applied to a silica gel column chromatography to obtain 112 mg of 3-ethylsulfonyl-5-phenyl-N-methyl-N-(4-trifluoromethylsulfanylphenyl)picolinamide (hereinafter, referred to as Compound of Present Invention 124).

Compound of Present Invention 124

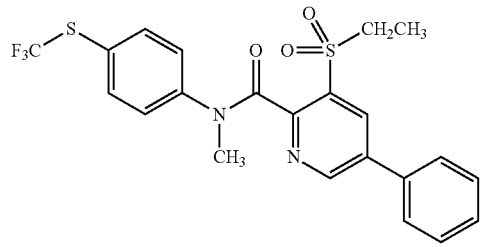 [SMILES: CCS(=O)(=O)c1cc(-c2ccccc2)cnc1C(=O)N(C)c1ccc(SC(F)(F)F)cc1]

$^1$H-NMR (CDCl$_3$)δ: 9.10 (0.2H, d), 8.65 (0.7H, d), 8.53 (0.2H, d), 8.41 (0.1H, d), 8.39 (0.7H, d), 8.19 (0.1H, d), 7.76 (0.5H, d), 7.68 (0.5H, d), 7.62-7.38 (8.0H, m), 3.70 (1.6H, q), 3.58 (2.0H, s), 3.53 (0.8H, dd), 3.28 (0.6H, s), 1.36 (3.0H, dt).

The compounds described in the production examples described above and the compounds produced by the production method according to the method described in the production examples described above are shown in the tables.

The compounds of the present invention represented by the formula (1):

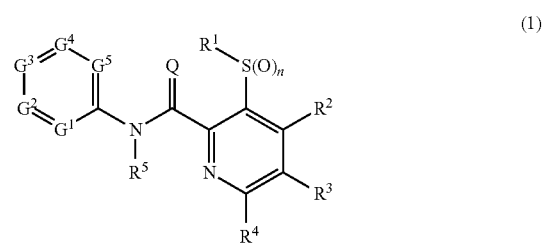

wherein $R^1$, $R^2$, $R^3$, $R^4$, $R^5$, $G^1$, $G^2$, $G^3$, $G^4$, $G^5$, n and Q represent the combinations shown in [Table 16] to [Table 22] shown below.

TABLE 16

| Compound of Present Invention | $R^1$ | $R^2$ | $R^3$ | $R^4$ | $R^5$ | $G^1$ | $G^2$ | $G^3$ | $G^4$ | $G^5$ | n | Q |
|---|---|---|---|---|---|---|---|---|---|---|---|---|
| 1 | Et | H | CF$_3$ | H | H | N | CH | CCF$_3$ | CH | CH | 0 | O |
| 2 | Et | H | H | H | H | N | CH | CCF$_3$ | CH | CH | 0 | O |
| 3 | Et | H | H | H | H | N | CH | CCF$_3$ | CH | CH | 2 | O |
| 4 | Et | H | CF$_3$ | H | H | N | CH | CCF$_3$ | CH | CH | 2 | O |
| 5 | Et | H | CF$_3$ | H | H | N | CH | CCF$_3$ | CH | CH | 1 | O |
| 6* | Et | H | H | H | H | N | CH | CCF$_3$ | CH | CH | 2 | O |
| 7 | Et | H | H | H | H | N | CCF$_3$ | CH | CH | CH | 0 | O |
| 8 | Et | H | H | H | H | N | CH | CH | CCF$_3$ | CH | 0 | O |
| 9 | Et | H | H | H | H | CH | CH | CCF$_3$ | CH | CH | 0 | O |
| 10 | Et | H | H | H | H | CH | CCF$_3$ | CH | CCF$_3$ | CH | 0 | O |
| 11 | Et | H | H | H | H | N | CCF$_3$ | CH | CH | CH | 2 | O |
| 12 | Et | H | H | H | H | N | CH | CH | CCF$_3$ | CH | 2 | O |
| 13 | Et | H | H | H | H | CH | CH | CCF$_3$ | CH | CH | 2 | O |
| 14 | Et | H | H | H | H | CH | CCF$_3$ | CH | CCF$_3$ | CH | 2 | O |
| 15 | Et | H | H | H | H | N | CH | CH | CH | CCF$_3$ | 2 | O |
| 16 | Et | H | H | H | Me | N | CH | CCF$_3$ | CH | CH | 0 | O |
| 17 | Et | H | H | H | Me | N | CH | CCF$_3$ | CH | CH | 2 | O |
| 18 | Et | H | H | H | H | CH | CH | COCF$_3$ | CH | CH | 0 | O |
| 19 | Et | H | H | H | H | CH | CCF$_3$ | CH | CH | CH | 0 | O |
| 20 | Et | H | H | H | H | CH | N | CCF$_3$ | CH | CH | 0 | O |

TABLE 16-continued

| Compound of Present Invention | R$^1$ | R$^2$ | R$^3$ | R$^4$ | R$^5$ | G$^1$ | G$^2$ | G$^3$ | G$^4$ | G$^5$ | n | Q |
|---|---|---|---|---|---|---|---|---|---|---|---|---|
| 21 | Et | H | H | H | H | CH | CH | COCF$_3$ | CH | CH | 2 | O |
| 22 | Et | H | H | H | H | CH | N | CCF$_3$ | CH | CH | 2 | O |
| 23 | Et | H | H | H | H | CH | CCF$_3$ | CH | CH | CH | 2 | O |
| 24 | Et | H | CF$_3$ | H | Me | N | CH | CCF$_3$ | CH | CH | 0 | O |

TABLE 17

| Compound of Present Invention | R$^1$ | R$^2$ | R$^3$ | R$^4$ | R$^5$ | G$^1$ | G$^2$ | G$^3$ | G$^4$ | G$^5$ | n | Q |
|---|---|---|---|---|---|---|---|---|---|---|---|---|
| 25 | Et | H | CF$_3$ | H | Me | N | CH | CCF$_3$ | CH | CH | 2 | O |
| 26 | Et | H | H | H | Et | N | CH | CCF$_3$ | CH | CH | 0 | O |
| 27 | Et | H | H | H | Et | N | CH | CCF$_3$ | CH | CH | 2 | O |
| 28 | Et | H | H | H | H | CH | N | CH | CCF$_3$ | CH | 0 | O |
| 29 | Et | H | H | H | H | CH | N | CH | CCF$_3$ | CH | 2 | O |
| 30 | Et | H | H | H | Me | N | CH | CCF$_2$CF$_3$ | CH | CH | 2 | O |
| 31 | Et | H | H | H | Me | N | CH | CCF$_2$CF$_3$ | CH | CH | 0 | O |
| 32 | Et | H | H | H | Me | N | CH | CSCF$_3$ | CH | CH | 0 | O |
| 33 | Et | H | H | H | Me | N | CH | CSCF$_3$ | CH | CH | 2 | O |
| 34 | Et | H | H | H | Me | CH | CH | CSCF$_3$ | CH | CH | 0 | O |
| 35 | Et | H | H | H | Me | CH | CH | CSCF$_3$ | CH | CH | 2 | O |
| 36 | Et | H | H | H | Me | CH | CH | CCF$_3$ | CH | CH | 0 | O |
| 37 | Et | H | H | H | Me | CH | CH | CCF$_3$ | CH | CH | 2 | O |
| 38 | Et | H | H | H | Me | CH | CCF$_3$ | CH | CCF$_3$ | CH | 2 | O |
| 39 | Et | H | H | H | Me | CH | CH | COCF$_3$ | CH | CH | 2 | O |
| 40 | Et | H | H | H | Me | CH | N | CCF$_3$ | CH | CH | 2 | O |
| 41 | Et | H | H | H | Me | N | CH | CS(O)CF$_3$ | CH | CH | 2 | O |
| 42 | Et | H | H | H | H | CH | CH | CC(OMe)$_2$CF$_3$ | CH | CH | 2 | O |
| 43 | Et | H | H | H | Me | CH | CH | CC(OMe)$_2$CF$_3$ | CH | CH | 2 | O |
| 44 | Et | H | H | H | Me | N | CH | CS(O)$_2$CF$_3$ | CH | CH | 2 | O |
| 45 | Et | H | H | H | CycPr | N | CH | CCF$_3$ | CH | CH | 2 | O |
| 46 | Et | H | H | H | H | N | CH | CCF$_2$CF$_3$ | CH | CH | 0 | O |
| 47 | Et | H | H | H | H | N | CH | CCF$_2$CF$_3$ | CH | CH | 2 | O |
| 48 | Et | H | H | H | H | N | CH | CSCF$_3$ | CH | CH | 0 | O |

TABLE 18

| Compound of Present Invention | R$^1$ | R$^2$ | R$^3$ | R$^4$ | R$^5$ | G$^1$ | G$^2$ | G$^3$ | G$^4$ | G$^5$ | n | Q |
|---|---|---|---|---|---|---|---|---|---|---|---|---|
| 49 | Et | H | H | H | H | N | CH | CSCF$_3$ | CH | CH | 2 | O |
| 50 | Et | H | CF$_3$ | H | Me | N | CH | CSCF$_3$ | CH | CH | 0 | O |
| 51 | Et | H | H | H | Me | N | CH | CSCF$_3$ | CH | CH | 1 | O |
| 52 | Et | H | CF$_3$ | H | Me | N | CH | CCF$_2$CF$_3$ | CH | CH | 2 | O |
| 53 | Et | H | CF$_3$ | H | Me | N | CH | CSCF$_3$ | CH | CH | 2 | O |
| 54 | Et | H | CF$_3$ | H | Me | N | CH | CSCF$_3$ | CH | CH | 1 | O |
| 55 | Et | H | CF$_3$ | H | Me | N | CH | CCF$_2$CF$_3$ | CH | CH | 0 | O |
| 56 | Et | H | H | H | H | N | CH | CH | CH | CCF$_3$ | 0 | O |
| 57 | Et | H | H | H | H | CH | CH | CSCF$_3$ | CH | CH | 0 | O |
| 58 | Et | H | H | H | H | CH | CH | CC(OMe)$_2$CF$_3$ | CH | CH | 0 | O |
| 59 | Et | H | H | H | CycPr | N | CH | CCF$_3$ | CH | CH | 0 | O |
| 60 | Et | H | H | H | H | CH | CH | CCF$_2$CF$_3$ | CH | CH | 0 | O |
| 61 | Et | H | H | H | Me | CH | CH | CCF$_2$CF$_3$ | CH | CH | 0 | O |
| 62 | Et | H | H | H | Me | CH | CH | CCF$_2$CF$_3$ | CH | CH | 2 | O |
| 63 | Et | H | CF$_3$ | H | H | CH | CH | CCF$_2$CF$_3$ | CH | CH | 0 | O |
| 64 | Et | H | CF$_3$ | H | Me | CH | CH | CCF$_2$CF$_3$ | CH | CH | 0 | O |
| 65 | Et | H | CF$_3$ | H | Me | CH | CH | CCF$_2$CF$_3$ | CH | CH | 2 | O |
| 66 | Et | H | CF$_3$ | H | H | CH | CH | CSCF$_3$ | CH | CH | 0 | O |

TABLE 18-continued

| Compound of Present Invention | R$^1$ | R$^2$ | R$^3$ | R$^4$ | R$^5$ | G$^1$ | G$^2$ | G$^3$ | G$^4$ | G$^5$ | n | Q |
|---|---|---|---|---|---|---|---|---|---|---|---|---|
| 67 | Et | H | CF$_3$ | H | Me | CH | CH | CSCF$_3$ | CH | CH | 0 | O |
| 68 | Et | H | CF$_3$ | H | Me | CH | CH | CSCF$_3$ | CH | CH | 2 | O |
| 69 | Et | H | H | H | H | N | CH | CCF$_2$CF$_3$ | CH | CH | 1 | O |
| 70 | Et | H | H | H | Me | N | CH | C(I) | CH | CH | 0 | O |
| 71 | Et | H | H | H | Me | N | CH | C(I) | CH | CH | 1 | O |
| 72 | Et | H | H | H | Me | N | CH | C(I) | CH | CH | 2 | O |

TABLE 19

| Compound of Present Invention | R$^1$ | R$^2$ | R$^3$ | R$^4$ | R$^5$ | G$^1$ | G$^2$ | G$^3$ | G$^4$ | G$^5$ | n | Q |
|---|---|---|---|---|---|---|---|---|---|---|---|---|
| 73 | Et | H | H | H | Et | N | CH | C(CF$_2$CF$_3$) | CH | CH | 2 | O |
| 74 | Et | H | H | H | Pr | N | CH | C(CF$_2$CF$_3$) | CH | CH | 2 | O |
| 75 | Et | H | H | H | iPr | N | CH | C(CF$_2$CF$_3$) | CH | CH | 2 | O |
| 76 | Et | H | H | H | CH$_2$C≡CH | N | CH | C(CF$_2$CF$_3$) | CH | CH | 2 | O |
| 77 | Et | H | H | H | CH$_2$CH=CH$_2$ | N | CH | C(CF$_2$CF$_3$) | CH | CH | 2 | O |
| 78 | Et | H | H | H | Me | N | CH | C(CF$_2$CF$_2$CF$_3$) | CH | CH | 2 | O |
| 79 | Et | H | H | H | Me | N | CH | C(Phenyl) | CH | CH | 2 | O |
| 80 | Et | H | H | H | Benzyl | N | CH | C(CF$_2$CF$_3$) | CH | CH | 2 | O |
| 81 | Et | H | H | H | 6-Chloropyridin-3-ylmethyl | N | CH | C(CF$_2$CF$_3$) | CH | CH | 2 | O |
| 82 | Et | H | H | H | 2-Chlorothiazol-5-ylmethyl | N | CH | C(CF$_2$CF$_3$) | CH | CH | 2 | O |
| 83 | Et | H | H | H | C(O)OMe | N | CH | C(CF$_2$CF$_3$) | CH | CH | 2 | O |
| 84 | Et | H | H | H | CH$_2$CF$_3$ | N | CH | C(CF$_2$CF$_3$) | CH | CH | 2 | O |
| 85 | Et | H | H | H | CH$_2$CF$_2$CF$_2$H | N | CH | C(CF$_2$CF$_3$) | CH | CH | 2 | O |
| 86 | Et | H | H | H | CH$_2$CF$_2$CF$_3$ | N | CH | C(CF$_2$CF$_3$) | CH | CH | 2 | O |
| 87 | Et | H | H | H | CH$_2$C(O)OMe | N | CH | C(CF$_2$CF$_3$) | CH | CH | 2 | O |
| 88 | Et | H | H | H | CH$_2$CN | N | CH | C(CF$_2$CF$_3$) | CH | CH | 2 | O |
| 89 | Et | H | H | H | Me | N | CH | C(2-Fluorophenyl) | CH | CH | 2 | O |
| 90 | Et | H | H | H | Me | N | CH | C(3-Fluorophenyl) | CH | CH | 2 | O |
| 91 | Et | H | H | H | Me | N | CH | C(4-Fluorophenyl) | CH | CH | 2 | O |
| 92 | Et | H | H | H | CH(Me)C(O)OMe | N | CH | C(CF$_2$CF$_3$) | CH | CH | 2 | O |
| 93 | Et | H | H | H | CH$_2$CycPr | N | CH | C(CF$_2$CF$_3$) | CH | CH | 2 | O |
| 94 | Et | H | H | H | Me | N | CH | C(3,5-Difluorophenyl) | CH | CH | 2 | O |
| 95 | Et | H | H | H | Me | N | CH | C(2-Trifluoromethylphenyl) | CH | CH | 2 | O |
| 96 | Et | H | H | H | Me | N | CH | C(3-Trifluoromethylphenyl) | CH | CH | 2 | O |

TABLE 20

| Compound of Present Invention | R$^1$ | R$^2$ | R$^3$ | R$^4$ | R$^5$ | G$^1$ | G$^2$ | G$^3$ | G$^4$ | G$^5$ | n | Q |
|---|---|---|---|---|---|---|---|---|---|---|---|---|
| 97 | Et | H | H | H | Me | N | CH | C(4-Trifluoromethylphenyl) | CH | CH | 2 | O |
| 98 | Et | H | H | H | C(O)NMe$_2$ | N | CH | C(CF$_2$CF$_3$) | CH | CH | 2 | O |
| 99 | Et | H | H | H | CH$_2$CH=CCl$_2$ | N | CH | C(CF$_2$CF$_3$) | CH | CH | 2 | O |
| 100 | Et | H | H | H | CH$_2$OCH$_3$ | N | CH | C(CF$_2$CF$_3$) | CH | CH | 2 | O |
| 101 | Et | H | H | H | Me | N | CH | C(OCH$_2$CF$_3$) | CH | CH | 2 | O |
| 102 | Et | H | H | H | Me | CH | CCl | C(CF$_3$) | CH | CH | 2 | O |
| 103 | Et | H | H | H | Me | CH | CH | C(CF$_3$) | CH | CH | 2 | O |
| 104 | Et | H | H | H | Me | CH | CF | C(CF$_3$) | CH | CH | 2 | O |
| 105 | Et | H | H | H | Me | CH | CBr | C(OCF$_3$) | CH | CH | 2 | O |
| 106 | Et | H | H | H | Me | CH | C(CF$_3$) | C(CF$_3$) | CH | CH | 2 | O |
| 107 | Et | H | H | H | Me | CH | CF | C(CF$_3$) | CH | CH | 2 | O |
| 108 | Et | H | CF$_3$ | H | Me | N | CH | C[S(O)CF$_3$] | CH | CH | 2 | O |
| 109 | Et | H | CF$_3$ | H | Me | CH | CH | C(SCF$_3$) | CH | CH | 1 | O |
| 110 | Et | H | H | H | Me | N | CCl | C(CF$_2$CF$_3$) | CH | CH | 0 | O |
| 111 | Et | H | H | H | Me | N | CCl | C(I) | CH | CH | 0 | O |
| 112 | Et | H | H | H | Me | N | CCl | C(CF$_2$CF$_3$) | CH | CH | 2 | O |
| 113 | Et | H | H | H | Me | N | CCl | C(I) | CH | CH | 2 | O |
| 114 | Et | H | H | H | Me | CH | CH | C[S(O)CF$_3$] | CH | CH | 2 | O |

TABLE 20-continued

| Compound of Present Invention | R¹ | R² | R³ | R⁴ | R⁵ | G¹ | G² | G³ | G⁴ | G⁵ | n | Q |
|---|---|---|---|---|---|---|---|---|---|---|---|---|
| 115* | Et | H | H | H | Me | CH | CH | C[S(O)CF₃] | CH | CH | 2 | O |
| 116 | Et | H | H | H | Me | CH | CH | C[S(O)₂CF₃] | CH | CH | 2 | O |
| 117 | Et | H | Cl | H | Me | CH | CH | C[S(O)CF₃] | CH | CH | 2 | O |
| 118 | Et | H | Cl | H | Me | CH | CH | C(SCF₃) | CH | CH | 2 | O |
| 119 | Et | H | NHCO₂Me | H | Me | CH | CH | C(SCF₃) | CH | CH | 2 | O |
| 120 | Et | H | NHC(O)Me | H | Me | CH | CH | C(SCF₃) | CH | CH | 2 | O |

TABLE 21

| Compound of Present Invention | R¹ | R² | R³ | R⁴ | R⁵ | G¹ | G² | G³ | G⁴ | G⁵ | n | Q |
|---|---|---|---|---|---|---|---|---|---|---|---|---|
| 121 | Et | H | N(Me)C(O)Me | H | Me | CH | CH | C(SCF₃) | CH | CH | 2 | O |
| 122 | Et | H | NMe₂ | H | Me | CH | CH | C(SCF₃) | CH | CH | 2 | O |
| 123 | Et | H | NH₂ | H | Me | CH | CH | C(SCF₃) | CH | CH | 2 | O |
| 124 | Et | H | Phenyl | H | Me | CH | CH | C(SCF₃) | CH | CH | 2 | O |
| 125 | Et | H | C(O)OEt | H | Me | CH | CH | C(SCF₃) | CH | CH | 2 | O |
| 126 | Et | H | C(O)OEt | H | Me | CH | CH | C[C(O)OEt] | CH | CH | 2 | O |
| 127 | Et | H | C(O)OH | H | Me | CH | CH | C(SCF₃) | CH | CH | 2 | O |
| 128 | Et | H | C(O)NHMe | H | Me | CH | CH | C(SCF₃) | CH | CH | 2 | O |
| 129 | Et | H | C(O)NHNHC(O)OEt | H | Me | CH | CH | C(SCF₃) | CH | CH | 2 | O |
| 130 | Et | H | N(SO₂Me)₂ | H | Me | CH | CH | C(SCF₃) | CH | CH | 2 | O |
| 131 | Et | H | Cl | H | Me | CH | CH | C(CF₃) | CH | CH | 0 | O |
| 132 | Et | H | Cl | H | Me | N | CH | C(CF₃) | CH | CH | 0 | O |
| 133 | Et | H | Cl | H | Me | CH | CH | C(CF₃) | CH | CH | 1 | O |
| 134 | Et | H | Cl | H | Me | N | CH | C(CF₃) | CH | CH | 1 | O |
| 135 | Et | H | NHC(O)NMe₂ | H | Me | CH | CH | C(SCF₃) | CH | CH | 2 | O |
| 136 | Et | H | Cl | H | Me | CH | CH | C(CF₃) | CH | CH | 2 | O |
| 137 | Et | H | Cl | H | Me | N | CH | C(CF₃) | CH | CH | 2 | O |
| 138 | Et | H | NH₂ | H | Me | CH | CH | C(CF₃) | CH | CH | 2 | O |
| 139 | Et | H | NH₂ | H | Me | N | CH | C(CF₃) | CH | CH | 2 | O |
| 140 | Et | H | NHC(O)Me | H | Me | CH | CH | C(CF₃) | CH | CH | 2 | O |
| 141 | Et | H | NHC(O)Me | H | Me | N | CH | C(CF₃) | CH | CH | 2 | O |
| 142 | Et | H | H | H | H | CH | CCl | C(CF₃) | CH | CH | 0 | O |
| 143 | Et | H | H | H | Me | CH | CCl | C(CF₃) | CH | CH | 0 | O |
| 144 | Et | H | H | H | H | CH | CH | C(CF₃) | CH | CF | 0 | O |

TABLE 22

| Compound of Present Invention | R¹ | R² | R³ | R⁴ | R⁵ | G¹ | G² | G³ | G⁴ | G⁵ | n | Q |
|---|---|---|---|---|---|---|---|---|---|---|---|---|
| 145 | Et | H | H | H | Me | CH | CH | C(CF₃) | CH | CF | 0 | O |
| 146 | Et | H | H | H | H | CH | CF | C(CF₃) | CH | CF | 0 | O |
| 147 | Et | H | H | H | Me | CH | CF | C(CF₃) | CH | CF | 0 | O |
| 148 | Et | H | H | H | H | CH | CBr | C(OCF₃) | CH | CH | 0 | O |
| 149 | Et | H | H | H | Me | CH | CBr | C(OCF₃) | CH | CH | 0 | O |
| 150 | Et | H | H | H | H | CH | C(CF₃) | C(CF₃) | CH | CH | 0 | O |
| 151 | Et | H | H | H | Me | CH | C(CF₃) | C(CF₃) | CH | CH | 0 | O |
| 152 | Et | H | H | H | H | CH | CF | C(CF₃) | CF | CH | 0 | O |
| 153 | Et | H | H | H | Me | CH | CF | C(CF₃) | CF | CH | 0 | O |
| 154 | Et | H | SEt | H | Me | CH | CH | C(SCF₃) | CH | CH | 2 | O |
| 155 | Et | H | Thiophen-2-yl | H | Me | CH | CH | C(SCF₃) | CH | CH | 2 | O |
| 156 | Et | H | F | H | Me | CH | CH | C(SCF₃) | CH | CH | 2 | O |
| 157 | Et | H | Pyridin-3-yl | H | Me | CH | CH | C(SCF₃) | CH | CH | 2 | O |
| 158 | Et | H | Cl | H | Me | CH | CH | C(SCF₃) | CH | CH | 2 | O |

(In [Table 16] to [Table 22] above, Me represents a methyl group, Et represents an ethyl group, Pr represents a propyl group, CycPr represents a cyclopropyl group, and iPr represents an isopropyl group.)

Here, "*" in the compound of the present invention in the tables means that the compound is an N-oxide. Specific examples are the following compounds.

Compound of Present Invention 6

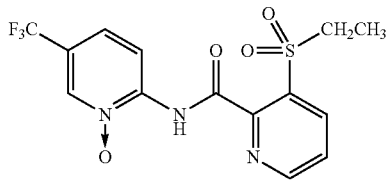 [SMILES: CCS(=O)(=O)c1cccnc1C(=O)Nc1ccc(C(F)(F)F)c[n+]1[O-]]

Compound of Present Invention 115

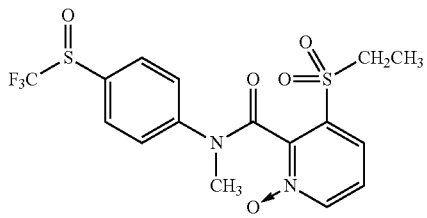 [SMILES: CCS(=O)(=O)c1ccc[n+]([O-])c1C(=O)N(C)c1ccc(S(=O)C(F)(F)F)cc1]

$^1$H-NMR data of the compounds of the present invention shown in [Table 16] to [Table 22] are shown below.

Compound of Present Invention 11

$^1$H-NMR (CDCl$_3$)δ: 10.21 (1H, brs), 8.95-8.81 (1H, m), 8.73-8.55 (2H, m), 8.02-7.88 (1H, m), 7.82-7.67 (1H, m), 7.56-7.42 (1H, m), 4.07-3.81 (2H, m), 1.46-1.29 (3H, m).

Compound of Present Invention 12

$^1$H-NMR (CDCl$_3$)δ: 10.26 (1H, brs), 8.86 (1H, dd), 8.70-8.64 (2H, m), 8.54 (1H, d), 7.75 (1H, dd), 7.34 (1H, d), 3.99 (2H, q), 1.38 (3H, t).

Compound of Present Invention 13

$^1$H-NMR (CDCl$_3$)δ: 9.69 (1H, brs), 8.84 (1H, d), 8.65 (1H, d), 7.86 (2H, d), 7.73 (1H, dd), 7.64 (2H, d), 3.97 (2H, q), 1.37 (3H, t).

Compound of Present Invention 15

$^1$H-NMR (CDCl$_3$)δ: 8.86 (1H, d), 8.76 (1H, brs), 8.68 (1H, d), 8.02 (1H, d), 7.75 (1H, dd), 7.32-7.24 (2H, m), 3.99 (2H, d), 1.35 (3H, t).

Compound of Present Invention 19

$^1$H-NMR (CDCl$_3$)δ: 10.30 (1H, brs), 8.41-8.30 (1H, m), 8.18-8.09 (1H, m), 7.96 (1H, d), 7.74 (1H, d), 7.55-7.35 (3H, m), 2.96 (2H, q), 1.45 (3H, t).

Compound of Present Invention 20

$^1$H-NMR (CDCl$_3$)δ: 10.45 (1H, brs), 8.78 (1H, s), 8.74 (1H, d), 8.36 (1H, s), 7.76 (1H, d), 7.70 (1H, d), 7.50-7.41 (1H, m), 2.98 (2H, d), 1.45 (3H, d).

Compound of Present Invention 22

$^1$H-NMR (CDCl$_3$)δ: 9.84 (1H, brs), 8.87 (1H, dd), 8.79 (1H, d), 8.71-8.61 (2H, m), 7.77 (1H, dd), 7.73 (1H, d), 3.95 (2H, q), 1.38 (3H, t).

Compound of Present Invention 23

$^1$H-NMR (CDCl$_3$)δ: 9.66 (1H, brs), 8.84 (1H, dd), 8.66 (1H, dd), 8.01 (1H, s), 7.95 (1H, d), 7.73 (1H, dd), 7.51 (1H, dd), 7.44 (1H, d), 3.99 (2H, q), 1.37 (3H, t).

Compound of Present Invention 28

$^1$H-NMR (CDCl$_3$)δ: 10.43 (1H, brs), 8.90 (1H, s), 8.84 (1H, s), 8.63 (1H, s), 8.36 (1H, d), 7.76 (1H, d), 7.46 (1H, dd), 2.98 (2H, q), 1.46 (3H, t).

Compound of Present Invention 29

$^1$H-NMR (CDCl$_3$)δ: 9.83 (1H, brs), 8.93 (1H, s), 8.86 (1H, d), 8.74-8.63 (3H, m), 7.77 (1H, dd), 3.97 (2H, q), 1.38 (3H, t).

Compound of Present Invention 34

$^1$H-NMR (CDCl$_3$)δ: 8.24 (1H, brs), 7.63-7.37 (3H, m), 7.28-7.06 (3H, m), 3.51 (3H, brs), 2.89 (2H, q), 1.27 (3H, t).

Compound of Present Invention 35

1H-NMR (CDCl$_3$, 22° C.)δ: 8.91 (0.2H, dd), 8.45 (0.8H, dd), 8.38 (0.2H, dd), 8.23 (0.8H, dd), 7.75 (0.4H, d), 7.65-7.56 (0.6H, m), 7.45 (1.6H, d), 7.42-7.38 (1.6H, m), 7.34 (0.8H, dd), 3.64 (1.6H, q), 3.56 (2.4H, s), 3.47 (0.4H, q), 3.23 (0.6H, s), 1.36-1.28 (3H, m).

Compound of Present Invention 36

$^1$H-NMR (DMSO-D$_6$, 80° C.)δ: 8.25 (1H, d), 7.78 (1H, d), 7.59 (2H, d), 7.43 (2H, d), 7.29 (1H, dd), 3.35 (3H, S) 2.95 (2H, q), 1.19 (3H, t).

Compound of Present Invention 37

$^1$H-NMR (CDCl$_3$, 22° C.)δ: 8.91 (0.2H, d), 8.47 (0.8H, d), 8.38 (0.2H, d), 8.22 (0.8H, d), 7.69 (0.9H, dd), 7.61 (0.2H, dd), 7.46 (3.1H, dd), 7.35 (0.8H, dd), 3.64 (1.5H, q), 3.56 (2.4H, s), 3.46 (0.5H, q), 3.23 (0.6H, s), 1.38-1.30 (3H, m).

Compound of Present Invention 40

$^1$H-NMR (CDCl$_3$, 22° C.)δ: 8.96-8.88 (0.6H, m), 8.74 (0.7H, d), 8.51 (0.7H, dd), 8.39 (0.3H, dd), 8.23 (0.7H, dd), 8.08 (0.3H, dd), 7.87 (0.7H, dd), 7.80 (0.3H, d), 7.64 (0.3H, dd), 7.50 (0.7H, d), 7.38 (0.7H, dd), 3.66-3.55 (3.6H, m), 3.44 (0.6H, q), 3.28 (0.8H, s), 1.34 (2.5H, t), 1.26 (0.5H, t).

Compound of Present Invention 41

$^1$H-NMR (DMSO-D$_6$, 80° C.)δ: 8.76-8.66 (2H, m), 8.38 (1H, dd), 8.23 (1H, d), 7.87-7.78 (1H, m), 7.73 (1H, dd), 3.48 (2H, q), 3.44 (3H, s), 1.20 (3H, t).

Compound of Present Invention 45

$^1$H-NMR (CDCl$_3$, 22° C.)δ: 8.92-8.53 (2H, m), 8.34 (1H, d), 7.88 (1H, d), 7.72-7.47 (2H, m), 3.55 (2H, q), 3.38-3.30 (1H, m), 1.33 (3H, t), 0.86-0.57 (4H, m).

Compound of Present Invention 50

$^1$H-NMR (CDCl$_3$)δ: 8.46 (1H, s), 8.44 (1H, s), 7.89 (1H, dd), 7.84 (1H, s), 7.67-7.45 (1H, m), 3.55 (3H, s), 3.02 (2H, q), 1.35 (3H, t).

Compound of Present Invention 51

$^1$H-NMR (CDCl$_3$)δ: 8.47 (1H, dd), 8.38 (1H, d), 8.28 (1H, dd), 7.86 (1H, dd), 7.49 (1H, dd), 7.21 (1H, d), 3.61 (3H, s), 3.48-3.34 (1H, m), 3.06-2.94 (1H, m), 1.35 (3H, t).

Compound of Present Invention 52

$^1$H-NMR (DMSO-D$_6$, 80° C.)δ: 9.15 (1H, brs), 8.64 (1H, s), 8.50 (1H, brs), 8.14 (1H, d), 7.78 (1H, brs), 3.56 (2H, q), 3.47 (3H, s), 1.23 (3H, t).

Compound of Present Invention 53

$^1$H-NMR (DMSO-D$_6$, 80° C.)δ: 9.12 (1H, brs), 8.63 (1H, d), 8.42 (1H, brs), 8.13 (1H, d), 7.67 (1H, brs), 3.56 (2H, q), 3.45 (3H, s), 1.23 (3H, t).

Compound of Present Invention 54

$^1$H-NMR (CDCl$_3$)δ: 8.71 (1H, d), 8.48 (1H, s), 8.27 (1H, d), 7.96 (1H, dd), 7.29 (1H, d), 3.62 (3H, s), 3.52-3.40 (1H, m), 3.08-2.97 (1H, m), 1.36 (3H, t).

Compound of Present Invention 55

$^1$H-NMR (CDCl$_3$)δ: 8.49 (1H, s), 8.47 (1H, s), 7.89-7.81 (2H, m), 7.75-7.57 (1H, m), 3.55 (3H, s), 3.02 (2H, q), 1.35 (3H, t).

Compound of Present Invention 56

$^1$H-NMR (CDCl$_3$)δ: 10.99 (1H, brs), 8.76 (1H, d), 8.35 (1H, d), 7.99 (1H, d), 7.73 (1H, d), 7.42 (1H, dd), 7.28-7.18 (1H, m), 2.94 (2H, q), 1.40 (3H, q).

Compound of Present Invention 57

$^1$H-NMR (CDCl$_3$)δ: 10.29 (1H, s), 8.33 (1H, dd), 7.90-7.83 (2H, m), 7.73 (1H, dd), 7.65 (2H, d), 7.42 (1H, dd), 2.96 (2H, q), 1.44 (3H, t).

Compound of Present Invention 59

$^1$H-NMR (CDCl$_3$)δ: 8.61 (1H, dd), 8.35 (1H, dd), 7.89 (1H, dd), 7.75-7.68 (2H, m), 7.25 (1H, dd), 3.35-3.25 (1H, m), 2.96 (2H, q), 1.30 (3H, t), 0.84-0.76 (2H, m), 0.64-0.57 (2H, m).

Compound of Present Invention 60

$^1$H-NMR (CDCl$_3$)δ: 10.34 (1H, s), 8.34 (1H, dd), 7.93 (2H, d), 7.74 (1H, dd), 7.59 (2H, d), 7.43 (1H, dd), 2.96 (2H, q), 1.45 (3H, t).

Compound of Present Invention 61

$^1$H-NMR (CDCl$_3$)δ: 8.24 (1H, s), 7.55-7.13 (6H, m), 3.52 (3H, s), 2.90 (2H, q), 1.27 (3H, t).

Compound of Present Invention 62

$^1$H-NMR (DMSO-D$_6$, 100° C.)δ: 8.82-8.51 (1H, m), 8.35-8.22 (1H, m), 7.73-7.41 (5H, m), 3.59-3.19 (5H, m), 1.18 (3H, t).

Compound of Present Invention 63

$^1$H-NMR (CDCl$_3$)δ: 10.21 (1H, s), 8.57 (1H, s), 7.96-7.89 (3H, m), 7.61 (2H, d), 3.00 (2H, q), 1.47 (3H, t).

Compound of Present Invention 64

$^1$H-NMR (CDCl$_3$)δ: 8.48-8.38 (1H, m), 7.73-7.28 (5H, m), 3.62-3.43 (3H, m), 3.05-2.92 (2H, m), 1.32 (3H, t).

Compound of Present Invention 65

$^1$H-NMR (CDCl$_3$)δ: 9.15 (0.2H, s), 8.69 (0.8H, s), 8.61 (0.2H, s), 8.45 (0.8H, s), 7.73 (0.5H, d), 7.66 (0.5H, d), 7.49 (1.5H, d), 7.45 (1.5H, d), 3.68 (1.6H, q), 3.57 (2.4H, s), 3.51 (0.4H, q), 3.25 (0.6H, s), 1.39-1.33 (3.0H, m).

Compound of Present Invention 66

$^1$H-NMR (CDCl$_3$)δ: 10.16 (1H, s), 8.56 (1H, s), 7.87 (3H, t), 7.66 (2H, d), 2.99 (2H, q), 1.46 (3H, t).

Compound of Present Invention 67

$^1$H-NMR (CDCl$_3$)δ: 8.46-8.36 (1H, m), 7.72-7.64 (2H, m), 7.52-7.44 (2H, m), 7.24-7.17 (1H, m), 3.58-3.49 (3H, m), 2.99-2.88 (2H, m), 1.32 (3H, t).

Compound of Present Invention 68

$^1$H-NMR (CDCl$_3$)δ: 9.15 (0.3H, s), 8.68 (0.7H, s), 8.60 (0.3H, s), 8.44 (0.7H, s), 7.77 (0.3H, d), 7.58 (0.3H, d), 7.48 (1.7H, d), 7.39 (1.7H, d), 3.66 (1.7H, t), 3.56 (2.1H, s), 3.50 (0.3H, t), 3.23 (0.9H, s), 1.36 (3.0H, t).

Compound of Present Invention 69

$^1$H-NMR (CDCl$_3$)δ: 10.75 (1H, s), 8.76 (1H, dd), 8.70 (1H, dd), 8.61 (1H, d), 8.51 (1H, dd), 7.97 (1H, dd), 7.81 (1H, dd), 3.40-3.29 (1H, m), 2.96-2.85 (1H, m), 1.32 (3H, t).

Compound of Present Invention 70

¹H-NMR (CDCl₃)δ: 8.52 (1H, s), 8.30 (1H, s), 7.80 (1H, d), 7.67 (1H, d), 7.29-7.20 (2H, m), 3.50 (3H, s), 2.94 (2H, q), 1.30 (3H, t).

Compound of Present Invention 72

¹H-NMR (CDCl₃)δ: 8.89 (0.3H, s), 8.67 (0.3H, s), 8.55 (0.7H, s), 8.50 (0.7H, s), 8.40-8.27 (1.0H, m), 8.01 (0.3H, s), 7.94 (0.3H, s), 7.69-7.57 (1.0H, m), 7.45-7.37 (0.7H, m), 6.90 (0.7H, d), 3.71-3.61 (3.6H, m), 3.48-3.44 (0.7H, m), 3.34-3.30 (0.7H, m), 1.35 (3.0H, t).

Compound of Present Invention 73

¹H-NMR (DMSO-D₆, 80° C.)δ: 8.67 (1H, brs), 8.63 (1H, brs), 8.37 (1H, dd), 8.05 (1H, d), 7.70 (1H, brs), 7.57 (1H, s), 4.04 (2H, q), 3.52 (2H, q), 1.23-1.17 (6H, m).

Compound of Present Invention 74

¹H-NMR (DMSO-D₆, 80° C.)δ: 8.65-8.59 (2H, m), 8.36 (1H, dd), 8.03 (1H, d), 7.68 (1H, dd), 7.51 (1H, brs), 4.06-3.96 (2H, m), 3.54 (2H, q), 1.70-1.59 (2H, m), 1.20 (3H, t), 0.85 (3H, t).

Compound of Present Invention 75

¹H-NMR (DMSO-D₆, 80° C.)δ: 8.75 (1H, brs), 8.60-8.56 (1H, m), 8.31 (1H, dd), 8.05-8.01 (1H, m), 7.62 (1H, dd), 7.44-7.40 (1H, m), 4.61 (1H, brs), 3.56 (2H, q), 1.35 (6H, d), 1.20 (3H, t).

Compound of Present Invention 76

¹H-NMR (DMSO-D₆, 80° C.)δ: 8.64 (1H, d), 8.57 (1H, s), 8.37 (1H, dd), 8.09 (1H, d), 7.70 (1H, dd), 7.57-7.51 (1H, m), 4.87 (2H, d), 3.52 (2H, q), 1.21 (3H, t).

Compound of Present Invention 77

¹H-NMR (DMSO-D₆, 80° C.)δ: 8.65-8.61 (1H, m), 8.53 (1H, s), 8.37 (1H, dd), 8.04 (1H, d), 7.69 (1H, dd), 7.53-7.47 (1H, m), 5.98-5.83 (1H, m), 5.25 (1H, d), 5.11 (1H, d), 4.70 (2H, brs), 3.53 (2H, q), 1.20 (3H, t).

Compound of Present Invention 78

¹H-NMR (CDCl₃)δ: 8.86-7.19 (6H, m), 3.66 (5H, s), 1.35 (3H, t).

Compound of Present Invention 79

¹H-NMR (DMSO-D₆, 100° C.)δ: 8.66 (2H, d), 8.35 (1H, d), 7.98 (1H, d), 7.69-7.35 (7H, m), 3.53-3.42 (5H, m), 1.21 (3H, t).

Compound of Present Invention 80

¹H-NMR (DMSO-D₆, 80° C.)δ: 8.62-8.58 (1H, m), 8.50 (1H, s), 8.38 (1H, d), 7.96 (1H, d), 7.70-7.65 (1H, m), 7.44-7.38 (3H, m), 7.30-7.25 (2H, m), 7.21 (1H, d), 5.35 (2H, s), 3.57 (2H, q), 1.22 (3H, t).

Compound of Present Invention 81

¹H-NMR (DMSO-D₆, 80° C.)δ: 8.61 (1H, d), 8.59 (1H, s), 8.44 (1H, s), 8.39 (1H, dd), 8.01 (1H, d), 7.89 (1H, dd), 7.70 (1H, dd), 7.42 (2H, d), 5.35 (2H, s), 3.56 (2H, q), 1.22 (3H, t).

Compound of Present Invention 82

¹H-NMR (DMSO-D₆, 80° C.)δ: 8.69 (1H, s), 8.67-8.63 (1H, m), 8.39 (1H, dd), 8.04 (1H, d), 7.73 (1H, dd), 7.56-7.51 (1H, m), 7.46-7.38 (1H, m), 5.40 (2H, s), 3.56 (2H, q), 1.22 (3H, t).

Compound of Present Invention 83

¹H-NMR (DMSO-D₆, 80° C.) δ: 8.98 (1H, s), 8.90 (1H, dd), 8.44-8.40 (2H, m), 7.81 (1H, dd), 7.75 (1H, d), 3.55 (3H, s), 3.38 (2H, q), 1.18 (3H, t).

Compound of Present Invention 84

¹H-NMR (DMSO-D₆, 80° C.)δ: 8.67 (1H, d), 8.58 (1H, dd), 8.38 (1H, dd), 8.06 (1H, dd), 7.70 (1H, dd), 7.39 (1H, d), 5.04 (2H, q), 3.55 (2H, q), 1.21 (3H, t).

Compound of Present Invention 85

¹H-NMR (DMSO-D₆, 80° C.)δ: 8.67 (1H, s), 8.56 (1H, d), 8.38 (1H, dd), 8.03 (1H, dd), 7.69 (1H, dd), 7.36 (1H, d), 6.61-6.35 (1H, m), 4.92 (2H, t), 3.56 (2H, q), 1.22 (3H, t).

Compound of Present Invention 86

¹H-NMR (DMSO-D₆, 80° C.)δ: 8.71-8.68 (1H, m), 8.57 (1H, dd), 8.38 (1H, dd), 8.03 (1H, dd), 7.70 (1H, dd), 7.34 (1H, d), 5.11 (2H, t), 3.55 (2H, q), 1.20 (3H, q).

Compound of Present Invention 87

¹H-NMR (DMSO-D₆, 80° C.)δ: 8.67 (1H, d), 8.58 (1H, s), 8.39 (1H, dd), 8.05 (1H, d), 7.73 (1H, dd), 7.57-7.48 (1H, m), 4.81 (2H, s), 3.66 (3H, s), 3.52 (2H, q), 1.20 (3H, t).

Compound of Present Invention 88

¹H-NMR (DMSO-D₆, 80° C.)δ: 8.74-8.69 (2H, m), 8.42 (1H, dd), 8.12 (1H, d), 7.77 (1H, dd), 7.53-7.47 (1H, m), 5.09 (2H, s), 3.53 (2H, q), 1.22 (3H, t).

Compound of Present Invention 89

¹H-NMR (DMSO-D₆)δ: 8.73 (1H, s), 8.50 (1H, s), 8.36 (1H, d), 7.90 (1H, s), 7.69 (1H, s), 7.54 (1H, t), 7.49-7.41 (1H, m), 7.32-7.27 (3H, m), 3.51 (2H, q), 3.42 (3H, s), 1.22-1.18 (3H, m).

Compound of Present Invention 90

¹H-NMR (DMSO-D₆)δ: 8.74-8.64 (2H, m), 8.36 (1H, d), 8.09-8.00 (1H, m), 7.73-7.47 (5H, m), 7.19 (1H, dd), 3.52 (2H, q), 3.42 (3H, s), 1.20 (3H, t).

Compound of Present Invention 91

¹H-NMR (DMSO-D₆)δ: 8.77-8.58 (2H, m), 8.36 (1H, d), 8.02-7.93 (1H, m), 7.74-7.65 (3H, m), 7.26 (3H, t), 3.52 (2H, q), 3.42 (3H, s), 1.20 (3H, t).

Compound of Present Invention 92

¹H-NMR (DMSO-D₆, 80° C.)δ: 8.62 (1H, d), 8.56 (1H, d), 8.36 (1H, dd), 7.98 (1H, dd), 7.66 (1H, dd), 7.33-7.27 (1H, m), 5.25 (1H, q), 3.66 (3H, s), 3.57 (2H, q), 1.58 (3H, d), 1.21 (3H, t).

Compound of Present Invention 93

¹H-NMR (DMSO-D₆, 80° C.)δ: 8.66-8.61 (2H, m), 8.36 (1H, dd), 8.04 (1H, d), 7.68 (1H, dd), 7.56-7.49 (1H, m), 3.97 (2H, d), 3.54 (2H, q), 1.20 (3H, t), 0.89-0.83 (1H, m), 0.41-0.34 (2H, m), 0.23-0.15 (2H, m).

Compound of Present Invention 94

¹H-NMR (DMSO-D₆)δ: 8.71 (2H, s), 8.37 (1H, d), 8.13-8.04 (1H, m), 7.73-7.41 (4H, m), 7.20-7.13 (1H, m), 3.51 (2H, q), 3.42 (3H, s), 1.21 (3H, t).

Compound of Present Invention 95

¹H-NMR (DMSO-D₆)δ: 8.70 (2H, s), 8.37 (1H, d), 8.10-7.78 (6H, m), 7.69 (1H, s), 3.52 (2H, q), 3.43 (3H, s), 1.21 (3H, t).

Compound of Present Invention 96

¹H-NMR (DMSO-D₆)δ: 8.71 (2H, s), 8.37 (1H, d), 8.13-8.07 (1H, m), 8.00-7.96 (2H, m), 7.75-7.67 (4H, m), 3.55-3.44 (5H, m), 1.29-1.16 (3H, m).

Compound of Present Invention 97

¹H-NMR (DMSO-D₆)δ: 8.68 (1H, s), 8.35 (1H, d), 8.28-8.21 (1H, m), 7.83-7.39 (7H, m), 3.52 (2H, q), 3.44 (3H, s), 1.20 (3H, t).

Compound of Present Invention 98

¹H-NMR (DMSO-D₆, 80° C.)δ: 8.71 (1H, d), 8.60 (1H, s), 8.42 (1H, dd), 8.17 (1H, dd), 7.76 (1H, dd), 7.64-7.57 (1H, m), 3.55 (2H, q), 2.96 (6H, d), 1.22 (3H, t).

Compound of Present Invention 99

¹H-NMR (DMSO-D₆, 80° C.)δ: 8.75-8.71 (1H, m), 8.68 (1H, s), 8.39 (1H, d), 8.10 (1H, d), 7.75 (1H, dd), 7.67-7.60 (1H, m), 6.23 (1H, t), 4.75 (2H, d), 3.51 (2H, q), 1.20 (3H, t).

Compound of Present Invention 100

¹H-NMR (DMSO-D₆, 80° C.)δ: 8.62 (1H, d), 8.55 (1H, s), 8.38 (1H, dd), 8.10 (1H, dd), 7.69 (1H, dd), 7.60 (1H, d), 5.46 (2H, s), 3.53 (2H, q), 3.35 (3H, s), 1.21 (3H, t).

Compound of Present Invention 101

¹H-NMR (DMSO-D₆)δ: 8.67 (1H, s), 8.32 (1H, d), 8.15 (1H, s), 7.65 (1H, s), 7.44 (2H, s), 4.73 (2H, q), 3.49 (2H, q), 3.34 (3H, s), 1.19 (3H, t).

Compound of Present Invention 102

¹H-NMR (DMSO-D₆)δ: 8.83-8.61 (1H, m), 8.37-8.27 (1H, m), 7.86-7.62 (3H, m), 7.56-7.42 (1H, m), 3.57-3.25 (5H, m), 1.22-1.14 (3H, m).

Compound of Present Invention 103

¹H-NMR (DMSO-D₆)δ: 9.03-7.24 (6H, m), 3.65-3.30 (5H, m), 1.25-1.13 (3H, m).

Compound of Present Invention 104

¹H-NMR (DMSO-D₆)δ: 8.40-8.28 (2H, m), 7.86-7.62 (3H, m), 3.57-3.19 (5H, m), 1.22-1.16 (3H, m).

Compound of Present Invention 105

¹H-NMR (DMSO-D₆)δ: 8.67-7.28 (6H, m), 3.58-3.25 (5H, m), 1.18 (3H, t).

Compound of Present Invention 106

¹H-NMR (DMSO-D₆)δ: 8.40-7.61 (6H, m), 3.58-3.31 (5H, m), 1.19 (3H, t).

Compound of Present Invention 107

¹H-NMR (DMSO-D₆)δ: 8.80 (1H, s), 8.37 (1H, d), 7.76-7.70 (1H, m), 7.45-7.36 (2H, m), 3.51 (2H, q), 3.33 (3H, s), 1.20 (3H, t).

Compound of Present Invention 108

¹H-NMR (CDCl₃)δ: 9.24-7.92 (5H, m), 3.69-3.45 (5H, m), 1.39 (3H, t).

Compound of Present Invention 109

¹H-NMR (CDCl₃)δ: 8.67-8.60 (1.0H, m), 8.55-8.41 (1.0H, m) 7.65-7.51 (2.0H, m), 7.18-7.05 (2.0H, m), 3.71-3.65 (0.2H, m), 3.60 (0.2H, s), 3.53 (2.8H, s), 3.48-3.43 (0.9H, m), 3.05-2.97 (0.9H, m), 1.35 (3.0H, t).

Compound of Present Invention 110

¹H-NMR (CDCl₃)δ: 8.34 (1H, dd), 7.83 (1H, d), 7.75 (1H, dd), 7.70 (1H, d), 7.29 (1H, dd), 3.50 (3H, s), 2.96 (2H, q), 1.31 (3H, t).

Compound of Present Invention 111

¹H-NMR (CDCl₃)δ: 8.32 (1H, d), 7.95 (1H, d), 7.71 (1H, dd), 7.27-7.24 (2H, m), 3.47 (3H, s), 2.95 (2H, q), 1.31 (3H, t).

Compound of Present Invention 112

¹H-NMR (CDCl₃)δ: 8.93-8.59 (1H, m), 8.36 (1H, dd), 7.99-7.74 (1H, m), 7.67-7.52 (1H, m), 7.28-7.26 (1H, m), 3.52 (5H, s), 1.39 (3H, dt).

Compound of Present Invention 113

¹H-NMR (CDCl₃)δ: 8.86-6.70 (5H, m), 3.73-3.09 (5H, m), 1.41-1.10 (3H, m).

Compound of Present Invention 114

¹H-NMR (CDCl₃)δ: 8.92 (0.2H, dd), 8.43 (0.8H, dd), 8.38 (0.2H, dd), 8.24 (0.8H, dd), 7.90 (0.4H, d), 7.79 (0.4H, d), 7.65-7.57 (3.4H, m), 7.35 (0.8H, dd), 3.65 (1.5H, q), 3.60 (2.3H, s), 3.49-3.42 (0.5H, m), 3.26 (0.7H, s), 1.33 (3.0H, t).

Compound of Present Invention 115

$^1$H-NMR (CDCl$_3$)δ: 8.46-7.29 (7H, m), 3.57-3.34 (5H, m), 1.36-1.30 (3H, m).

Compound of Present Invention 116

$^1$H-NMR (CDCl$_3$)δ: 8.93 (0.3H, s), 8.48-8.37 (1.0H, m), 8.27 (0.7H, d), 8.15-7.38 (5.00H, m), 3.69-3.60 (3.5H, m), 3.52-3.43 (0.7H, m), 3.34-3.26 (0.8H, m), 1.35 (3.0H, t).

Compound of Present Invention 119

$^1$H-NMR (CDCl$_3$)δ: 8.95-8.92 (0.2H, m), 8.48-8.44 (1.0H, m), 8.36 (0.8H, s), 7.74 (0.4H, d), 7.57 (0.4H, d), 7.46 (1.6H, d), 7.37 (1.6H, d), 6.99-6.96 (0.2H, m), 6.80-6.75 (0.8H, m), 3.87 (0.6H, s), 3.80 (2.4H, s), 3.66 (1.6H, q), 3.54 (2.4H, s), 3.48 (0.4H, q), 3.23 (0.6H, s), 1.33 (3.0H, dt).

Compound of Present Invention 120

$^1$H-NMR (CDCl$_3$)δ: 9.13 (0.2H, d), 8.65 (0.8H, d), 8.52 (0.2H, d), 8.41 (0.8H, d), 7.76 (0.2H, s), 7.74 (0.4H, d), 7.56 (0.4H, d), 7.52 (0.8H, s), 7.46 (1.6H, d), 7.37 (1.6H, d), 3.65 (1.6H, q), 3.54 (2.4H, s), 3.48 (0.4H, q), 3.22 (0.6H, s), 2.29 (0.5H, s), 2.20 (2.5H, s), 1.37-1.30 (3.0H, m).

Compound of Present Invention 121

$^1$H-NMR (CDCl$_3$)δ: 8.84 (0.2H, s), 8.34 (0.8H, s), 8.24 (0.2H, s), 8.10 (0.8H, s), 7.76 (0.4H, d), 7.58 (0.4H, d), 7.48 (1.6H, d), 7.40 (1.6H, dd), 3.71-3.26 (8H, m), 2.23-1.71 (3.0H, m), 1.34 (3.0H, dt).

Compound of Present Invention 122

$^1$H-NMR (CDCl$_3$)δ: 7.75 (1.2H, s), 7.53-7.31 (4.8H, m), 3.77-3.63 (2.0H, m), 3.57-3.52 (3.0H, m), 3.28-3.21 (0.6H, m), 3.17-3.10 (0.9H, m), 2.99 (4.5H, s), 1.38-1.33 (3.0H, m).

Compound of Present Invention 123

$^1$H-NMR (CDCl$_3$)δ: 8.27-7.34 (6.0H, m), 4.21 (0.5H, s), 4.03 (1.5H, s), 3.68 (1.4H, q), 3.55-3.51 (2.9H, m), 3.41-3.36 (0.2H, m), 3.23 (0.5H, s), 1.34 (3.0H, t).

Compound of Present Invention 126

$^1$H-NMR (CDCl$_3$)δ: 9.46 (0.1H, d), 9.00 (0.9H, d), 8.91 (0.1H, d), 8.75 (0.9H, d), 8.16 (0.2H, d), 7.86 (1.8H, d), 7.59 (0.2H, d), 7.41 (1.8H, d), 4.51 (0.2H, q), 4.41 (2.0H, q), 4.32 (1.8H, q), 3.65 (1.8H, q), 3.56 (2.6H, s), 3.49 (0.2H, q), 3.23 (0.4H, s), 1.42-1.32 (9.0H, m).

Compound of Present Invention 127

$^1$H-NMR (CDCl$_3$)δ: 9.35 (0.2H, s), 8.98 (0.8H, s), 8.86 (0.2H, s), 8.75 (0.8H, s), 7.75 (0.4H, d), 7.56 (0.4H, d), 7.46 (1.6H, d), 7.39 (1.6H, d), 3.64-3.15 (5.0H, m), 1.35-1.23 (3.0H, m).

Compound of Present Invention 128

$^1$H-NMR (CDCl$_3$)δ: 9.28 (0.2H, d), 8.83 (0.8H, d), 8.65 (0.2H, d), 8.50 (0.8H, d), 7.76 (0.4H, d), 7.57 (0.4H, d), 7.46 (1.6H, d), 7.39 (1.6H, d), 6.36 (0.2H, s), 6.16 (0.8H, s), 3.65 (1.6H, q), 3.55 (2.4H, s), 3.49 (0.4H, q), 3.21 (0.6H, s), 3.11 (0.6H, d), 3.01 (2.4H, d), 1.34 (3.0H, t).

Compound of Present Invention 129

$^1$H-NMR (CDCl$_3$)δ: 9.29 (0.2H, s), 8.84 (0.8H, d), 8.76 (0.2H, s), 8.61 (0.8H, s), 8.54 (1.0H, m), 7.76 (0.3H, d), 7.57 (0.3H, d), 7.48 (1.7H, d), 7.39 (1.7H, d), 7.01-6.86 (1.0H, m), 4.24 (2.0H, td), 3.65 (1.6H, q), 3.55 (2.4H, s), 3.48 (0.4H, q), 3.21 (0.6H, s), 1.36-1.29 (6.0H, m).

Compound of Present Invention 130

$^1$H-NMR (CDCl$_3$)δ: 8.85 (0.2H, d), 8.40 (0.8H, d), 8.34 (0.2H, d), 8.18 (0.8H, d), 7.76 (0.5H, d), 7.57 (0.5H, d), 7.50 (1.5H, d), 7.38-7.34 (1.5H, m), 3.70-3.24 (11.0H, m), 1.33 (3.0H, q).

Compound of Present Invention 131

$^1$H-NMR (CDCl$_3$) δ: 8.16-8.10 (1H, m), 7.53-7.45 (3H, m), 7.34-7.29 (2H, m), 3.50 (3H, s), 2.93 (2H, q), 1.33 (3H, t).

Compound of Present Invention 132

$^1$H-NMR (CDCl$_3$) δ: 8.56 (1H, d), 8.17 (1H, d), 7.83-7.78 (1H, m), 7.63 (1H, d), 7.56-7.46 (1H, m), 3.55 (3H, s), 2.98 (2H, q), 1.35 (3H, t).

Compound of Present Invention 133

$^1$H-NMR (CDCl$_3$) δ: 8.37 (1H, s), 8.20 (1H, s), 7.53 (2H, d), 7.19 (2H, d), 3.52 (3H, s), 3.48-3.41 (1H, m), 3.04-2.94 (1H, m), 1.37 (3H, t).

Compound of Present Invention 134

$^1$H-NMR (CDCl$_3$) δ: 8.46-8.43 (2H, m), 8.22-8.20 (1H, m), 7.90-7.87 (1H, m), 7.27 (1H, d), 3.62-3.60 (3H, m), 3.49-3.40 (1H, m), 3.06-2.96 (1H, m), 1.40-1.35 (3H, m).

Compound of Present Invention 135

$^1$H-NMR (DMSO-D$_6$, 100° C.) δ: 8.56 (1H, s), 8.49 (1H, s), 7.62 (2H, d), 7.45 (2H, d), 3.57-3.48 (2H, m), 2.94 (3H, s), 2.68 (3H, s), 1.18 (3H, t).

Compound of Present Invention 136

$^1$H-NMR (CDCl$_3$) δ: 8.85 (0.2H, d), 8.41 (0.8H, d), 8.36 (0.2H, d), 8.20 (0.8H, d), 7.74 (0.3H, d), 7.62 (0.4H, d), 7.47 (3.3H, d), 3.66 (1.7H, q), 3.54 (2.4H, s), 3.49 (0.3H, q), 3.23 (0.6H, s), 1.38-1.33 (3.0H, m).

Compound of Present Invention 137

$^1$H-NMR (CDCl$_3$) δ: 8.70-7.64 (4.4H, m), 7.23-7.14 (0.6H, m), 3.72-3.55 (5.0H, m), 1.38 (3.0H, t).

Compound of Present Invention 138

$^1$H-NMR (CDCl$_3$) δ: 8.27-7.17 (6.0H, m), 4.22 (0.3H, s), 4.05 (1.7H, s), 3.68 (1.6H, q), 3.54-3.47 (2.7H, m), 3.23 (0.7H, s), 1.31 (3.0H, t).

Compound of Present Invention 139

¹H-NMR (CDCl₃) δ: 8.69-7.14 (5H, m), 4.20 (2H, s), 3.66 (2H, q), 3.58 (3H, s), 1.36 (3H, t).

Compound of Present Invention 140

¹H-NMR (CDCl₃) δ: 8.98 (0.2H, s), 8.53-8.49 (1.0H, m), 8.37 (0.8H, d), 7.46-7.45 (3.2H, m), 7.21 (0.8H, s), 3.85 (0.6H, s), 3.78 (2.4H, s), 3.65 (1.6H, q), 3.53 (2.4H, s), 3.50-3.44 (0.4H, m), 3.23 (0.6H, s), 1.36-1.29 (3.0H, m).

Compound of Present Invention 141

¹H-NMR (CDCl₃) δ: 8.66 (1H, s), 8.51 (1H, d), 7.72-7.63 (1H, m), 7.23-7.14 (2H, m), 3.83 (3H, s), 3.70-3.53 (5H, m), 1.37 (3H, t).

Compound of Present Invention 142

¹H-NMR (CDCl₃) δ: 10.35 (1H, s), 8.33 (1H, d), 8.13 (1H, s), 7.74 (1H, d), 7.71 (1H, d), 7.65 (1H, d), 7.43 (1H, dd), 2.96 (2H, q), 1.45 (3H, t).

Compound of Present Invention 143

¹H-NMR (CDCl₃) δ: 8.31-8.25 (1H, m), 7.60 (1H, d), 7.51 (1H, d), 7.43-7.38 (1H, m), 7.23-7.14 (2H, m), 3.48 (3H, s), 2.93 (2H, q), 1.30 (3H, t).

Compound of Present Invention 144

¹H-NMR (CDCl₃) δ: 10.62 (1H, s), 8.82 (1H, t), 8.36 (1H, dd), 7.74 (1H, dd), 7.47-7.38. (3H, m), 2.97 (2H, q), 1.45 (3H, t).

Compound of Present Invention 145

¹H-NMR (CDCl₃) δ: 8.59-7.01 (6H, m), 3.65-2.86 (5H, m), 1.31 (3H, t).

Compound of Present Invention 146

¹H-NMR (CDCl₃) δ: 10.67 (1H, s), 8.68 (1H, dd), 8.36 (1H, d), 7.75 (1H, d), 7.44 (1H, dd), 7.36 (1H, dd), 2.97 (2H, q), 1.45 (3H, t).

Compound of Present Invention 147

¹H-NMR (CDCl₃) δ: 8.30-8.11 (1H, m), 7.72-7.59 (1H, m), 7.36-7.03 (3H, m), 3.43 (3H, brs), 2.96 (2H, q), 1.33 (3H, t).

Compound of Present Invention 148

¹H-NMR (CDCl₃) δ: 10.22 (1H, s), 8.32 (1H, dd), 8.26 (1H, d), 7.73 (1H, dd), 7.68 (1H, dd), 7.41 (1H, dd), 7.28 (1H, dd), 2.95 (2H, q), 1.44 (3H, t).

Compound of Present Invention 149

¹H-NMR (CDCl₃) δ: 8.38-8.14 (1H, m), 7.69-7.46 (2H, m), 7.29-7.00 (3H, m), 3.49 (3H, brs), 2.92 (2H, q), 1.30 (3H, t).

Compound of Present Invention 150

¹H-NMR (CDCl₃) δ: 10.49 (1H, s), 8.34 (1H, d), 8.23-8.17 (2H, m), 7.83 (1H, d), 7.75 (1H, d), 7.44 (1H, dd), 2.97 (2H, q), 1.45 (3H, t).

Compound of Present Invention 151

¹H-NMR (CDCl₃) δ: 8.26 (1H, brs), 7.70 (1H, d), 7.65 (1H, brs), 7.59 (1H, d), 7.56-7.49 (1H, m), 7.18 (1H, dd), 3.52 (3H, s), 2.92 (2H, q), 1.29 (3H, t).

Compound of Present Invention 152

¹H-NMR (CDCl₃) δ: 10.41 (1H, s), 8.33 (1H, dd), 7.75 (1H, d), 7.53 (2H, d), 7.44 (1H, dd), 2.97 (2H, q), 1.45 (3H, t).

Compound of Present Invention 153

¹H-NMR (CDCl₃) δ: 8.31 (1H, dd), 7.66 (1H, dd), 7.24 (1H, dd), 6.93 (2H, d), 3.44 (3H, s), 2.96 (2H, q), 1.31 (3H, t).

Compound of Present Invention 154

¹H-NMR (CDCl₃) δ: 8.71 (0.2H, d), 8.26 (0.8H, d), 8.15 (0.2H, d), 8.01 (0.8H, d), 7.73 (0.4H, d), 7.62 (0.4H, d), 7.46 (3.2H, s), 3.66 (1.6H, q), 3.54 (2.4H, s), 3.47 (0.4H, q), 3.24 (0.6H, s), 3.11 (0.5H, q), 2.98 (1.5H, q), 1.36-1.31 (3.0H, m), 1.31-1.24 (3.0H, m).

Compound of Present Invention 155

¹H-NMR (CDCl₃) δ: 9.10-8.19 (2H, m), 7.78-7.41 (6H, m), 7.20-7.06 (1H, m), 3.73-3.50 (5H, m), 1.37 (3H, dt).

Compound of Present Invention 156

¹H-NMR (DMSO-D₆, 60° C.) δ: 8.21-8.16 (1H, m), 7.74 (1H, d), 7.58 (2H, d), 7.33 (2H, d), 3.35 (3H, s), 3.00 (2H, dt), 1.19 (3H, td).

Compound of Present Invention 157

¹H-NMR (CDCl₃) δ: 9.16-7.00 (10H, m), 3.72-3.47 (5H, m), 1.36 (3H, t).

Next, formulation examples of the compound of the present invention are shown. The part means part by weight.

Formulation Example 1

10 parts of any one of Compounds of Present Invention 1 to 158 are dissolved in a mixture of 35 parts of xylene and 35 parts of N,N-dimethylformamide, 14 parts of polyoxyethylenestyrylphenyl ether and 6 parts of calcium dodecylbenzenesulfonate are added thereto. The mixture is mixed to obtain each emulsifiable concentrate.

Formulation Example 2

4 parts of sodium lauryl sulfate, 2 parts of calcium lignosulfonate, 20 parts of synthetic hydrous silicon oxide fine powder and 54 parts of diatomaceous earth are mixed, and 20 parts of any one of Compounds of Present Invention 1 to 158 are further added thereto. The mixture is mixed to obtain each wettable powder.

Formulation Example 3

1 part of synthetic hydrous silicon oxide fine powder, 2 parts of calcium lignosulfonate, 30 parts of bentonite and 65 parts of kaolin clay are added to 2 parts of any one of Compounds of Present Invention 1 to 158 and mixed. Subsequently, an appropriate amount of water is added to this mixture, and the mixture is further stirred, granulated with a granulator, and forced-air dried to obtain each granule.

Formulation Example 4

1 part of any one of Compounds of Present Invention 1 to 158 is dissolved in an appropriate amount of acetone, and 5 parts of synthetic hydrous silicon oxide fine powder, 0.3 parts of PAP and 93.7 parts of Fubasami clay are added thereto. The mixture is sufficiently stirred and mixed to evaporate and eliminate acetone to obtain each dust formulation.

Formulation Example 5

35 parts of a mixture of polyoxyethylene alkyl ether sulfate ammonium salt and white carbon (weight ratio 1:1), 10 parts of any one of Compounds of Present Invention 1 to 158 and 55 parts of water are mixed, and finely pulverized by wet grinding method to obtain each flowable.

Formulation Example 6

0.1 parts of any one of Compounds of Present Invention 1 to 158 are dissolved in 5 parts of xylene and 5 parts of trichloroethane, and the mixture is mixed with 89.9 parts of deodorized kerosene to obtain each oil solution.

Formulation Example 7

10 mg of any one of Compounds of Present Invention 1 to 158 is dissolved in 0.5 ml of acetone, and this solution is applied to 5 g of solid feed powder for animal (solid feed powder for breeding CE-2, product of CLEA Japan, Inc.), and the mixture is uniformly mixed. Subsequently, acetone is evaporated to dryness to obtain each poisonous bait.

Formulation Example 8

0.1 parts of any one of Compounds of Present Invention 1 to 158 and 49.9 parts of Neothiozol (Chuo Kasei Co., Ltd.) are filled into an aerosol can, and an aerosol valve is attached, then the container is filled with 25 parts of dimethyl ether and 25 parts of LPG and shaken, and an actuator is attached to obtain an oil-based aerosol.

Formulation Example 9

0.6 parts of any one of Compounds of Present Invention 1 to 158, 0.01 parts of BHT (2,6-di-tert-butyl-4-methylphenol), 5 parts of xylene, 3.39 parts of deodorized kerosene and 1 part of emulsifier {Atmos 300 (registered trade name for Atmos Chemical Ltd.)} are mixed and dissolved, and the resulting solution and 50 parts of distilled water are filled into an aerosol container. A valve is attached to the container, and then 40 parts of a propellant (LPG) is filled under pressure through the valve to obtain an aqueous aerosol.

Formulation Example 10

0.1 g of any one of Compounds of Present Invention 1 to 158 is dissolved in 2 ml of propylene glycol, and the solution is impregnated in a porous ceramic plate with a size of 4.0 cm×4.0 cm and 1.2 cm in thickness to obtain a heating type smoking agent.

Formulation Example 11

5 parts of any one of Compounds of Present Invention 1 to 158 and 95 parts of an ethylene-methyl methacrylate copolymer (a ratio of methyl methacrylate in the copolymer: 10% by weight, Acryft WD301, manufactured by SUMITOMO CHEMICAL Co., Ltd.) are melt-kneaded with a closed pressurizing kneader (manufactured by Moriyama Works), and the resulting kneaded matter is extruded from an extrusion molding machine through a molding die to obtain a rod-shaped molded body with a size of 15 cm in length and 3 mm in diameter.

Formulation Example 12

5 parts of any one of Compounds of Present Invention 1 to 158 and 95 parts of a soft vinyl chloride resin are melt-kneaded with a closed pressurizing kneader (manufactured by Moriyama Works), and the resulting kneaded matter is extruded from an extrusion molding machine through a molding die to obtain a rod-shaped molded body with a size of 15 cm in length and 3 mm in diameter.

Formulation Example 13

100 mg of any one of Compounds of Present Invention 1 to 158, 68.75 mg of lactose, 237.5 mg of corn starch, 43.75 mg of microcrystalline cellulose, 18.75 mg of polyvinylpyrrolidone, 28.75 mg of sodium carboxymethyl starch and 2.5 mg of magnesium stearate are mixed, and the resulting mixture is compressed to an appropriate size to obtain a tablet.

Formulation Example 14

25 mg of any one of Compounds of Present Invention 1 to 158, 60 mg of lactose, 25 mg of corn starch, 6 mg of carmellose calcium and an appropriate amount of 5% hydroxypropyl methylcellulose are mixed, and the resulting mixture is filled into a hard shell gelatin capsule or a hydroxypropyl methylcellulose capsule to obtain an encapsulated formulation.

Formulation Example 15

Distilled water is added to 1000 mg of any one of Compounds of Present Invention 1 to 158, 500 mg of fumaric acid, 2000 mg of sodium chloride, 150 mg of methylparaben, 50 mg of propylparaben, 25000 mg of granulated sugar, 13000 mg of sorbitol (70% solution), 100 mg of Veegum K (Vanderbilt Co.), 35 mg of flavor and 500 mg of colorant, such that a final volume is 100 ml, and the mixture is mixed to obtain a suspension for oral administration.

Formulation Example 16

5 parts of any one of Compounds of Present Invention 1 to 158 are dissolved in 5 parts of polysorbate 85, 3 parts of benzyl alcohol and 30 parts of propylene glycol, a phosphate buffer is added to this solution so as to have a pH of 6.0 to 6.5, and then water is added until a total amount is 100 parts to obtain a liquid formulation for oral administration.

Formulation Example 17

5 parts of aluminum distearate are dispersed in 57 parts of fractionated palm oil and 3 parts of polysorbate 85 by heating. This dispersion is cooled to room temperature, and 25 parts of saccharin are dispersed in an oily vehicle thereof. 10 parts of any one of Compounds of Present Invention 1 to 158 are added thereto to obtain a paste formulation for oral administration.

Formulation Example 18

5 parts of any one of Compounds of Present Invention 1 to 158 and 95 parts of limestone filler are mixed, and a granule for oral administration is obtained using wet granulation method.

Formulation Example 19

5 parts of any one of Compounds of Present Invention 1 to 158 are dissolved in 80 parts of diethylene glycol monoethyl ether, and 15 parts of propylene carbonate are mixed therewith to obtain a spot-on solution.

Formulation Example 20

5 parts of any one of Compounds of Present Invention 1 to 158 are dissolved in 70 parts of diethylene glycol monoethyl ether, and 20 parts of 2-octyl dodecanol are mixed therewith to obtain a pour-on solution.

Formulation Example 21

60 parts of NIKKOL TEALS-42 (Nikko Chemicals Co., Ltd., 42% aqueous solution of triethanolamine lauryl sulfate) and 20 parts of propylene glycol are added to 0.5 parts of any one of Compounds of Present Invention 1 to 158, the mixture is sufficiently stirred and mixed until it becomes a uniform solution, and then 19.5 parts of water are added and further sufficiently stirred and mixed to obtain a shampoo agent as a uniform solution.

Formulation Example 22

0.15 parts of any one of Compounds of Present Invention 1 to 158, 95 parts of an animal feed and 4.85 parts of a mixture of secondary calcium phosphate, diatomaceous earth, Aerosil and carbonate (or chalk) are sufficiently stirred and mixed to obtain a feed premix for animal.

Formulation Example 23

7.2 g of any one of Compounds of Present Invention 1 to 158 and 92.8 g of VOSCO S-55 (manufactured by Maruishi Pharmaceutical Co., Ltd.) are dissolved and mixed at 100° C., poured into a suppository mold, and cooled and solidified to obtain a suppository.

Next, the pest control effect of the compound of the present invention and the intermediate compound is shown as test examples.

Test Example 1

The formulations of Compounds of Present Invention 3, 6, 13, 16 to 17, 21 to 22, 26 to 27, 30 to 41, 43 to 44, 47, 49 to 55, 61 to 62, 64 to 65, 67 to 78, 80 to 81, 83 to 88, 90, 92 to 93, 95, 97 to 98, 101 to 107, 109 to 110, 112, 114 to 128, and 130 to 141 as obtained in Formulation Example 5 were diluted with water, so as to have a concentration of the active ingredient of 500 ppm, to prepare a test drug solution.

On the other hand, on a cucumber seedling (the first true leaf stage) planted in a plastic cup was inoculated with about 30 Aphis gossypii (whole stage), and leaving it for a day.

20 ml of the test drug solution was sprayed on the seedling.

Six days after spraying, the number of surviving Aphis gossypii parasitic on the leaves of the cucumber was examined, and the controlling value was calculated according to the following equation:

Controlling value (%)={1−($Cb \times Tai$)/($Cai \times Tb$)}×100 wherein the symbols represent as follows:
Cb: the number of insects in a non-treated section before treatment,
Cai: the number of surviving parasitic insects in a non-treated section on observation,
Tb: the number of insects in a treated section before treatment,
Tai: the number of surviving parasitic insects in a treated section on observation,
wherein the non-treated section refers to a section where the test drug solution prepared by diluting the formulation not containing the compound of the present invention as in Formulation Example 5 with the same amount of water as in the treated section was sprayed.

As a result, in the treated section using each test drug solution of Compounds of Present Invention 3, 6, 13, 16 to 17, 21 to 22, 26 to 27, 30 to 41, 43 to 44, 47, 49 to 55, 61 to 62, 64 to 65, 67 to 78, 80 to 81, 83 to 88, 90, 92 to 93, 95, 97 to 98, 101 to 107, 109 to 110, 112, 114 to 128, and 130 to 141, the controlling value was 90% or more.

Test Example 2

The formulations of Compounds of Present Invention 3, 6, 13, 16 to 17, 21 to 22, 26 to 27, 30 to 35, 37 to 41, 43 to 44, 47, 50 to 53, 55, 61 to 62, 64, 67 to 68, 73 to 78, 83, 87 to 88, 93, 101, 104, 106 to 109, 114 to 119, and 121 to 122 as obtained in Formulation Example 5 were diluted with water, so as to have a concentration of the active ingredient of 500 ppm, to prepare a test drug solution.

On the other hand, a cucumber seedling (the second true leaf stage) planted in a plastic cup was drenched at its foot with 5 ml of the test drug solution, and kept in a greenhouse at 25° C. for 7 days. On the cucumber leaf surface was inoculated about 30 Aphis gossypii (whole stage), and further kept in the greenhouse for 6 days, then the number of surviving Aphis gossypii parasitic on the leaves of the cucumber was examined, and the controlling value was calculated according to the following equation:

Controlling value (%)={1−($Cb \times Tai$)/($Cai \times Tb$)}×100 wherein the symbols represent as follows:
Cb: the number of insects in a non-treated section before treatment,
Cai: the number of surviving parasitic insects in a non-treated section on observation,
Tb: the number of insects in a treated section before treatment,
Tai: the number of surviving parasitic insects in a treated section on observation,
wherein the non-treated section refers to a section where the test drug solution prepared by diluting the formulation not containing the compound of the present invention as in Formulation Example 5 with the same amount of water as in the treated section was sprayed.

As a result, in the treated section using each test drug solution of Compounds of Present Invention 3, 6, 13, 16 to 17, 21 to 22, 26 to 27, 30 to 35, 37 to 41, 43 to 44, 47, 50 to 53, 55, 61 to 62, 64, 67 to 68, 73 to 78, 83, 87 to 88, 93, 101, 104, 106 to 109, 114 to 119, and 121 to 122, the controlling value was 90% or more.

Test Example 3

The formulations of Compounds of Present Invention 3, 16, 21, 27, 30 to 41, 47, 50 to 53, 55, 61 to 62, 64 to 68, 73 to 78, 83, 88, 93, 107, 109 to 110, 114, 118 to 119, 121, 124 to 125, and 141 as obtained in Formulation Example 5 were diluted with water, so as to have a concentration of the active ingredient of 500 ppm, to prepare a test drug solution.

On a rice seedling in the second leaf stage planted in a polyethylene cup was sprayed 10 ml of each test drug solution. After air-drying, 20 third-fourth instar larvae of *Nilaparvata lugens* were released, and kept in the greenhouse at 25° C. After 6 days, the number of surviving *Nilaparvata lugens* parasitic on the rice was examined, and the controlling value was calculated according to the following equation:

Controlling value (%)={1−($Cb \times Tai$)/($Cai \times Tb$)}×100 wherein the symbols represent as follows:
Cb: the number of insects in a non-treated section before treatment,
Cai: the number of surviving parasitic insects in a non-treated section on observation,
Tb: the number of insects in a treated section before treatment,
Tai: the number of surviving parasitic insects in a treated section on observation,
wherein the non-treated section refers to a section where the test drug solution prepared by diluting the formulation not containing the compound of the present invention as in Formulation Example 5 with the same amount of water as in the treated section was sprayed.

As a result, in the treated section using each test drug solution of Compounds of Present Invention 3, 16, 21, 27, 30 to 41, 47, 50 to 53, 55, 61 to 62, 64 to 68, 73 to 78, 83, 88, 93, 107, 109 to 110, 114, 118 to 119, 121, 124 to 125, and 141, the controlling value was 90% or more.

Test Example 4

The formulations of Compounds of Present Invention 13, 16 to 17, 21 to 22, 26 to 27, 29 to 33, 35 to 41, 44, 47, 49, 51 to 53, 55, 61 to 62, 64, 67 to 68, 73 to 78, 83, 88, 93, 107 to 109, 112, 114, 116 to 117, and 119 to 121 as obtained in Formulation Example 5 were diluted with water, so as to have a concentration of the active ingredient of 500 ppm, to prepare a test drug solution.

On the other hand, a rice seedling (2 weeks after sowing, the second leaf stage) planted in a plastic cup was drenched at its foot with 5 ml of each test drug solution, and kept in a greenhouse of 25° C. for 7 days. 20 third-fourth instar larvae of *Nilaparvata lugens* were released, and further kept in the greenhouse for 6 days, then the number of surviving *Nilaparvata lugens* parasitic on the rice was examined, and the controlling value was calculated according to the following equation:

Controlling value (%)={1−($Cb \times Tai$)/($Cai \times Tb$)}×100 wherein the symbols represent as follows:
Cb: the number of insects in a non-treated section before treatment,
Cai: the number of surviving parasitic insects in a non-treated section on observation,
Tb: the number of insects in a treated section before treatment,
Tai: the number of surviving parasitic insects in a treated section on observation,
wherein the non-treated section refers to a section where the test drug solution prepared by diluting the formulation not containing the compound of the present invention as in Formulation Example 5 with the same amount of water as in the treated section was sprayed.

As a result, in the treated section using each test drug solution of Compounds of Present Invention 13, 16 to 17, 21 to 22, 26 to 27, 29 to 33, 35 to 41, 44, 47, 49, 51 to 53, 55, 61 to 62, 64, 67 to 68, 73 to 78, 83, 88, 93, 107 to 109, 112, 114, 116 to 117, and 119 to 121, the controlling value was 90% or more.

Test Example 5

The formulations of Compounds of Present Invention 13, 16 to 17, 21 to 22, 26 to 27, 29 to 33, 35 to 41, 44, 47, 49, 51 to 53, 55, 61 to 62, 64, 67 to 68, 73 to 78, 83, 88, 93, 107 to 109, 112, 114, 116 to 117, and 119 to 121 as obtained in Formulation Example 5 were diluted with water, so as to have a concentration of the active ingredient of 500 ppm, to prepare a test drug solution.

On the other hand, *Bemisia tabaci* adult was released on a tomato seedling (the third true leaf stage) planted in a polyethylene cup, and made to lay eggs for about 72 hours. The tomato seedling was kept in a greenhouse for 8 days, and when instar larvae hatched from the eggs, the above test drug solution was sprayed at a rate of 20 ml/cup, and the cup was kept in a greenhouse at 25° C. After 7 days, the number of surviving instar larvae on the tomato leaves was examined, and the controlling value was calculated according to the following equation:

Controlling value (%)={1−($Cb \times Tai$)/($Cai \times Tb$)}×100 wherein the symbols represent as follows:
Cb: the number of insects in a non-treated section before treatment,
Cai: the number of surviving insects in a non-treated section on observation,
Tb: the number of insects in a treated section before treatment,
Tai: the number of surviving insects in a treated section on observation,
wherein the non-treated section refers to a section where the test drug solution prepared by diluting the formulation not containing the compound of the present invention as in Formulation Example 5 with the same amount of water as in the treated section was sprayed.

As a result, in the treated section using each test drug solution of Compounds of Present Invention 13, 16 to 17, 21 to 22, 26 to 27, 29 to 33, 35 to 41, 44, 47, 49, 51 to 53, 55, 61 to 62, 64, 67 to 68, 73 to 78, 83, 88, 93, 107 to 109, 112, 114, 116 to 117, and 119 to 121, the controlling value was 90% or more.

Test Example 6

The formulations of Compounds of Present Invention 3, 6 to 7, 9, 11 to 14, 17 to 18, 21 to 22, 25, 27, 31, 33 to 34, 36 to 39, 41, 44, 46 to 53, 55, 60 to 65, 67 to 69, 73 to 78, 80 to 83, 85 to 89, 91 to 93, 96, 98, 102 to 103, 105 to 107, 109 to 110, 112, 114, 116 to 125, and 132 as obtained in Formulation Example 5 were diluted with water, so as to have a concentration of the active ingredient of 500 ppm, to prepare a test drug solution.

On the other hand, on cabbage at the third leaf stage planted in a polyethylene cup was sprayed at a rate of 20 mL/cup of the test drug solution. After the drug solution was dried, the foliage part was cut off, and then placed in a 50 mL volume cup. Five second instar larvae of *Plutella xylostella* were released into the cup, and the cup was sealed with a lid. After the cup was kept at 25° C. for 5 days, the number of surviving insects was counted. The death rate was calculated according to the following equation:

Death rate (%)=(Number of dead insects/Number of tested insects)×100.

As a result, in the treated section using each test drug solution of Compounds of Present Invention 3, 6 to 7, 9, 11 to 14, 17 to 18, 21 to 22, 25, 27, 31, 33 to 34, 36 to 39, 41, 44, 46 to 53, 55, 60 to 65, 67 to 69, 73 to 78, 80 to 83, 85 to 89, 91 to 93, 96, 98, 102 to 103, 105 to 107, 109 to 110, 112, 114, 116 to 125, and 132, the death rate was 80% or more.

Test Example 7

The formulations of Compounds of Present Invention 3 to 5, 11, 13 to 14, 16 to 18, 27, 30 to 31, 34, 36 to 39, 41, 43 to 44, 47, 49 to 55, 60 to 62, 64 to 65, 67 to 69, 73 to 78, 80 to 83, 85 to 88, 91 to 93, 98, 102, 104 to 110, 112, 114, 116 to 119, 122, and 124 to 125 as obtained in Formulation Example 5 were diluted with water, so as to have a concentration of the active ingredient of 500 ppm, to prepare a test spray solution.

On the other hand, an apple tree was planted in a plastic cup, and grown until the seventh-eighth true leaf was spread. To the apple tree was sprayed at a rate of 20 mL/cup of the test drug solution. After the drug solution was dried, 60 first-instar *Adoxophyes orana fasciata* were released, and the plastic cup the bottom of which was cut off and on which a filter paper was put was upside-down and covered. After 7 days, the number of surviving insects was counted, and the death rate was calculated according to the following equation:

Death rate (%)=(Number of dead insects/Number of tested insects)×100.

As a result, in the treated section using each test drug solution of Compounds of Present Invention 3 to 5, 11, 13 to 14, 16 to 18, 27, 30 to 31, 34, 36 to 39, 41, 43 to 44, 47, 49 to 55, 60 to 62, 64 to 65, 67 to 69, 73 to 78, 80 to 83, 85 to 88, 91 to 93, 98, 102, 104 to 110, 112, 114, 116 to 119, 122, and 124 to 125, the death rate was 90% or more.

Test Example 8

The formulations of Compounds of Present Invention 31, 41, 55, 62, 64 to 65, 67 to 70, 73 to 75, 88, 119, 124 and 131 as obtained in Formulation Example 5 were diluted with water, so as to have a concentration of the active ingredient of 500 ppm, to prepare a test drug solution.

A filter paper having a diameter of 5.5 cm was spread on the bottom of a polyethylene cup having the same diameter and 0.7 ml of the test drug solution was added dropwise onto the filter paper, and 30 mg of sucrose was uniformly placed as bait. Into the polyethylene cup, 10 female imagoes of *Musca domestica* were released, and the cup was sealed with a lid. After 24 hours, the life and death of *Musca domestica* was examined, and the death rate was calculated.

Death rate (%)=(Number of dead insects/Number of tested insects)×100

As a result, in the treated section using each test drug solution of Compounds of Present Invention 31, 41, 55, 62, 64 to 65, 67 to 70, 73 to 75, 88, 119, 124 and 131, the death rate was 100%.

Test Example 9

The formulations of Compounds of Present Invention 31, 50, 55, 62, 69 and 88 as obtained in Formulation Example 5 were diluted with water, so as to have a concentration of the active ingredient of 500 ppm, to prepare a test drug solution.

A filter paper having a diameter of 5.5 cm was spread on the bottom of a polyethylene cup having the same diameter and 0.7 ml of the test drug solution was added dropwise onto the filter paper, and 30 mg of sucrose was uniformly placed as bait. Into the polyethylene cup, 2 male imagoes of *Blattella germanica* were released, and the cup was sealed with a lid. After 6 days, the life and death of *Blattella germanica* was examined, and the death rate was calculated.

Death rate (%)=(Number of dead insects/Number of tested insects)×100

As a result, in the treated section using each test drug solution of Compounds of Present Invention 31, 50, 55, 62, 69 and 88, the death rate was 100%.

Test Example 10

The formulations of Compounds of Present Invention 2, 7, 13, 18, 20, 31, 34, 44, 46 to 47, 49, 52, 55, 60 to 62, 64 to 65, 67 to 69, 73 to 74, 76 to 78, 80 to 88, 93, 95, 105 to 106, 110, 112, 116, 119 to 125, 128 and 131 as obtained in Formulation Example 5 were diluted with water, so as to have a concentration of the active ingredient of 500 ppm, to prepare a test drug solution.

0.7 ml of the test drug solution was added to 100 ml of ion-exchanged water (active ingredient concentration: 3.5 ppm). 20 last-instar larvae of *Culex pipiens pallens* were released into the solution. One day later, the life and death of the *Culex pipiens pallens* was examined, and the death rate of the pest was calculated.

Death rate (%)=(Number of dead insects/Number of tested insects)×100

As a result, in the treated section using each test drug solution of Compounds of Present Invention 2, 7, 13, 18, 20, 31, 34, 44, 46 to 47, 49, 52, 55, 60 to 62, 64 to 65, 67 to 69, 73 to 74, 76 to 78, 80 to 88, 93, 95, 105 to 106, 110, 112, 116, 119 to 125, 128 and 131, the death rate was 95% or more.

Test Example 11

2 mg of each of Compounds of Present Invention 7, 20, 25, 28, 48, 55, 65 and 110 was weighed in a screw tube (Maruemu No. 5; 27×55 mm), and 0.2 mL of acetone was added thereto and sealed with a cap to dissolve the compound. The screw tube was rotated and inverted to uniformity coat the drug solution onto the whole inner wall of the tube. After removing the cap, the solution was air-dried for about 2 hours, then non-blood-sucking nymphal ticks, *Haemaphysalis longicornis* (5 ticks/group) were released, and the tube was sealed with the cap. After 2 days, the number of dead ticks was examined, and the death rate was calculated according to the following equation:

Death rate (%)=100×(Number of dead ticks/Number of tested ticks).

As a result, in the treated section using each test drug solution of Compounds of Present Invention 7, 20, 25, 28, 48, 55, 65 and 110, the death rate was 100%.

Industrial Applicability

The compound of the present invention has a controlling effect on pests and is useful as an active ingredient of a pest control agent.

The invention claimed is:
1. An amide compound represented by formula (1) or an N-oxide thereof,

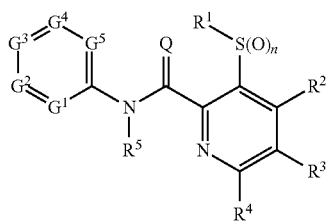

wherein
R$^1$ represents a C1 to C6 chain hydrocarbon group optionally having one or more atoms or groups selected from group X or a C3 to C9 alicyclic hydrocarbon group optionally having one or more atoms or groups selected from group Y, R$^2$, R$^3$ and R$^4$ are the same or different and represent a C1 to C6 chain hydrocarbon group optionally having one or more atoms or groups selected from group X, a C3 to C9 alicyclic hydrocarbon group optionally having one or more atoms or groups selected from group Y, a phenyl group optionally having one or more atoms or groups selected from group Z, a 5- or 6-membered heterocyclic group optionally having one or more atoms or groups selected from group Z, OR$^{11}$, S(O)$_m$R$^{11}$, S(O)$_2$NR$^{11}$R$^{12}$, NR$^{11}$R$^{12}$, NR$^{15}$C(O)R$^{11}$, NR$^{15}$C(O)OR$^{11}$, NR$^{15}$C(O)NR$^{11}$R$^{12}$, NR$^{16}$S(O)$_2$R$^{13}$, C(O)R$^{11}$, C(O)OR$^{11}$, C(O)NR$^{11}$R$^{12}$, C(O)NR$^{11}$NR$^{15}$R$^{16}$, SF$_5$, a cyano group, a nitro group, a halogen atom or a hydrogen atom, R$^5$ represents a C1 to C6 chain hydrocarbon group optionally having one or more atoms or groups selected from group W, a C3 to C9 alicyclic hydrocarbon group optionally having one or more atoms or groups selected from group Y, a C1 to C6 chain hydrocarbon group having one phenyl group (wherein the phenyl group optionally has one or more atoms or groups selected from group Z), a C1 to C6 chain hydrocarbon group having one 5- or 6-membered heterocyclic group (wherein the 5- or 6-membered heterocyclic group optionally has one or more atoms or groups selected from group Z), C(O)R$^{11}$, C(O)OR$^{11}$, C(O)NR$^{11}$R$^{12}$ or a hydrogen atom, G$^1$ represents a nitrogen atom or CR$^6$,
G$^2$ represents a nitrogen atom or CR$^7$,
G$^3$ represents a nitrogen atom or CR$^8$,
G$^4$ represents a nitrogen atom or CR$^9$,
G$^5$ represents a nitrogen atom or CR$^{10}$ (wherein not all of G$^2$, G$^3$ and G$^4$ represent a nitrogen atom), R$^6$ and R$^{10}$ are the same or different and represent a C1 to C6 chain hydrocarbon group optionally having one or more atoms or groups selected from group X, a C3 to C9 alicyclic hydrocarbon group optionally having one or more atoms or groups selected from group Y, OR$^{14}$, S(O)$_m$R$^{14}$, a fluorine atom or a hydrogen atom, R$^7$, R$^8$ and R$^9$ are the same or different and represent a C1 to C6 chain hydrocarbon group optionally having one or more atoms or groups selected from group X, a C3 to C9 alicyclic hydrocarbon group optionally having one or more atoms or groups selected from group Y, a phenyl group optionally having one or more atoms or groups selected from group Z, a 5- or 6-membered heterocyclic group optionally having one or more atoms or groups selected from group Z, OR$^{14}$, S(O)$_m$R$^{11}$, S(O)$_2$NR$^{11}$R$^{12}$, NR$^{11}$R$^{12}$, NR$^{11}$C(O)R$^{12}$, NR$^{11}$C(O)OR$^{12}$, NR$^{11}$S(O)$_2$R$^{13}$, C(O)R$^{11}$, C(O)OR$^{11}$, C(O)NR$^{11}$R$^{12}$, SF$_5$, a hydroxy group, a cyano group, a nitro group, a halogen atom or a hydrogen atom (wherein at least one of R$^7$, R$^8$ and R$^9$ represents a C1 to C6 chain hydrocarbon group optionally having one or more atoms or groups selected from group X, a C3 to C9 alicyclic hydrocarbon group optionally having one or more atoms or groups selected from group Y, a phenyl group optionally having one or more atoms or groups selected from group Z, a 5- or 6-membered heterocyclic group optionally having one or more atoms or groups selected from group Z, OR$^{14}$, S(O)$_m$R$^{11}$, S(O)$_2$NR$^{11}$R$^{12}$, NR$^{11}$R$^{12}$, NR$^{11}$C(O)R$^{12}$, NR$^{11}$C(O)OR$^{12}$, NR$^{11}$S(O)$_2$R$^{13}$, C(O)R$^{11}$, C(O)OR$^{11}$, C(O)NR$^{11}$R$^{12}$, SF$_5$, a cyano group, a nitro group, or a halogen atom), R$^{11}$ and R$^{12}$ are the same or different and represent a C1 to C6 chain hydrocarbon group optionally having one or more atoms or groups selected from group V, a C3 to C9 alicyclic hydrocarbon group optionally having one or more atoms or groups selected from group Y, a phenyl group optionally having one or more atoms or groups selected from group Z, a 4-, 5- or 6-membered heterocyclic group optionally having one or more atoms or groups selected from group Z or a hydrogen atom, R$^{13}$ represents a C1 to C6 chain hydrocarbon group optionally having one or more atoms or groups selected from group V, a C3 to C9 alicyclic hydrocarbon group optionally having one or more atoms or groups selected from group Y, a phenyl group optionally having one or more atoms or groups selected from group Z or a 4-, 5- or 6-membered heterocyclic group optionally having one or more atoms or groups selected from group Z, R$^{14}$ represents a C1 to C6 chain hydrocarbon group optionally having one or more atoms or groups selected from the group consisting of halogen atoms and C3 to C9 alicyclic hydrocarbon groups (wherein the C3 to C9 alicyclic hydrocarbon group optionally has one or more halogen atoms or one or more C1 to C3 alkyl groups) or a C3 to C9 alicyclic hydrocarbon group optionally having one or more atoms or groups selected from the group consisting of halogen atoms and C1 to C3 alkyl groups, R$^{15}$ represents a C1 to C6 chain hydrocarbon group optionally having one or more atoms or groups selected from group V, a C3 to C9 alicyclic hydrocarbon group optionally having one or more atoms or groups selected from group Y, a phenyl group optionally having one or more atoms or groups selected from group Z, a 5- or 6-membered heterocyclic group optionally having one or more atoms or groups selected from group Z, C(O)R$^{11}$, C(O)OR$^{11}$, C(O)NR$^{11}$R$^{12}$ or a hydrogen atom, R$^{16}$ represents a C1 to C6 chain hydrocarbon group optionally having one or more atoms or groups selected from group V, a C3 to C9 alicyclic hydrocarbon group optionally having one or more atoms or groups selected from group Y, a phenyl group optionally having one or more atoms or groups selected from group Z, a 5- or 6-membered heterocyclic group optionally having one or more atoms or groups selected from group Z, $C(O)R^{11}$, $C(O)OR^{11}$, $C(O)NR^{11}R^{12}$, $S(O)_2R^{11}$, $S(O)_2NR^{11}R^{12}$ or a hydrogen atom, Q represents an oxygen atom or a sulfur atom, m represents 0, 1 or 2, and n represents 0, 1 or 2;

Group X: a group consisting of C3 to C9 alicyclic hydrocarbon groups optionally having one or more atoms or groups selected from the group consisting of halogen atoms and C1 to C3 alkyl groups, C1 to C6 alkoxy groups optionally having one or more halogen atoms, C1 to C6 alkylsulfanyl groups optionally having one or more halogen atoms, C1 to C6 alkylsulfinyl groups optionally having one or more halogen atoms, C1 to C6 alkylsulfonyl groups optionally having one or more halogen atoms, C2 to C6 alkylcarbonyl groups optionally having one or more halogen atoms, C2 to C6 alkoxycarbonyl groups optionally having one or more halogen atoms, hydroxy groups, mercapto groups, cyano groups, and halogen atoms, Group Y: a group consisting of C1 to C6 alkyl groups optionally having one or more halogen atoms, C1 to C6 alkoxy groups optionally having one or more halogen atoms, C1 to C6 alkylsulfanyl groups optionally having one or more halogen atoms, C1 to C6 alkylsulfinyl groups optionally having one or more halogen atoms, C1 to C6 alkylsulfonyl groups optionally having one or more halogen atoms, and halogen atoms, Group Z: a group consisting of C1 to C6 alkyl groups optionally having one or more halogen atoms, C1 to C6 alkoxy groups optionally having one or more halogen atoms, C1 to C6 alkylsulfanyl groups optionally having one or more halogen atoms, C1 to C6 alkylsulfinyl groups optionally having one or more halogen atoms, C1 to C6 alkylsulfonyl groups optionally having one or more halogen atoms, C1 to C6 alkylamino groups optionally having one or more halogen atoms, C2 to C8 dialkylamino groups optionally having one or more halogen atoms, C2 to C6 alkylcarbonyl groups optionally having one or more halogen atoms, C2 to C6 alkoxycarbonyl groups optionally having one or more halogen atoms, hydroxy groups, mercapto groups, amino groups, cyano groups, nitro groups, and halogen atoms, Group W: a group consisting of C3 to C9 alicyclic hydrocarbon groups optionally having one or more atoms or groups selected from the group consisting of halogen atoms and C1 to C3 alkyl groups, C1 to C6 alkoxy groups optionally having one or more halogen atoms, C1 to C6 alkylsulfanyl groups optionally having one or more halogen atoms, C1 to C6 alkylsulfinyl groups optionally having one or more halogen atoms, C1 to C6 alkylsulfonyl groups optionally having one or more halogen atoms, C2 to C6 alkylcarbonyl groups optionally having one or more halogen atoms, C2 to C6 alkoxycarbonyl groups optionally having one or more halogen atoms, hydroxy groups, cyano groups, and halogen atoms, Group V: a group consisting of C3 to C9 alicyclic hydrocarbon groups optionally having one or more atoms or groups selected from group Y, a phenyl group optionally having one or more atoms or groups selected from group Z, a 5- or 6-membered heterocyclic group optionally having one or more atoms or groups selected from group Z, a C1 to C6 alkoxy group optionally having one or more halogen atoms, a C2 to C6 alkenyloxy group optionally having one or more halogen atoms, a C2 to C6 alkynyloxy group optionally having one or more halogen atoms, a C1 to C6 alkylsulfanyl group optionally having one or more halogen atoms, a C1 to C6 alkylsulfinyl group optionally having one or more halogen atoms, a C1 to C6 alkylsulfonyl group optionally having one or more halogen atoms, a C1 to C6 alkylaminosulfonyl group optionally having one or more halogen atoms, a C2 to C8 dialkylaminosulfonyl group optionally having one or more halogen atoms, a C1 to C6 alkylamino group optionally having one or more halogen atoms, a C2 to C8 dialkylamino group optionally having one or more halogen atoms, a C2 to C6 alkylcarbonylamino group optionally having one or more halogen atoms, a C2 to C6 alkoxycarbonylamino group optionally having one or more halogen atoms, a C2 to C6 alkylcarbonyl group optionally having one or more halogen atoms, a C2 to C6 alkoxycarbonyl group optionally having one or more halogen atoms, a C2 to C6 alkylaminocarbonyl group optionally having one or more halogen atoms, a C3 to C10 dialkylaminocarbonyl group optionally having one or more halogen atoms, cyano groups, hydroxy groups, and halogen atoms;

when m is 1 or 2 in $S(O)_mR^{11}$, $R^{11}$ does not represent a hydrogen atom.

2. The amide compound according to claim 1, wherein $R^1$ is a C1 to C6 alkyl group optionally having one or more atoms or groups selected from the group consisting of halogen atoms and cyclopropyl groups (wherein the cyclopropyl group optionally has one or more halogen atoms or one or more C1 to C3 alkyl groups), a C3 to C6 cycloalkyl group optionally having one or more atoms or groups selected from the group consisting of halogen atoms and C1 to C3 alkyl groups, a C2 to C6 alkenyl group optionally having one or more halogen atoms or a C2 to C6 alkynyl group optionally having one or more halogen atoms, $R^2$, $R^3$ and $R^4$ are the same or different and are a C1 to C6 chain hydrocarbon group optionally having one or more atoms or groups selected from group X, a phenyl group optionally having one or more atoms or groups selected from group Z, a 5- or 6-membered heterocyclic group optionally having one or more atoms or groups selected from group Z, $OR^{11}$, $S(O)_mR^{11}$, $S(O)_2NR^{11}R^{12}$, $NR^{11}R^{12}$, $NR^{15}C(O)R^{11}$, $NR^{15}C(O)OR^{11}$, $NR^{15}C(O)NR^{11}R^{12}$, $NR^{16}S(O)_2R^{13}$, $C(O)R^{11}$, $C(O)OR^{11}$, $C(O)NR^{11}R^{12}$, $C(O)NR^{11}NR^{15}R^{16}$, a cyano group, a halogen atom or a hydrogen atom, $R^5$ is a C1 to C6 alkyl group optionally having one or more atoms or groups selected from the group consisting of halogen atoms and cyclopropyl groups (wherein the cyclopropyl group optionally has one or more halogen atoms or one or more C1 to C3 alkyl groups), a C3 to C6 cycloalkyl group optionally having one or more atoms or groups selected from the group consisting of halogen atoms and C1 to C3 alkyl groups, a (C1 to C6 alkoxy)C1 to C6 alkyl group optionally having one or more halogen atoms, a C2 to C6 alkenyl group optionally having one or more halogen atoms, a C2 to C6 alkynyl group optionally having one or more halogen atoms, a C1 to C6 alkyl group having one thiazolyl group (wherein the thiazolyl group optionally has one or more atoms or groups selected from the group consisting of C1 to C3 alkyl groups optionally having one or more halogen atoms and halogen atoms), a C1 to C6 alkyl group having one pyridyl group (wherein the pyridyl group optionally has one or more atoms or groups selected from the group consisting of C1 to C3 alkyl groups optionally having one or more halogen atoms and halogen atoms), $C(O)R^{11}$, $C(O)OR^{11}$ or a hydrogen atom, $R^6$ and $R^{10}$ are the same or different and are a C1 to C6 alkyl group optionally having one or more halogen atoms, a fluorine atom or a hydrogen atom, $R^7$, $R^8$ and $R^9$ are the same or different and are a C1 to C6 chain hydrocarbon group optionally having one or more atoms or groups selected from group X, a C1 to C6 alkoxy group optionally having one or more halogen atoms, $OR^{14}$, $S(O)_m R^{11}$, a halogen atom or a hydrogen atom (wherein at least one of $R^7$, $R^8$ and $R^9$ represents a C1 to C6 chain hydrocarbon group optionally having one or more atoms or groups selected from group X, a C1 to C6 alkoxy group optionally having one or more halogen atoms, $OR^{14}$, $S(O)_m R^{11}$, or a halogen atom), $R^{11}$ and $R^{12}$ are the same or different and are a C1 to C6 alkyl group optionally having one or more halogen atoms, a phenyl group optionally having one or more atoms or groups selected from the group consisting of C1 to C3 alkyl groups optionally having one or more halogen atoms and halogen atoms, a 5- or 6-membered heterocyclic group optionally having one or more atoms or groups selected from the group consisting of C1 to C3 alkyl groups optionally having one or more halogen atoms and halogen atoms, a C3 to C6 cycloalkyl group optionally having one or more atoms or groups selected from the group consisting of halogen atoms and C1 to C3 alkyl groups or a hydrogen atom, and Q is an oxygen atom, or an N-oxide thereof.

3. The amide compound according to claim 1, wherein $R^1$ is a C3 to C6 cycloalkyl group optionally having one or more atoms or groups selected from the group consisting of halogen atoms and C1 to C3 alkyl groups, a C1 to C6 alkyl group optionally having one or more halogen atoms or a (C3 to C6 cycloalkyl)C1 to C3 alkyl group optionally having one or more halogen atoms, $R^2$, $R^3$ and $R^4$ are the same or different and are a C1 to C6 alkyl group optionally having one or more halogen atoms, a 5- or 6-membered heterocyclic group optionally having one or more atoms or groups selected from C1 to C3 alkyl groups optionally having one or more halogen atoms and halogen atoms, $OR^{11}$, $S(O)_m R^{11}$, $NR^{11}R^{12}$, $NR^{15}C(O)R^{11}$, $NR^{15}C(O)OR^{11}$, $NR^{15}C(O)NR^{11}R^{12}$, $NR^{16}S(O)_2 R^{13}$, $C(O)OR^{11}$, $C(O)NR^{11}R^{12}$, $C(O)NR^{11}NR^{15}R^{16}$, a cyano group, a halogen atom or a hydrogen atom, $R^5$ is a C1 to C6 alkyl group optionally having one or more atoms or groups selected from the group consisting of halogen atoms and cyclopropyl groups (wherein the cyclopropyl group optionally has one or more halogen atoms or one or more C1 to C3 alkyl groups), a C3 to C6 cycloalkyl group optionally having one or more atoms or groups selected from the group consisting of halogen atoms and C1 to C3 alkyl groups, a (C1 to C6 alkoxy)C1 to C6 alkyl group optionally having one or more halogen atoms, a C2 to C6 alkenyl group optionally having one or more halogen atoms, a C2 to C6 alkynyl group optionally having one or more halogen atoms, a C2 to C6 alkylcarbonyl group optionally having one or more halogen atoms, a C2 to C6 alkoxycarbonyl group optionally having one or more halogen atoms or a hydrogen atom, $R^6$ and $R^{10}$ are the same or different and are a fluorine atom or a hydrogen atom, $R^7$, $R^8$ and $R^9$ are the same or different and are a C1 to C6 alkyl group optionally having one or more atoms or groups selected from the group consisting of C1 to C3 alkoxy groups and halogen atoms, a C2 to C6 alkenyl group optionally having one or more halogen atoms, a C2 to C6 alkynyl group optionally having one or more halogen atoms, a C1 to C6 alkoxy group optionally having one or more halogen atoms, a C1 to C6 alkylsulfanyl group optionally having one or more halogen atoms, a C1 to C6 alkylsulfinyl group optionally having one or more halogen atoms, a C1 to C6 alkylsulfonyl group optionally having one or more halogen atoms, a halogen atom or a hydrogen atom (wherein at least one of $R^7$, $R^8$ and $R^9$ represents a C1 to C6 alkyl group optionally having one or more atoms or groups selected from the group consisting of C1 to C3 alkoxy groups and halogen atoms, a C2 to C6 alkenyl group optionally having one or more halogen atoms, a C2 to C6 alkynyl group optionally having one or more halogen atoms, a C1 to C6 alkoxy group optionally having one or more halogen atoms, a C1 to C6 alkylsulfanyl group optionally having one or more halogen atoms, a C1 to C6 alkylsulfinyl group optionally having one or more halogen atoms, a C1 to C6 alkylsulfonyl group optionally having one or more halogen atoms, or a halogen atom), $R^{11}$ is a C1 to C6 alkyl group optionally having one or more halogen atoms or a hydrogen atom, and Q is an oxygen atom, or an N-oxide thereof.

4. The amide compound according to claim 1, wherein $R^1$ is a C1 to C6 alkyl group, a cyclopropyl group or a cyclopropylmethyl group, $R^2$, $R^3$ and $R^4$ are the same or different and are a C1 to C3 alkyl group optionally having one or more halogen atoms, a C1 to C3 alkylsulfanyl group optionally having one or more halogen atoms, a C1 to C3 alkylsulfinyl group optionally having one or more halogen atoms, a C1 to C3 alkylsulfonyl group optionally having one or more halogen atoms, an amino group, a C1 to C3 alkylamino group optionally having one or more halogen atoms, a C2 to C6 dialkylamino group optionally having one or more halogen atoms, a C2 to C6 alkylcarbonylamino group optionally having one or more halogen atoms, a C2 to C6 alkoxycarbonylamino group optionally having one or more halogen atoms, a C2 to C6 alkylaminocarbonyl group optionally having one or more halogen atoms, a C2 to C6 dialkylaminocarbonyl group optionally having one or more halogen atoms, a C2 to C6 alkoxycarbonyl group optionally having one or more halogen atoms, a 5- or 6-membered heterocyclic group optionally having one or more atoms or groups selected from the group consisting of C1 to C3 alkyl groups optionally having one or more halogen atoms and halogen atoms, a halogen atom or a hydrogen atom, $R^5$ is a C1 to C6 alkyl group optionally having one or more atoms or groups selected from the group consisting of halogen atoms and cyclopropyl groups (wherein the cyclopropyl group optionally has one or more halogen atoms or one or more C1 to C3 alkyl groups), a C3 to C6 cycloalkyl group optionally having one or more atoms or groups selected from the group consisting of halogen atoms and C1 to C3 alkyl groups, a C2 to C6 alkenyl group optionally having one or more halogen atoms, a C2 to C6 alkynyl group optionally having one or more halogen atoms, a (C1 to C6 alkoxy)C1 to C6 alkyl group optionally having one or more halogen atoms, a C2 to C6 alkylcarbonyl group optionally having one or more halogen atoms, a C2 to C6 alkoxycarbonyl group optionally having one or more halogen atoms or a hydrogen atom, $R^6$ and $R^{10}$ are the same or different and are a fluorine atom or a hydrogen atom, $R^7$, $R^8$ and $R^9$ are the same or different and are a C1 to C6 haloalkyl group, a C2 to C6 haloalkenyl group, a C1 to C6 haloalkoxy group, a C1 to C6 haloalkylsulfanyl group, a C1 to C6 haloalkylsulfinyl group, a C1 to C6 haloalkylsulfonyl group, a halogen atom or a hydrogen atom, and Q is an oxygen atom, or an N-oxide thereof.

5. The amide compound according to claim 1, wherein $R^5$ is a C1 to C6 alkyl group optionally having one or more atoms or groups selected from the group consisting of halogen atoms and cyclopropyl groups (wherein the cyclopropyl group optionally has one or more halogen atoms or one or more C1 to C3 alkyl groups), a C2 to C6 alkenyl group optionally having one or more halogen atoms, a C2 to C6 alkynyl group optionally having one or more halogen atoms, a (C1 to C6 alkoxy)C1 to C6 alkyl group optionally having one or more halogen atoms, a C3 to C6 cycloalkyl group optionally having one or more atoms or groups selected from the group consisting of halogen atoms and C1 to C3 alkyl groups, a C2 to C6 alkylcarbonyl group optionally having one or more halogen atoms or a C2 to C6 alkoxycarbonyl group optionally having one or more halogen atoms, or an N-oxide thereof.

6. The amide compound according to claim 1, wherein $R^5$ is a hydrogen atom, or an N-oxide thereof.

7. The amide compound according to claim 1, wherein one or two of $G^1$, $G^2$, $G^3$, $G^4$ and $G^5$ are a nitrogen atom, or an N-oxide thereof.

8. The amide compound according to claim 7, wherein $G^1$ is a nitrogen atom or $CR^6$, $G^2$ is a nitrogen atom or $CR^7$, $G^3$ is $CR^8$, $G^4$ is $CR^9$, $G^5$ is a nitrogen atom or $CR^{10}$, and one or two of $G^1$, $G^2$ and $G^5$ are a nitrogen atom, or an N-oxide thereof.

9. The amide compound according to claim 7, wherein $G^1$ is a nitrogen atom or CH, $G^5$ is a nitrogen atom or CH (wherein one or two of $G^1$, $G^2$ and $G^5$ represent a nitrogen atom), and $R^7$, $R^8$ and $R^9$ are the same or different and are a C1 to C6 haloalkyl group, a C2 to C6 haloalkenyl group, a C1 to C6 haloalkoxy group, a C1 to C6 haloalkylsulfanyl group, a C1 to C6 haloalkylsulfinyl group, a C1 to C6 haloalkylsulfonyl group, a halogen atom or a hydrogen atom, or an N-oxide thereof.

10. The amide compound according to claim 7, wherein $G^1$ is a nitrogen atom or CH, $G^5$ is a nitrogen atom or CH (wherein one or two of $G^1$, $G^2$ and $G^5$ represent a nitrogen atom), and $R^7$, $R^8$ and $R^9$ are the same or different and are a C1 to C3 perfluoroalkyl group, a C1 to C3 perfluoroalkoxy group, a C1 to C3 perfluoroalkylsulfanyl group, a C1 to C3 perfluoroalkylsulfinyl group, a C1 to C3 perfluoroalkylsulfonyl group, a halogen atom or a hydrogen atom, or an N-oxide thereof.

11. The amide compound according to claim 7, wherein one of $G^1$, $G^2$ and $G^5$ is a nitrogen atom, or an N-oxide thereof.

12. The amide compound according to claim 7, wherein $G^1$ is a nitrogen atom, $G^2$ is $CR^7$, $G^3$ is $CR^8$, $G^4$ is $CR^9$, and $G^5$ is $CR^{10}$, or an N-oxide thereof.

13. The amide compound according to claim 7, wherein $G^1$ is $CR^6$, $G^2$ is a nitrogen atom, $G^3$ is $CR^8$, $G^4$ is $CR^9$, and $G^5$ is $CR^{10}$, or an N-oxide thereof.

14. The amide compound according to claim 1, wherein $G^1$ is $CR^6$, $G^2$ is $CR^7$, $G^3$ is $CR^8$, $G^4$ is $CR^9$, and $G^5$ is $CR^{10}$, or an N-oxide thereof.

15. The amide compound according to claim 14, wherein $G^1$ is CH, $G^2$ is $CR^7$, $G^3$ is $CR^8$, $G^4$ is $CR^9$, and $G^5$ is CH, and $R^7$, $R^8$ and $R^9$ are the same or different and are a C1 to C6 haloalkyl group, a C2 to C6 haloalkenyl group, a C1 to C6 haloalkoxy group, a C1 to C6 haloalkylsulfanyl group, a C1 to C6 haloalkylsulfinyl group, a C1 to C6 haloalkylsulfonyl group, a halogen atom or a hydrogen atom, or an N-oxide thereof.

16. The amide compound according to claim 14, wherein $G^1$ is CH, $G^2$ is $CR^7$, $G^3$ is $CR^8$, $G^4$ is $CR^9$, and $G^5$ is CH, and $R^7$, $R^8$ and $R^9$ are the same or different and are a C1 to C3 perfluoroalkyl group, a C1 to C3 perfluoroalkoxy group, a C1 to C3 perfluoroalkylsulfanyl group, a C1 to C3 perfluoroalkylsulfinyl group, a C1 to C3 perfluoroalkylsulfonyl group, a halogen atom or a hydrogen atom, or an N-oxide thereof.

17. A pest control composition comprising the compound as defined in claim 1, and an inert carrier.

18. A method for controlling pests comprising applying an effective amount of the compound as defined in claim 1 to a pest or a pest-infested area.

* * * * *